US011033616B2

(12) United States Patent
Poulet et al.

(10) Patent No.: US 11,033,616 B2
(45) Date of Patent: Jun. 15, 2021

(54) RECOMBINANT VIRAL VECTOR SYSTEMS EXPRESSING EXOGENOUS FELINE PARAMYXOVIRUS GENES AND VACCINES MADE THEREFROM

(71) Applicants: Boehringer Ingelheim Vetmedica GmbH, Ingelheim am Rhein (DE); BOEHRINGER INGELHEIM ANIMAL HEALTH USA INC., Duluth, GA (US)

(72) Inventors: Hervé Poulet, Ste Foy-lès-Lyon (FR); Veljko Nikolin, Hannover (DE); Abraham Johannes De Smit, Wijchen (NL); Teshome Mebatsion, Watkinsville, GA (US)

( * ) Notice: Subject to any disclaimer, the term of this patent is extended or adjusted under 35 U.S.C. 154(b) by 0 days.

(21) Appl. No.: 16/337,636

(22) PCT Filed: Feb. 20, 2019

(86) PCT No.: PCT/EP2019/054151
§ 371 (c)(1),
(2) Date: Mar. 28, 2019

(87) PCT Pub. No.: WO2019/162294
PCT Pub. Date: Aug. 29, 2019

(65) Prior Publication Data
US 2020/0206339 A1 Jul. 2, 2020

(30) Foreign Application Priority Data
Feb. 23, 2018 (EP) ..................................... 18158450

(51) Int. Cl.
*A61K 39/12* (2006.01)
*C12N 15/86* (2006.01)
*A61K 39/00* (2006.01)

(52) U.S. Cl.
CPC .............. *A61K 39/12* (2013.01); *C12N 15/86* (2013.01); *A61K 2039/5254* (2013.01); *A61K 2039/5256* (2013.01); *C12N 2710/24043* (2013.01); *C12N 2760/18034* (2013.01); *C12N 2760/18434* (2013.01)

(58) Field of Classification Search
CPC ............ A61K 39/12; A61K 2039/5254; A61K 2039/5256; C12N 15/86; C12N 2710/24043; C12N 2760/18034; C12N 2760/18434
See application file for complete search history.

(56) References Cited

U.S. PATENT DOCUMENTS

2013/0230529 A1* 9/2013 Yuen .................... C07K 14/005
424/139.1

FOREIGN PATENT DOCUMENTS

| JP | 2015198654 | | 11/2015 |
|---|---|---|---|
| WO | 2005013918 | A2 | 2/2005 |
| WO | 2013107290 | A1 | 7/2013 |
| WO | 2018037100 | A1 | 3/2018 |

OTHER PUBLICATIONS

Marcacci et al; "Genome characterization of feline morbillivirus from Italy"; J. of Virological Methods (2016), vol. 234, p. 160-163.
S. Sakaguchi et al; "Genetic diversity of feline morbilliviruses isolated in Japan"; J. of General Virology (2014), vol. 95, No. Pt 7, p. 1464-1468.
Taylor et al., 1991, Vaccine, vol. 9, No. 3, pp. 190-193.
Taylor et al., 1992, Virology, vol. 187, No. 1, pp. 321-328.
Taylor et al., 1994, Dev Biol Stand., vol. 82, pp. 131-135.
Tartaglia et al., Journal of Virology, 1993, vol. 67, No. 4, pp. 2370-2375.
Woo et al., Proceedings of the National Academy of Sciences, Apr. 3, 2012, vol. 109, No. 14, pp. 5435-5440.
Woo et al.,Proceedings of the National Academy of Sciences, Mar. 19, 2012, vol. 109, No. 14, pp. 1-7.
Database EMBL Apr. 17, 2012, EBI accession No. EM_STD:JQ411016, Database accession No. JQ411016.
Database EMBL Apr. 17, 2012, EBI accession No. EM_STD:JQ411014, Database accession No. JQ411014.
Database EMBL Apr. 17, 2012, EBI accession No. EM_STD:JQ411015, Database accession No. JQ411015.
Sieg Michael et al., Aug. 12, 2015, Virus Genes, Kluwer Academic Publishers, Boston, US, vol. 51, No. 2, pp. 294-297.
Database EMBL, Dec. 11, 2014, EBI accession No. EM_STD:KP159803, Database accession No. KP159803.
Database EMBL, Jul. 6, 2015, EBI accession No. EM_STD:KR269599, Database accession No. KR269599.
Weli et al., Feb. 3, 2011, Virology Journal, Biomed Central, London, GB, vol. 8, No. 1, p. 49 (15 pages).
Sieg Michael et al., Apr. 19, 2018, Genome Announcements, vol. 6, No. 16, pp. e00244-18.
Database EMBL, Mar. 8, 2018, EBI accession No. EM_STD:MG563820, Database accession No. MG563820.
De Vries et al., J. gen. Virol., Jan. 1, 1988, vol. 69, pp. 2071-2083.
Marciani et al., Vaccine, Feb. 1, 1991, vol. 9, No. 2, pp. 89-96.
McEachern et al., Vaccine, Jul. 23, 2008, vol. 26, No. 31, pp. 3842-3852.
Park et al.; Virology 468-470 (2014) 524-531.

* cited by examiner

*Primary Examiner* — Rachel B Gill
(74) *Attorney, Agent, or Firm* — Steffan Finnegan

(57) ABSTRACT

The present invention relates to exogenous feline paramyxovirus genes, which are expressed from recombinant viral vector systems.

27 Claims, 17 Drawing Sheets

Specification includes a Sequence Listing.

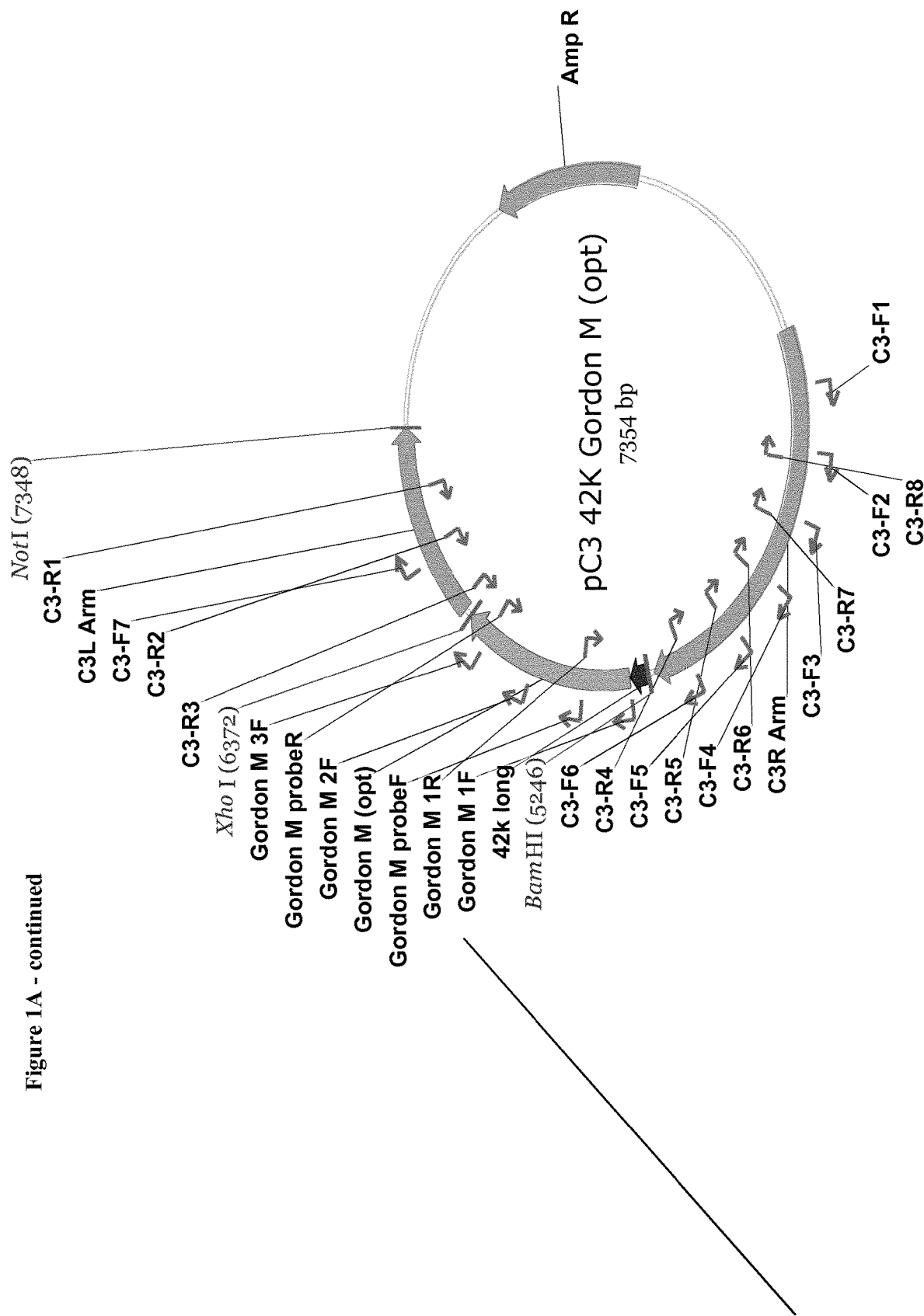
Figure 1A - continued

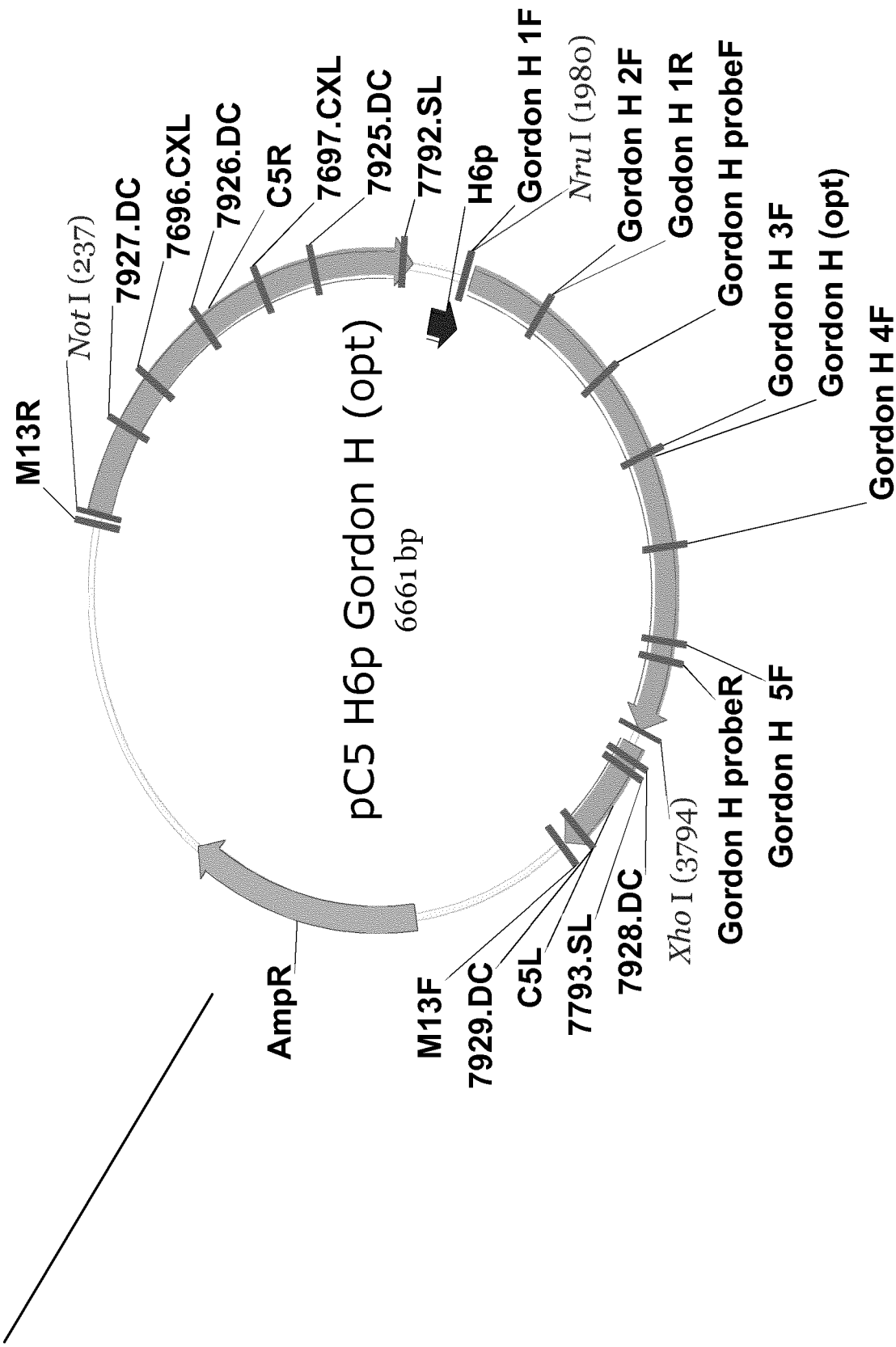
Figure 1A - continued

Figure 1B
From a single IVR, two constructs were isolated
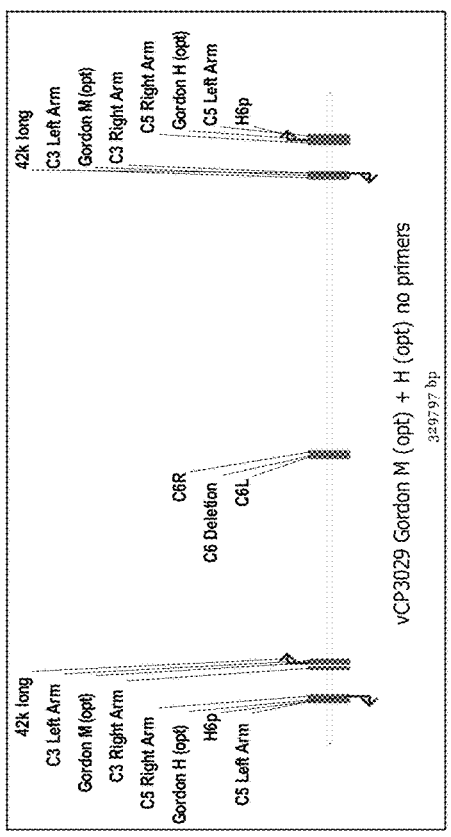
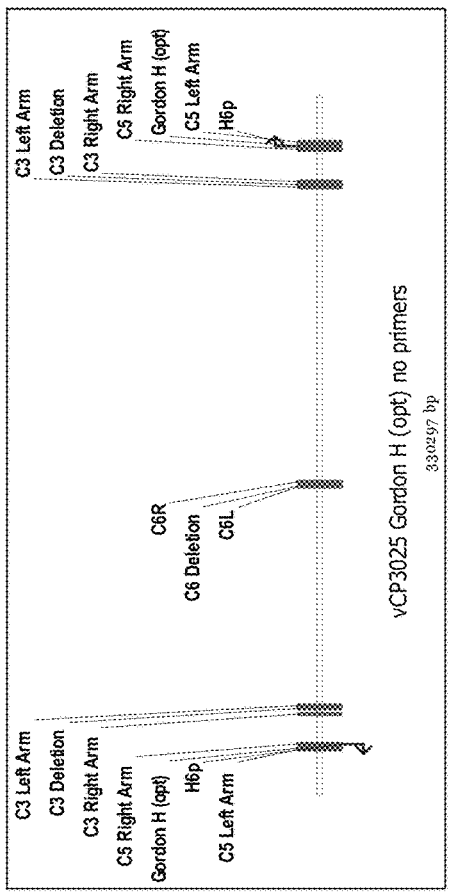

Figure 2 vCP3025
C5 Sequence: sequence confirmed 304,701 - 308,870

```
C5 Right Arm: 304,779 - 306,314
H6 promoter: 306,412 - 306,535
Gordon H (opt): 306,536 – 308,323
C5 Left Arm: 308,374 – 308,878
```

```
304674                              AAA TGACTATGTA CCGTTATTGC ATGAACGATA TTATAAATAT
                                    TTT ACTGATACAT GGCAATAACG TACTTGCTAT AATATTTATA
304744  AGGTTCTCGT AGGAGAGAAC TATTGACTAT GGCAATGAAT GTTAATGTT ATACTTTGGA TGAAGCTATA
        TCCAAGAGCA TCCTCTCTTG ATAACTGATA CCGTTACTTA CAATTACAA TATGAAACCT ACTTCGATAT
304814  AATATGCATT GGAAAATAA TCCATTTAAA GAAACGATTC AAATACTACA AAACCTAAGT GATAATATGT
        TTATACGTAA CCTTTTTATT AGGTAAATTT CTTTCCTAAG TTTATGATGT TTTGGATTCG CTATTATACA
304884  TAACTAAGCT TATTCTTAAC GACCCTTTAA ATATACAACAA ATAACATAA TTTTGTATA ACCTAACAAA
        ATTGATTCGA ATAAGAATTG CTGGGAAATT TATATGTGTT TATTTGTATT AAAAACATAT TGGATTGTTT
304954  TAACTAAAAC ATAAAATAA TAAAGGAAA TGTAATATCG TAATTATTTT ACTCAGGAAT GGGGTTAAAT
        ATTGATTTTG TATTTTTATT ATTTTCCTTT ACATTATAGC ATTAATAAAA TGAGTCCTTA CCCCAATTTA
305024  ATTTATATCA CGTGTATAC TATACTGTTA TCGTATCTC TTTACAATTA CTATTACGAA TATGCAAGAG
        TAAATATAGT GCACATATAC ATATGACAAT AGCATATGAC AAATGTTAAT GATAATGCTT ATACGGTTCTC
305094  ATAATAAGAT TACGTATTTA AGAGAATCTT GTCATGATAA TTGGGTACGA CATAGTGATA AATGCTATTT
        TATTATTCTA ATGCATAAAT TCTCTTAGAA CAGTACTATT AACCCATGCT GTATCGCTAT TTACGATAAA
305164  CGCATCGTTA CATAAAGTCA GTTGGAAAGA TGGATTGAC AGATGTAACT TAATAGGTCC AAAAATGTTA
        GCGTAGCAAT GTATTTCAGT CAACCTTTCT ACCTAAACTG TCTACATTGA ATTATCCACG TTTTTACAAT
305234  AATACACGA TTCTATCCGA AGATAGGATA CCAGTTATAT TATACAAAAA TCAGCTCGTTG GATAAAACAG
        TTATTGTCGT AAGATAGCCT TCTATCCTAT GGTCAATATA ATATGTTTTT AGTGCCAAC CTATTTTGTC
305304  ATTCTGCAAT ATTCGTAAAA GATGAAGATT ACTGCCAATT TGTAAACTAT GACAATAAAA AGCCATTTAT
        TAAGACGTTA TAAGCATTTT CTACTTCTAA TGACGGTTAA ACATTTGATA CTGTTATTTT TCGGTAAATA
305374  CTCAACGACA TCGTGTAATT CTTCCATGTT TTATGTATGT GTTTCAGATA TTATGAGATT ACTATAAACT
        GAGTTGCTGT AGCACATTAA GAAGGTACAA AATACATCTAT CAAAGTCTAT AATACTCTAA TGATATTTGA
305444  TTTTGTATAC TTATATTCCG TAAACTATAT TAATCATGAA GAAAATGAAA AAGTATAGAA GCTGTTCACG
        AAAACATATG AATATAAGGC ATTTGATATA ATTAGTACTT CTTTTACTTT TTCATATGTT CGACAAGTGC
305514  AGCGGTTGTT GAAAACAACA AAATTATACA TTCAAGATGG CTTACATATA CGTCTGTGAG GCTATCATGG
        TCGCCAACAA CTTTTGTTGT TTTAATATGT AAGTTCTACC GAATGTATAT GCAGACACTC CGATAGTACC
305584  ATAATGACAA TGCATCTCTA AATGGTTTT TGGACAATGG ATTCGACCCT AACACGGAAT ATGGTACTCT
        TATTACTGTT ACGTAGAGAT TTATCCAAAA ACCTGTTACC TAAGCTGGGA TTGTGCCTTA TACCATGAGA
305654  ACAATCTCCT CTTGAAATGG CTGTAATGTT CAAGAATACC GAGGGTATAA AAATCTTGAT GAGCTATGGA
        TGTTAGAGGA GAACTTTACC GACATTACAA GTTCTTATGG CTCGATATT TTAGAACTA CTCCATACCT
305724  GCTAAACCTG TAGTTACTGA ATGCACAACT TCTTGTCTGC ATGATGCGCT GTTGAGAGAC GACTACAAAA
        CGATTTGGAC ATCAATGACT TACGTGTTGA AGAACAGACG TACTACGCCA CAACTCTCTG CTGATGTTTT
305794  TAGTGAAAGA TCTGTTGAAG AATAACTATG TAAACAATGT TCTTTACAGC GGAGGCTTTA CTCCTTTGTG
        ATCACTTTCT AGACAACTTC TTATTGATAC ATTTGTTACA AGAAATGTCG CCTCCGAAAT GAGGAAACAC
305864  TTTGGCAGCT TACCTTAACA AAGTTAATTT GGTAAACTTC CTATTGGCTC ATTCGGCGGA TGTAGATATT
        AAACCGTCGA ATGGAATTGT TTCAATTAAA CCAATTTGAA GATAACCGAG TAAGCCGCCT ACATCTATAA
305934  TCAAACACGG ATCGGTTAAC TCCTCTACAT ATAGCCGTAT CAAATAAAAA TTTAACAATG GTTAAACTTC
        AGTTTGTGCT TAGCCAATTG AGGAGATGTA TATCGGCATA GTTTATTTTT AAATTGTTAC CAATTGAAG
306004  TATTGAACAA AGTTGCTGAT ACTGATTTGC TGAATAACAT GGGACGTACT CCTTAATGA TCGCTGTACA
        ATAACTTGTT TCCACGACTA TGACTGAACG ACCTATTGTA CCCTGCATGA GGAAATTACT AGCGACATGT
306074  ATCTGCAAAT ATTGAAATAT GTAGCACGCT ACTTAAAAAA AATAABATGT CCAGACTGG GAAAATTGA
        TAGACGTTTA TAACTTTATA CATCGTGCGA TGAATTTTTT TTATTTTACA GGTCTTGACC CTTTTAACT
306144  TCTTGCCAGC TGTAATTCAT GGTAGAAAG AAGTGCTCGA GCTACTTTTC AACAAGGGAG CAGATGTAAA
        AGAACGGTCG ACATTAAGTA CCATCTTTC TTCACGAGTC CGATGAAGTC GATGAAAAG TGTTCCCTC GTCTACATTT
306214  CTACATCTTT GAAAGAAATG GAAAATCATA TACTGTTTTG GAATTGATTA AAGAAGTTA CTCTGAGACA
        GATGTAGAAA CTTTCTTAC CTTTAGTAT ATGACAAAC CTTAACTAAT TTCTTTAAT GAGACTCTGT
306284  CAAAAGAGGT AGCTGAAGTG GTACTCTCAA AGGTACGTGA CTAATTAGCT ATAAAAAGGA TCCGGGTAAA
        GTTTTCTCCA TCGACTTCAC CATGAGAGTT TCCATGCACT GATTAATCGA TATTTTTCCT AGGCCCATT
306354  TTAATTAGTC ATCAGGCAGG GCGAGAACGA GACTACTTGT TGTTAATTA ATTAGAGCTT CTTTATTCTA
        AATTAATCAG TAGTCCGTCC CGCTCTTGCT CTGATAGACG AGCAATTAAT TAATCTCGA GAAATAAGAT
306424  TACTTAAAAA GTGAAAATAA ATACAAAGGT TCTTGAGGGT TGTGTTAAAT TGAAAGCGAG AAAAATCAT
        ATGAATTTTT CACTTTTATT TATGTTTCCA AGAACTCCCA ACACAATTTA ACTTTCGCTC TTTATTAGTA
306494  AAATTATTTC ATTATCGCGA TATCCGTTAA GTTTGTATCG TAATGGAAAG CAATAATAAC AAATACTATA
        TTTAATAAAG TAATAGCGCT ATAGGCAATT CAAACATGTA ATTACCTTTG GTTATTATTG TTTATGATAT
306564  AAGACAGCAA TCGGTACTTC AGCAAGATCG TGGACGAGAA TAAGACAGTC AATAATCACC TGTACTCCCT
        TTCTGTCGTT AGCCATGAAG TCGTTCTAGG ACCTGCTCTT ATTCTGTCAG TTATTAGTGG ACATGAGGGA
```

Figure 2 - continued

```
306634  GTCTATCAGG ATCATCACCG TGATCGCCAT CGTGGTGTCC CTGATCGCAA CCACTATCAC TATCATCAAT
        CAGATAGTCC TAGTAGTGGC ACTAGCGGTA GCACCACAGG GACTAGCGTT GGTGATAGTG ATAGTAGTTA
306704  GCCATCTCTG GCAGAACCAC TCTGAACAAT AACATGGACA TGCTGCTGAA CCAGCAGGAT AAGATCAATA
        CGGTAGAGAC CGTCTTGGTG AGACTTGTTA TTGTACCTGT ACGACGACTT GGTCGTCCTA TTCTAGTTAT
306774  ACATCAAAGA GATGATCTTC GACAGGATCT ATCCACTGAT CAACGCAATG AGCACCGAGC TGGGGCTGCA
        TGTAGTTTCT CTACTAGAAG CTGTCCTAGA TAGGTGACTA GTTGCGTTAC TCGTGGCTCG ACCCCGACGT
306844  CATCCCTACC CTGCTGGACG AACTGACTAA GTCCATCGAT CAGAAGATCA AAATCATGAC TCCACCTCTG
        GTAGGGATGG GACGACCTGC TTGACTGATT CAGGTAGCTA GTCTTCTAGT TTTAGTACTG AGGTGGAGAC
306914  GAAACCACTA CCTCTAATCT GAACTGGTGC ATCAATCCCC CAAACGGAAT CATCGTGGAC CCAAAAGGCT
        CTTTGGTGAT GGAGATTAGA CTTGACCACG TAGTTAGGGG GTTTGCCTTA GTAGCACCTG GGTTTTCCGA
306984  ACTGTGAGGG GCTGGAACTG TCCAAGACCT ATAAACTGCT GCTGGACCAG CTGGATATGC TGAGGAAGAA
        TGACACTCCC CGACCTTGAC AGGTTCTGGA TATTTGACGA CGACCTGGTC GACCTATACG ACTCCTTCTT
307054  AAGCCTGATC ATCAATAAGA AATCCATCAA CCAGTGCAGA CTGGTGGATA GCTCCAATAT CGTGTTCGCC
        TTCGGACTAG TAGTTATTCT TTAGGTAGTT GGTCACGTCT GACCACCTAT CGAGGTTATA GCACAAGCGG
307124  ACCGTGAACA TCCAGAGCAC TCCTAGGTTT CTGAATCTGG GACATACCGT GTCCAACCAG AGAATCACTT
        TGGCACTTGT AGGTCTCGTG AGGATCCAAA GACTTAGACC CTGTATGGCA CAGGTTGGTC TCTTAGTGAA
307194  TCGGACAGGG TACTTACTCT AGCACCTATA TCATCACTAT CCAGGAGGAC GGTCTGACCG ATGTGCAGTA
        AGCCTGTCCC ATGAATGAGA TCGTGGATAT AGTAGTGATA GGTCCTCCTG CCAGACTGGC TACACGTCAT
307264  CAGAGTGTTT GAAATCGGCT ATATCTCTGA CCAGTTCGGG ACTTTTCCTT CTCTGATCGT GAGCAGGGTG
        GTCTCACAAA CTTTAGCCGA TATAGAGACT GGTCAAGCCC TGAAAGGACT AGAGCTAGCA CTCGTCCCAC
307334  CTGCCCGTGA GAATGGTGCT GGGGATGGAG TCCTGCACTC TGACCTCTGA TAAGTTCGGC GGGTACTTCC
        GACGGGCACT CTTACCACGA CCCCTACCTC AGGACGTGAG ACTGGAGACT ATTCAAGCCG CCCATGAAGG
307404  TGTGCATGAA TATCCCCACC AGGTCTATCT ACGACTATGT GAACATCAGA GATCTGAAGA GCCTGTACGT
        ACACGTACTT ATAGGGGTGG TCCAGATAGA TGCTGATACA CTTGTAGTCT CTAGACTTCT CGGACATGCA
307474  GACCATCCCC CACTACGGCA AAATCAATTA CACTTATTTC AACTTTGGGA AGGTGAGGAG CCCACATGAG
        CTGGTAGGGG GTGATGCCGT TTTAGTTAAT GTGAATAAAG TTGAAACCCT TCCACTCCTC GGGTGTACTC
307544  ATCGACAAAA TCTGGCTGAC TTCTGAAAGA GGACAGATGA TCAGCGGTTA CTTCGCCGCA TTTGTGACTA
        TAGCTGTTTT AGACCGACTG AAGACTTTCT CCTGTCTACT AGTCGCCAAT GAAGCGGCGT AAACACTGAT
307614  TCACCATCAG GAACTACAAC AACTACCCTT ACAAGTGCCT GCACAACCCA TGTCTGGAGA GAAGCGAATC
        AGTGGTAGTC CTTGATGTTG TTGATGGGAA TGTTCACGGA CGTGTTGGGT ACAGACCTCT CTTCGCTTAG
307684  CTACTGCAAG GGATGGTATA AGAACATCAC TGGTACCGAC GATGTGCCCA TCCTGGCCTA CCTGCTGGTG
        GATGACGTTC CCTACCTATAT TCTTGTAGTG ACCATGGCTG CTACACGGGT AGGACCGGAT GGACGACCAC
307754  GAGATGAACG ATGAGGAAGG TCCACTGATC ACCCTGGTGG AAATCCCTCC CTACAATTAT ACTGCACCTA
        CTCTACTTGC TACTCCTTCC AGGTGACTAG TGGGACCACC TTTAGGGAGG GATGTTAATA TGACGTGGAT
307824  GCCATAACTC CCTGTACTAT GACGATAAGA TCAACAAGCT GATCATGACT ACCTCCCACA TCGGATATAT
        CGGTATTGAG GGACATGATA CTGCTATTCT AGTTGTTCGA CTAGTACTGA TGGAGGGTGT AGCCTATATA
307894  CCAGATCAAC GAGGTGCATG AAGTGATCGT GGGTGACAAT CTGAAGGCCA TCCTGCTGAA CAGGCTGAGC
        GGTCTAGTTG CTCCACGTAC TTCACTAGCA CCCACTGTTA GACTTCCGGT AGGACGACTT GTCCGACTCG
307964  GATGAGCACC CAACTCTGAC CGCATGTAGG TTCAATCAGG AGATCAAAGA AAGACATATC TCCGACGGCC
        CTACTCGTGG GTTGAGACTG GCGTACATCC AAGTTAGTCC TCTAGTTTCT TTCTGTATAG AGGCTGCCGG
308034  TGATCATCTC TAACAGCGCC CTGATCGATA TCCAGGAGAG GATGTACGTG ACCGTGAAGG CAGTGCCACC
        ACTAGTAGAG ATTGTCGCGG GACTAGCTAT AGGTCCTCTC CTACATGCAC TGGCACTTCC GTCACGGTGG
308104  TATCGGCAAT TATAACTTTA CCGTGGAACT GCACTCCAGA TCTAATACTA GCTACGTGGG GCTGCCTAGG
        ATAGCCGTTA ATATTGAAAT GGCACCTTGA CGTGAGGTCT AGATTATGAT CGATGCACCC CGACGGATCC
308174  CAGTTCAACG CAAGATATGA CAAACTGCAT CTGGAATGCT TTGCCTGGGA TAGATCCTGG TGGTGTGCAC
        GTCAAGTTGC GTTCTATACT GTTTGACGTA GACCTTACGA AACGGACCCT ATCTAGGACC ACCACACGTG
308244  TGATCCCCCA GTTTTCTCTG TCCTGGAATG AGAGCCTGTC CGTGGATACT GCTATTTTCA ACCTGATAAA
        ACTAGGGGGT CAAAAGAGAC AGGACCTTAC TCTCGGACAG GCACCTATGA CGATAAAAGT TGGACTATTT
308314  CTGTAACTAA CTCGAGTCTA GAATCGATCC CGGGTTTTTA TGACTAGTTA ATCACGGCCG CTTATAAAGA
        GACATTGATT GAGCTCAGAT CTTAGCTAGG GCCCAAAAAT ACTGATCAAT TAGTGCCGGC GAATATTTCT
308384  TCTAAAATGC ATAATTTCTA AATATGAAA AAAGTACAT CATGAGCAAC GCGTTAGTAT ATTTTACAAT
        AGATTTTACG TATTAAAGAT TTATTACTTT TTTTCATGTA GTACTCGTTG CGCAATCATA TAAAATGTTA
308454  GGAGATTAGC GCTCTATACC GTTCTATGTT TATTGATTCA GATGATGTTT TAGAAAAGAA AGTTATTGAA
        CCTCTAATTG CGAGATATGG CAAGATACAA ATAACTAAGT CTACTACAAA ATCTTTTCTT TCAATAACTT
308524  TATGAAAACT TTAATGAAGA TGAAGATGAC GACGATGATT ATTGTTGTAA ATCTGTTTTA GATGAAGAAG
        ATACTTTTGA AATTACTTCT ACTTCTACTG CTGCTACTAA TAACAACATT TAGACAAAAT CTACTTCTTC
308594  ATGACGCGCT AAAGTATACT ATGGTTACAA AGTATAGTCT TATACTACTA ATGGCGACTT GTGCAAGAAG
        TACTGCGCGA TTTCATATGA TACCAATGTT TCATATTCAGA ATATGATGAT TACCGCTGAA CACGTTCTTC
308664  GTATAGTATA GTGAAAATGT TGTTAGATTA TGATTATGAA AAACCAAATA AATCAGATCC ATATCTAAAG
        CATATCATAT CACTTTTACA ACAATCTAAT ACTAATACTT TTTGGTTTAT TTAGTCTAGG TATAGATTTC
308734  GTATCTCCTT TGCACATAAT TTCATCTATT CCTAGTTTAG AATACTTTTC ATTATATTTG TTTACAGCTG
        CATAGAGGAA ACGTGTATTA AAGTAGATAA GGATCAAATC TTATGAAAAG TAATATAAAC AAATGTCGAC
308804  AAGACCAAAA AAATATATCG ATAATACAAG AGTATGTTAA CTCCTAAT AAGATGAAAT TGAATCA
        TTCTGGTTTT TTTATATAGC TATTATGTTC TCATACAATT GAGGACGATTA TTCTACTTTA ACTTACT
```

Figure 3 vCP3029
C5 Sequence: sequence confirmed 304,166 – 308,380

```
C5 Right Arm: 304,279 – 305,814
H6 promoter: 305,912 - 306,035
Gordon H(opt): 306,036 – 307,823
C5 Left Arm: 307,874-308,378
```

```
304119                                                            TAG TTACTTGGAT AAATTAATCG
                                                                  ATC AATGAACCTA TTTAATTAGC
304189  AGACGCGTGA TAAAATGACT ATGTACCGTT ATTGCATGAA CGATATTATA AATATAGGTT CTCGTAGGAG
        TCTGCGCACT ATTTTACTGA TACATGGCAA TAACGTACTT GCTATAATAT TTATATCCAA GAGCATCCTC
304259  AGAACTATTG ACTATGGCAA TGAATGTTAA ATGTTATACT TTGGATGAAG CTATAAATAT GCATTGGAAA
        TCTTGATAAC TGATACCGTT ACTTACAATT TACAATATGA AACCTACTTC GATATTTATA CGTAACCTTT
304329  AATAATCCAT TTAAGAAAG GATTCAAATA CTACAAACC TAAGCGATAA TATGTTAACT AAGCTTATTC
        TTATTAGGTA AATTCTTTC GATGTTTG ATTCGCTATT ATACAATTGA TTCGAATAAG
304399  TTACGACGC TTTAAATATA CACAAATAAA CATAATTTTT GTATAACCTA ACAAATAACT AAAACATAAA
        AATGCTGCG AAATTTATAT GTGTTATATT GTATTAAAAA CATATTGGAT TGTTATTGA TTTGTATTT
304469  AATAATAAAA GGAAATGTAA TATCGTAATT ATTTTACTCA GGAATGGGT TAATATTTA TATCACGTGT
        TTATTATTTT CCTTTACATT ATAGCATTAA TAAAATGAGT CCTTACCCCA ATTATAAAT ATAGTGCACA
304539  ATATCTATAC TGTTATCGTA TACTCTTTAC AATTACTATT ACGAATATGC AAGAGATAAT AAGATTACGT
        TATAGATATG ACAATAGCAT ATGAGAAATG TTAATGATAA TGCTTATACG TTCTCTATTA TTCTAATGCA
304609  ATTTAAGAGA ATCTTGTCAT GATAATTGCG TACGACATAG TGATAAATGC TATTCGCAT CGTTACATAA
        TAAATTCTCT TAGAACAGTA CTATTAACCC ATGCTGTATC ACTATTTACG ATAAAGCGTA GCAATGTATT
304679  AGTCAGTTGG AAAGATGCAT TTGACAGATG TAACTTAATA GGTGCAAAAA TGTTAAATAA CAGCATTCTA
        TCAGTCAACC TTTCTACCTA AACTGTCTAC ATTGAATTAT CCACGTTTTT ACAATTTATT GTCGTAAGAT
304749  TCGGAGATA GGATACCAGT TATATTATAC AAAAATCACT GGTTGGATAA AACAGATTCT GCAATATTCG
        AGCCTCTAT CCTATGGTCA ATATAATATG TTTTTAGTGA CCAACCTATT TTGTCTAAGA CGTTATAAGC
304819  TAAAAGATGA AGATTACTGC GAATTTGTAA ACTATGACAA TAAAAAGCCA TTTATCTCAA CGACATCGTG
        ATTTTCTACT TCTAATGACG CTTAAACATT TGATACTGTT ATTTTTCGGT AAATAGAGTT GCTGTAGCAC
304889  TAATTCTTCC ATGTTTATG TATCTGTTTC AGTATATTATG AGATTACTAT AAACTTTTTG TATACTATA
        ATTAAGAAGG TACAAATAC ATACACAAAG TCTATAATAC TCTAATGATA TTTGAAAAAC ATATGAATAT
304959  TTCGTAAAC TATATTAATC ATGAAGAAAA TGAAAAGTA TAGAAGCTGT CACGAGCGG TTGTTGAAAA
        AAGGCATTTG ATATAATTAG TACTTCTTTT ACTTTTCAT ATCTTCGACA AGTGCTCGCC AACAACTTTT
305029  CAACAAAATT ATACATTCAA GATGGCTTAC ATATACGTCT GTGAGGCTAT CATGGATAAT GACAATGCAT
        GTTGTTTAA TATGTAAGTT CTACCGAATG TATATGCAGA CACTCCGATA GTACCTATTA CTGTTACGTA
305099  CTCTAAATAG GTTTTTGGAC AATGGATTCG ACCCTAACAC GGAATATGGT ACTCTACAAT CTCTCTTTGA
        GAGATTTATC CAAAAACCTG TTACCTAAGC TGGGATTGTG CCTTATACCA TGAGATGTTA GAGGAGAACT
305169  AATGGCTGTA ATGTTCAAGA ATACCGAGCG TATAAAAATC TTGATGAGCT ATGGAGCTAA ACCTGTAGTT
        TTACCGACAT TACAAGTTCT TATGGCTCCG ATATTTTTAG AACTACTCCA TACCTCGATT TGGACATCAA
305239  ACTGAATCGA CAACTTCTTG TCTGCATGAT GCGGTGTTCA GAGACGACTA CAAAATAGTG AAAGATCTGT
        TGACTTACGT GTTGAAGAAC AGACGTACTA CGCCACAACT CTCTGCTGAT GTTTATCAC TTTCTAGACA
305309  TGAAGAATAA CTATGTAAAC AATGTTCTTT ACAGCCGAGG CTTACTCCT TTGTGTTGG CAGCTTACCT
        ACTTCTTATT GATACATTTG TTACAAGAAA TGTCGGCCTCC GAATGAGGA AACACAAACC GTCGAATGGA
305379  TAACAAAGTT AATTGGTTA AACTTCTATT GGCTCATTCG GCGGATGTAG ATATTCAAA CACGGATCGG
        ATTGTTTCAA TTAACCAAT TGGAGATAA CGGAGTAGC CGCCTACATC TATAAAGTTT GTGCCTAGCC
305449  TTAACTCCTC TACATATAGC CGTATCAAAT AAAAATTTAA CAATGGTTAA ACTTCTATTG AACAAGGTG
        AATTGAGCAG ATGTATATCG GCATAGTTTA TTTTTAAATT GTTACCAATT TGAAGATAAC TTGTTCCAC
305519  CTGATACTGA CTTCCTGGAT AACATGGGAC GTGCTCCTTT AATGATCGCT GTACAATCTG GAATATTGA
        GACTATGACT GAACGACCTA TTGTACCCTG CATGACGAAA TTACTAGCCA CATGTTAGAC CTTTATAACT
305589  AATATGTAGC ACACTACTTA AAAAAAATAA AATGTCCAGA ACTGGGAAGA ATTGATCTTS CCAGCTGTAA
        TTATACATGT TGTGATGAAT TTTTTTATT TTACAGGTCT TGACCCTTTT TAACTAGAAC GGTCGACATT
305659  TTCATGGTAG AAAAGAAGTG CTCAGGCTAC TTTCAACAA AGGAGCAGAT GTAAACTACA TCTTTGAAAG
        AAGTACCATC TTTTCTTCAC GAGTCCGATG AAAAGTTGTT TCCTCGTCTA CATTGATGT AGAAACTTTC
305729  AAATGGAAAA TCATATACTG TTTTGGAATT CATTAAGAA AGTTACTCTG AGACACAAAA GAGGTAGCTG
        TTTACCTTTT AGTATATGAC AAAACCTTAA CTAATTCTT TCAATGACAC TCTGTGTTT CTCCATCGAC
305799  AAGTGCGTACT CTCAAGGTA CGTGACTAAT TAGCTATAAA AAGGATCCGG GTTAATTAAT TAGTCATCAG
        TTCACCATGA GAGTTTCCAT GCACTGATTA ATCGATATTT TTCCTAGGCC CAATTAATTA ATCAGTAGTC
305869  GCAGGGCGAG AACGAGACTA TCTGCTCGTT AATTAATTAG AGCTTCTTTA TTCTATACTT AAAAAGTGAA
        CGTCCCGCTC TTGCTCTGAT AGACGAGCAA TTAATTAATC TCGAAGAAAT AAGATATGAA TTTTTCACTT
305939  AATAAATACA AAGGTTCTTG AGGGTTGTGT TAAATTGAAA GCGAGAAATA ATCATAAATT ATTTCATTAT
        TTATTTATGT TTCCAAGAAC TCCCAACACA ATTTAACTTT CGCTCTTTAT TAGTATTTAA TAAAGTAATA
306009  CGTGATACC GTTAAGTTTG TATCGTAATG GAAAGCAATA ATAACAATA CTAAAAGAC AGCAATCGGT
        GCACTATGG CAATTCAAAC ATAGCATTAC CTTTCGTTAT TATTGTTAT GATATTTCTG TCGTTAGCCA
```

Figure 3 - continued

Figure 4 vCP3029
C3 Sequence: sequence confirmed 38,608 – 42,807

C3 Right Arm: 38,666 – 40,664
    42K promoter: 40,703 – 40,808
    Gordon M (opt): 40,809 – 41,822
    C3 Left Arm: 41,866 – 42,791

```
38591                       CGT ATTACCGTGA TTATTTAGAG AATTATAGTC GGCGTTATAA GATAAAAGTA
                            GCA TAATGGCACT AATAAATCTC TTAATATCAG CCGCAATATT CTATTTTCAT
38661  ATTTTATATT ATTAAAACTA TTAGATAACA TAGCTTTATG TAAAGGAGTA TTTCAGATA  ACTTAGCTTT
       TAAAATATAA TAATTTTGAT AATCTATTGT ATCGAAATAC ATTTCCTCAT AAAGGTCTAT TGAATCGAAA
38731  AGCATTACG  TAAGCACCGT GGTCAAGTAA GAGTTAACA  AATTCTGTTT TCATAGAACT AACTGCCATG
       TCGTAAATGC ATTCGTGGCA CCAGTTCATT CTCAATTGT  TTAAGACAAA AGTATCTTGA TTGACGGTAC
38801  TATAGAGGAC TGAACCTTT  ATGATTATAG ACGTTACAT  AGCAACCATA TAATAAGATC GCATTCAGTA
       ATATCTCCTG ACTTGGAAA  TACTAATATC TGCAATGTA  TGTTGGTAT  ATTATTCTAG CGTAAGTCAT
38871  TATTAATATC TTTCATTCT  ATGCTATGT  GAATAACATG TTTATCTAAT CCTACCAACT TTGTATCAGT
       ATAATTATAG AAAGTAAAGA TACGATACA  CTTATTGTAC AAATAGATTA GGATGGTTGA AACATAGTCA
38941  ACCGTACTTC AGTAATAAGT TTACTATAGT TTTGTTTTTA GATGCAACAG CTATATTTAG AACGGTATCT
       TGGCATGAAG TCATTATTCA AATGATATCA AAACAAAAAT CTACGTTGTC GATATAAATC TTGCCATAGA
39011  ATATGATTAT TAACCACATT AACAATAGAT CCTCTTTCTA AAAGTGTCTT TGTTGTTTCG ATATCGTTAC
       TATACTAATA ATTGGTGTAA TTGTTATCTA GGAGAAAGAT TTTCACAGAA ACAACAAAGC TATAGCAATG
39081  GTGAAACAGC GTAATGTAAG GGACTGCCCA TACAGTCATC TATTACGTTT ATATCAGCTC CTAGATTTAA
       CACTTTGTCG CATTACATTC CCTGACGGGT ATGTCAGTAG ATAATGCAAA TATAGTCGAG GATCTAAATT
39151  CAGGAGTCGT GTTACATCTT TTCTTCTATT AATTACCGAA TGATGTAATG CGGTTTTACC TAAATCATCT
       GTCTTCACGA CAATGTAGAA AAGAAGATAA TTAATGGCTT ACTACATTAC CCCAAAATGG ATTAGTAGA
39221  TGTTCGTTTA TAGGCACTCC GTGATTTATA AGTAACGCTA TTATATCGTA ACTACAATTA TTTTTAAGTG
       ACAAGCAAAT ATCCGTGAGG CACTAAATAT TCATTGCGAT AATATAGCAT TGATGTTAAT AAAAATTCAC
39291  CCTTTATGAG ATACTGTTTA TGCAAAAATA AACTTTATC  TATTTTAATA CTATTATCTA ACAATATCCT
       GGAAATACTC TATGACAAAT ACGTTTTTAT TTGAAAATAG ATAAATTAT  GATAATAGAT TGTTATAGGA
39361  AATTAATCT  ATATTCTTAT ACTTTATAGC GTAATGTAAC GCAGTTTCAA AATTTCTAGT TTGTATATTA
       TTAATTAGA  TATAAGAATA TGAAATATCG CATTACATTG CGTCAAAGTT TTAAGATCA  AACATATAAT
39431  AGATCAATAT TAAAATCTAT AAATATTTTA TACATATCAT CAGATATCTT ATCATACAGT ACATCGTAAT
       TCTAGTTATA ATTTTAGATA TTTATAAAAT ATGTATAGTA GTCTATAGAA TAGTATCTCA TGTAGCATTA
39501  AATTTAGAAA GAATCTATTA CAATTAACAC CTTTTTTTAA TAAATATCTA GTTAATGACT TATTGTTTCT
       TTAAATCTTT CTTAGATAAT GTTAATTGTG GAAAAAAATT ATTTATAGAT CAATTACTGA ATAACAAAGA
39571  ATATACAGAA ATATATAACG GACTATTTCC AGAATGTATC TGTTCTATGT CAGCGCCAGA ATCTATTCGT
       TATATGTCTT TATATATTGC CTGATAAAGG TCTTACATAG ACAAGATACA GTCGCGGTCT TAGATAAGCA
39641  AGTTAGCAA  TTTCTGTATT ATCAAACTA  GCAGCTTTAT GAAGAGGAGC ATTTTTACAT TTTAAAATAT
       TCAAATCGTT AAAGACATAA TAGATTTGAT CGTCGAAATA CTTCTCCTCG TAAAAATGTA AAATTTTATA
39711  CGGCACCGTG CCTAGATAAT AATTTTGCCA TTTCTATATC AGAATTACTT ACGGCTAAAT ACAAAGACGT
       GCCGTGGCAC AAGATCATTA TTAAAATGGT AAAGATATAG TCTTTAATGAA TGCCGATTTA TGTTTCTGCA
39781  TGATAGTATA TTTACGTTAT TGTATTTGCA TTTTTAAGT  ATAGACCTTA CTAAATTAT  ATCTCTATAC
       ACTATCATAT AAATGCAATA ACATAAACGT AAAAAATTCA TATCTGGAAT GATTTAAATA TAGACATATG
39851  CTTATAGCTT TATGCAGTTC ATTTATAGT  CTTCCATTAC TCATTCTGG  TAATGAAGTA TTATATATCA
       GAATATCGAA ATACGTCAAG TAAATATTCA GAAGGTATG  AGTAAAGACC ATTACTTCAT AATATATAGT
39921  TTATGATATT ATCTCTATTT TATTCTAATA AAAACCGTTA TCATGTTATT TATTATTTGT TATAATTATA
       AATACTATAA TAGAGATAAA ATAAGATTAT TTTTGGCAAT AGTACAATAA ATAATAAATA ATATTAATAT
39991  CTATTTAATA AATTATACCA AATACTTAGA TACTTATTAA TACCATCCTA GAACTTGTAT TTCTTGCCCC
       GATAAATTAT TTAATATCGT TTATGAATCT ATGAATAATT ATGCTAGGAT CTTGAACATA AAGAACGGGG
40061  CTAAACTTGG ACATGCACTC CATTAGCCGT TTCTTGTTTT CGACATCGTC CTCCTTAACA TATCCTACTG
       GATTTGAACC TGTACGTGAG GTAATCCGCA AAGAACAAAA GCTGTAGCAG GAGGAATTGT ATACGATGAC
40131  TTATGTGAGG ATTCCACGGA TTATCTACTC TGTATATCACC AAACACGTCC TTCGAACAGG GTACCGCATT
       AATACACTCC TAAGGTGCCT AATAGATGAC ACTATAGTGG TTTGTGCAGG AAGCTTGCC  CATGGCGTAA
40201  CAGCAGAACA TTTCTTAGGG CCTCAAGTTC ATCAGATACC TCCAGTTCA  TAACTACAGC GCATCCTTTC
       GTCGTCTTGT AAAGAATCCC GGAGTTCAAG TAGTCTATGG AGGTCAAAGT ATTGATGTCG CGTAGGAAAG
40271  GCTCCCAACT GTTTACAGCC GTTATCTGA  GGAAAACACA TCTCTCTTT  ACAGACTATA GAAATAGTCT
       CGAGGGTTGA CAAATGTCGG CAATGAGACT CCTTTTGTGT AGAGAGAAA  TGTCTGATAT CTTTATCAGA
40341  GTAAATCTTG ATCAGTTATT TGCTTTTTGA AATTTCAAA  TCTATCACAT TGATCCATAT TTGCTATTCC
       CATTTAGAAC TAGTCAATAA ACGAAAAACT TTAAAGTTT  AGATAGTGTA ACTAGGTATA AACGATAAGG
40411  AAGAGTTATA TGAGGAAAA  TATCACATCC TGTCATGTAT TTTATTGTAA CATTATTATA ATCTGTAACA
       TTCTCAATAT ACTCCTTTT  ATAGTGTAGG ACAGTACATA AAATAACATT GTAATAATAT TAGACATTGT
40481  TCAGTATCTA ACCTAACGTC GTAAAGTTA  ACAGATGCCG AGTTACTGTA ATCCAAGGA  ACCTAACAT
       AGTCATAGAT TGGATTGCAG CATTTTCAAT TGTCTACGGC TCAATGATAT TAGGGTTCCT TGGAATTGTA
```

Figure 4 - continued

```
40551  CTAATCCCAT TAAAATAGTA TCCTTTCTAC TATTTTTTC ATTGGCAAGT ATGTGGCTTA GTTTACACAA
       GATTAGGGTA ATTTTATCAT AGGAAAGATG ATAAAAAAG TACCGTTCA TACACCGAAT CAAATGTGTT
40621  AATTCCTGCC ATTTTGTAC GATAGCGAAG CAATAGCTTG TATGCTTTTT ATTTGATTAA CTAGTCATAA
       TTAAGGACGG TAAAACATTG CTATCGCTTC GTTATCGAAC ATACGAAAAA TAAACTAATT GATCAGTATT
40691  AAATCGGGAT CCTCAAAAAA ATATAAATGA TTCACCATCT GATAGAAAAA AAATTTATTG GGAGAATATG
       TTTAGCCCTA GGAGTTTTTT TATATTTACT AAGTGGTAGA CTATCTTTT TTTAAATAAC CCTCTTATAC
40761  ATAATATTTT GGGATTTCAA AATTGAAAAT ATATAATTAC AATATAAAAT GACTGAGATC TTCAACCTGG
       TATTATAAAA CCCTAAAGTT TTAACTTTTA TATATTAATG TTATATTTTA CTGACTCTAG AAGTTGGACC
40831  ACGAAAGCTC TTGGAGTGTT AAAGGGACCC TGGACCCTCT GACCCCCGAT ACCTACCCCG ATGGGAGGCT
       TGCTTTCGAG AACCTCACAA TTTCCCTGGG ACCTGGGAGA CTGGGGGCTA TGGATGGGGC TACCCTCCGA
40901  GGTGCCAAAG ATCAGAGTGA TCGACCCTGG GCTGGGGGAT AGGAAAAGCG GGGGCTACAT GTATCTGCTG
       CCACGGTTTC TAGTCTCACT AGCTGGGACC CGACCCCCTA TCCTTTTCGC CCCCGATGTA CATAGACGAC
40971  CTGCACGGGG TGATCGAGGA CTCTGAAACC GTGATCAACC CCAAGGGGAG AGCCTTCGGG GCATTTCCAC
       GACGTGCCCC ACTAGCTCCT GAGACTTTGG CACTAGTTGG GGTTCCCCTC TCGGAAGCCC CGTAAAGGTG
41041  TGGGGGTGGG GCAGAGCACC GAGAATCCCG AAGATCTGTT CAAGGAGATC CTGACTCTGA ACATCGTGAC
       ACCCCCACCC CGTCTCGTGG CTCTTAGGGC TTCTAGACAA GTTCCTCTAG GACTGAGACT TGTAGCACTG
41111  CAGGAGAACT GCCGGGTTTA ATGAAAAACT GGTGTACTAT AACACCACTC CTCTGAATCT GCTGACTCCC
       GTCCTCTTGA CGGCCCAAAT TACTTTTTGA CCACATGATA TTGTGGTGAG GAGACTTAGA CGACTGAGGG
41181  TGGAAGAAAG TGCTGGCCTA CCGGTCTATC TTCACCGCAA ACCAAGTGTG TAACAATACT AGCTCCATCC
       ACCTTCTTTC ACGACCGGAT GCCCAGATAG AAGTGGCGTT TGGTTCACAC ATTGTTATGA TCGAGGTAGG
41251  CCATCGACAT CCCACAGAAG TTTAGGCCTG TGTATCTGAC CGTGACTAAA CTGAGCGACG ATGGGTACTA
       GGTAGCTGTA GGGTGTCTTC AAATCCGGAC ACATAGACTG GCACTGATTT GACTCGCTGC TACCCATGAT
41321  TCAGATCCCC AAGATGATCC AGGACTTCAA ATCTAGCAAC TCTGTGGCAT TTAATATCCT GGTGCACCTG
       AGTCTAGGGG TTCTACTAGG TCCTGAAGTT TAGATCGTTG AGACACCGTA AATTATAGGA CCACGTGGAC
41391  AGCATGGGGA CCATCCTGCT GGATTCCTCT AAGGGGAGCA GGGTGGGGAA CCCAGCCGAG AATCTGATCA
       TCGTACCCCT GGTAGGACGA CCTAAGGAGA TTCCCCTCGT CCCACCCCTT GGGTCGGCTC TTAGACTAGT
41461  CTTTCATGAT CCATATCGGG AACTTCAAGA GAAAGAACAA CAAGGCATAC TCCCCTGAAT ATTGCAAGAG
       GAAAGTACTA GGTATAGCCC TTGAAGTTCT CTTTCTTGTT GTTCCGTATG AGGGGACTTA TAACGTTCTC
41531  GAAAATCATG AGACTGGGGC TGATCTTCAG CCTGGGGGCA ATCGGGGCA CCTCCCTGCA TATCAGGTGC
       CTTTTAGTAC TCTGACCCCG ACTAGAAGTC GGACCCCGT TAGCCCCCGT GGAGGGACGT ATAGTCCACG
41601  ACTGGGAAGA TGTCCAAAAG ACTGCAGGCA TACCTGGGGT TTAAGAGGAC CCTGTGTTAC CCTCTGATGT
       TGACCCTTCT ACAGGTTTTC TGACGTCCGT ATGGACCCA AATTCTCCTG GGACACAATG GGAGACTACA
41671  ATGTGAACGA GGGGCTGAAT AAAACTCTGT GGAGAAACGA GTGCAAGATC GAAAAAGTGC AGGCCGTGCT
       TACACTTGCT CCCCGACTTA TTTTGAGACA CCTCTTTGCT CACGTTCTAG CTTTTTCACG TCCGGCACGA
41741  GCAGCCATCT GTGCCTAATG AGTTCAAAAT ATACGACGAC ATTATCATAG ACAATACAAA CGGGCTGTTC
       CGTCGGTAGA CACGGATTAC TCAAGTTTTA TATGCTGCTG TAATAGTATC TGTTATGTTT GCCCGACAAG
41811  AAAGTCAAGT AACTCGAGGA ATTCCTGCAG CCCGGGTTTT TATAGCTAAT TAGTCAAATG TGAGTTAATA
       TTTCAGTTCA TTGAGCTCCT TAAGGACGTC GGGCCCAAAA ATATCGATTA ATCAGTTTAC ACTCAATTAT
41881  TTAGTATACT ACATTACTAA TTTATTACAT ATTCATTTAT ATCAATCTAG TAGCATTTAG CTTTTATAAA
       AATCATATGA TGTAATGATT AAATAATGTA TAAGTAAATA TAGTTAGATC ATCGTAAATC GAAAATATTT
41951  ACAATATAAC TGAATAGTAC ATACTTTACT AATAAGTTAT AAATAAGAGA TACATATTTA TAGTATTTTA
       TGTTATATTG ACTTATCATG TATGAAATGA TTATTCAATA TTTATTCTCT ATGTATAAAT ATCATAAAAT
42021  CTTTCTACGC TGAATATAAT AATATAATTA TACAAATATA ATTTTTAATA CTATATACTA TATAACTGAA
       GAAAGATGTG ACTTATATTA TTATATTAAT ATGTTTATAT TAAAAATTAT GATATATCAT ATATTGACTT
42091  ATAAAATACC AGTGTAATAT AGTTATTATA CATTTATACC ACATCAAAGA TGACTTATAA CATCAGTGTC
       TATTTTATGG TCACATTATA TCAATAATAT GTAAATATGG TGTAGTTTCT ACTCAATATT GTAGTCACAG
42161  ACTGTTACCA ACAGTAGTTA TACGATGAGT AGTTACTCTC GTATGGCGTT AGTATGTATG TATCTTCTAG
       TGACAATCGT TGTCATCAAT ATGCTACTCA TCAATGATGA CATACCGCAA TCATACATAC ATAGAAGATC
42231  TTTTCTTAGT AGGCATTATA GGAAACGTCA AGCTTATAAG GTTATTAATG GTATCTAGAA ATATATCTAT
       AAAAGAATCA TCCGTAATAT CCTTGCAGT TCGAATATTC CAATAATTAC CATAGATCTT TATATAGATA
42301  TATACCGTTT CTCAACTTGG GAATAGCCGA TTTGCTGTTT GTGATATTCA TACCTTATA CATTATATAC
       ATATGCCAAA GAGTTGAACC CTTATCGGCT AAACGACAAA CACTATAAGT ATGGAAATAT GTAATATATG
42371  ATACTAAGTA ATTTCCATTG GCATTTTGGT AAACGCTTTT GTAAAATTGG TTCTTTCTTT TTTACTTCTA
       TATGATTCAT TAAAGGTAAC CGTAAAAGCCA TTTCGTGAAA CATTTTAATC AAGAAAGTAAA AATGAAGAT
42441  ACATGTTTGC AAGTATATTT TTAATAACTG TAATAAGCGT ATATAGATAT GTAAAAATTA CCCTTCCTGG
       TGTACAAACG TTCATATAAA AATTATTGAC ATTATTCGCA TATATCTATA CATTTTAAT GGGAAGGACC
42511  ATTTACCTAT AAATATGTTA ACATTAGAAA TATGTACATT ACTATATTT TCATATGGAT TATTTCTATT
       TAAATGGATA TTTATACAAT TGTAATCTTT ATACATGTAA TGATATAAAA AGTATACCCTA ATAAAGATAA
42581  ATACTAGGGA TTCCTGCTCT TTACTTTAGA AATACTATCG TAACAAAAAA TAACGACACG CTGTGTATTA
       TATGATCCCT AAGGACGAGA AATGAAATCT TTATGATAGC ATTGTTTTTT ATTGCTGTGC GACACATAAT
42651  ATCATTATCA TGAATAATAGA GAAATTGCTG AATTGATTTA CAAAGTTATT ATCTGTATCA GATTATTTT
       TAGTAATAGT ACTATTATCT CTTTAACGAC TTAACTAAAT GTTTCAATAA TAGACATAGT CTAAATAAAA
42721  AGGATGCCTA CTACCTACGA TAATTATACT CGTATGCTAT ACGTTACTGA TCTACAGAAC TAACAATGCA
       TCCTATGGAT GATGCATGCT ATTAATATGA GCATACGATA TGCAATGACT AGATGTCTTG ATTGTTACGT
42791  TCTAATATAT CTGATAA
       AGATTATATA GACTATT
```

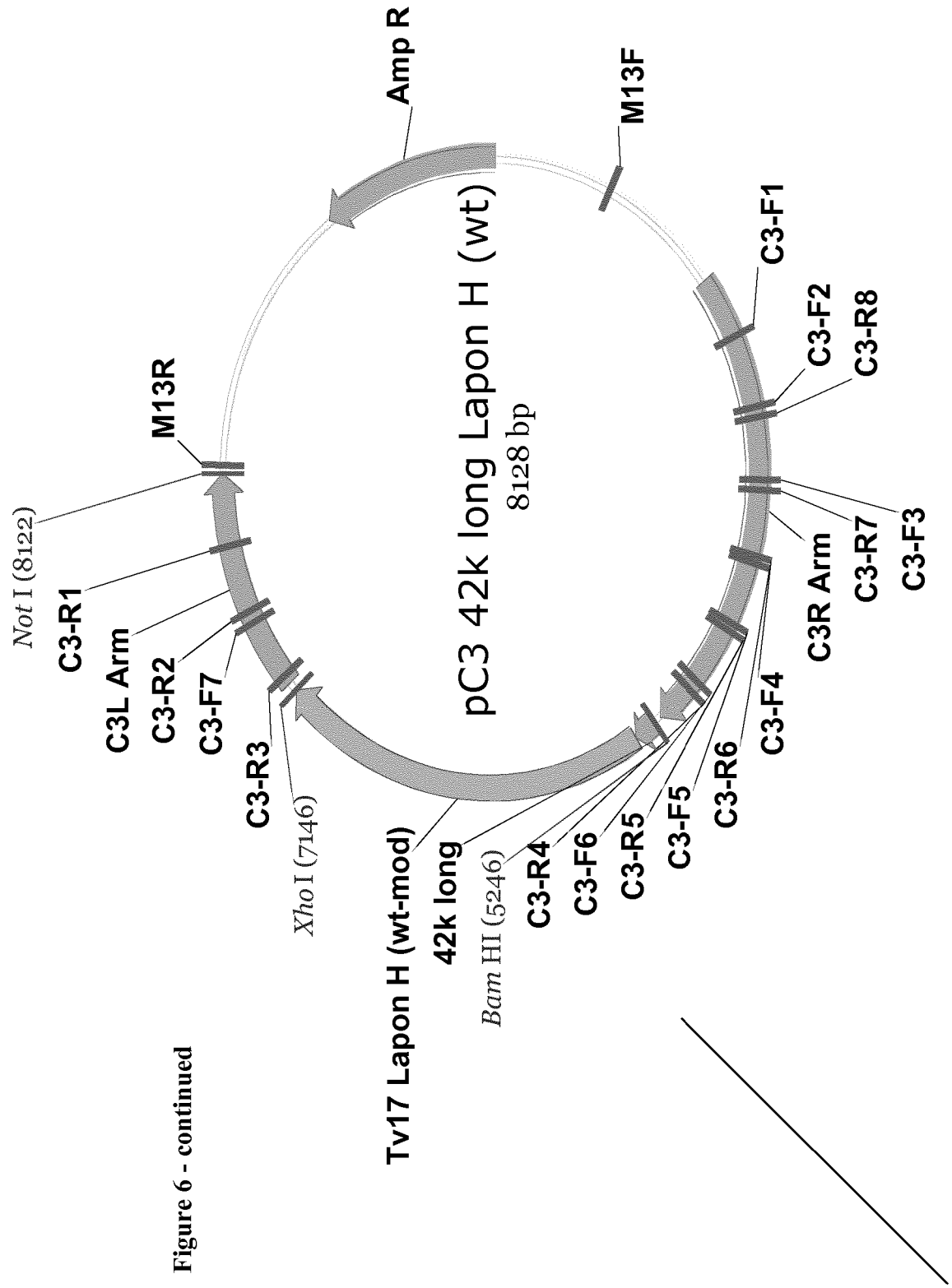
Figure 6 - continued

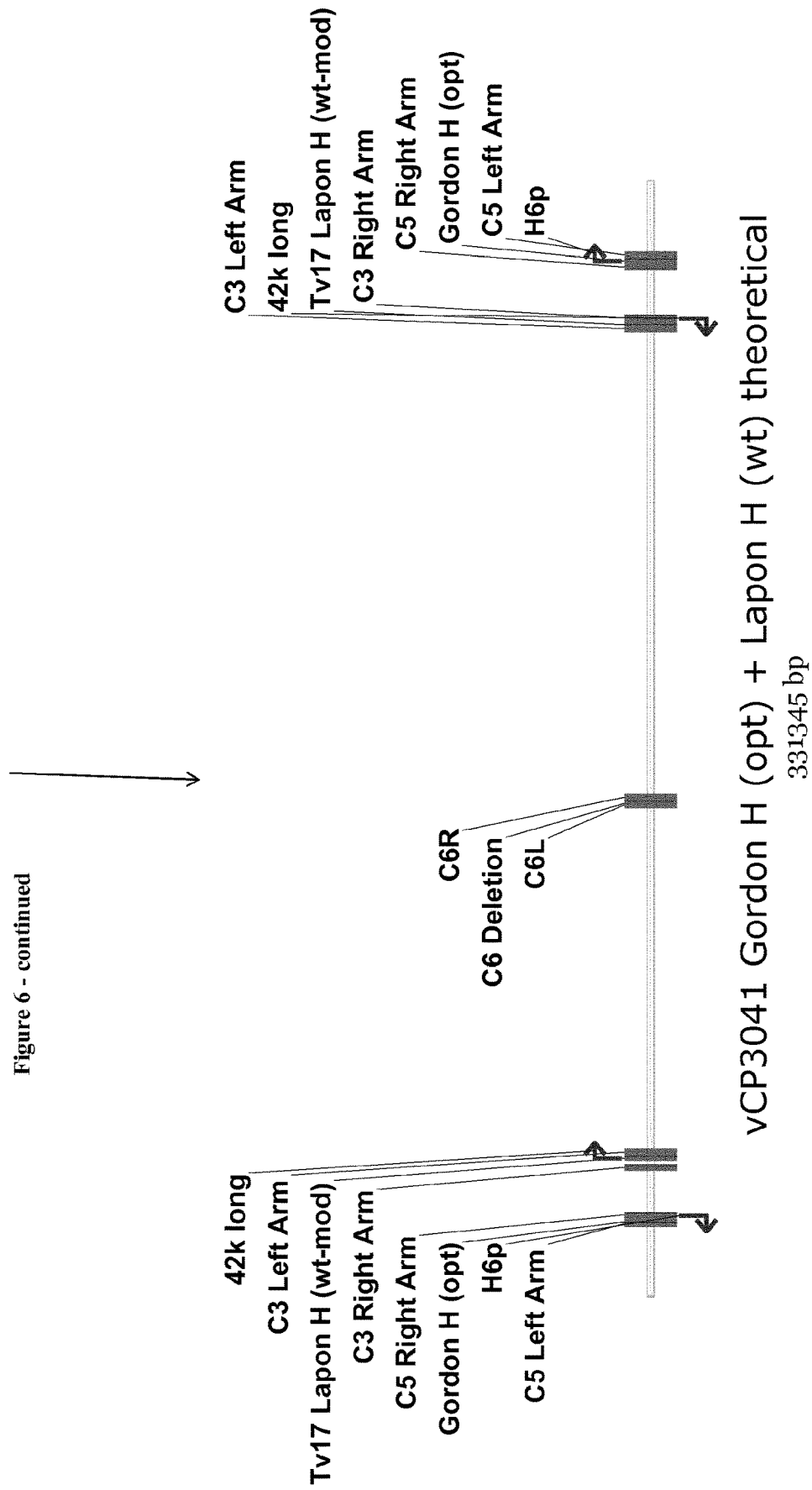
Figure 6 - continued

Figure 7 vCP3041
C3 Sequence: theoretical sequence

C3 Right Arm: 38,666-40,674
42K long promoter: : 40703-40808
Lapon H (wt-no BamHI site): 40,809-42,596
C3 Left Arm: 42,641-43,585

```
38619  GATTATTTAG AGAATTATAG TCGGCGTTAT AAGATAAAAG TAATTTTATA TTATTAAAAC TATTAGATAA
       CTAATAAATC TCTTAATATC AGCCGCAATA TTCTATTTTC ATTAAAATAT AATAATTTTG ATAATCTATT
38689  CATAGCTTTA TGTAAAGGAG TATTTCCAGA TAACTAGCT  TTAGCATTTA CGTAAGCACC GTGGTCAAGT
       GTATCGAAAT ACATTTCCTC ATAAAGGTCT ATTGAATCGA AATCGTAAAT GCATTCGTGG CACCAGTTCA
38759  AAGAGTTTAA CAAATTCTGT TTTCATAGAA CTAACTGCCA TGTATAGAGG AGTGAAACCT TTATGATTAT
       TTCTCAAATT GTTTAAGACA AAAGTATCTT GATTGACGGT ACATATCTCC TCACTTTGGA AATACTAATA
38829  AGAGTTTAC  ATAGCAACCA TATAATAAGA TCGTATTCAG TATATTAATA TCTTTCATTT CTATAGCTAT
       TCTGCAAATG TATCGTTGGT ATATTATTCT AGCGTAAGCA ATATAATTAT AGAAAGTAAA GATATCGATA
38899  GTGAATAACA TGTTTATCTA ATCCTACCAA CTTTGTATCA GTACCGTACT TCAGTAATAA GTTACTATA
       CACTTATTGT ACAAATAGAT TACGATGGTT GAAACATAGT CATGGCATGA AGTCATTATT CAATGATAT
38969  GTTTGTTTT  TAGATGCAAC AGCTATATTT AGAACGGTAT CTATATGATT ATTAACCACA TTAACATTAG
       CAAAACAAAA ATCTACGTTG TCGATATAAA TCTTGCCATA GATATACTAA TAATTGGTGT AATTGTAATC
39039  ATCCTCTTTC TAAAAGTGTC TTTGTTGTTT CGATATCGTT ACGTGAAACA GCGTAATGTA AGGGACTGCC
       TAGCAGAAAC ATTTTCACAG AAACAACAAA GCTATACGCA TGCACTTTGT CGCATTACAT TCCCTGACGG
39109  CATACAGTCA TCTATTACGT TTATATCAGC TCCTAGATTT AACAGAAGTG CTGTTACATC TTTCTTCTA
       GTATGTCAGT AGATAATGCA AATATAGTCG AGGATCTAAA TTGTCTTCAC GACAATGTAG AAAGAAGAT
39179  TTAATTACGG AATGATGTAA TGCGGTTTTA CCTAAATCAT CTTGTTCGTT TATAGGCACT CCGTGATTTA
       AATTAATGCC TTACTACATT ACCCCAAAAT GGATTTAGTA GAACAAGCAA ATATCCGTGA GGCACTAAAT
39249  TAAGTAACGC TATTATATCG TAACTACAAT TATTTTTAAG TGCCTTTATG AGATACTGTT TATGCAAAAA
       ATTCATGCG  ATAATATAGC ATTGATGTTA ATAAAAATTC ACGGAAATAC TCTATGACAA ATACGTTTTT
39319  TAAACTTTTA TCTATTTTAA TACTATTATC TAACAATATC CTAATTAAAT CTATATTCTT ATACTTTATA
       ATTTGAAAAT AGATAAAATT ATGATAATAG ATTGTTATAG GATTAATTTA GATATAAGAA TATGAAATAT
39389  GCGTAATGTA ACGCAGTTTC AAAATTTCTA GTTTGTATAT TAAGATCAAT ATTAAAATCT ATAAATATTT
       CGCATTACAT TGCCTCAAAG TTTTAAAGAT CAAACATATA ATTCTACTTA TAATTTAGA  TATTTATAA
39459  TATACATATC ATCAGATATC TTATCATACA GTACATCGTA ATAATTTAGA AAGAATCTAT TACAATTAAC
       ATATGTATAG TAGTCTATAG AATAGTATGT CATGTAGCAT TATTAAATCT TTCTTAGATA ATGTTAATTG
39529  ACCTTTTTTT AATAAATATC TAGTTAATGA CTTATTGTTT CTATATACAG AAATATATAA CGGACTATTT
       TGGAAAAAAA TTATTTATAG ATCAATTACT GAATAACAAA GATATATGTC TTTATATATT GCCTGATAAA
39599  CCGAATGTA  TCTGTTCTAT GTCAGCGCCA GAATCTATTA GTAGTTTAGC AATTTCTGTA TTATCTAAAC
       GGTCTACAT  AGACAAGATA CAGTCGCGGT CTTAGATAAT CATCAAATCG TTAAAGACAT AATAGATTTG
39663  TAGCAGCTTT ATGAAGAGGA GGATTTTTAC ATTTTAAAAT ATCGGCACCG TGTTCTAGTA ATAATTTAC
       ATCGTCGAAA TACTTCCT   CCTAAAAATG TAAAATTTTA TAGCCGTGGC ACAAGATCAT TATTAAAATG
39739  CATTTCTATA TCAGAAATAC TTACGGCTAA ATACAAGAC  GTTGATAGTA TATTTACGTT ATTGTATTTC
       GTAAAGATAT AGTCTTTATG AATGCCGATT TATGTTTCTG CAACTATCAT ATAAATGCAA TAACATAAAC
39809  CATTTTTAA  GTATATACCT TACTAAATTT ATATCCTAT  ACCTTATGCA TTTATGCAGT TCATTTATAA
       GTAAAAATT  CATATATGGA ATGATTTAAA TATAGAGATA TCGAATATCG AAATACGTCA AGTAAATATT
39879  GTCTTCCATT ACTCATTTCT GGTAATGAAG TATTATATAT CATTATGATA TTACTCTAT  TTTATTCTAA
       CAGAAGGTAA TGAGTAAGA  CCATTACTTC ATAATATATA GTAATACTAT AATGAGATA  AAATAAGATT
39949  TAAAAACCGT TATCAGTTA  TTTATTATTT GTTATAATTA TACTATTTA  TAAATTATAC CAAATACTTA
       ATTTTTGCA  ATAGTACAAT AAATAATAAA CAATATTTAT AGATAAATT  ATTTAATATG GTTTATGAAT
40019  GATACTTATT AATACCATCC TAGAACTTGT ATTTCTTGCC CCCTAAACTT GGACATGACG TCCATTAGGC
       CTATGAATAA TTATGGTAGG ATCTTGAACA TAAAGAACGG GGATTTGAA  CCTGTACGTG AGGTAATCCG
40089  GTTTCTTGT  TTCGACATCG TCTTCCTTAA CATATCCTAC TGTTATGTGA GGATTCCACG GATTATCTAC
       CAAAGAACAA AAGCTGTAGC AGCAGGAATT GTATACGATG ACAATACACT CCTAAGGTGC CTAATAGATG
40159  TGTGATATCA CCAAACACGT CCTTCGAACA GGGTACCGCA TTCAGCAGAA CATTTCTTAG GGCTCTAAGT
       ACACTATAGT GGTTTGTGCA GGAAGCTTGT CCCATGGCGT AAGTCGTCTT GTAAAGAATC CCGAGATTCA
40229  TCATCAGATA CCTCCAGTTT CATAACTACA GCGCATCTT  TCGCTCCCAA CTGTTTAGAG GCGGTACTCT
       AGTAGTCTAT GGAGGTCAAA GTATTGATGT CGCGTAGGAA AGCGAGGGTT GACAATCTC  CGCATGAGA
40293  GAGGAAACA  CATCTCTTCT TTACAGACTA TAGAAATAGT CTGTAAATCT TGATCAGTTA TTTGCTTTTT
       CTCCTTTTGT GTAGAGAAGA AATGTCTGAT ATCTTTATCA GACATTTAGA ACTAGTCAAT AAACGAAAAA
40369  GAAATTTCA  AATCTATCAC ATTGATCCAT ATTTCGTTT  CCAAGACTTA TATGACGAAA AATATCACAT
       CTTTAAAAGT TTAGATAGTG TAACTAGGTA TAAACGATAA GGTTCTCAAT ATACTCCTTA TTATAGTGTA
40439  CCTGTCATGT ATTTTATTGT AACATTATTA TAATCTGTAA CATCAGTATC TAACCTAACG TCGTAAAAGT
       GGACAGTACA TAAAATAACA TTGTAATAAT ATTAGACATT GTAGTCATAG ATTGGATTGC AGCATTTTCA
40509  TAACAGATGC CCAGTTACTA TAATCCCAAG GAACCTTAAC ATCTAATCCC ATTAAAATAG TATCCTTCT
       ATTGTCTACG GGTCAATGAT ATTAGGGTTC CTTGAATTG  TAGATAGGG  TAATTTATC  ATAGGAAGA
40579  ACTATTTTTT TCATTGGCAA GTATCTGGCT TAGTTTACAC AAAATTCCTG CCATTTGCTA ACGATAGCGA
       TGATAAAAAA AGTACCGTT  CATACACCGA ATCAAATGTG TTTTAAGGAC GGTAAACAT  TGCTATCGCT
40649  AGAATAGCT  TGTATCGTTT TTATTTGATT AACTAGTCAT AAAAATCGGG ATCCTCAAAA AATATATAAT
       TCGTTATCGA ACATACGAAA AATAAACTAA TTGATCAGTA TTTTAGCCC  TAGGAGTTT  TTTATATTTA
```

Figure 7 - continued

```
40719  GATTCACCAT CTGATAGAAA AAAAATTTAT TGGGAGAATA TGATAATATT TTGGGATTTC AAAATTGAAA
       CTAAGTGGTA GACTATCTTT TTTTTAAATA ACCCTCTTAT ACTATTATAA AACCCTAAAG TTTTAACTTT
40789  ATATATAATT ACAATATAAA ATGGAGTCCA ACAACATTAA ATATTACAAA GACTCTAATC GGTATCTTGG
       TATATATTAA TGTTATATTT TACCTCAGGT TGTTGTAATT TATAATGTTT CTGAGATTAG CCATAGAACC
40859  TAAAATATTA GATGAACACA AGACAGTTAA TAATCAATTG TACAGGTTGA GTATTAAAGT AATTACCATT
       ATTTTATAAT CTACTTGTGT TCTGTCAATT ATTAGTTAAC ATGTCCAACT CATAATTTCA TTAATGGTAA
40929  ATTGCTATTA TTGTAAGCTT AATTGCAACA ATAATAACTA TTATTAATGC CACAAGTGGA AGAACTACCC
       TAACGATAAT AACATTCGAA TTAACGTTGT TATTATTGAT AATAATTACG GTGTTCACCT TCTTGATGGG
40999  TAAACAGTAA TACAGACATA CTGCTTAGCC AAAGAGATGA GATTCATAGT ATTCATGAAA TGATATTTGA
       ATTTGTCATT ATGTCTGTAT GACGAATCGG TTTCTCTACT CTAAGTATCA TAAGTACTTT ACTATAAACT
41069  CCGTATTTAT CCTTTGATAA CTGCTATGAG TACAGAGCTA GGACTTCATA TTCCTACTTT ATTAGATGAA
       GGCATAAATA GGAAACTATT GACGATACTC ATGTCTCGAT CCTGAAGTAT AAGGATGAAA TAATCTACTT
41139  CTTACTAAAG CAATTGATCA AAAAATTAAA ATAATGAATC CTCCCGTTGA TACTGTAACA TCTGATCTTA
       GAATGATTTC GTTAACTAGT TTTTTAATTT TATTACTTAG GAGGGCAACT ATGACATTGT AGACTAGAAT
41209  ACTGGTGTAT CAAACCTCCT AATGGGATTA TTATGGACCC AAAAGGTTAT TGCGAAAGTA TGGAATTATC
       TGACCACATA GTTGGAGGA TTACCCTAAT AATACCTGGG TTTTCCAATA ACGCTTTCAT ACCTTAATAG
41279  TAAAACTTAC AAATTATTGC TTGATCAGTT AGATGTCTCA AGAAAGAAAT CGGTCATTAT AAATAGAAAG
       ATTTTGAATG TTTAATAACG AACTAGTCAA TCTACAGAGT TCTTTCTTTA GCGAGTAATA TTTATCTTTC
41349  AATATCAACC AGTGTCAATT AGTTGATGAC TCAAAGATCA CTTTTGCTAC TGTTAATATA CAATCTACAC
       TTATAGTTGG TCACAGTTAA TCAACTACTG AGTTTCTAGT GAAAACGATG ACAATTATAT GTTAGATGTG
41419  CAAGGTTTTT AAATTTTGGT CATACAGTCA GCAATCAACG TATAACATTT GGTCAAGGAA CTTATAGTAG
       GTTCCAAAAA TTTAAAACCA GTATGTCAGT CGTTAGTTGC ATATTGTAAA CCAGTTCCTT GAATATCATC
41489  TACTTATATT ATAACTATCC AAGAAGATGG AATAAATGAT GTTCAATATC GAGTGTTTGA AATTGGATAT
       ATGAATATAA TATTGATAGG TTCTTCTACC TTATTTACTA CAAGTTATAG CTCACAAACT TTAACCTATA
41559  ATCTCTGATC AGTTTGGTTT TTTCCCCTCA TTAATAGTAT CTAGGGTATT GCCTATACGT ATGGTATTGG
       TAGAGACTAG TCAAACCAAA AAAGGGGAGT AATTATCATA GATCCCATAA CGGATATGCA TACCATAACC
41629  GAATGGAATC CTGTACCTTG ACGAGTGATC GACAAGGTGG GTATTCTTA TGTATGAATA CATTAACACG
       CTTACCTTAG GACATGGAAC TGCTCACTAG CTGTTCCACC CATAAAGAAT ACATACTTAT GTAATTGTGC
41699  GTCTATATAT GATTATGTCA ATATAAGAGA TTTGAAATCA CTATACATAA CACTTCCTCA TTATGGTAAG
       CAGATATATA CTAATACAGT TATATTCTCT AAACTTTAGT GATATGTATT GTGAAGGAGT AATACCATTC
41769  GTTAATTATA CTTACTTCAA TTTTGGGAAA ATAGGAGCC CACATGAGAT TGATAAAATT TGGCTAACGT
       CAATTAATAT GAATGAAGTT AAAACCCTTT TAATCCTCGG GTGTACTCTA ACTATTTTAA ACCGATTGCA
41839  CCGAAAGAGG TCAAATTATT TCTGGTTATT TTGCAGCATT TGTCACAATT ACGATTCGAA ATTATAATAA
       GGCTTTCTCC AGTTTAATAA AGACCAATAA AACGTCGTAA ACAGTGTTAA TGCTAAGCTT TAATATTATT
41909  TTATCCCTAC AAATGTTTGA ATAATCCATG TTTTGACAAC TCTGAGAATT ACTGTAGGGG ATGGTATAAG
       AATAGGGATG TTTACAAACT TATTAGGTAC AAAACTGTTG AGACTCTTAA TGACATCCCC TACCATATTC
41979  AACATAACAG GCACCGATGA TGTTCCAATA CTAGCATACT TACTAGTTGA AATGTATGAT GAAGAAGGAC
       TTGTATTGTC CGTGGCTACT ACAAGGTTAT GATCGTATGA ATGATCAACT TTACATACTA CTTCTTCCTG
42049  CTTTAATTAC ACTTGTAGCA ATACCACCTT ACAATTATAC AGCTCCATCT CATAATTCTC TTTACTATGA
       GAAATTAATG TGAACATCGT TATGGTGGAA TGTTAATATG TCGAGGTAGA GTATTAAGAG AAATGATACT
42119  TGACAAAATT AATAAGTTGA TAATGATAC ATCTCACACT GGGTATTAC AGATCAATGA GGTGCATGAG
       ACTGTTTTAA TTATTCAACT ATTACTGATG TAGAGTGTGA CCCATATATG TCTAGTTACT CCACGTACTC
42189  GTGATTGTTG GTGATGATTT AAAGGCTATT CTCCTGAACA GATTATCTGA TGAACACCCT AATCTTACAG
       CACTAACAAC CACTACTAAA TTTCCGATAA GAGGACTTGT CTAATAGACT ACTTGTGGGA TTAGAATGTC
42259  CCTGTAGACT TAATCAAGGC ATTAAAGAGC AGTACAAGTC CGATGGAACG ATAATTCAA ATTCTGCACT
       GGACATCTGA ATTAGTTCCG TAATTTCTCG TCATGTTCAG GCTACCTTGC TATTAAAGTT TAAGACGTGA
42329  TATTGATATA CAAGAACGAA TGTATATTAC AGTCAAGCT ATTCCACCAG TAGGTAACTA TAACTTTACA
       ATAACTATAT GTTCTTGCTT ACATATAATG TCAGTTTCGA TAAGGTGGTC ATCCATTGAT ATTGAAATGT
42399  GTTGAGTTGC ACTCTAGATC AAACACATCT TATATATTGT TACCGAAACA GTTCAATGCC AAGTATGACA
       CAACTCAACG TGAGATCTAG TTTGTGTAGA ATATATAACA ATGGCTTTGT CAAGTTACGG TTCATACTGT
42469  AATTACATCT TGAGTGCTTT AATTGGGACA AGTCTTGGTG GTGTGCTTTG ATACCTCAAT TTTCATTAAG
       TTAATGTAGA ACTCACGAAA TTAACCCTGT TCAGAACCA CACACGAACA TATGGAGTTA AAAGTAATTC
42539  TTGGAATGAA TCCCTTTCTG TTGATACTGC TATTTTTAAT TTAATAAATT GTAAATGACT CGAGGAATTC
       AACCTTACTT AGGGAAAGAC AACTATGACG ATAAAAATTA AATTATTTAA CATTTACTGA GCTCCTTAAG
42609  CTGCAGCCCG GGTTTTTATA GCTAATTAGT CAAATGTCAG TTAATATTAG TATACTACAT TACTAATTTA
       GACGTCGGGC CCAAAAATAT CGATTAATCA GTTTACACTC AATTATAATC ATATCATGTA ATGATTAAAT
42679  TTACATATTC ATTATATCA ATCTAGTAGC ATTTACTTT TATAAACAA TATACTGAA TAGTACATAC
       AATGTATAAG TAAATATAGT TAGATCATCG TAAATCGAAA ATATTTGTT ATATTGACTT ATCATGTAG
42749  TTTACTAATA AGTTATAAAT AAGAGATACA TATTTATAGT ATTTTACTTT CTACACTGAA TATAATAATA
       AAATGATTAT TCAATATTTA TTCTCTATGT ATAAATATCA TAAATGAAA GATGTGACTT ATATTATTAT
42819  TAATTATACA AATATAATTT TTAATACTAT ATAGTATATA ACTGAAATAA AATACCAGTG TAATATAGTT
       ATTAATATGT TTATATTAAA AATTATGATA TATCATATAT TGACTTTATT TTATGGTCAC ATTATATCAA
42889  ATTATACATT TATACCACAT CAAGATGAG TTATAACAC AGTGTCGTG TTAGCAACAG TAGTTATACG
       TAATATGTAA ATATGGTGTA GTTCTACTC AATATTGTAG TCACAGTGAC AATCGTTGTC ATCAATATGC
42959  ATGAGTAGTT ACTCTCGTAT GGCGTTAGTA TGTATGTATC TTCTAGTTT CTTAGTAGGC ATTATAGAA
       TACTCATCAA TGAGAGCATA CCGCAATCAT ACATACATAG AAGATCAAAA GAATCATCCG TAATATCCTT
43029  ACGTCAACGT TATAGGTTA TTAATGGTAT CTAGAAATAT ATCTATTATA CCGTTTCTCA ACTTGGGAAT
       TGCAGTTGCA ATATTCCAAT AATTACCATA GATCCTATAT TAGATAATAT GGCAAAGAGT TGAACCTTTA
43099  AGCCGATTTG CTGTTTGTGA TATTGCATAC CTTTATACATT ATATACATAC TAAGTAATTT CCATTGGCAT
       TCGGCTAAAC GACAAACACT ATAAGTATGG AAATATGTAA TATATGTATG ATTCATTAAA GGTAACCGTA
```

Figure 7 - continued

```
43169  TTTGGTAAAG CACTTTGTAA AATTAGTTCT TTCTTTTTA CTTCTAACAT GTTTGCAAGT ATATTTTAA
       AAACCATTTC GTGAAACATT TTAATCAAGA AAGAAAAAT GAAGATTGTA CAAACGTTCA TATAAAAATT
43239  TAACTGTAAT AAGCGTATAT AGATATGTAA AAATTACCCT TCCTGGATTT ACCTATAAAT ATGTTAACAT
       ATTGACATTA TTCGCATATA TCTATACATT TTTAATGGCA AGGACCTAAA TGGATATTTA TACAATTGTA
43309  TAGAAATATG TACATTACTA TATTTTTCAT ATGGATTATT TCTATTATAC TAGGGATTCC TGCTCTTTAC
       ATCTTTATAC ATGTAATGAT ATAAAAAGTA TACCTAATAA AGATAATATG ATCCCTAAGG ACGAGAAATG
43379  TTTAGAAATA CTATCGTAAC AAAAAATAAC GACACGCTGT GTATTAATCA TTATCATGAT AATAGAGAAA
       AAATCTTTAT GATAGCATTG TTTTTTATTG CTGTGCGACA CATAATTAGT AATAGTACTA TTATCTCTTT
43449  TTGCTGAATT GATTTACAAA GTTATTATCT GTATCAGATT TATTTTAGGA TACCTACTAC CTACGATAAT
       AACGACTTAA CTAATGTTTT CAATAATAGA CATACTCTAA ATAAAATCCT ATGGATGATG GATGCTATTA
43519  TATACTCGTA TGCTATACGT TACTGATCTA CAGAACTAAC AATGCATCTA ATATATCTGA TAAGATATTC
       ATATGAGCAT ACGATATGCA ATGACTAGAT GTCTTGATTG TTACGTAGAT TATATAGACT ATTCTATAAG
```

RECOMBINANT VIRAL VECTOR SYSTEMS EXPRESSING EXOGENOUS FELINE PARAMYXOVIRUS GENES AND VACCINES MADE THEREFROM

CROSS-REFERENCE TO RELATED APPLICATIONS

This application is a U.S. national stage of International Application No. PCT/EP2019/054151 filed on Feb. 20, 2019 and is based on European patent application EP 18158450.9 filed on Feb. 23, 2018, the disclosures of which are hereby incorporated by reference.

SEQUENCE LISTING

The Sequence Listing associated with this application is provided in text format in lieu of a paper copy, and is hereby incorporated by reference into the specification. The name of the text file containing the Sequence Listing is Sequence-Listing.txt. The text file is 294 KB; it was created on 16 Jan. 2020; and it is being submitted electronically via EFS-Web, concurrent with the filing of the specification.

BACKGROUND OF THE INVENTION

A. Field of the Invention

The present invention relates to the field of (vector) vaccines, and specifically to exogenous feline paramyxovirus genes, which are expressed from recombinant viral vector systems. Further, the present invention relates to recombinant viral vector-based feline paramyxovirus vaccines.

B. Background and Description of the Related Art

Feline Paramyxoviruses

Paramyxoviruses are enveloped, negative-sense single-stranded RNA [(−)ssRNA] viruses that have been associated with a number of infectious diseases in humans and animals There are two subfamilies of Paramyxoviruses, Paramyxovirinae and Pneumovirinae and at least five genera within the subfamily Paramyxovirinae, namely Respirovims, Rubulavirus, Morbillivirus, Henipavims, and Avulavirus. Examples of Paramyxoviruses include canine distemper virus, measles virus, rinderpest virus, mumps virus and human parainfluenza viruses. Paramyxoviruses have a linear genome encoding seven viral polypeptides: a nucleocapsid protein, a phospho-protein, a matrix protein, a fusion protein, a haemagglutinin protein and a polymerase. Paramyxovirus virions are enveloped and can be spherical, filamentous or pleomorphic with a diameter of around 150 nm. Fusion proteins and attachment proteins (hemagglutinin, "H") appear as spikes on the virion surface. Matrix proteins ("M") inside the envelope stabilize the structure of the virus. The nucleocapsid core is composed of the genomic RNA, nucleocapsid proteins ("N"), phosphoproteins ("P") and polymerase proteins ("L" for "large protein"). The fusion protein ("F") projects from the envelope surface as a trimer, and mediates cell entry by inducing fusion between the viral envelope and the cell membrane.

Paramyxoviruses have for example been isolated from wild-living and domestic animals including cats, rodents and bats but also humans Paramyxovirus infections, particularly of the Paramyxovirinae subfamily, have been associated with kidney diseases due to renal tissue damage shown in various species. Kidney disease, especially chronic kidney disease (CKD) is, for instance, among the most common diseases and one of the most common causes of death in domestic cats, particularly in older individuals. Lulich et al. (Compendium on continuing education for the practicing veterinarian (1992) 14(2):127-152) report a prevalence of chronic kidney disease among total domestic cat populations of about 1.5% and about 7.5% in domestic cats older than 10 years. The causes of these diseases can be very diverse. In many cases the exact etiology cannot be determined. On the other hand, it is known that chronic kidney disease most often occurs as a result of inflammation of the renal tubules and renal interstitial tissue. This is called idiopathic tubulointerstitial nephritis (TIN).

Several feline paramyxoviruses have been described in the art. US 2013/0230529 A1 (WO 2013/107290 A1) and Woo et al. (Proc. Nat. Acad. Sci. (2012) 109(14):5435-5440) describe a feline morbillivirus (FmoPV) isolated in Hong Kong which is associated with TIN in domestic cats. Other research groups from Japan (Sakaguchi et al. (2014) General Virology, 95(7), 1464-1468; Furuya et al. (2014) Archives of virology, 159(2), 371-373), Italy (Lorusso et al. (2013) Vet Ital. 51(3):235-237) and the USA (Sharp et al. (2016) Emerging Infectious Diseases 22(4):760) also detected paramyxoviruses in urine samples from cats. Sieg et al. (Virus Genes (2015) 51(2):294-297) describe the discovery of feline paramyxoviruses in domestic cats with chronic kidney disease.

Further prior art in this regard is as follows: JP 2015 198654 A relates to means of isolating/identifying a novel strain of feline morbillivirus and effective preventive measure against feline morbillivirus infection. Marcacci M et al. (Journal of Virological Methods 2016, 234: 160-163) describe the genome characterization of feline morbillivirus from Italy.

Viral Vector Systems

Avipox virus viral vector systems are based on avipox viruses, which are naturally host-restricted poxviruses. Among such avipox viruses canarypox virus (CPV) has been engineered to express foreign, heterologous, extrinsic, exogenous gene products (Taylor J et al., Vaccine 1991, 9(3): 190-193; Taylor J et al., Virology 1992, 187(1): 321-328; Taylor J et al., Dev Biol Stand 1994, 82: 131-135).

Recombinant poxviruses can be constructed in two steps known in the art and analogous to the methods for creating synthetic recombinants of poxviruses such as the vaccinia virus and avipox virus described in U.S. Pat. Nos. 4,769, 330; 4,722,848; 4,603,112; 5,110,587; 5,174,993; 5,494, 807; and 5,505,941, the disclosures of which are incorporated herein by reference.

Specifically, ALVAC is an engineered poxvirus vector derived from canarypox virus (e.g. U.S. Pat. No. 5,756,103). ALVAC is an attenuated canarypox virus-based vector that was a plaque-cloned derivative of the human canarypox vaccine, Kanapox ALVAC-based recombinant viruses expressing extrinsic immunogens have also been demonstrated efficacious as vaccine vectors (see for instance Tartaglia J et al., J Virology 1993, 67(4): 2370-2375). This avipox vector is restricted to avian species for productive replication and does not productively replicate in non-avian hosts, a characteristic thought to improve its safety profile. On human cell cultures, canarypox virus replication is aborted early in the viral replication cycle prior to viral DNA synthesis. Nevertheless, when engineered to express extrinsic immunogens, authentic expression and processing is observed in vitro in mammalian cells and inoculation into numerous mammalian species induces antibody and cellular immune responses to extrinsic immunogen and provides protection against challenge with the cognate pathogen (Taylor J et al., Vaccine 1991, 9(3): 190-193; Taylor J et al., Virology 1992, 187(1): 321-328). ALVAC was deposited under the terms of the Budapest Treaty with the American Type Culture Collection (ATCC) under accession number VR-2547 (U.S. Pat. No. 5,756,103, the disclosure of which is incorporated herein by reference).

TROVAC refers to an attenuated fowlpox viral vector that was a plaque-cloned isolate derived from FP1-vaccine strain of fowlpox virus that is licensed for vaccination of 1-day-old chicks (e.g. U.S. Pat. No. 5,766,599). The parental virus strain Duvette was obtained in France as a fowlpox scab from a chicken. The virus was attenuated by approximately 50 serial passages in chicken embryonated eggs followed by 25 passages on chicken embryo fibroblast cells. The virus was subjected to four successive plaque purifications. One plaque isolate was further amplified in primary CEF cells and a stock virus, designated as TROVAC, established. TROVAC was deposited under the terms of the Budapest Treaty with the American Type Culture Collection (ATCC) under accession number VR-2553 (U.S. Pat. No. 5,766,599, the disclosure of which is incorporated herein by reference).

Specific applications of ALVAC and TROVAC vector based vaccination approaches are for instance described in WO 2006/073431, WO 2006/115843, and WO 2013/123242, the disclosures of which are incorporated herein by reference.

Further prior art is as follows: Weli S C et al. (Virology J. 2011, 8 (1): 49) describes avipoxviruses: infection biology and their use as vaccine vectors. WO 2005/013918 is directed to a poxvirus vaccine comprising a soluble truncated poxvirus envelope protein. De Vries P et al. (J. Gen. Virol. 1988, 69: 2071-2083) disclose that canine distemper virus (CDV) immune-stimulating complexes (Iscoms), but not measles vims iscoms protect dogs against CDV infection. Marciani D J et al. (Vaccine 1991, 9(2): 89-96) describe the protective immune response of a genetically engineered subunit vaccine against feline leukaemia virus in cats. McEachern J A et al. (Vaccine 2008, 26(31): 3842-3852) describe that a recombinant subunit vaccine formulation protects against lethal Nipah virus challenge in cats.

Most available paramyxoviruses vaccines and more especially morbilliviruses are modified live virus vaccines. They are usually safe and efficacious. However, as with some classical modified live vims, reversion to virulence may occasionally occur. As an example, some cases of reversion to virulence of some distemper vaccine strains have been reported. Therefore, there is an unmet need for safe vectors as a way to overcome the potential safety issues of classical attenuated strains.

SUMMARY OF THE INVENTION

In order to overcome the deficiencies in the prior art, the invention provides novel target antigens which are expressed from viral vector vaccines and feline paramyxovirus/feline morbillivirus vaccines.

The present invention concerns among others the development of efficacious viral vector vaccines that immunize felines against feline paramyxovirus (infections), preferably by means of an avipox virus viral vector, such as an attenuated canarypox or attenuated fowlpox vector, e.g. ALVAC or TROVAC. Such attenuated vectors encode at least one feline paramyxovirus antigen so there can be expression of the heterologous proteins with limited or no productive replication.

The present invention concerns a viral vector, preferably a recombinant and/or non-naturally occurring viral vector, comprising at least one exogenous antigen encoding sequence relating to at least one pathogen infecting felines, wherein the at least one pathogen infecting felines is feline paramyxovirus. Preferably, the viral vector is selected from the group consisting of: avipox virus viral vector, canine morbillivirus viral vector, herpes virus viral vector, varicella virus viral vector.

The present invention concerns a mammalian host cell characterized in that it comprises the viral vector as herein described and claimed.

The present invention concerns the use of the viral vector as herein described and claimed or the mammalian host cell as herein described and claimed for the manufacture of an immunogenic composition or vaccine.

The present invention concerns an immunogenic composition comprising
 (a) the viral vector as herein described and claimed or the mammalian host cell as herein described and claimed, and/or
 (b) a polypeptide encoded by the viral vector as herein described and claimed, such as a virus, a modified live virus, a virus like particle (VLP) or the like, and
 (c) optionally a pharmaceutical- or veterinary-acceptable carrier or excipient, preferably said carrier being suitable for oral, intradermal, intramuscular or intranasal application;
 wherein preferably said immunogenic composition comprises a virus, such as an infectious virus.

The present invention concerns a vaccine or pharmaceutical composition comprising
 (a) the viral vector as herein described and claimed or the mammalian host cell as herein described and claimed, and/or
 (b) a polypeptide encoded by the viral vector as herein described and claimed, such as a virus, a modified live virus, a virus like particle (VLP) or the like, and
 (c) a pharmaceutical- or veterinary-acceptable carrier or excipient, preferably said carrier being suitable for oral, intradermal, intramuscular or intranasal application,
 (d) optionally said vaccine or pharmaceutical composition further comprising an adjuvant.

The present invention concerns a method for the preparation of an immunogenic composition or a vaccine for reducing the incidence and/or the severity of one or more clinical signs associated with or caused by an infection with at least one pathogenic paramyxovirus, comprising the following steps:
 (a) infecting the mammalian host cell as herein described and claimed with the viral vector as herein described and claimed,
 (b) cultivating the infected cells under suitable conditions,
 (c) collecting infected cell cultures,
 (d) optionally purifying the collected infected cell cultures of step (c),
 (e) optionally mixing said collected infected cell culture with a pharmaceutically acceptable carrier.

The present invention concerns an immunogenic composition as herein described and claimed or the vaccine as herein described and claimed for use in a method of reducing or preventing the clinical signs or disease caused by an infection with at least one pathogenic paramyxovirus or for use in a method of treating and/or preventing an infection with at least one pathogenic paramyxovirus, wherein preferably said feline is a cat, more preferably a domestic cat, wherein preferably the at least one pathogenic paramyxovirus is at least one feline paramyxovirus, wherein preferably said clinical signs or disease caused by an infection with at least one pathogenic paramyxovirus or said infection with at least one pathogenic paramyxovirus are selected from the group consisting of: viremia, fever, virus shedding in the environment, infections of the urogenital system, infections of the urinary system, kidney disease, chronic kidney disease (CKD), inflammation of the renal tubules and renal interstitial tissue, idiopathic tubulointerstitial nephritis (TIN).

The present invention concerns a method of immunizing a feline, such as a cat, more preferably a domestic cat, against a clinical disease caused by at least one pathogenic paramyxovirus in said feline, said method comprising the step of administering to the feline the immunogenic composition as herein described and claimed or the vaccine as herein described and claimed, wherein said immunogenic composition or vaccine fails to cause clinical signs of infection but is capable of inducing an immune response that immunizes the feline against pathogenic forms of said at least one paramyxovirus, wherein preferably the at least one pathogenic paramyxovirus is at least one feline paramyxovirus, wherein preferably said clinical disease or said clinical signs of infection are selected from the group consisting of: viremia, fever, virus shedding in the environment, infections of the urogenital system, infections of the urinary system, kidney disease, chronic kidney disease (CKD), inflammation of the renal tubules and renal interstitial tissue, idiopathic tubulointerstitial nephritis (TIN).

The present invention concerns a kit for vaccinating a feline, preferably a cat, more preferably a domestic cat, against a disease associated with and/or reducing the incidence or the severity of one or more clinical signs associated with or caused by at least one pathogenic paramyxovirus in a feline comprising:
(a) a dispenser capable of administering a vaccine to said feline; and
(b) the immunogenic composition as herein described and claimed or the vaccine as herein described and claimed, and
(c) optionally an instruction leaflet;
wherein preferably the at least one pathogenic paramyxovirus is at least one feline paramyxovirus, wherein preferably said disease or said clinical signs are selected from the group consisting of: viremia, fever, virus shedding in the environment, infections of the urogenital system, infections of the urinary system, kidney disease, chronic kidney disease (CKD), inflammation of the renal tubules and renal interstitial tissue, idiopathic tubulointerstitial nephritis (TIN).

Among others, advantages of the underlying invention are as follows:
(1) Increased safety of the vectored vaccines in comparison with attenuated live vaccines
(2) Directed immunization towards the given (immunodominant) antigen, avoiding the expression of potential immunosuppressive proteins of feline paramyxoviruses
(3) Ability to grow the vectored vaccines to high titers compatible with commercial vaccine production Thus, the solution to the above technical problem is achieved by the description and the embodiments characterized in the claims and the invention in its different aspects is implemented according to the claims.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A and FIG. 1B depict the schematic overview about the in vitro recombination (IVR) with the two donor plasmids pC3 42 k Gordon M (opt) and pC5 H6p Gordon H (opt) and the resulting two constructs vCP3025 and vCP3029.

FIG. 2 depicts SEQ ID NO:49, the vCP3025 cloned insertion locus C5 and its confirmed nucleotide sequence from base pair 304,701 to 308,870 including right flanking sequence of the insertion locus C5, H6 promoter, Gordon H (opt) and left flanking sequence of the insertion locus C5.

FIG. 3 depicts SEQ ID NO:50, the vCP3029 cloned insertion locus C5 and its confirmed nucleotide sequence from base pair 304,166 to 308,380 including right flanking sequence of the insertion locus C5, H6 promoter, Gordon H (opt) and left flanking sequence of the insertion locus C5.

FIG. 4 depicts SEQ ID NO:51, the vCP3029 cloned insertion locus C3 and its confirmed nucleotide sequence from base pair 38,608 to 42,807 including right flanking sequence of the insertion locus C3, 42k promoter, Gordon M (opt) and left flanking sequence of the insertion locus C3.

FIG. 7 depicts SEQ ID NO:95, the vCP3041 cloned insertion locus C3 and its theoretical nucleotide sequence from base pair 38,619 to 43,588 including right flanking sequence of the insertion locus C3, 42k long promoter, Lapön H (wt; no BamH I restriction enzyme site) and left flanking sequence of the insertion locus C3.

DETAILED DESCRIPTION OF THE INVENTION

Figure 1A:
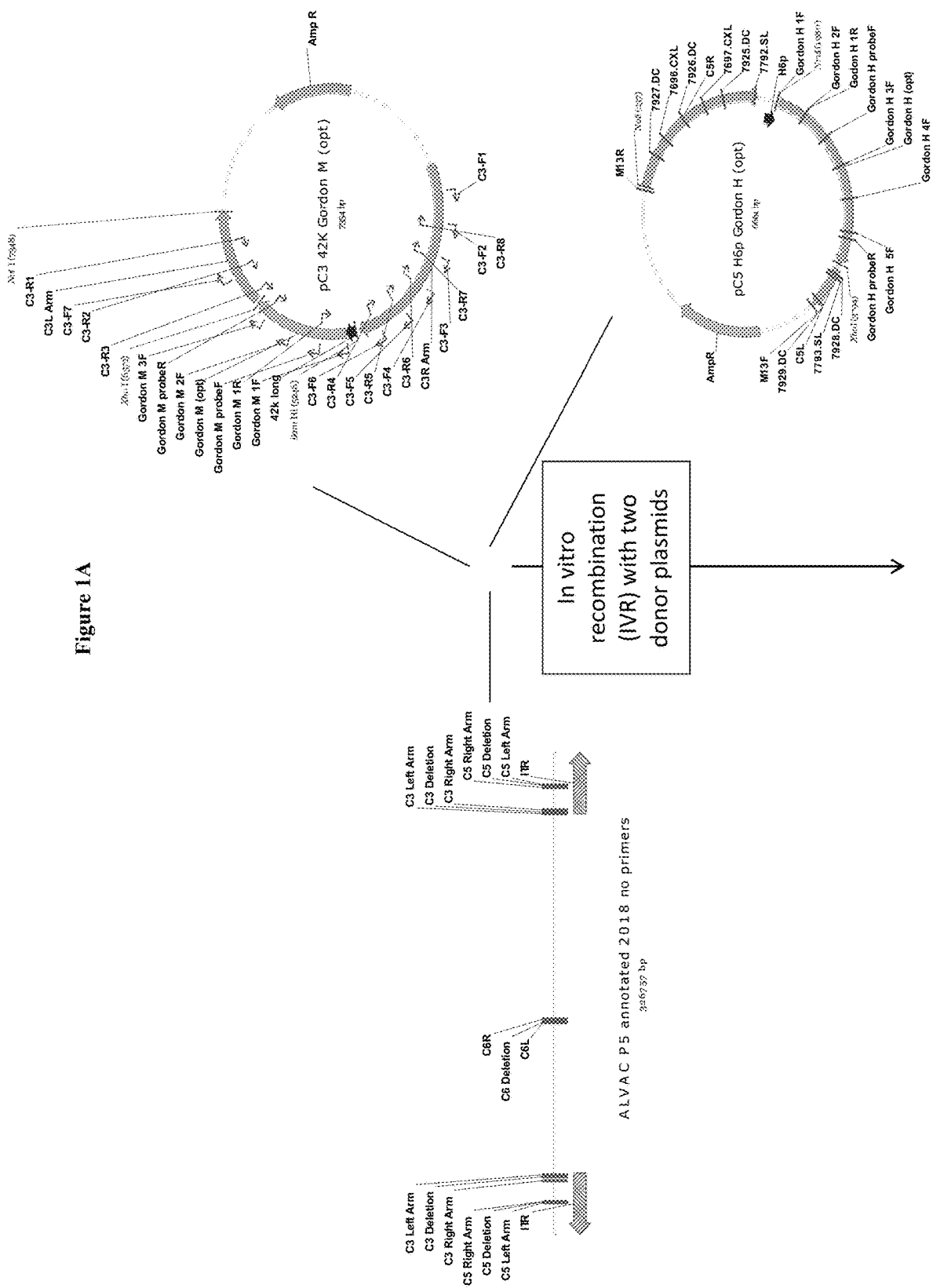
Figure 5:
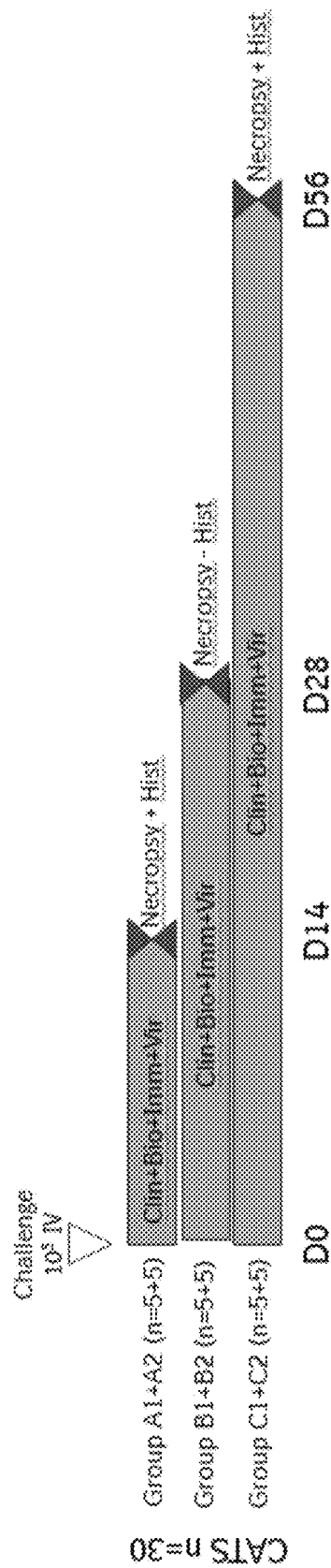
FIG. 5 depicts a graphical overview about the experimental plan and follow-up of the challenge model clinical study (Example 4).

The present invention solves the problems inherent in the prior art and provides a distinct advance in the state of the art.

Generally, the present invention concerns a viral vector comprising at least one exogenous antigen encoding sequence relating to at least one pathogen infecting felines, wherein the at least one pathogen infecting felines is feline paramyxovirus.

In a specific aspect, such viral vector as herein described and claimed is selected from the group consisting of: avipox virus viral vector, canine morbillivirus viral vector, herpes virus viral vector, varicella virus viral vector.

In another specific aspect, the at least one pathogen infecting felines being feline paramyxovirus as herein described and claimed is selected from the group consisting of:
(a) a feline paramyxovirus type 2 (FPaV-2);
(b) a feline paramyxovirus type 2 (FPaV-2), the genome of which comprises a ribonucleic acid complementary to the nucleic acid sequence selected from the group consisting of:
  (i) a nucleic acid sequence according to SEQ ID NO: 1,
  (ii) a nucleic acid sequence which is at least 70% identical to SEQ ID NO:1, at least 75% identical to SEQ ID NO:1, at least 80% identical to SEQ ID NO:1, at least 85% identical to SEQ ID NO:1, at least 90% identical to SEQ ID NO:1, at least 91% identical to SEQ ID NO:1, at least 92% identical to SEQ ID NO:1, at least 93% identical to SEQ ID NO:1, at least 94% identical to SEQ ID NO:1, at least 95% identical to SEQ ID NO:1, at least 96% identical to SEQ ID NO:1, at least 97% identical to SEQ ID NO:1, at least 98% identical to SEQ ID NO:1, at least 99% identical to SEQ ID NO:1;
(c) feline paramyxovirus type 2 (FPaV-2) as deposited at Collection Nationale de Culture de Microorganismes (CNCM) under accession number CNCM I-5123;
(d) a feline paramyxovims type 2 (FPaV-2), the genome of which comprises a ribonucleic acid complementary to the nucleic acid sequence selected from the group consisting of:
  (i) a nucleic acid sequence according to SEQ ID NO: 2,
  (ii) a nucleic acid sequence which is at least 70% identical to SEQ ID NO:2, at least 75% identical to SEQ ID NO:2, at least 80% identical to SEQ ID NO:2, at least 85% identical to SEQ ID NO:2, at least 90% identical to SEQ ID NO:2, at least 91% identical to SEQ ID NO:2, at least 92% identical to SEQ ID NO:2, at least 93% identical to SEQ ID NO:2, at least 94% identical to SEQ ID NO:2, at least 95% identical to SEQ ID NO:2, at least 96% identical to SEQ ID NO:2, at least 97% identical to SEQ ID NO:2, at least 98% identical to SEQ ID NO:2, at least 99% identical to SEQ ID NO:2;
(e) a feline morbillivirus (FeMoV);
(f) a feline morbillivirus (FeMoV), the genome of which comprises a ribonucleic acid complementary to the nucleic acid sequence selected from the group consisting of:
  (i) a nucleic acid sequence according to SEQ ID NO: 3,
  (ii) a nucleic acid sequence which is at least 70% identical to SEQ ID NO:3, at least 75% identical to SEQ ID NO:3, at least 80% identical to SEQ ID NO:3, at least 85% identical to SEQ ID NO:3, at least 90% identical to SEQ ID NO:3, at least 91% identical to SEQ ID NO:3, at least 92% identical to SEQ ID NO:3, at least 93% identical to SEQ ID NO:3, at least 94% identical to SEQ ID NO:3, at least 95% identical to SEQ ID NO:3, at least 96% identical to SEQ ID NO:3, at least 97% identical to SEQ ID NO:3, at least 98% identical to SEQ ID NO:3, at least 99% identical to SEQ ID NO:3.

In another specific aspect, the at least one pathogen infecting felines being feline paramyxovirus as herein described and claimed is selected from the group consisting of:
(b) a feline paramyxovirus type 2 (FPaV-2), the genome of which comprises a ribonucleic acid complementary to the nucleic acid sequence selected from the group consisting of:
  (i) a nucleic acid sequence according to SEQ ID NO: 1,
  (ii) a nucleic acid sequence which is at least 70% identical to SEQ ID NO:1, at least 75% identical to SEQ ID NO:1, at least 80% identical to SEQ ID NO:1, at least 85% identical to SEQ ID NO:1, at least 90% identical to SEQ ID NO:1, at least 91% identical to SEQ ID NO:1, at least 92% identical to SEQ ID NO:1, at least 93% identical to SEQ ID NO:1, at least 94% identical to SEQ ID NO:1, at least 95% identical to SEQ ID NO:1, at least 96% identical to SEQ ID NO:1, at least 97% identical to SEQ ID NO:1, at least 98% identical to SEQ ID NO:1, at least 99% identical to SEQ ID NO:1;
(c) feline paramyxovirus type 2 (FPaV-2) as deposited at Collection Nationale de Culture de Microorganismes (CNCM) under accession number CNCM I-5123;
(d) a feline paramyxovirus type 2 (FPaV-2), the genome of which comprises a ribonucleic acid complementary to the nucleic acid sequence selected from the group consisting of:
  (i) a nucleic acid sequence according to SEQ ID NO: 2,
  (ii) a nucleic acid sequence which is at least 70% identical to SEQ ID NO:2, at least 75% identical to SEQ ID NO:2, at least 80% identical to SEQ ID NO:2, at least 85% identical to SEQ ID NO:2, at least 90% identical to SEQ ID NO:2, at least 91% identical to SEQ ID NO:2, at least 92% identical to SEQ ID NO:2, at least 93% identical to SEQ ID NO:2, at least 94% identical to SEQ ID NO:2, at least 95% identical to SEQ ID NO:2, at least 96% identical to SEQ ID NO:2, at least 97% identical to SEQ ID NO:2, at least 98% identical to SEQ ID NO:2, at least 99% identical to SEQ ID NO:2.

In another specific aspect, the viral vector is recombinant and/or non-naturally occurring.

In another specific aspect, the viral vector as herein described and claimed is a canarypox vector, preferably an attenuated canarypox vector, more preferably ALVAC, even more preferably ALVAC-1 or ALVAC-2, most preferably ALVAC as deposited under the terms of the Budapest Treaty at the American Type Culture Collection (ATCC) under accession number VR-2547.

In another specific aspect, the viral vector as herein described and claimed is a fowlpox vector, preferably an attenuated fowlpox vector, more preferably TROVAC, most preferably TROVAC as deposited under the terms of the Budapest Treaty at the American Type Culture Collection (ATCC) under accession number VR-2553.

In another specific aspect, the viral vector as herein described and claimed is selected from the group consisting of: vCP3025, vCP3029, vCP3041.

In yet another specific aspect, the at least one exogenous antigen encoding sequence as herein described and claimed is selected from the group consisting of: hemagglutinin protein ("H") encoding sequence, matrix protein ("M") encoding sequence, fusion protein ("F") encoding sequence, nucleocapsid protein ("N") encoding sequence, phosphoprotein ("P") encoding sequence, RNA-dependent RNA polymerase protein ("L") encoding sequence, and more preferably is a hemagglutinin protein ("H") encoding sequence and/or a matrix protein ("M") encoding sequence and/or a fusion protein ("F") encoding sequence.

In yet another specific aspect, the at least one exogenous antigen encoding sequence as herein described and claimed is a hemagglutinin protein ("H") encoding sequence and the hemagglutinin protein ("H") encoding sequence comprises a nucleic acid sequence which is at least 70% identical to SEQ ID NO:4, at least 75% identical to SEQ ID NO:4, at least 80% identical to SEQ ID NO:4, at least 85% identical to SEQ ID NO:4, at least 90% identical to SEQ ID NO:4, at least 91% identical to SEQ ID NO:4, at least 92% identical to SEQ ID NO:4, at least 93% identical to SEQ ID NO:4, at least 94% identical to SEQ ID NO:4, at least 95% identical to SEQ ID NO:4, at least 96% identical to SEQ ID NO:4, at least 97% identical to SEQ ID NO:4, at least 98% identical to SEQ ID NO:4, at least 99% identical to SEQ ID NO:4, and preferably is selected from the group consisting of: SEQ ID NO:4, SEQ ID NO:5.

In yet another specific aspect, the at least one exogenous antigen encoding sequence as herein described and claimed is a hemagglutinin protein ("H") encoding sequence and the hemagglutinin protein ("H") encoding sequence comprises a nucleic acid sequence encoding a polypeptide having an amino acid sequence which is at least 70% identical to SEQ ID NO:6, at least 75% identical to SEQ ID NO:6, at least 80% identical to SEQ ID NO:6, at least 85% identical to SEQ ID NO:6, at least 90% identical to SEQ ID NO:6, at least 91% identical to SEQ ID NO:6, at least 92% identical to SEQ ID NO:6, at least 93% identical to SEQ ID NO:6, at least 94% identical to SEQ ID NO:6, at least 95% identical to SEQ ID NO:6, at least 96% identical to SEQ ID NO:6, at least 97% identical to SEQ ID NO:6, at least 98% identical to SEQ ID NO:6, at least 99% identical to SEQ ID NO:6, and preferably is the amino acid sequence according to SEQ ID NO:6.

In yet another specific aspect, the at least one exogenous antigen encoding sequence as herein described and claimed is a matrix protein ("M") encoding sequence and the matrix protein ("M") encoding sequence comprises a nucleic acid sequence which is at least 70% identical to SEQ ID NO:7, at least 75% identical to SEQ ID NO:7, at least 80% identical to SEQ ID NO:7, at least 85% identical to SEQ ID NO:7, at least 90% identical to SEQ ID NO:7, at least 91% identical to SEQ ID NO:7, at least 92% identical to SEQ ID NO:7, at least 93% identical to SEQ ID NO:7, at least 94% identical to SEQ ID NO:7, at least 95% identical to SEQ ID NO:7, at least 96% identical to SEQ ID NO:7, at least 97% identical to SEQ ID NO:7, at least 98% identical to SEQ ID NO:7, at least 99% identical to SEQ ID NO:7, and preferably is selected from the group consisting of: SEQ ID NO:7, SEQ ID NO:8.

In yet another specific aspect, the at least one exogenous antigen encoding sequence as herein described and claimed is a matrix protein ("M") encoding sequence and the matrix protein ("M") encoding sequence comprises a nucleic acid sequence encoding a polypeptide having an amino acid sequence which is at least 70% identical to SEQ ID NO:9, at least 75% identical to SEQ ID NO:9, at least 80% identical to SEQ ID NO:9, at least 85% identical to SEQ ID NO:9, at least 90% identical to SEQ ID NO:9, at least 91% identical to SEQ ID NO:9, at least 92% identical to SEQ ID NO:9, at least 93% identical to SEQ ID NO:9, at least 94% identical to SEQ ID NO:9, at least 95% identical to SEQ ID NO:9, at least 96% identical to SEQ ID NO:9, at least 97% identical to SEQ ID NO:9, at least 98% identical to SEQ ID NO:9, at least 99% identical to SEQ ID NO:9, and preferably is the amino acid sequence according to SEQ ID NO:9.

In yet another specific aspect, the at least one exogenous antigen encoding sequence as herein described and claimed is a fusion protein ("F") encoding sequence and the fusion protein ("F") encoding sequence comprises a nucleic acid sequence which is at least 70% identical to SEQ ID NO:10, at least 75% identical to SEQ ID NO:10, at least 80% identical to SEQ ID NO:10, at least 85% identical to SEQ ID NO:10, at least 90% identical to SEQ ID NO:10, at least 91% identical to SEQ ID NO:10, at least 92% identical to SEQ ID NO:10, at least 93% identical to SEQ ID NO:10, at least 94% identical to SEQ ID NO:10, at least 95% identical to SEQ ID NO:10, at least 96% identical to SEQ ID NO:10, at least 97% identical to SEQ ID NO:10, at least 98% identical to SEQ ID NO:10, at least 99% identical to SEQ ID NO:10, and preferably is selected from the group consisting of: SEQ ID NO:10, SEQ ID NO:11.

In yet another specific aspect, the at least one exogenous antigen encoding sequence as herein described and claimed is a fusion protein ("F") encoding sequence and the fusion protein ("F") encoding sequence comprises a nucleic acid sequence encoding a polypeptide having an amino acid sequence which is at least 70% identical to SEQ ID NO:12, at least 75% identical to SEQ ID NO:12, at least 80% identical to SEQ ID NO:12, at least 85% identical to SEQ ID NO:12, at least 90% identical to SEQ ID NO:12, at least 91% identical to SEQ ID NO:12, at least 92% identical to SEQ ID NO:12, at least 93% identical to SEQ ID NO:12, at least 94% identical to SEQ ID NO:12, at least 95% identical to SEQ ID NO:12, at least 96% identical to SEQ ID NO:12, at least 97% identical to SEQ ID NO:12, at least 98% identical to SEQ ID NO:12, at least 99% identical to SEQ ID NO:12, and preferably is the amino acid sequence according to SEQ ID NO:12.

In yet another specific aspect, the at least one exogenous antigen encoding sequence as herein described and claimed is a nucleocapsid protein ("N") encoding sequence and the nucleocapsid protein ("N") encoding sequence comprises a nucleic acid sequence which is at least 70% identical to SEQ ID NO:13, at least 75% identical to SEQ ID NO:13, at least 80% identical to SEQ ID NO:13, at least 85% identical to SEQ ID NO:13, at least 90% identical to SEQ ID NO:13, at least 91% identical to SEQ ID NO:13, at least 92% identical to SEQ ID NO:13, at least 93% identical to SEQ ID NO:13, at least 94% identical to SEQ ID NO:13, at least 95% identical to SEQ ID NO:13, at least 96% identical to SEQ ID NO:13, at least 97% identical to SEQ ID NO:13, at least 98% identical to SEQ ID NO:13, at least 99% identical to SEQ ID NO:13, and preferably is selected from the group consisting of: SEQ ID NO:13.

In yet another specific aspect, the at least one exogenous antigen encoding sequence as herein described and claimed is a nucleocapsid protein ("N") encoding sequence and the nucleocapsid protein ("N") encoding sequence comprises a nucleic acid sequence encoding a polypeptide having an amino acid sequence which is at least 70% identical to SEQ ID NO:14, at least 75% identical to SEQ ID NO:14, at least 80% identical to SEQ ID NO:14, at least 85% identical to SEQ ID NO:14, at least 90% identical to SEQ ID NO:14, at least 91% identical to SEQ ID NO:14, at least 92% identical to SEQ ID NO:14, at least 93% identical to SEQ ID NO:14, at least 94% identical to SEQ ID NO:14, at least 95% identical to SEQ ID NO:14, at least 96% identical to SEQ ID NO:14, at least 97% identical to SEQ ID NO:14, at least 98% identical to SEQ ID NO:14, at least 99% identical to SEQ ID NO:14, and preferably is the amino acid sequence according to SEQ ID NO:14.

In yet another specific aspect, the at least one exogenous antigen encoding sequence as herein described and claimed is a phosphoprotein ("P") encoding sequence and the phosphoprotein ("P") encoding sequence comprises a nucleic acid sequence which is at least 70% identical to SEQ ID NO:15, at least 75% identical to SEQ ID NO:15, at least 80% identical to SEQ ID NO:15, at least 85% identical to SEQ ID NO:15, at least 90% identical to SEQ ID NO:15, at least 91% identical to SEQ ID NO:15, at least 92% identical to SEQ ID NO:15, at least 93% identical to SEQ ID NO:15, at least 94% identical to SEQ ID NO:15, at least 95% identical to SEQ ID NO:15, at least 96% identical to SEQ ID NO:15, at least 97% identical to SEQ ID NO:15, at least 98% identical to SEQ ID NO:15, at least 99% identical to SEQ ID NO:15, and preferably is selected from the group consisting of: SEQ ID NO:15.

In yet another specific aspect, the at least one exogenous antigen encoding sequence as herein described and claimed is a phosphoprotein ("P") encoding sequence and the phosphoprotein ("P") encoding sequence comprises a nucleic acid sequence encoding a polypeptide having an amino acid sequence which is at least 70% identical to SEQ ID NO:16, at least 75% identical to SEQ ID NO:16, at least 80% identical to SEQ ID NO:16, at least 85% identical to SEQ ID NO:16, at least 90% identical to SEQ ID NO:16, at least 91% identical to SEQ ID NO:16, at least 92% identical to SEQ ID NO:16, at least 93% identical to SEQ ID NO:16, at least 94% identical to SEQ ID NO:16, at least 95% identical to SEQ ID NO:16, at least 96% identical to SEQ ID NO:16, at least 97% identical to SEQ ID NO:16, at least 98% identical to SEQ ID NO:16, at least 99% identical to SEQ ID NO:16, and preferably is the amino acid sequence according to SEQ ID NO:16.

In yet another specific aspect, the at least one exogenous antigen encoding sequence as herein described and claimed is a RNA-dependent RNA polymerase protein ("L") encoding sequence and the RNA-dependent RNA polymerase protein ("L") encoding sequence comprises a nucleic acid sequence which is at least 70% identical to SEQ ID NO:17, at least 75% identical to SEQ ID NO:17, at least 80% identical to SEQ ID NO:17, at least 85% identical to SEQ ID NO:17, at least 90% identical to SEQ ID NO:17, at least 91% identical to SEQ ID NO:17, at least 92% identical to SEQ ID NO:17, at least 93% identical to SEQ ID NO:17, at least 94% identical to SEQ ID NO:17, at least 95% identical to SEQ ID NO:17, at least 96% identical to SEQ ID NO:17, at least 97% identical to SEQ ID NO:17, at least 98% identical to SEQ ID NO:17, at least 99% identical to SEQ ID NO:17, and preferably is selected from the group consisting of: SEQ ID NO:17.

In yet another specific aspect, the at least one exogenous antigen encoding sequence as herein described and claimed is a RNA-dependent RNA polymerase protein ("L") encoding sequence and the RNA-dependent RNA polymerase protein ("L") encoding sequence comprises a nucleic acid sequence encoding a polypeptide having an amino acid sequence which is at least 70% identical to SEQ ID NO:18, at least 75% identical to SEQ ID NO:18, at least 80% identical to SEQ ID NO:18, at least 85% identical to SEQ ID NO:18, at least 90% identical to SEQ ID NO:18, at least 91% identical to SEQ ID NO:18, at least 92% identical to SEQ ID NO:18, at least 93% identical to SEQ ID NO:18, at least 94% identical to SEQ ID NO:18, at least 95% identical to SEQ ID NO:18, at least 96% identical to SEQ ID NO:18, at least 97% identical to SEQ ID NO:18, at least 98% identical to SEQ ID NO:18, at least 99% identical to SEQ ID NO:18, and preferably is the amino acid sequence according to SEQ ID NO:18.

In yet another specific aspect, the at least one exogenous antigen encoding sequence as herein described and claimed is a hemagglutinin protein ("H") encoding sequence and the hemagglutinin protein ("H") encoding sequence comprises a nucleic acid sequence which is at least 70% identical to SEQ ID NO:19, at least 75% identical to SEQ ID NO:19, at least 80% identical to SEQ ID NO:19, at least 85% identical to SEQ ID NO:19, at least 90% identical to SEQ ID NO:19, at least 91% identical to SEQ ID NO:19, at least 92% identical to SEQ ID NO:19, at least 93% identical to SEQ ID NO:19, at least 94% identical to SEQ ID NO:19, at least 95% identical to SEQ ID NO:19, at least 96% identical to SEQ ID NO:19, at least 97% identical to SEQ ID NO:19, at least 98% identical to SEQ ID NO:19, at least 99% identical to SEQ ID NO:19, and preferably is selected from the group consisting of: SEQ ID NO:19.

In yet another specific aspect, the at least one exogenous antigen encoding sequence as herein described and claimed is a hemagglutinin protein ("H") encoding sequence and the hemagglutinin protein ("H") encoding sequence comprises a nucleic acid sequence encoding a polypeptide having an amino acid sequence which is at least 70% identical to SEQ ID NO:20, at least 75% identical to SEQ ID NO:20, at least 80% identical to SEQ ID NO:20, at least 85% identical to SEQ ID NO:20, at least 90% identical to SEQ ID NO:20, at least 91% identical to SEQ ID NO:20, at least 92% identical to SEQ ID NO:20, at least 93% identical to SEQ ID NO:20, at least 94% identical to SEQ ID NO:20, at least 95% identical to SEQ ID NO:20, at least 96% identical to SEQ ID NO:20, at least 97% identical to SEQ ID NO:20, at least 98% identical to SEQ ID NO:20, at least 99% identical to SEQ ID NO:20, and preferably is the amino acid sequence according to SEQ ID NO:20.

In yet another specific aspect, the at least one exogenous antigen encoding sequence as herein described and claimed is a matrix protein ("M") encoding sequence and the matrix protein ("M") encoding sequence comprises a nucleic acid sequence which is at least 70% identical to SEQ ID NO:21, at least 75% identical to SEQ ID NO:21, at least 80% identical to SEQ ID NO:21, at least 85% identical to SEQ ID NO:21, at least 90% identical to SEQ ID NO:21, at least 91% identical to SEQ ID NO:21, at least 92% identical to SEQ ID NO:21, at least 93% identical to SEQ ID NO:21, at least 94% identical to SEQ ID NO:21, at least 95% identical to SEQ ID NO:21, at least 96% identical to SEQ ID NO:21, at least 97% identical to SEQ ID NO:21, at least 98% identical to SEQ ID NO:21, at least 99% identical to SEQ ID NO:21, and preferably is selected from the group consisting of: SEQ ID NO:21.

In yet another specific aspect, the at least one exogenous antigen encoding sequence as herein described and claimed is a matrix protein ("M") encoding sequence and the matrix protein ("M") encoding sequence comprises a nucleic acid sequence encoding a polypeptide having an amino acid sequence which is at least 70% identical to SEQ ID NO:22, at least 75% identical to SEQ ID NO:22, at least 80% identical to SEQ ID NO:22, at least 85% identical to SEQ ID NO:22, at least 90% identical to SEQ ID NO:22, at least 91% identical to SEQ ID NO:22, at least 92% identical to SEQ ID NO:22, at least 93% identical to SEQ ID NO:22, at least 94% identical to SEQ ID NO:22, at least 95% identical to SEQ ID NO:22, at least 96% identical to SEQ ID NO:22, at least 97% identical to SEQ ID NO:22, at least 98% identical to SEQ ID NO:22, at least 99% identical to SEQ ID NO:22, and preferably is the amino acid sequence according to SEQ ID NO:22.

In yet another specific aspect, the at least one exogenous antigen encoding sequence as herein described and claimed is a fusion protein ("F") encoding sequence and the fusion protein ("F") encoding sequence comprises a nucleic acid sequence which is at least 70% identical to SEQ ID NO:23, at least 75% identical to SEQ ID NO:23, at least 80% identical to SEQ ID NO:23, at least 85% identical to SEQ ID NO:23, at least 90% identical to SEQ ID NO:23, at least 91% identical to SEQ ID NO:23, at least 92% identical to SEQ ID NO:23, at least 93% identical to SEQ ID NO:23, at least 94% identical to SEQ ID NO:23, at least 95% identical to SEQ ID NO:23, at least 96% identical to SEQ ID NO:23, at least 97% identical to SEQ ID NO:23, at least 98% identical to SEQ ID NO:23, at least 99% identical to SEQ ID NO:23, and preferably is selected from the group consisting of: SEQ ID NO:23.

In yet another specific aspect, the at least one exogenous antigen encoding sequence as herein described and claimed is a fusion protein ("F") encoding sequence and the fusion protein ("F") encoding sequence comprises a nucleic acid sequence encoding a polypeptide having an amino acid sequence which is at least 70% identical to SEQ ID NO:24, at least 75% identical to SEQ ID NO:24, at least 80% identical to SEQ ID NO:24, at least 85% identical to SEQ ID NO:24, at least 90% identical to SEQ ID NO:24, at least 91% identical to SEQ ID NO:24, at least 92% identical to SEQ ID NO:24, at least 93% identical to SEQ ID NO:24, at least 94% identical to SEQ ID NO:24, at least 95% identical to SEQ ID NO:24, at least 96% identical to SEQ ID NO:24, at least 97% identical to SEQ ID NO:24, at least 98% identical to SEQ ID NO:24, at least 99% identical to SEQ ID NO:24, and preferably is the amino acid sequence according to SEQ ID NO:24.

In yet another specific aspect, the at least one exogenous antigen encoding sequence as herein described and claimed is a nucleocapsid protein ("N") encoding sequence and the nucleocapsid protein ("N") encoding sequence comprises a nucleic acid sequence which is at least 70% identical to SEQ ID NO:25, at least 75% identical to SEQ ID NO:25, at least 80% identical to SEQ ID NO:25, at least 85% identical to SEQ ID NO:25, at least 90% identical to SEQ ID NO:25, at least 91% identical to SEQ ID NO:25, at least 92% identical to SEQ ID NO:25, at least 93% identical to SEQ ID NO:25, at least 94% identical to SEQ ID NO:25, at least 95% identical to SEQ ID NO:25, at least 96% identical to SEQ ID NO:25, at least 97% identical to SEQ ID NO:25, at least 98% identical to SEQ ID NO:25, at least 99% identical to SEQ ID NO:25, and preferably is selected from the group consisting of: SEQ ID NO:25.

In yet another specific aspect, the at least one exogenous antigen encoding sequence as herein described and claimed is a nucleocapsid protein ("N") encoding sequence and the nucleocapsid protein ("N") encoding sequence comprises a nucleic acid sequence encoding a polypeptide having an amino acid sequence which is at least 70% identical to SEQ ID NO:26, at least 75% identical to SEQ ID NO:26, at least 80% identical to SEQ ID NO:26, at least 85% identical to SEQ ID NO:26, at least 90% identical to SEQ ID NO:26, at least 91% identical to SEQ ID NO:26, at least 92% identical to SEQ ID NO:26, at least 93% identical to SEQ ID NO:26, at least 94% identical to SEQ ID NO:26, at least 95% identical to SEQ ID NO:26, at least 96% identical to SEQ ID NO:26, at least 97% identical to SEQ ID NO:26, at least 98% identical to SEQ ID NO:26, at least 99% identical to SEQ ID NO:26, and preferably is the amino acid sequence according to SEQ ID NO:26.

In yet another specific aspect, the at least one exogenous antigen encoding sequence as herein described and claimed is a phosphoprotein ("P") encoding sequence and the phosphoprotein ("P") encoding sequence comprises a nucleic acid sequence which is at least 70% identical to SEQ ID NO:27, at least 75% identical to SEQ ID NO:27, at least 80% identical to SEQ ID NO:27, at least 85% identical to SEQ ID NO:27, at least 90% identical to SEQ ID NO:27, at least 91% identical to SEQ ID NO:27, at least 92% identical to SEQ ID NO:27, at least 93% identical to SEQ ID NO:27, at least 94% identical to SEQ ID NO:27, at least 95% identical to SEQ ID NO:27, at least 96% identical to SEQ ID NO:27, at least 97% identical to SEQ ID NO:27, at least 98% identical to SEQ ID NO:27, at least 99% identical to SEQ ID NO:27, and preferably is selected from the group consisting of: SEQ ID NO:27.

In yet another specific aspect, the at least one exogenous antigen encoding sequence as herein described and claimed is a phosphoprotein ("P") encoding sequence and the phosphoprotein ("P") encoding sequence comprises a nucleic acid sequence encoding a polypeptide having an amino acid sequence which is at least 70% identical to SEQ ID NO:28, at least 75% identical to SEQ ID NO:28, at least 80% identical to SEQ ID NO:28, at least 85% identical to SEQ ID NO:28, at least 90% identical to SEQ ID NO:28, at least 91% identical to SEQ ID NO:28, at least 92% identical to SEQ ID NO:28, at least 93% identical to SEQ ID NO:28, at least 94% identical to SEQ ID NO:28, at least 95% identical to SEQ ID NO:28, at least 96% identical to SEQ ID NO:28, at least 97% identical to SEQ ID NO:28, at least 98% identical to SEQ ID NO:28, at least 99% identical to SEQ ID NO:28, and preferably is the amino acid sequence according to SEQ ID NO:28.

In yet another specific aspect, the at least one exogenous antigen encoding sequence as herein described and claimed is a RNA-dependent RNA polymerase protein ("L") encoding sequence and the RNA-dependent RNA polymerase protein ("L") encoding sequence comprises a nucleic acid sequence which is at least 70% identical to SEQ ID NO:29, at least 75% identical to SEQ ID NO:29, at least 80% identical to SEQ ID NO:29, at least 85% identical to SEQ ID NO:29, at least 90% identical to SEQ ID NO:29, at least 91% identical to SEQ ID NO:29, at least 92% identical to SEQ ID NO:29, at least 93% identical to SEQ ID NO:29, at least 94% identical to SEQ ID NO:29, at least 95% identical to SEQ ID NO:29, at least 96% identical to SEQ ID NO:29, at least 97% identical to SEQ ID NO:29, at least 98% identical to SEQ ID NO:29, at least 99% identical to SEQ ID NO:29, and preferably is selected from the group consisting of: SEQ ID NO:29.

In yet another specific aspect, the at least one exogenous antigen encoding sequence as herein described and claimed is a RNA-dependent RNA polymerase protein ("L") encoding sequence and the RNA-dependent RNA polymerase protein ("L") encoding sequence comprises a nucleic acid sequence encoding a polypeptide having an amino acid sequence which is at least 70% identical to SEQ ID NO:30, at least 75% identical to SEQ ID NO:30, at least 80% identical to SEQ ID NO:30, at least 85% identical to SEQ ID NO:30, at least 90% identical to SEQ ID NO:30, at least 91% identical to SEQ ID NO:30, at least 92% identical to SEQ ID NO:30, at least 93% identical to SEQ ID NO:30, at least 94% identical to SEQ ID NO:30, at least 95% identical to SEQ ID NO:30, at least 96% identical to SEQ ID NO:30, at least 97% identical to SEQ ID NO:30, at least 98% identical to SEQ ID NO:30, at least 99% identical to SEQ ID NO:30, and preferably is the amino acid sequence according to SEQ ID NO:30.

In yet another specific aspect, the at least one exogenous antigen encoding sequence as herein described and claimed is a hemagglutinin protein ("H") encoding sequence and the hemagglutinin protein ("H") encoding sequence comprises a nucleic acid sequence which is at least 70% identical to SEQ ID NO:31, at least 75% identical to SEQ ID NO:31, at least 80% identical to SEQ ID NO:31, at least 85% identical to SEQ ID NO:31, at least 90% identical to SEQ ID NO:31, at least 91% identical to SEQ ID NO:31, at least 92% identical to SEQ ID NO:31, at least 93% identical to SEQ ID NO:31, at least 94% identical to SEQ ID NO:31, at least 95% identical to SEQ ID NO:31, at least 96% identical to SEQ ID NO:31, at least 97% identical to SEQ ID NO:31, at least 98% identical to SEQ ID NO:31, at least 99% identical to SEQ ID NO:31, and preferably is selected from the group consisting of: SEQ ID NO:31, SEQ ID NO:32.

In yet another specific aspect, the at least one exogenous antigen encoding sequence as herein described and claimed is a hemagglutinin protein ("H") encoding sequence and the hemagglutinin protein ("H") encoding sequence comprises a nucleic acid sequence encoding a polypeptide having an amino acid sequence which is at least 70% identical to SEQ ID NO:33, at least 75% identical to SEQ ID NO:33, at least 80% identical to SEQ ID NO:33, at least 85% identical to SEQ ID NO:33, at least 90% identical to SEQ ID NO:33, at least 91% identical to SEQ ID NO:33, at least 92% identical to SEQ ID NO:33, at least 93% identical to SEQ ID NO:33, at least 94% identical to SEQ ID NO:33, at least 95% identical to SEQ ID NO:33, at least 96% identical to SEQ ID NO:33, at least 97% identical to SEQ ID NO:33, at least 98% identical to SEQ ID NO:33, at least 99% identical to SEQ ID NO:33, and preferably is the amino acid sequence according to SEQ ID NO:33.

In yet another specific aspect, the at least one exogenous antigen encoding sequence as herein described and claimed is a matrix protein ("M") encoding sequence and the matrix protein ("M") encoding sequence comprises a nucleic acid sequence which is at least 70% identical to SEQ ID NO:34, at least 75% identical to SEQ ID NO:34, at least 80% identical to SEQ ID NO:34, at least 85% identical to SEQ ID NO:34, at least 90% identical to SEQ ID NO:34, at least 91% identical to SEQ ID NO:34, at least 92% identical to SEQ ID NO:34, at least 93% identical to SEQ ID NO:34, at least 94% identical to SEQ ID NO:34, at least 95% identical to SEQ ID NO:34, at least 96% identical to SEQ ID NO:34, at least 97% identical to SEQ ID NO:34, at least 98% identical to SEQ ID NO:34, at least 99% identical to SEQ ID NO:34, and preferably is selected from the group consisting of: SEQ ID NO:34, SEQ ID NO:35.

In yet another specific aspect, the at least one exogenous antigen encoding sequence as herein described and claimed is a matrix protein ("M") encoding sequence and the matrix protein ("M") encoding sequence comprises a nucleic acid sequence encoding a polypeptide having an amino acid sequence which is at least 70% identical to SEQ ID NO:36, at least 75% identical to SEQ ID NO:36, at least 80% identical to SEQ ID NO:36, at least 85% identical to SEQ ID NO:36, at least 90% identical to SEQ ID NO:36, at least 91% identical to SEQ ID NO:36, at least 92% identical to SEQ ID NO:36, at least 93% identical to SEQ ID NO:36, at least 94% identical to SEQ ID NO:36, at least 95% identical to SEQ ID NO:36, at least 96% identical to SEQ ID NO:36, at least 97% identical to SEQ ID NO:36, at least 98% identical to SEQ ID NO:36, at least 99% identical to SEQ ID NO:36, and preferably is the amino acid sequence according to SEQ ID NO:36.

In yet another specific aspect, the at least one exogenous antigen encoding sequence as herein described and claimed is a fusion protein ("F") encoding sequence and the fusion protein ("F") encoding sequence comprises a nucleic acid sequence which is at least 70% identical to SEQ ID NO:37, at least 75% identical to SEQ ID NO:37, at least 80% identical to SEQ ID NO:37, at least 85% identical to SEQ ID NO:37, at least 90% identical to SEQ ID NO:37, at least 91% identical to SEQ ID NO:37, at least 92% identical to SEQ ID NO:37, at least 93% identical to SEQ ID NO:37, at least 94% identical to SEQ ID NO:37, at least 95% identical to SEQ ID NO:37, at least 96% identical to SEQ ID NO:37, at least 97% identical to SEQ ID NO:37, at least 98% identical to SEQ ID NO:37, at least 99% identical to SEQ ID NO:37, and preferably is selected from the group consisting of: SEQ ID NO:37.

In yet another specific aspect, the at least one exogenous antigen encoding sequence as herein described and claimed is a fusion protein ("F") encoding sequence and the fusion protein ("F") encoding sequence comprises a nucleic acid sequence encoding a polypeptide having an amino acid sequence which is at least 70% identical to SEQ ID NO:38, at least 75% identical to SEQ ID NO:38, at least 80% identical to SEQ ID NO:38, at least 85% identical to SEQ ID NO:38, at least 90% identical to SEQ ID NO:38, at least 91% identical to SEQ ID NO:38, at least 92% identical to SEQ ID NO:38, at least 93% identical to SEQ ID NO:38, at least 94% identical to SEQ ID NO:38, at least 95% identical to SEQ ID NO:38, at least 96% identical to SEQ ID NO:38, at least 97% identical to SEQ ID NO:38, at least 98% identical to SEQ ID NO:38, at least 99% identical to SEQ ID NO:38, and preferably is the amino acid sequence according to SEQ ID NO:38.

In yet another specific aspect, the at least one exogenous antigen encoding sequence as herein described and claimed is a nucleocapsid protein ("N") encoding sequence and the nucleocapsid protein ("N") encoding sequence comprises a nucleic acid sequence which is at least 70% identical to SEQ ID NO:39, at least 75% identical to SEQ ID NO:39, at least 80% identical to SEQ ID NO:39, at least 85% identical to SEQ ID NO:39, at least 90% identical to SEQ ID NO:39, at least 91% identical to SEQ ID NO:39, at least 92% identical to SEQ ID NO:39, at least 93% identical to SEQ ID NO:39, at least 94% identical to SEQ ID NO:39, at least 95% identical to SEQ ID NO:39, at least 96% identical to SEQ ID NO:39, at least 97% identical to SEQ ID NO:39, at least 98% identical to SEQ ID NO:39, at least 99% identical to SEQ ID NO:39, and preferably is selected from the group consisting of: SEQ ID NO:39.

In yet another specific aspect, the at least one exogenous antigen encoding sequence as herein described and claimed is a nucleocapsid protein ("N") encoding sequence and the nucleocapsid protein ("N") encoding sequence comprises a nucleic acid sequence encoding a polypeptide having an amino acid sequence which is at least 70% identical to SEQ ID NO:40, at least 75% identical to SEQ ID NO:40, at least 80% identical to SEQ ID NO:40, at least 85% identical to SEQ ID NO:40, at least 90% identical to SEQ ID NO:40, at least 91% identical to SEQ ID NO:40, at least 92% identical to SEQ ID NO:40, at least 93% identical to SEQ ID NO:40, at least 94% identical to SEQ ID NO:40, at least 95% identical to SEQ ID NO:40, at least 96% identical to SEQ ID NO:40, at least 97% identical to SEQ ID NO:40, at least 98% identical to SEQ ID NO:40, at least 99% identical to SEQ ID NO:40, and preferably is the amino acid sequence according to SEQ ID NO:40.

In yet another specific aspect, the at least one exogenous antigen encoding sequence as herein described and claimed is a phosphoprotein ("P") encoding sequence and the phosphoprotein ("P") encoding sequence comprises a nucleic acid sequence which is at least 70% identical to SEQ ID NO:41, at least 75% identical to SEQ ID NO:41, at least 80% identical to SEQ ID NO:41, at least 85% identical to SEQ ID NO:41, at least 90% identical to SEQ ID NO:41, at least 91% identical to SEQ ID NO:41, at least 92% identical to SEQ ID NO:41, at least 93% identical to SEQ ID NO:41, at least 94% identical to SEQ ID NO:41, at least 95% identical to SEQ ID NO:41, at least 96% identical to SEQ ID NO:41, at least 97% identical to SEQ ID NO:41, at least 98% identical to SEQ ID NO:41, at least 99% identical to SEQ ID NO:41, and preferably is selected from the group consisting of: SEQ ID NO:41.

In yet another specific aspect, the at least one exogenous antigen encoding sequence as herein described and claimed is a phosphoprotein ("P") encoding sequence and the phosphoprotein ("P") encoding sequence comprises a nucleic acid sequence encoding a polypeptide having an amino acid sequence which is at least 70% identical to SEQ ID NO:42, at least 75% identical to SEQ ID NO:42, at least 80% identical to SEQ ID NO:42, at least 85% identical to SEQ ID NO:42, at least 90% identical to SEQ ID NO:42, at least 91% identical to SEQ ID NO:42, at least 92% identical to SEQ ID NO:42, at least 93% identical to SEQ ID NO:42, at least 94% identical to SEQ ID NO:42, at least 95% identical to SEQ ID NO:42, at least 96% identical to SEQ ID NO:42, at least 97% identical to SEQ ID NO:42, at least 98% identical to SEQ ID NO:42, at least 99% identical to SEQ ID NO:42, and preferably is the amino acid sequence according to SEQ ID NO:42.

In yet another specific aspect, the at least one exogenous antigen encoding sequence as herein described and claimed is a RNA-dependent RNA polymerase protein ("L") encoding sequence and the RNA-dependent RNA polymerase protein ("L") encoding sequence comprises a nucleic acid sequence which is at least 70% identical to SEQ ID NO:43, at least 75% identical to SEQ ID NO:43, at least 80% identical to SEQ ID NO:43, at least 85% identical to SEQ ID NO:43, at least 90% identical to SEQ ID NO:43, at least 91% identical to SEQ ID NO:43, at least 92% identical to SEQ ID NO:43, at least 93% identical to SEQ ID NO:43, at least 94% identical to SEQ ID NO:43, at least 95% identical to SEQ ID NO:43, at least 96% identical to SEQ ID NO:43, at least 97% identical to SEQ ID NO:43, at least 98% identical to SEQ ID NO:43, at least 99% identical to SEQ ID NO:43, and preferably is selected from the group consisting of: SEQ ID NO:43.

In yet another specific aspect, the at least one exogenous antigen encoding sequence as herein described and claimed is a RNA-dependent RNA polymerase protein ("L") encoding sequence and the RNA-dependent RNA polymerase protein ("L") encoding sequence comprises a nucleic acid sequence encoding a polypeptide having an amino acid sequence which is at least 70% identical to SEQ ID NO:44, at least 75% identical to SEQ ID NO:44, at least 80% identical to SEQ ID NO:44, at least 85% identical to SEQ ID NO:44, at least 90% identical to SEQ ID NO:44, at least 91% identical to SEQ ID NO:44, at least 92% identical to SEQ ID NO:44, at least 93% identical to SEQ ID NO:44, at least 94% identical to SEQ ID NO:44, at least 95% identical to SEQ ID NO:44, at least 96% identical to SEQ ID NO:44, at least 97% identical to SEQ ID NO:44, at least 98% identical to SEQ ID NO:44, at least 99% identical to SEQ ID NO:44, and preferably is the amino acid sequence according to SEQ ID NO:44.

In yet another specific aspect, the viral vector as herein described and claimed comprises two or more exogenous antigen encoding sequences, preferably a hemagglutinin protein ("H") encoding sequence and a matrix protein ("M") encoding sequence, or a hemagglutinin protein ("H") encoding sequence and a fusion protein ("F") encoding sequence, or a matrix protein ("M") encoding sequence and a fusion protein ("F") encoding sequence, or a hemagglutinin protein ("H") encoding sequence and a matrix protein ("M") encoding sequence and a fusion protein ("F") encoding sequence.

In yet another specific aspect, the viral vector as herein described and claimed comprises two or more exogenous antigen encoding sequences, preferably the same two exogenous antigen coding sequences (i.e. H+H, F+F, M+M, P+P, L+L, N+N), but from two different strains, such as one exogenous antigen coding sequence from a feline paramyxovirus type 2 (FPaV-2) strain, more preferably the "Gordon strain" or the "TV25 strain", and the other one exogenous antigen coding sequence from a feline morbillivirus strain, more preferably the "Lapön strain"—for instance, a hemagglutinin protein ("H") encoding sequence of one strain and a hemagglutinin protein ("H") encoding sequence of another strain. Preferably, the one strain of "the hemagglutinin protein ("H") encoding sequence of one strain" is a feline paramyxovirus type 2 (FPaV-2) strain, more preferably the "Gordon strain" or the "TV25 strain", and the another strain of the "hemagglutinin protein ("H") encoding sequence of another strain" is a feline morbillivirus strain, more preferably the "Lapön strain". Most preferably, the one strain of "the hemagglutinin protein ("H") encoding sequence of one strain" is a hemagglutinin protein ("H") encoding sequence and the hemagglutinin protein ("H") encoding sequence comprises a nucleic acid sequence which is at least 70% identical to SEQ ID NO:4 or 19, at least 75% identical to SEQ ID NO:4 or 19, at least 80% identical to SEQ ID NO:4 or 19, at least 85% identical to SEQ ID NO:4 or 19, at least 90% identical to SEQ ID NO:4 or 19, at least 91% identical to SEQ ID NO:4 or 19, at least 92% identical to SEQ ID NO:4 or 19, at least 93% identical to SEQ ID NO:4 or 19, at least 94% identical to SEQ ID NO:4 or 19, at least 95% identical to SEQ ID NO:4 or 19, at least 96% identical to SEQ ID NO:4 or 19, at least 97% identical to SEQ ID NO:4 or 19, at least 98% identical to SEQ ID NO:4 or 19, at least 99% identical to SEQ ID NO:4 or 19, and preferably is selected from the group consisting of: SEQ ID NO:4, SEQ ID NO:5, SEQ ID NO:19; and the another strain of the "hemagglutinin protein ("H") encoding sequence of another strain" is a hemagglutinin protein ("H") encoding sequence and the hemagglutinin protein ("H") encoding sequence comprises a nucleic acid sequence which is at least 70% identical to SEQ ID NO:31 or 94, at least 75% identical to SEQ ID NO:31 or 94, at least 80% identical to SEQ ID NO:31 or 94, at least 85% identical to SEQ ID NO:31 or 94, at least 90% identical to SEQ ID NO:31 or 94, at least 91% identical to SEQ ID NO:31 or 94, at least 92% identical to SEQ ID NO:31 or 94, at least 93% identical to SEQ ID NO:31 or 94, at least 94% identical to SEQ ID NO:31 or 94, at least 95% identical to SEQ ID NO:31 or 94, at least 96% identical to SEQ ID NO:31 or 94, at least 97% identical to SEQ ID NO:31 or 94, at least 98% identical to SEQ ID NO:31 or 94, at least 99% identical to SEQ ID NO:31 or 94, and preferably is selected from the group consisting of: SEQ ID NO:31, SEQ ID NO:32, SEQ ID NO:94.

In yet another specific aspect, the at least one exogenous antigen encoding sequence as herein described and claimed is inserted in at least one insertion locus, preferably in a non-essential region of the viral vector genome.

In yet another specific aspect, the at least one exogenous antigen encoding sequence as herein described and claimed is inserted in two or more insertion loci.

In yet another specific aspect, the insertion locus as herein described and claimed is insertion locus C3.

In yet another specific aspect, the viral vector as herein described and claimed comprises flanking sequences of the insertion locus C3, preferably according to SEQ ID NO:45 (C3 flanking region left arm) and SEQ ID NO:46 (C3 flanking region right arm).

In yet another specific aspect, the insertion locus as herein described and claimed is insertion locus C5.

In yet another specific aspect, the viral vector as herein described and claimed comprises flanking sequences of the insertion locus C5, preferably according to SEQ ID NO:47 (C5 flanking region left arm) and SEQ ID NO:48 (C5 flanking region right arm).

In yet another specific aspect, the insertion locus as herein described and claimed is insertion locus C6.

In yet another specific aspect, the at least one exogenous antigen encoding sequence as herein described and claimed is operably linked to at least one promoter sequence, preferably at least one weak promoter sequence.

In yet another specific aspect, the promoter sequence as herein described and claimed is H6 vaccinia promoter.

In yet another specific aspect, the promoter sequence as herein described and claimed is I3L vaccinia promoter.

In yet another specific aspect, the promoter sequence as herein described and claimed is 42 k (long) poxviral promoter.

In yet another specific aspect, the promoter sequence as herein described and claimed is 7.5 k vaccinia promoter.

In yet another specific aspect, the promoter sequence as herein described and claimed is Pi vaccinia promoter.

In yet another specific aspect, the viral vector as herein described and claimed further comprises additional regulatory sequences, such as a termination signal and/or polyadenylation sequence.

In yet another specific aspect, the viral vector as herein described and claimed comprises a nucleic acid sequence which is at least 70%, 75%, 80%, 85%, 90%, 91%, 92%, 93%, 94%, 95%, 96%, 97%, 98%, 99% identical to the nucleic acid sequence selected from the group consisting of SEQ ID NO:49, SEQ ID NO:50, SEQ ID NO:51, and preferably is the nucleic acid sequence selected from the group consisting of: SEQ ID NO:49, SEQ ID NO:50, SEQ ID NO:51.

In yet another specific aspect, the feline as herein described and claimed is a cat, preferably a domestic cat.

The present invention concerns a mammalian host cell characterized in that it comprises the viral vector as herein described and claimed.

The present invention concerns the use of the viral vector as herein described and claimed or the mammalian host cell as herein described and claimed for the manufacture of an immunogenic composition or vaccine.

The present invention concerns an immunogenic composition comprising
(a) the viral vector as herein described and claimed or the mammalian host cell as herein described and claimed, and/or
(b) a polypeptide encoded by the viral vector as herein described and claimed, such as a virus, a modified live virus, a virus like particle (VLP) or the like, and
(c) optionally a pharmaceutical- or veterinary-acceptable carrier or excipient, preferably said carrier being suitable for oral, intradermal, intramuscular or intranasal application;
wherein preferably said immunogenic composition comprises a virus, such as an infectious virus.

The present invention concerns a vaccine or pharmaceutical composition comprising
(a) the viral vector as herein described and claimed or the mammalian host cell as herein described and claimed, and/or
(b) a polypeptide encoded by the viral vector as herein described and claimed, such as a virus, a modified live virus, a virus like particle (VLP) or the like, and
(c) a pharmaceutical- or veterinary-acceptable carrier or excipient, preferably said carrier being suitable for oral, intradermal, intramuscular or intranasal application,
(d) optionally said vaccine or pharmaceutical composition further comprising an adjuvant.

The present invention concerns a method for the preparation of an immunogenic composition or a vaccine for reducing the incidence and/or the severity of one or more clinical signs associated with or caused by an infection with at least one pathogenic paramyxovirus, comprising the following steps:
(a) infecting the mammalian host cell as herein described and claimed with the viral vector as herein described and claimed,
(b) cultivating the infected cells under suitable conditions,
(c) collecting infected cell cultures,
(d) optionally purifying the collected infected cell cultures of step (c),
(e) optionally mixing said collected infected cell culture with a pharmaceutically acceptable carrier.

The present invention concerns the immunogenic composition as herein described and claimed or the vaccine as herein described and claimed for use in a method of reducing or preventing the clinical signs or disease caused by an infection with at least one pathogenic paramyxovims or for use in a method of treating and/or preventing an infection with at least one pathogenic paramyxovirus, wherein preferably said feline is a cat, more preferably a domestic cat, wherein preferably the at least one pathogenic paramyxovirus is at least one feline paramyxovims, wherein preferably said clinical signs or disease caused by an infection with at least one pathogenic paramyxovirus or said infection with at least one pathogenic paramyxovirus are selected from the group consisting of: viremia, fever, virus shedding in the environment, infections of the urogenital system, infections of the urinary system, kidney disease, chronic kidney disease (CKD), inflammation of the renal tubules and renal interstitial tissue, idiopathic tubulointerstitial nephritis (TIN).

The present invention concerns a method of immunizing a feline, such as a cat, more preferably a domestic cat, against a clinical disease caused by at least one pathogenic paramyxovirus in said feline, said method comprising the step of administering to the feline the immunogenic composition as herein described and claimed or the vaccine as herein described and claimed, wherein said immunogenic composition or vaccine fails to cause clinical signs of infection but is capable of inducing an immune response that immunizes the feline against pathogenic forms of said at least one paramyxovirus, wherein preferably the at least one pathogenic paramyxovirus is at least one feline paramyxovirus, wherein preferably said clinical disease or said clinical signs of infection are selected from the group consisting of: viremia, fever, virus shedding in the environment, infections of the urogenital system, infections of the urinary system, kidney disease, chronic kidney disease (CKD), inflammation of the renal tubules and renal interstitial tissue, idiopathic tubulointerstitial nephritis (TIN).

The present invention concerns a kit for vaccinating a feline, preferably a cat, more preferably a domestic cat, against a disease associated with and/or reducing the incidence or the severity of one or more clinical signs associated with or caused by at least one pathogenic paramyxovirus in a feline comprising:
(a) a dispenser capable of administering a vaccine to said feline; and
(b) the immunogenic composition as herein described and claimed or the vaccine as herein described and claimed, and
(c) optionally an instruction leaflet;
wherein preferably the at least one pathogenic paramyxovirus is at least one feline paramyxovirus, wherein preferably said disease or said clinical signs are selected from the group consisting of: viremia, fever, virus shedding in the environment, infections of the urogenital system, infections of the urinary system, kidney disease, chronic kidney disease (CKD), inflammation of the renal tubules and renal interstitial tissue, idiopathic tubulointerstitial nephritis (TIN).

Definitions

Unless defined otherwise, all technical and scientific terms used herein have the same meaning as is commonly understood by one of skill in the art to which this invention belongs at the time of filing. The meaning and scope of terms should be clear; however, in the event of any latent ambiguity, definitions provided herein take precedent over any dictionary or extrinsic definition. Further, unless otherwise required by context, singular terms shall include pluralities and plural terms shall include the singular. Herein, the use of "or" means "and/or" unless stated otherwise. Furthermore, the use of the term "including", as well as other forms such as "includes" and "included" is not limiting. All patents and publications referred to herein are incorporated by reference herein.

The practice of the present invention will employ, unless otherwise indicated, conventional techniques of virology, molecular biology, microbiology, recombinant DNA technology, protein chemistry and immunology, which are within the skill of the art. Such techniques are explained fully in the literature. See, e.g., Sambrook, Fritsch & Maniatis, Molecular Cloning: A Laboratory Manual, Vols. I, II and III, Second Edition (1989); DNA Cloning, Vols. I and II (D. N. Glover ed. 1985); Oligonucleotide Synthesis (M. J. Gait ed. 1984); Nucleic Acid Hybridization (B. D. Hames & S. J. Higgins eds. 1984); Animal Cell Culture (R. K. Freshney ed. 1986); Immobilized Cells and Enzymes (IRL press, 1986); Perbal, B., A Practical Guide to Molecular Cloning (1984); the series, Methods In Enzymology (S. Colowick and N. Kaplan eds., Academic Press, Inc.); Protein purification methods—a practical approach (E. L. V. Harris and S. Angal, eds., IRL Press at Oxford University Press); and Handbook of Experimental Immunology, Vols. I-IV (D. M. Weir and C. C. Blackwell eds., 1986, Blackwell Scientific Publications).

Before describing the present invention in detail, it is to be understood that this invention is not limited to particular DNA, polypeptide sequences or process parameters as such may, of course, vary. It is also to be understood that the terminology used herein is for the purpose of describing particular embodiments of the invention only, and is not intended to be limiting. It must be noted that, as used in this specification and the appended claims, the singular forms "a", "an" and "the" include plural referents unless the content clearly dictates otherwise. Thus, for example, reference to "an antigen" includes a mixture of two or more antigens, reference to "an excipient" includes mixtures of two or more excipients, and the like.

The term "vector" as it is known in the art refers to a polynucleotide construct, typically a plasmid or a bacterial artificial chromosome, used to transmit genetic material to a host cell. Vectors can be, for example, bacteria, viruses, phages, bacterial artificial chromosomes, cosmids, or plasmids. A vector as used herein can be composed of or contain either DNA or RNA. In some embodiments, a vector is composed of DNA. In some embodiments a vector is an infectious virus. Such a viral vector contains a viral genome which was manipulated in a way that it carries a foreign gene which has no function in the replication of the viral vector neither in cell culture nor in a host animal According to specific aspects of the present disclosure a vector may be used for various aspects such as mere transmission of genetic material, for the transfection of host cells or organisms, for use as vaccines, e.g. DNA vaccines or for gene expression purposes. Gene expression is a term describing the biosynthesis of a protein in a cell as directed by a specific polynucleotide sequence called gene. In a specific aspect a vector may be an "expression vector", which is a vector that is capable of directing the expression of a protein encoded by one or more genes carried by the vector when it is present in the appropriate environment.

Vectors and methods for making and/or using vectors (or recombinants) for expression can be by or analogous to the methods disclosed in: U.S. Pat. Nos. 4,603,112, 4,769,330, 5,174,993, 5,505,941, 5,338,683, 5,494,807, 4,722,848, 5,942,235, 5,364,773, 5,762,938, 5,770,212, 5,942,235, 382, 425, PCT publications WO 94/16716, WO 96/39491, WO 95/30018; Paoletti, "Applications of pox virus vectors to vaccination: An update, "PNAS USA 93: 11349-11353, October 1996; Moss, "Genetically engineered poxviruses for recombinant gene expression, vaccination, and safety," PNAS USA 93: 11341-11348, October 1996; Smith et al., U.S. Pat. No. 4,745,051 (recombinant baculovirus); Richardson, C. D. (Editor), Methods in Molecular Biology 39, "Baculovirus Expression Protocols" (1995 Humana Press Inc.); Smith et al., "Production of Human Beta Interferon in Insect Cells Infected with a Baculovirus Expression Vector", Molecular and Cellular Biology, December, 1983, Vol. 3, No. 12, p. 2156-2165; Pennock et al., "Strong and Regulated Expression of *Escherichia coli* B-Galactosidase in Infect Cells with a Baculovirus vector, "Molecular and Cellular Biology March 1984, Vol. 4, No. 3, p. 406; EPA 0 370 573; U.S. application No. 920,197, filed Oct. 16, 1986; EP Patent publication No. 0 265 785; U.S. Pat. No. 4,769,331 (recombinant herpesvirus); Roizman, "The function of herpes simplex virus genes: A primer for genetic engineering of novel vectors," PNAS USA 93:11307-11312, October 1996; Andreansky et al., "The application of genetically engineered herpes simplex viruses to the treatment of experimental brain tumors," PNAS USA 93: 11313-11318, October 1996; Robertson et al., "Epstein-Barr virus vectors for gene delivery to B lymphocytes", PNAS USA 93: 11334-11340, October 1996; Frolov et al., "Alphavirus based expression vectors: Strategies and applications," PNAS USA 93: 11371-11377, October 1996; Kitson et al., J. Virol. 65, 3068-3075, 1991; U.S. Pat. Nos. 5,591,439, 5,552,143; WO 98/00166; allowed U.S. application Ser. Nos. 08/675, 556, and 08/675,566 both filed Jul. 3, 1996 (recombinant adenovirus); Grunhaus et al., 1992, "Adenovirus as cloning vectors," Seminars in Virology (Vol. 3) p. 237-52, 1993; Ballay et al. EMBO Journal, vol. 4, p. 3861-65, Graham, Tibtech 8, 85-87, April, 1990; Prevec et al., J. Gen Virol. 70, 42434; PCT WO 91/11525; Feigner et al. (1994), J. Biol. Chem. 269, 2550-2561, Science, 259: 1745-49, 1993; and McClements et al, "Immunization with DNA vaccines encoding glycoprotein D or glycoprotein B, alone or in combination, induces protective immunity in animal models of herpes simplex virus-2 disease", PNAS USA 93: 11414-11420, October 1996; and U.S. Pat. Nos. 5,591,639, 5,589, 466, and 5,580,859, as well as WO 90/11092, WO93/19183, WO94/21797, WO95/11307, WO95/20660; Tang et al., Nature, and Furth et al., Analytical Biochemistry, relating to DNA expression vectors, inter alia. See also WO 98/33510; Ju et al., Diabetologia, 41: 736-739, 1998 (lentiviral expression system); Sanford et al., U.S. Pat. No. 4,945,050; Fischbach et al. (Intracel); WO 90/01543; Robinson et al., Seminars in Immunology vol. 9, pp. 271-283 (1997), (DNA vector systems); Szoka et al., U.S. Pat. No. 4,394,448 (method of inserting DNA into living cells); McCormick et al., U.S. Pat. No. 5,677,178 (use of cytopathic viruses); and U.S. Pat. No. 5,928,913 (vectors for gene delivery); as well as other documents cited herein.

The term "viral vector" describes a genetically modified virus which was manipulated by recombinant DNA technique in a way so that its entry into a host cell results in a specific biological activity, e.g. the expression of a transgene carried by the vector. In a specific aspect the transgene is an antigen. A viral vector may or may not be replication competent in the target cell, tissue, or organism.

Generation of a viral vector can be accomplished using any suitable genetic engineering techniques well known in the art, including, without limitation, the standard techniques of restriction endonuclease digestion, ligation, transformation, plasmid purification, DNA sequencing, transfection in cell cultures, for example as described in Sambrook et al. (Molecular Cloning: A Laboratory Manual Cold Spring Harbor Laboratory Press, N.Y. (1989)) or K. Maramorosch and H. Koprowski (Methods in Virology Volume VIII, Academic Press Inc. London, UK (2014)).

A viral vector can incorporate sequences from the genome of any known organism. The sequences can be incorporated in their native form or can be modified in any way to obtain a desired activity. For example, the sequences can comprise insertions, deletions or substitutions.

A viral vector can include coding regions for two or more proteins of interest. For example, the viral vector can include the coding region for a first protein of interest and the coding region for a second protein of interest. The first protein of interest and the second protein of interest can be the same or different. In some embodiments, the viral vector can include the coding region(s) for a third or a fourth protein of interest. The third and the fourth protein of interest can be the same or different. The total length of the two or more proteins of interest encoded by one viral vector can vary. For example, the total length of the two or more proteins can be at least about 200 amino acids. At least about 250 amino acids, at least about 300 amino acids, at least about 350 amino acids, at least about 400 amino acids, at least about 450 amino acids, at least about 500 amino acids, at least about 550 amino acids, at least about 600 amino acids, at least about 650 amino acids, at least about 700 amino acids, at least about 750 amino acids, at least about 800 amino acids, or longer.

Preferred viral vectors include avipox virus viral vector, canine morbillivirus viral vector, herpes vims viral vector and varicella vims viral vector.

According to specific aspects of the present invention, the term "viral vector" or alternatively "viral construct" refers to a recombinant viral construct derived from a virus, which is selected from avipox vims viral vector, canine morbillivirus viral vector, herpes virus viral vector and varicella virus viral vector. Preferred viral vectors include avipox virus viral vectors, such as ALVAC and TROVAC.

According to specific aspects of the present invention, the term "avipox virus viral vector" or alternatively "avipox viral vector" refers to vector systems which are based on avipox viruses, which are naturally host-restricted poxviruses. Among such avipox viruses canarypox virus (CPV) has been engineered to express foreign, heterologous, extrinsic, exogenous gene products. Specifically, ALVAC is an engineered poxvirus vector derived from canarypox virus (U.S. Pat. No. 5,756,103, the disclosure of which is incorporated herein by reference). ALVAC is an attenuated canarypox virus-based vector that was a plaque-cloned derivative of the human canarypox vaccine, Kanapox This avipox vector is restricted to avian species for productive replication and does not productively replicate in non-avian hosts, a characteristic thought to improve its safety profile. On human cell cultures, canarypox virus replication is aborted early in the viral replication cycle prior to viral DNA synthesis. Nevertheless, when engineered to express extrinsic immunogens, authentic expression and processing is observed in vitro in mammalian cells and inoculation into numerous mammalian species induces antibody and cellular immune responses to extrinsic immunogen and provides protection against challenge with the cognate pathogen. ALVAC was deposited under the terms of the Budapest Treaty with the American Type Culture Collection (ATCC) under accession number VR-2547 (U.S. Pat. No. 5,756,103, the disclosure of which is incorporated herein by reference). ALVAC ATCC VR-2547 deposit-derived ALVAC vectors according to the present invention comprise vCP3025 and vCP3029 which include C3 and C5 insertion loci as the parental deposited ALVAC ATCC VR-2547 vector. TROVAC refers to an attenuated fowlpox viral vector that was a plaque-cloned isolate derived from FP1-vaccine strain of fowlpox virus that is licensed for vaccination of 1-day-old chicks (U.S. Pat. No. 5,766,599, the disclosure of which is incorporated herein by reference). The parental virus strain Duvette was obtained in France as a fowlpox scab from a chicken. The virus was attenuated by approximately 50 serial passages in chicken embryonated eggs followed by 25 passages on chicken embryo fibroblast cells. The vims was subjected to four successive plaque purifications. One plaque isolate was further amplified in primary CEF cells and a stock virus, designated as TROVAC, established. TROVAC was deposited under the terms of the Budapest Treaty with the American Type Culture Collection (ATCC) under accession number VR-2553 (U.S. Pat. No. 5,766,599, the disclosure of which is incorporated herein by reference).

The terms "viral vector" and "viral construct" can be used interchangeably.

The term "construct," as used herein, refers to a recombinant nucleic acid such as a plasmid, a BAC, or a recombinant virus that has been artificially generated.

The term "plasmid" refers to cytoplasmic DNA that replicates independently of the bacterial chromosome within a bacterial host cell. In a specific aspect of the present invention the term "plasmid" and/or "transfer plasmid" refers to an element of recombinant DNA technology useful for construction of e.g. an expression cassette for insertion into a viral vector. In another specific aspect the term "plasmid" may be used to specify a plasmid useful for DNA vaccination purposes.

As used herein, the terms "nucleic acid" and "polynucleotide" are interchangeable and refer to any nucleic acid.

The term "nucleic acid", "nucleic acid sequence", "nucleotide sequence", "polynucleotide", "polynucleotide sequence", "RNA sequence", cDNA sequences or "DNA sequence" as used herein refers to an oligonucleotide, nucleotide or polynucleotide and fragments and portions thereof and to DNA or RNA of genomic or synthetic origin, which may be single or double stranded and represent the sense or antisense strand. The sequence may be a non-coding sequence, a coding sequence or a mixture of both. The nucleic acid sequences of the present invention can be prepared using standard techniques well known to one of skill in the art.

The terms "nucleic acid" and "polynucleotide" also specifically include nucleic acids composed of bases other than the five biologically occurring bases (adenine, guanine, thymine, cytosine and uracil).

The terms "regulatory nucleic acid", "regulatory element" and "expression control element" are used interchangeably and refer to nucleic acid molecules that can influence the expression of an operably linked coding sequence in a particular host organism. These terms are used broadly to and cover all elements that promote or regulate transcription, including promoters, promoter sequences, core elements required for basic interaction of RNA polymerase and transcription factors, upstream elements, enhancers, and response elements. Exemplary regulatory elements in prokaryotes include promoters, operator sequences and ribosome binding sites. Regulatory elements that are used in eukaryotic cells can include, without limitation, transcriptional and translational control sequences, such as promoters, enhancers, splicing signals, polyadenylation signals, terminators, protein degradation signals, internal ribosome-entry sites (IRES), picornaviridal 2A sequences, and the like, that provide for and/or regulate expression of a coding sequence and/or production of an encoded polypeptide in a host cell.

An "internal ribosome entry site" or "IRES" describes a sequence which functionally promotes translation initiation independent from the gene 5' of the IRES and allows two cistrons (open reading frames) to be translated from a single transcript in an animal cell. The IRES provides an independent ribosome entry site for translation of the open reading frame immediately downstream of it. Unlike bacterial mRNA which can be polycistronic, i.e., encode several different polypeptides that are translated sequentially from the mRNAs, most mRNAs of animal cells are monocistronic and code for the synthesis of only one polypeptide. With a polycistronic transcript in a eukaryotic cell, translation would initiate from the 5' most translation initiation site, terminate at the first stop codon, and the transcript would be released from the ribosome, resulting in the translation of only the first encoded polypeptide in the mRNA. In a eukaryotic cell, a polycistronic transcript having an IRES operably linked to the second or subsequent open reading frame in the transcript allows the sequential translation of that downstream open reading frame to produce the two or more polypeptides encoded by the same transcript. The IRES can be of varying length and from various sources, e.g. Encephalomyocarditis virus (EMCV), picornaviruses, e.g. Foot-and-mouth disease virus, FMDV or Polio virus (PV), or Hepatitis C virus (HCV). Various IRES sequences and their use in vector construction have been described and are well known in the art. The downstream coding sequence is operably linked to the 3' end of the IRES at any distance that will not negatively affect the expression of the downstream gene. The optimum or permissible distance between the IRES and the start of the downstream gene can be readily determined by varying the distance and measuring expression as a function of the distance.

The term "2a" or "2a peptide" means short oligopeptide sequences, described as 2a and '2a-like', serve as linkers which are able to mediate a co-translational cleavage between proteins by a process defined as ribosomal-skipping. Such 2a and '2a-like' sequences (from Picornaviridae and other viruses or cellular sequences) can be used to concatenate multiple gene sequences into a single gene, ensuring their co-expression within the same cell (see Luke and Ryan, 2013).

As used herein, the term "promoter" or "promoter sequence" means a nucleotide sequence that permits binding of RNA polymerase and directs the transcription of a gene. Typically, a promoter is located in the 5' non-coding region of a gene, proximal to the transcriptional start site of the gene. Sequence elements within promoters that function in the initiation of transcription are often characterized by consensus nucleotide sequences. Examples of promoters include, but are not limited to, promoters from bacteria, yeast, plants, viruses, and animals such as mammals (including horses, pigs, cattle and humans), birds or insects. A promoter can be inducible, repressible, and/or constitutive. Inducible promoters initiate increased levels of transcription from DNA under their control in response to some change in culture conditions, such as a change in temperature (Ptashne, 2014). Examples of promoters well known to the person skilled in the art are for example SV40 large T, HCMV and MCMV immediate early gene 1, human elongation factor alpha promoter, baculovirus polyhedrin promoter.

As used herein in the context of the present invention the term promoter refers especially to a weak promoter (sequence), preferably H6 vaccinia promoter, I3L vaccinia promoter, 42 k (long) poxviral promoter, 7.5 k vaccinia promoter and/or Pi vaccinia promoter, or the complementary nucleotide sequence thereof, preferably the sequence identity is (at least) 72% over the entire length (or higher).

The term "enhancer" denotes a polynucleotide sequence which in the cis location acts on the activity of a promoter and thus stimulates the transcription of a gene or coding sequence functionally connected to this promoter. Unlike promoters the effect of enhancers is independent of position and orientation and they can therefore be positioned in front of or behind a transcription unit, within an intron or even within the coding region. The enhancer may be located both in the immediate vicinity of the transcription unit and at a considerable distance from the promoter. It is also possible to have a physical and functional overlap with the promoter. The skilled artisan will be aware of a number of enhancers from various sources (and deposited in databanks such as GenBank, e.g. SV40 enhancers, CMV enhancers, polyoma enhancers, adenovirus enhancers) which are available as independent elements or elements cloned within polynucleotide sequences (e.g. deposited at the ATCC or from commercial and individual sources). A number of promoter sequences also contain enhancer sequences such as the frequently used CMV promoter. The human CMV enhancer is one of the strongest enhancers identified hitherto. One example of an inducible enhancer is the metallothionein enhancer, which can be stimulated by glucocorticoids or heavy metals.

The term "complementary nucleotide sequences" describes one strand of the two paired strands of polynucleotides such as DNA or RNA. The nucleotide sequence of the complementary strand mirrors the nucleotide sequence of its paired strand so that for each adenosin it contains a thymin (or uracil for RNA), for each guanine a cytosin, and vice versa. The complementary nucleotide sequence of e.g. 5'-GCATAC-3' is 3'-CGTATG-5' or for RNA 3'-CGUAUG-5'.

The terms "gene", "gene of interest", as used herein have the same meaning and refer to a polynucleotide sequence of any length that encodes a product of interest. The gene may further comprise regulatory sequences preceding (5' non-coding or untranslated sequences) and following (3' non-coding or untranslated sequences) the coding sequence. The selected sequence can be full length or truncated, a fusion or tagged gene, and can be a cDNA, a genomic DNA, or a DNA fragment. It is generally understood that genomic DNA encoding for a polypeptide or RNA may include non-coding regions (i.e. introns) that are spliced from mature messenger RNA (mRNA) and are therefore not present in cDNA encoding for the same polypeptide or RNA. It can be the native sequence, i.e. naturally occurring form(s), or can be mutated, or comprising sequences derived from different sources or otherwise modified as desired. These modifications include codon optimizations to optimize codon usage in the selected host cell or tagging. Furthermore they can include removal or additions of cis-acting sites such as (cryptic) splice donor, acceptor sites and branch points, polyadenylation signals, TATA-boxes, chi-sites, ribosomal entry sites, repeat sequences, secondary structures (e.g. stem loops), binding sites for transcription factors or other regulatory factors, restriction enzyme sites etc. to give just a few, but not limiting examples. The selected sequence can encode a secreted, cytoplasmic, nuclear, membrane bound or cell surface polypeptide.

The term "nucleotide sequence of interest" as used herein is a more general term than gene of interest as it does not necessarily comprise a gene but may comprise elements or parts of a gene or other genetic information, e.g. on (origin of replication). A nucleotide sequence of interest may be any DNA or RNA sequence independently of whether it comprises a coding sequence or not.

"Open reading frame" or "ORF" refers to a length of nucleic acid sequence, either DNA or RNA that comprises a translation start signal or initiation codon, such as an ATG or AUG, and a termination codon and can be potentially translated into a polypeptide sequence.

The term "transcription" describes the biosynthesis of mRNA in a cell.

The term "expression" as used herein refers to transcription and/or translation of a nucleic acid sequence within a host cell. According to specific aspects of the present invention the term "expression" refers to transcription and/or translation of a heterologous and/or exogenous nucleic acid sequence within a host cell. The level of expression of a desired product in a host cell may be determined on the basis of either the amount of corresponding RNA or mRNA that is present in the cell, or the amount of the desired polypeptide encoded by the selected sequence. For example, mRNA transcribed from a selected sequence can be quantitated by Northern blot hybridization, ribonuclease RNA protection, in situ hybridization to cellular RNA or by RTqPCR (reverse transcription followed by quantitative PCR). Proteins expressed from a selected sequence can be quantitated by various methods, e.g. by ELISA, by Western blotting, by radioimmunoassays, by immunoprecipitation, by assaying for the biological activity of the protein, or by immunostaining of the protein followed by FACS analysis.

The term "expression cassette" or "transcription unit" or "expression unit" defines a region within a vector, construct or polynucleotide sequence that contains one or more genes to be transcribed, wherein the nucleotide sequences encoding the transcribed gene(s) as well as the polynucleotide sequences containing the regulatory elements contained within an expression cassette are operably linked to each other. They are transcribed from a promoter and transcription is terminated by at least one polyadenylation signal. In one specific aspect, they are transcribed from one single promoter. As a result, the different genes are at least transcriptionally linked. More than one protein or product can be transcribed and expressed from each transcription unit (multicistronic transcription unit). Each transcription unit will comprise the regulatory elements necessary for the transcription and translation of any of the selected sequences that are contained within the unit. And each transcription unit may contain the same or different regulatory elements. For example, each transcription unit may contain the same terminator, IRES element or introns may be used for the functional linking of the genes within a transcription unit. A vector or polynucleotide sequence may contain more than one transcription unit.

By the term "increased expression", "increased titer or productivity" or "improved expression or productivity" is meant the increase in expression, synthesis or secretion of a heterologous and/or exogenous sequence introduced into a host cell, for example of a gene coding for a therapeutic protein, by comparison with a suitable control, for example a protein encoded by a cDNA versus a protein encoded by an intron-containing gene. There is increased titer or productivity if a cell according to the invention is cultivated according to a method according to the invention described here, and if this cell has at least a 1.2-fold, a 1.5-fold, a two-fold, a three-fold, a four-fold or a five-fold increase in specific productivity or titer. There is also increased titer or productivity if a cell according to the invention is cultivated according to a method according to the invention described here, and if this cell has at least a 1.2-fold or at least a 1.5-fold or at least a two-fold or at least a three-fold increase in specific productivity or titer. There is also in particular increased titer or productivity if a cell according to the invention is cultivated according to a method according to the invention described here, and if this cell has at least a 1.2-fold to five-fold, preferably a 1.5-fold to five-fold, more preferably two-fold to five-fold, particularly preferably a three-fold to five-fold increase in specific productivity or titer. "Increased expression" may mean as well that more cells are actually expressing the gene/sequence of interest. For example increased expression may mean that the promoters of the present invention are active for a longer period of time during the viral replication cycle relative to other promoters.

An increased expression, titer or productivity may be obtained by using a heterologous viral vector according to the invention. This may be combined with other approaches such as a FACS-assisted selection of recombinant host cells which contain, as additional selectable marker, one or more fluorescent proteins (e.g. GFP) or a cell surface marker. Other methods of obtaining increased expression, and a combination of different methods may also be used, are based for example on the use of cis-active elements for manipulating the chromatin structure (e.g. LCR, UCOE, EASE, isolators, S/MARs, STAR elements), on the use of (artificial) transcription factors, treatment of the cells with natural or synthetic agents for up-regulating endogenous or heterologous and/or exogenous gene expression, improving the stability (half-life) of mRNA or the protein, improving the initiation of mRNA translation, increasing the gene dose by the use of episomal plasmids (based on the use of viral sequences as replication origins, e.g. SV40, polyoma, adenovirus, EBV or BPV), the use of amplification-promoting sequences or in vitro amplification systems based on DNA concatemers.

An assay to measure "increased expression" is LC-MS/MS-based protein measurements such as multiple reaction monitoring (MRM); antibody-based detection methods such as Western blot, dot blot, or Immunodiffusion, and flow cytometry; and measures of biological activity by hemagglutination assay.

"Promoter activity" is measured indirectly by quantification of mRNA transcribed under control of the respective promoter. mRNA is quantified by RTqPCR relative to an endogenous standard.

The term "virus load" is well known to the person skilled in that art. The term virus load is interchangeable used with the term "viral titer" herein. The virus load or virus titer is a measure of the severity of an active viral infection, and can be determined by methods known to the person skilled in the art. The determination can be based on the detection of viral proteins such as by antibody binding to the viral proteins and further detection or, alternatively, by detection of viral nucleic acids by amplification methods such as RT-PCR. Monitoring of virion associated viral RNA in plasma by nucleic acid amplification methods is a widely used parameter to assess the status and progression of retroviral disease, and to evaluate the effectiveness of prophylactic and therapeutic interventions. Exemplary, the vims load or vims titer can be calculated by estimating the live amount of virus in an involved body fluid such as a number of RNA copies per milliliter of blood plasma. Preferably, the term "virus load" or "virus titer" is a measure of infectious units per volume of a virus preparation. Viral titer is an endpoint in a biological procedure and is defined as the dilution at which a certain proportion of tests carried out in parallel show an effect (Reed and Muench, 1938). Specifically the tissue culture infectious dose fifty per milliliter (TCID50/ml) gives the dilution of a virus preparation at which 50% of a number of cell cultures inoculated in parallel with that dilution are infected.

"Transcription-regulatory elements" normally comprise a promoter upstream of the gene sequence to be expressed, transcription initiation and termination sites and a polyadenylation signal.

The term "transcription initiation site" refers to a nucleic acid in the construct corresponding to the first nucleic acid incorporated into the primary transcript, i.e. the mRNA precursor. The transcription initiation site may overlap with the promoter sequences.

The "termination signal" or "terminator" or "polyadenylation signal" or "polyA" or transcription termination site" or "transcription termination element" is a signal sequence which causes cleavage at a specific site at the 3' end of the eukaryotic mRNA and post-transcriptional incorporation of a sequence of about 100-200 adenine nucleotides (polyA tail) at the cleaved 3' end, and thus causes RNA polymerase to terminate transcription. The polyadenylation signal comprises the sequence AATAAA about 10-30 nucleotides upstream of the cleavage site and a sequence located downstream. Various polyadenylation elements are known such as tk polyA, SV40 late and early polyA, BGH polyA (described for example in U.S. Pat. No. 5,122,458) or hamster growth hormone polyA (WO2010/010107).

"Translation regulatory elements" comprise a translation initiation site (AUG), a stop codon and a polyA signal for each individual polypeptide to be expressed. An internal ribosome entry site (IRES) may be included in some constructs. In order to optimize expression it may be advisable to remove, add or alter 5'- and/or 3'-untranslated regions of the nucleic acid sequence to be expressed to eliminate any potentially extra inappropriate alternative translation initiation codons or other sequences that may interfere with or reduce expression, either at the level of transcription or translation. Consensus ribosome binding sites (Kozak sequence) can be inserted immediately upstream of the start codon to enhance translation and thus expression. Increased A/U contents around this ribosome binding site further a more efficient ribosome binding.

By definition, every polynucleotide sequence or every gene inserted in a host cell and the respective protein or RNA encoded thereby is referred to as "exogenous", "exogenous sequence", "exogenous gene", "exogenous coding sequence", "exogenous antigen encoding sequence" with respect to the host cell, when it comes from a different (virus) species. Accordingly, the feline paramyxovirus antigens of the present invention are exogenous in view of an avipox virus viral vector, such as ALVAC. As used herein in respect to a sequence or gene of interest such as an antigen the term "exogenous" or "exogenous antigen encoding sequence" means that said sequence or gene of interest, specifically said antigen is expressed out of its natural species context. Accordingly, the H antigen from FPaV-2 strain "Gordon" is one example of an exogenous antigen in respect to the avipox virus viral vector, such as ALVAC. Any feline paramyxovirus sequence or gene of interest such as a feline paramyxovirus antigen is therefore an exogenous sequence or gene of interest or antigen according to a specific aspect of the present invention.

By definition, every polynucleotide sequence or every gene inserted in a host cell and the respective protein or RNA encoded thereby is referred to as "heterologous, "heterologous sequence", "heterologous gene", "heterologous coding sequence", "transgene" or "heterologous protein" with respect to the host cell. This applies even if the sequence to be introduced or the gene to be introduced is identical to an endogenous sequence or an endogenous gene of the host cell. For example, an ALVAC promoter sequence introduced into an ALVAC viral vector at a different site or in modified form than in the ALVAC wild type virus is by definition a heterologous sequence. As used herein in respect to a sequence or gene of interest such as an antigen, the term "heterologous" means that said sequence or gene of interest, specifically said antigen, is expressed out of its natural subspecies context.

Accordingly, any feline paramyxovirus specific sequence or gene of interest such as an antigen, for example an H antigen from FPaV-2 "Gordon" strain, in respect to another (feline) paramyxovirus viral vector, is therefore a heterologous sequence or gene of interest or antigen according to a specific aspect of the present invention.

The term "non-naturally occurring" means any sequence or gene of interest such as an antigen, which is not occurring in this context naturally, such as a hybrid sequence or a sequence or gene of interest such as an antigen from a different species, or sequence or gene of interest such as an antigen, which is not a product of nature due to artificial mutation, insertion, deletion or the like.

The term "recombinant" is used interchangeably with the terms "non-naturally occurring", "heterologous" and "exogenous" throughout the specification of this present invention. Thus, a "recombinant" protein is a protein expressed from a either a heterologous or an exogenous polynucleotide sequence. The term recombinant as used with respect to a virus means a virus produced by artificial manipulation of the viral genome. A vims comprising a heterologous or an exogenous sequence such as an exogenous antigen encoding sequence is a recombinant virus. The term recombinant virus and the term non-naturally occurring vims are used interchangeably.

Thus, the term "heterologous vector" means a vector that comprises a heterologous or an exogenous polynucleotide sequence. The term "recombinant vector" means a vector that comprises a heterologous or a recombinant polynucleotide sequence.

As used herein, the term "operably linked" is used to describe the connection between regulatory elements and a gene or its coding region. Typically, gene expression is placed under the control of one or more regulatory elements, for example, without limitation, constitutive or inducible promoters, tissue-specific regulatory elements, and enhancers. A gene or coding region is said to be "operably linked to" or "operatively linked to" or "operably associated with" the regulatory elements, meaning that the gene or coding region is controlled or influenced by the regulatory element. For instance, a promoter is operably linked to a coding sequence if the promoter effects transcription or expression of the coding sequence.

Furthermore, within the scope of the present description the terms "functional linking", "functionally linked" or "operably linked" means that two or more nucleic acid sequences or sequence elements are positioned in a way that permits them to function in their intended manner. For example, a promoter/enhancer or terminator is functionally linked to a coding gene sequence if it is able to control or modulate the transcription of the linked gene sequence in the cis position. Generally, but not necessarily, the DNA sequences that are functionally linked are contiguous and, where necessary to join two polypeptide coding regions or in the case of a secretion signal peptide, contiguous and in reading frame. However, although an operably linked promoter is generally located upstream or an operably linked terminator is generally located downstream of the coding sequence, it is not necessarily contiguous with it. Enhancers do not have to be contiguous as long as they increase the transcription of the coding sequence. For this they can be located upstream or downstream of the coding sequence and even at some distance. A polyadenylation site is operably linked to a coding sequence if it is located at the 3' end of the coding sequence in a way that transcription proceeds through the coding sequence into the polyadenylation signal. Linking is accomplished by recombinant methods known in the art, e.g. by ligation at suitable restriction sites or blunt ends or by using fusion PCR methodology. Synthetic oligonucleotide linkers or adapters can be used in accord with conventional practice if suitable restriction sites are not present.

Accordingly, the term "functional fragment or derivative" of a promoter sequence means that the fragment or derivative still effects promoter activity. Functional assays of how to assess promoter activity are well known to one of ordinary skill in the art (Bustin 2000, Nolan et al. 2006). An exemplary embodiment of such a functional assay includes e.g. a promoter kinetics experiment. Cells infected with vector viruses carrying expression cassettes where a promoter or fragment thereof directs transcription of a reporter transgene are incubated for different times. Total RNA is prepared from samples collected at different times after infection. After destruction of contaminating DNA by DNAse I digestion, the RNA is reverse transcribed. One replicate sample is processed with addition of reverse transcriptase (RT), the second replicate is processed without addition of RT in order to demonstrate successful removal of contaminating DNA from the RNA preparation. The resulting cDNA is purified and used as template in a conventional PCR. Only the samples processed with the addition of RT shall produce a PCR product. These cDNAs can then be used for qPCR with primers for the reporter transgene and in parallel with primers for an essential gene of the viral vector (internal standard gene), the transcription of which provides an internal standard for the efficiency of infection and replication. qPCR values of the reporter are normalized between the different constructs and times after infection using the qPCR values of the internal standard gene. This allows an interpretation of promoter activities of different promoters and fragments thereof.

"Sequence homology", as used herein, refers to a method of determining the relatedness of two sequences. To determine sequence homology, two or more sequences are optimally aligned, and gaps are introduced if necessary. However, in contrast to "sequence identity", conservative amino acid substitutions are counted as a match when determining sequence homology. In other words, to obtain a polypeptide or polynucleotide having 95% sequence homology with a reference sequence, 85%, preferably 90%, 91%, 92%, 93%, 94%, even more preferably 95%, 96%, 97%, 98%, 99%, 99.9% of the amino acid residues or nucleotides in the reference sequence must match or comprise a conservative substitution with another amino acid or nucleotide, or a number of amino acids or nucleotides up to 15%, preferably up to 10%, 9%, 8%, 7%, 6%, even more preferably up to 5%, 4%, 3%, 2%, 1%, 0.1% of the total amino acid residues or nucleotides, not including conservative substitutions, in the reference sequence may be inserted into the reference sequence. Preferably the homolog sequence comprises at least a stretch of 50, even more preferred of 100, even more preferred of 250, even more preferred of 500 nucleotides.

"Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, 91%, 92%, 93%, 94%, even more preferably 95%, 96%, 97%, 98%, 99%, 99.9% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, 91%, 92%, 93%, 94%, even more preferably 95%, 96%, 97%, 98%, 99%, 99.9% identity relative to the reference nucleotide sequence, up to 15%, preferably 10%, 9%, 8%, 7%, 6%, even more preferably 5%, 4%, 3%, 2%, 1%, 0.1% of the nucleotides in the reference sequence may be deleted or substituted with another nucleotide, or a number of nucleotides up to 15%, preferably 10%, 9%, 8%, 7%, 6%, even more preferably 5%, 4%, 3%, 2%, 1%, 0.1% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, 91%, 92%, 93%, 94%, even more preferably 95%, 96%, 97%, 98%, 99% sequence identity to a reference amino acid sequence, it is intended that the given amino acid sequence of the polypeptide is identical to the reference sequence except that the given polypeptide sequence may include up to 15, preferably up to 10, 9, 8, 7, 6, even more preferably up to 5, 4, 3, 2, 1 amino acid alterations per each 100 amino acids of the reference amino acid sequence. In other words, to obtain a given polypeptide sequence having at least 85%, preferably 90%, 91%, 92%, 93%, 94%, even more preferably 95%, 96%, 97%, 98%, 99% sequence identity with a reference amino acid sequence, up to 15%, preferably up to 10%, 9%, 8%, 7%, even more preferably up to 5%, 4%, 3%, 2%, 1% of the amino acid residues in the reference sequence may be deleted or substituted with another amino acid, or a number of amino acids up to 15%, preferably up to 10%, 9%, 8%, 7%, even more preferably up to 5%, 4%, 3%, 2%, 1% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

The terms "sequence identity" or "percent identity" are used interchangeably herein. For the purpose of this invention, it is defined here that in order to determine the percent identity of two amino acid sequences or two nucleic acid sequences, the sequences are aligned for optimal comparison purposes (e.g., gaps can be introduced in the sequence of a first amino acid or nucleic acid for optimal alignment with a second amino or nucleic acid sequence). The amino acid or nucleotide residues at corresponding amino acid or nucleotide positions are then compared. When a position in the first sequence is occupied by the same amino acid or nucleotide residue as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100). Preferably, the two sequences are the same length.

A sequence comparison may be carried out over the entire lengths of the two sequences being compared or over fragment of the two sequences. Typically and preferred in the scope of the present invention, the comparison will be carried out over the full length of the two sequences being compared. However, sequence identity may be carried out over a region of, for example, twenty, fifty, one hundred or more contiguous amino acid residues.

As used herein, it is in particular understood that the term "having at least X % sequence identity with the nucleic acid/amino acid sequence according to SEQ ID NO:Y" (or, alternatively, the term "having at least X % sequence identity with the nucleic acid/amino acid sequence of/set forth in SEQ ID NO:Y") is equivalent to the term "having at least X % sequence identity with the nucleic acid/amino acid sequence according to SEQ ID NO:Y over the length of SEQ ID NO:Y" or to the term "having at least X % sequence identity with the nucleic acid/amino acid sequence according to SEQ ID NO:Y over the whole length of SEQ ID NO:Y", respectively.

The skilled person will be aware of the fact that several different computer programs are available to determine the homology between two sequences. For instance, a comparison of sequences and determination of percent identity between two sequences can be accomplished using a mathematical algorithm. In a specific aspect, the percent identity between two amino acid or nucleic acid sequences is determined using the Needleman and Wunsch (J. Mol. Biol. (48): 444-453 (1970)) algorithm which has been incorporated into the GAP program in the Accelrys GCG software package, using either a Blosum 62 matrix or a PAM250 matrix, and a gap weight of 16, 14, 12, 10, 8, 6, or 4 and a length weight of 1, 2, 3, 4, 5, or 6. The skilled person will appreciate that all these different parameters will yield slightly different results but that the overall percentage identity of two sequences is not significantly altered when using different algorithms.

The protein sequences or nucleic acid sequences of the present invention can further be used as a "query sequence" to perform a search against public databases to, for example, identify other family members or related sequences. Such searches can be performed using the BLASTN and BLASTP programs (version 2.0) of Altschul, et al. (1990) J. Mol. Biol. 215:403-10. BLAST protein searches can be performed with the BLASTP program, score=50, wordlength=3 to obtain amino acid sequences homologous to protein molecules of the invention. To obtain gapped alignments for comparison purposes, Gapped BLAST can be utilized as described in Altschul et al. (1997) Nucleic Acids Res. 25(17): 3389-3402. When utilizing BLAST and Gapped BLAST programs, the default parameters of the respective programs (e.g., BLASTP and BLASTN) can be used. See the homepage of the National Center for Biotechnology Information.

The term "feline" in the scope of the present invention refers to a member of the family of Felidae, particularly of the genera of *Felis* (which is preferred herein), Lynx, Panthera, Neofelis, Caracal, *Leopardus*, Puma, Acinonyx, Prionailurus, and Otocolobus. The *Felis* genus includes for example the species of *Felis silvestris*, e.g. *Felis silvestris silvestris* (European wildcat), feral cat, preferably *Felis silvestris catus* (also known as *Felis catus*, i.e. the domestic cat), *Felis chaus, Felis nigripes, Felis margarita*, and *Felis bieti*. The genus Panthera e.g. includes Tiger (Panthera tigris), Lion (Panthera leo), Jaguar (Panthera onca), Leopard (Panthera pardus), Snow leopard (Panthera uncial), and Liger. Other Felidae include but are not limited to Lynx lynx, *Lynx rufus, Acinonyx jubatus* (Cheetah), *Puma concolor* (Cougar), *Leopardus pardalis* (Ocelot). Preferably, the "feline" is a cat, most preferably a domestic cat.

An "immunogenic or immunological composition" refers to a composition of matter that comprises at least one antigen, or immunogenic portion thereof, that elicits an immunological response in the host of a cellular or antibody-mediated immune response to the composition. Preferably, the immunogenic composition induces an immune response and, more preferably, confers protective immunity against one or more of the clinical signs of a feline paramyxovirus infection. In case where the host displays a protective immunological response such that resistance to new infection will be enhanced and/or the clinical severity of the disease reduced, the immunogenic composition is described as a "vaccine".

The term "antigen" used herein is well understood in the art and includes substances which are immunogenic, i.e., immunogens, as well as substances which induce immunological unresponsiveness, or anergy, i.e., a lack of reactions by the body's defense mechanisms to foreign substances. As used herein, the term "antigen" is intended to mean full length proteins as well as peptide fragments thereof containing or comprising epitope. Further, the term "antigen encoding sequence" relates to sequences encoding an antigen. Preferably the antigen encoding sequence is a nucleic acid sequence such as a cDNA sequence. However, the term "nucleic acid sequence" has been defined elsewhere herein.

The term "at least one exogenous antigen encoding sequence" also encompasses more than one exogenous antigen encoding sequence. Thus, it has to be understood that the term "at least one exogenous antigen encoding sequence" encompasses two, three, four, five or six exogenous antigen encoding sequences. Accordingly, the term "at least two exogenous antigen encoding sequences" encompasses three, four, five or six exogenous antigen encoding sequences.

The term "different exogenous antigen encoding sequences" are sequences that differ in their sequence compared to each other.

An "immunogenic composition" as used herein can refer to a polypeptide or a protein, such as for example a viral surface protein that elicits an immunological response as described herein. The term "immunogenic fragment" or "immunogenic portion" refers to a fragment or truncated and/or substituted form of a protein or polypeptide that includes one or more epitopes and thus elicits the immunological response described herein. In general, such truncated and/or substituted forms, or fragments will comprise at least six contiguous amino acids from a full-length protein. Such fragments can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N. J. For example, linear epitopes may be determined by concurrently synthesizing large numbers of peptides on solid supports, the peptides corresponding to portions of the protein molecule, and reacting the peptides with antibodies while the peptides are still attached to the supports. Such techniques are known and described in the art, see e.g., U.S. Pat. No. 4,708,871; Geysen et al. (1984) Proc. Natl. Acad. Sci. USA 81:3998-4002; and Geysen et al. (1986) Molec. Immunol. 23:709-715. Similarly, conformational epitopes are readily identified by determining spatial conformation of amino acids such as by, e.g., x-ray crystallography and two-dimensional nuclear magnetic resonance. See Epitope Mapping Protocols, supra. Synthetic antigens are also included within the definition, for example, polyepitopes, flanking epitopes, and other recombinant or synthetically derived antigens. See, e.g., Bergmann et al. (1993) Eur. J. Immunol. 23:2777-2781; Bergmann et al. (1996), J. Immunol. 157:3242-3249; Suhrbier, A. (1997), Immunol. and Cell Biol. 75:402-408; and Gardner et al., (1998) 12th World AIDS Conference, Geneva, Switzerland, Jun. 28-Jul. 3, 1998. The teachings and content of which are all incorporated by reference herein.

The term "immunizing" relates to an active immunization by the administration of an immunogenic composition to a feline to be immunized, thereby causing an immunological response against the antigen included in such immunogenic composition.

The term "in need" or "of need", as used herein means that the administration/treatment is associated with the boosting or improvement in health or clinical signs or any other positive medicinal effect on health of the animals which receive the immunogenic composition in accordance with the present invention.

The term "vaccine" as used herein refers to a pharmaceutical composition comprising at least one immunologically active component that induces an immunological response in an animal and possibly but not necessarily one or more additional components that enhance the immunological activity of the active component. A vaccine may additionally comprise further components typical to pharmaceutical compositions. By way of distinction the immunologically active component of a vaccine may comprise complete virus particles in either their original form or as attenuated particles in a so called modified live vaccine (MLV) or particles inactivated by appropriate methods in a so called killed vaccine (KV). In another form the immunologically active component of a vaccine may comprise appropriate elements of the organisms (subunit vaccines) whereby these elements are generated either by destroying the whole particle or the growth cultures containing such particles and optionally subsequent purification steps yielding the desired structure(s), or by synthetic processes including an appropriate manipulation by use of a suitable system based on, for example, bacteria, insects, mammalian, or other species plus optionally subsequent isolation and purification procedures, or by induction of the synthetic processes in the animal needing a vaccine by direct incorporation of genetic material using suitable pharmaceutical compositions (polynucleotide vaccination). A vaccine may comprise one or simultaneously more than one of the elements described above. As used within specific aspects of the present invention "vaccine" refers to a live vaccine or live virus, also called recombinant vaccine. In another specific aspect of the present invention "vaccine" refers to an inactivated or killed virus including virus like particles (VLPs). Thus, a vaccine may be a subunit vaccine or a killed (KV) or inactivated vaccine.

The term "DNA vaccination" or "polynucleotide vaccination" means direct inoculation of genetic material using suitable pharmaceutical compositions.

Various physical and chemical methods of inactivation are known in the art. The term "inactivated" refers to a previously virulent or non-virulent virus that has been irradiated (ultraviolet (UV), X-ray, electron beam or gamma radiation), heated, or chemically treated to inactivate or kill such virus while retaining its immunogenicity. Suitable inactivating agents include beta-propiolactone, binary or beta- or acetyl-ethyleneimine, gluteraldehyde, ozone, and formalin (formaldehyde).

For inactivation by formalin or formaldehyde, formaldehyde is typically mixed with water and methyl alcohol to create formalin. The addition of methyl alcohol prevents degradation or cross reaction during the in activation process. One embodiment uses about 0.1 to 1% of a 37% solution of formaldehyde to inactivate the virus. It is critical to adjust the amount of formalin to ensure that the material is inactivated but not so much that side effects from a high dosage occur.

More particularly, the term "inactivated" in the context of a virus means that the virus is incapable of replication in vivo or in vitro. For example, the term "inactivated" may refer to a virus that has been propagated in vitro, and has then been inactivated using chemical or physical means so that it is no longer capable of replicating.

As used herein, the terms "inactivated", "killed" or "KV" are used interchangeably.

The term "live vaccine" refers to a vaccine comprising either a living organism or a replication competent virus or viral vector.

A "pharmaceutical composition" essentially consists of one or more ingredients capable of modifying physiological, e.g., immunological functions, of the organism it is administered to, or of organisms living in or on the organism. The term includes, but is not restricted to, antibiotics or antiparasitics, as well as other constituents commonly used to achieve certain other objectives such as, but not limited to, processing traits, sterility, stability, feasibility to administer the composition via enteral or parenteral routes such as oral, intranasal, intravenous, intramuscular, subcutaneous, intradermal, or other suitable route, tolerance after administration, or controlled release properties. One non-limiting example of such a pharmaceutical composition, solely given for demonstration purposes, could be prepared as follows: cell culture supernatant of an infected cell culture is mixed with a stabilizer (e.g., spermidine and/or bovine serum albumin (BSA) and the mixture is subsequently lyophilized or dehydrated by other methods. Prior to vaccination, the mixture is then rehydrated in aqueous (e.g., saline, phosphate buffered saline (PBS) or non-aqueous solutions (e.g., oil emulsion, aluminum-based adjuvant).

As used herein, "pharmaceutical- or veterinary-acceptable carrier" includes any and all solvents, dispersion media, coatings, adjuvants, stabilizing agents, diluents, preservatives, antibacterial and antifungal agents, isotonic agents, adsorption delaying agents, and the like. In some specific aspects, and especially those that include lyophilized immunogenic compositions, stabilizing agents for use in the present invention include stabilizers for lyophilization or freeze-drying.

In some embodiments, the immunogenic composition of the present invention contains an adjuvant. "Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.), John Wiley and Sons, NY, pp 51-94 (1995) and Todd et al., Vaccine 15:564-570 (1997). Exemplary adjuvants are the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name CARBOPOL®; (BF Goodrich, Ohio, USA) are particularly appropriate. They are cross-linked with an allyl sucrose or with allyl pentaerythritol. Among then, there may be mentioned Carbopol 974P, 934P and 971P. Most preferred is the use of CARBOPOL® 971P. Among the copolymers of maleic anhydride and alkenyl derivative, are the copolymers EMA (Monsanto), which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from E. coli (recombinant or otherwise), cholera toxin, IMS 1314 or muramyl dipeptide, or naturally occurring or recombinant cytokines or analogs thereof or stimulants of endogenous cytokine release, among many others.

It is expected that an adjuvant can be added in an amount of about 100 µg to about 10 mg per dose, preferably in an amount of about 100 µg to about 10 mg per dose, more preferably in an amount of about 500 µg to about 5 mg per dose, even more preferably in an amount of about 750 µg to about 2.5 mg per dose, and most preferably in an amount of about 1 mg per dose. Alternatively, the adjuvant may be at a concentration of about 0.01 to 50%, preferably at a concentration of about 2% to 30%, more preferably at a concentration of about 5% to 25%, still more preferably at a concentration of about 7% to 22%, and most preferably at a concentration of 10% to 20% by volume of the final product.

"Diluents" can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

"Isolated" means altered "by the hand of man" from its natural state, i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein.

"Attenuation" means reducing the virulence of a pathogen. In the present invention "attenuation" is synonymous with "avirulent". In the present invention, an attenuated virus is one in which the virulence has been reduced so that it does not cause clinical signs of infection but is capable of inducing an immune response in the target animal, but may also mean that the clinical signs are reduced in incidence or severity in animals infected with the attenuated virus, especially the ALVAC viral vector as claimed, in comparison with a "control group" of animals infected with non-attenuated virus or pathogen and not receiving the attenuated virus. In this context, the term "reduce/reduced" means a reduction of at least 10%, preferably 25%, even more preferably 50%, still more preferably 60%, even more preferably 70%, still more preferably 80%, even more preferably 90% and most preferably of 100% as compared to the control group as defined above. Thus, an attenuated, avirulent pathogen such as for example an attenuated viral vector as claimed, especially the ALVAC viral vector as claimed, is suitable for the generation of a modified live vaccine (MLV) or modified live immunogenic composition.

The term "attenuated" paramyxovirus, as described herein, is in particular directed to a paramyxovirus which is attenuated in vitro and/or in vivo, more particular in susceptible cell lines and/or the host. In this context, "attenuated" particularly relates to a reduced virulence of the paramyxovirus, wherein "virulence" is understood to be the degree of pathogenicity, and wherein "pathogenicity" is directed to the ability of the pathogen to induce clinical signs in the host or the offspring of the host. Possible clinical signs of the infection with the paramyxovirus of the present invention comprise, for example, an increased thirst, increased urination, weight loss, decreased appetite, lethargy, and vomiting in the subject. Possible laboratory findings associated with an infection with the paramyxovirus of the present invention in a subject comprise, for example, increased levels of creatinine and symmetric dimethyl arginine (SDMA). Possible histological findings associated with an infection with the paramyxovirus of the present invention in a subject comprise, for example, cortical and medullary scarring, tubular degeneration, interstitial inflammation due to infiltration of primarily lymphocytes, plasma cells, macrophages and granulocytes.

The term "treatment and/or prophylaxis" refers to the lessening of the incidence of the particular feline paramyxovirus infection or the reduction in the severity of clinical signs caused by or associated with the particular feline paramyxovirus infection. Thus, the term "treatment and/or prophylaxis" also refers to the reduction of the number of animals that become infected with the particular feline paramyxovirus (=lessening of the incidence of the feline paramyxovirus infection) or to the reduction of the severity of clinical signs normally associated with or caused by a feline paramyxovirus infection in a group of animals which animals have received an effective amount of the immunogenic composition as provided herein in comparison to a group of animals which animals have not received such immunogenic composition. The term "treatment and/or prophylaxis" generally involves the administration of an effective amount of the immunogenic composition of the present invention to an animal or animals in need of or that could benefit from such a treatment/prophylaxis. The term "treatment" refers to the administration of the effective amount of the immunogenic composition once the animal or at least some animals is/are already infected with such feline paramyxovims and wherein such animals already show some clinical signs caused by or associated with such feline paramyxovirus infection. The term "prophylaxis" refers to the administration to an animal prior to any infection of such animal with feline paramyxovirus or at least where such animal or none of the animals in a group of animals do not show any clinical signs caused by or associated with the infection by such feline paramyxovirus. The terms "prophylaxis" and "preventing" are used interchangeably in this application.

The term "clinical signs" as used herein refers to signs of infection of an animal from feline paramyxovirus. The clinical signs of infection depend on the pathogen selected. Examples for such clinical signs include but are not limited to increased thirst, increased urination, weight loss, decreased appetite, lethargy, vomiting in the subject, viremia, fever, and shedding of the virus in the environment. Possible laboratory findings associated with an infection with the feline paramyxovirus of the present invention in a subject comprise, for example, increased levels of creatinine and symmetric dimethyl arginine (SDMA). Possible histological findings associated with an infection with the paramyxovirus of the present invention in a subject comprise, for example, cortical and medullary scarring, tubular degeneration, interstitial inflammation due to infiltration of primarily lymphocytes, plasma cells, macrophages and granulocytes. However, the clinical signs also include but are not limited to clinical signs that are directly observable from a live animal.

Preferably, the clinical signs lessened in incidence or severity in a treated animal compared to animals that are either not treated or treated with an immunogenic composition that was available prior to the present invention but subsequently infected by the particular feline paramyxovims refer to increased thirst, increased urination, weight loss, decreased appetite, lethargy, vomiting in the subject, viremia, fever, shedding of the virus in the environment, infections of the urogenital system, infections of the urinary system, kidney disease, chronic kidney disease (CKD), inflammation of the renal tubules and renal interstitial tissue, and idiopathic tubulointerstitial nephritis (TIN) stitial nephritis (TIN).

Herein, "effective dose" means, but is not limited to, an amount of antigen that elicits, or is able to elicit, an immune response that yields a reduction of clinical symptoms in an animal to which the antigen is administered.

As used herein, the term "effective amount" means, in the context of a composition, an amount of an immunogenic composition capable of inducing an immune response that reduces the incidence of or lessens the severity of infection or incident of disease in an animal Such effective amount is able to lessen the incidence of the particular feline paramyxovirus infection in felines or to reduce the severity of clinical signs of the particular feline paramyxovirus infection. Particularly, an effective amount refers to colony forming units (CFU) per dose. Alternatively, in the context of a therapy, the term “effective amount” refers to the amount of a therapy which is sufficient to reduce or ameliorate the severity or duration of a disease or disorder, or one or more symptoms thereof, prevent the advancement of a disease or disorder, cause the regression of a disease or disorder, prevent the recurrence, development, onset, or progression of one or more symptoms associated with a disease or disorder, or enhance or improve the prophylaxis or treatment of another therapy or therapeutic agent.

An “immune response” or “immunological response” means, but is not limited to, the development of a cellular and/or antibody-mediated immune response to the (immunogenic) composition or vaccine of interest. Usually, an immune or immunological response includes, but is not limited to, one or more of the following effects: the production or activation of antibodies, B cells, helper T cells, suppressor T cells, and/or cytotoxic T cells, directed specifically to an antigen or antigens included in the composition or vaccine of interest. Preferably, the host will display either a therapeutic or a protective immunological (memory) response such that resistance to new infection will be enhanced and/or the clinical severity of the disease reduced. Such protection will be demonstrated by either a reduction in number of symptoms, severity of symptoms, or the lack of one or more of the symptoms associated with the infection of the pathogen, a delay in the of onset of viremia, reduced viral persistence, a reduction in the overall viral load and/or a reduction of viral excretion.

“Protection against disease”, “protective immunity”, “functional immunity”, “reduction of clinical symptoms”, “induction/production of neutralizing antibodies and/or serum conversion”, and similar phrases, means a partial or complete response against a disease or condition generated by administration of one or more therapeutic compositions of the invention, or a combination thereof, that results in fewer deleterious effects than would be expected in a non-immunized animal that has been exposed to disease or infection. That is, the severity of the deleterious effects of the infection is lessened in a vaccinated animal Infection may be reduced, slowed, or possibly fully prevented, in a vaccinated animal Herein, where complete prevention of infection is meant, it is specifically stated. If complete prevention is not stated then the term includes partial prevention. A “protective immunological response” or “protective immunity” will be demonstrated by either a reduction or lack of clinical signs normally displayed by an infected host, a quicker recovery time and/or a lowered duration of infectivity or lowered pathogen titer in the tissues or body fluids or excretions of the infected host.

Herein, “reduction of the incidence and/or severity of clinical signs” or “reduction of clinical symptoms” means, but is not limited to, reducing the number of infected animals in a group, reducing or eliminating the number of animals exhibiting clinical signs of infection, or reducing the severity of any clinical signs that are present in one or more animals, in comparison to wild-type infection. For example, it should refer to any reduction of pathogen load, pathogen shedding, reduction in pathogen transmission, or reduction of any clinical sign symptomatic of feline paramyxovirus infections. Preferably these clinical signs are reduced in one or more animals receiving the therapeutic composition of the present invention by at least 10% in comparison to animals not receiving the composition and that become infected. More preferably clinical signs are reduced in animals receiving a composition of the present invention by at least 20%, preferably by at least 30%, more preferably by at least 40%, and even more preferably by at least 50%.

The term “increased protection” herein means, but is not limited to, a statistically significant reduction of one or more clinical symptoms which are associated with infection by an infectious agent in a vaccinated group of animals vs. a non-vaccinated control group of animals. The term “statistically significant reduction of clinical symptoms” means, but is not limited to, the frequency in the incidence of at least one clinical symptom in the vaccinated group of animals is at least 10%, preferably 20%, more preferably 30%, even more preferably 50%, and even more preferably 70% lower than in the non-vaccinated control group after the challenge the infectious agent.

The term “pathogen” is well known to the person skilled in the art. The term “pathogen” comprises bacteria and viruses. In the course of the present invention the term “pathogen infecting felines” preferably is feline paramyxovirus.

“Long-lasting protection” shall refer to “improved efficacy” that persists for at least 3 weeks, but more preferably at least 3 months, still more preferably at least 6 months.

The term “shedding” refers to secretions such as nasal discharges and, further, to aerosols created by coughing or sneezing. Thus, shedding may be determined by examining the virus titer in nasal swabs or by the virus titer in the lungs. The term “shedding” further encompasses the transfer of virus to susceptible animals (i e sentinels). It is in the general knowledge of a person skilled in the art how to measure the viral shedding.

“Safety” refers to the absence of adverse consequences in a vaccinated animal following vaccination, including but not limited to: potential reversion of a bacterium-based vaccine to virulence, clinically significant side effects such as persistent, systemic illness or unacceptable inflammation at the site of vaccine administration.

The terms “vaccination” or “vaccinating” or variants thereof, as used herein means, but is not limited to, a process which includes the administration of an immunogenic composition of the invention that, when administered to an animal, elicits, or is able to elicit—directly or indirectly—an immune response in said animal.

“Mortality”, in the context of the present invention, refers to death caused by an infection, and includes the situation where the infection is so severe that an animal is euthanized to prevent suffering and provide a humane ending to its life.

The formulations of the invention comprise an effective immunizing amount of one or more immunogenic compositions and a physiologically acceptable vehicle. Vaccines comprise an effective immunizing amount of one or more immunogenic compositions and a physiologically acceptable vehicle. The formulation should suit the mode of administration.

The immunogenic composition, if desired, can also contain minor amounts of wetting or emulsifying agents, or pH buffering agents. The immunogenic composition can be a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

Preferred routes of administration include but are not limited to intranasal, oral, intradermal, subcutaneous and intramuscular. Administration in drinking water, most preferably in a single dose, is desirable. The skilled artisan will recognize that compositions of the invention may also be administered in one, two or more doses, as well as, by other routes of administration. For example, such other routes include subcutaneously, intracutaneously, intraperitoneally, and depending on the desired duration and effectiveness of the treatment, the compositions according to the invention may be administered once or several times, also intermittently, for instance on a daily basis for several days, weeks or months and in different dosages such as about $1\times10^4$ to $1\times10^9$ (see viral titer above). In a specific aspect of the present invention the dosage is about $1\times10^4$ to $1\times10^8$ $TCID_{50}$.

The term "sample" refers to a sample of a body fluid, to a sample of separated cells or to a sample from a tissue or an organ. Samples of body fluids can be obtained by well-known techniques and include, preferably, samples of blood, plasma, serum, or urine, more preferably, samples of blood, plasma or serum. Tissue or organ samples may be obtained from any tissue or organ by, e.g., biopsy. Separated cells may be obtained from the body fluids or the tissues or organs by separating techniques such as centrifugation or cell sorting.

The term "obtained" may comprise an isolation and/or purification step known to the person skilled in the art, preferably using precipitation, columns etc.

The term "immunotest" and "genomic analytical test" is the basis for differentiating animals vaccinated with the immunogenic composition according to the present invention and animals infected with the naturally occurring (disease-associated) feline paramyxovirus. Examples of immunotests include any enzyme-immunological or immunochemical detection method such as ELISA (enzyme linked immunosorbent assay), EIA (enzyme immunoassay), RIA (radioimmunoassay), sandwich enzyme immune tests, fluorescent antibody test (FAT) electrochemiluminescence sandwich immunoassays (ECLIA), dissociation-enhanced lanthanide fluoro immuno assay (DELFIA) or solid phase immune tests, immunofluorescent test (IFT), immunohistological staining, Western blot analysis or any other suitable method available to technicians skilled in the art. Depending upon the assay used, the antigens or the antibodies can be labeled by an enzyme, a fluorophore or a radioisotope. See, e.g., Coligan et al. Current Protocols in Immunology, John Wiley & Sons Inc., New York, N.Y. (1994); and Frye et al., Oncogen 4: 1153-1157, 1987.

The term "genomic analytical test" refers to a genomic analytical method based upon the polymerase chain reaction (PCR), reverse transcription polymerase chain reaction (RT-PCR), real-time PCR (r-PCR) or real time reverse transcription PCR (rRT-PCR), Templex-PCR, nucleic-acid sequence based amplification (NASBA), and isothermal amplification methods using polymerases and specific oligonucleotides as primers. The aforementioned amplification methods are well known in the art.

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

Hybridization reactions can be performed under conditions of different "stringency." Conditions that increase stringency of a hybridization reaction are well known. See for examples, "Molecular Cloning: A Laboratory Manual", second edition (Sambrook et al. 1989). Examples of relevant conditions include (in order of increasing stringency): incubation temperatures of 25° C., 37° C., 50° C., and 68° C.; buffer concentrations of 10×SSC, 6×SSC, 1×SSC, 0.1×SSC (where SSC is 0.15 M NaCl and 15 mM citrate buffer) and their equivalent using other buffer systems; formamide concentrations of 0%, 25%, 50%, and 75%; incubation times from 5 minutes to 24 hours; 1, 2 or more washing steps; wash incubation times of 1, 2, or 15 minutes; and wash solutions of 6×SSC, 1×SSC, 0.1×SSC, or deionized water.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

SEQUENCE LISTING

This application contains a sequence listing. The sequence listing comprises the following sequences:

SEQ ID NO:1 FPaV-2 "Gordon strain" full genome sequence; given as a DNA sequence that correspond to the positive RNA-strand into which the negative RNA strand viral genome is transcribed, i.e. it comprises the ORFs in 5' to 3' direction like an mRNA SEQ ID NO:2 FPaV-2 "TV25 strain" full genome sequence; given as a DNA sequence that correspond to the positive RNA-strand into which the negative RNA strand viral genome is transcribed, i.e. it comprises the ORFs in 5' to 3' direction like an mRNA SEQ ID NO:3 FeMoV "Lapön strain" full genome sequence; given as a DNA sequence that correspond to the positive RNA-strand into which the negative RNA strand viral genome is transcribed, i.e. it comprises the ORFs in 5' to 3' direction like an mRNA SEQ ID NO:4 FPaV-2 "Gordon strain" H antigen "wild-type" nucleic acid; given as DNA sequence SEQ ID NO:5 FPaV-2 "Gordon strain" H antigen nucleic acid that has been codon-optimized for expression primarily in felines; given as DNA sequence SEQ ID NO:6 FPaV-2 "Gordon strain" H antigen translated amino acid sequence SEQ ID NO:7 FPaV-2 "Gordon strain" M antigen "wild-type" nucleic acid; given as DNA sequence SEQ ID NO:8 FPaV-2 "Gordon strain" M antigen nucleic acid that has been codon-optimized for expression primarily in felines; given as DNA sequence SEQ ID NO:9 FPaV-2 "Gordon strain" M antigen translated amino acid sequence SEQ ID NO:10 FPaV-2 "Gordon strain" F antigen "wild-type" nucleic acid; given as DNA sequence SEQ ID NO:11 FPaV-2 "Gordon strain" F antigen nucleic acid that has been codon-optimized for expression primarily in felines; given as DNA sequence SEQ ID NO:12 FPaV-2 "Gordon strain" F antigen translated amino acid sequence SEQ ID NO:13 FPaV-2 "Gordon strain" N antigen "wild-type" nucleic acid; given as DNA sequence SEQ ID NO:14 FPaV-2 "Gordon strain" N antigen translated amino acid sequence SEQ ID NO:15 FPaV-2 "Gordon strain" P antigen "wild-type" nucleic acid; given as DNA sequence SEQ ID NO:16 FPaV-2 "Gordon strain" P antigen translated amino acid sequence SEQ ID NO:17 FPaV-2 "Gordon strain" L antigen "wild-type" nucleic acid; given as DNA sequence SEQ ID NO:18 FPaV-2 "Gordon strain" L antigen translated amino acid sequence SEQ ID NO:19 FPaV-2 "TV25 strain" H antigen "wild-type" nucleic acid; given as DNA sequence SEQ ID NO:20 FPaV-2 "TV25 strain" H antigen translated amino acid sequence SEQ ID NO:21 FPaV-2 "TV25 strain" M antigen "wild-type" nucleic acid; given as DNA sequence SEQ ID NO:22 FPaV-2 "TV25 strain" M antigen translated amino acid sequence SEQ ID NO:23 FPaV-2 "TV25 strain" F antigen "wild-type" nucleic acid; given as DNA sequence SEQ ID NO:24 FPaV-2 "TV25 strain" F antigen translated amino acid sequence SEQ ID NO:25 FPaV-2 "TV25 strain" N antigen "wild-type" nucleic acid; given as DNA sequence SEQ ID NO:26 FPaV-2 "TV25 strain" N antigen translated amino acid sequence SEQ ID NO:27 FPaV-2 "TV25 strain" P antigen "wild-type" nucleic acid; given as DNA sequence SEQ ID NO:28 FPaV-2 "TV25 strain" P antigen translated amino acid sequence SEQ ID NO:29 FPaV-2 "TV25 strain" L antigen "wild-type" nucleic acid; given as DNA sequence SEQ ID NO:30 FPaV-2 "TV25 strain" L antigen translated amino acid sequence SEQ ID NO:31 FeMoV "Lapön strain" H antigen "wild-type" nucleic acid; given as DNA sequence SEQ ID NO:32 FeMoV "Lapön strain" H antigen nucleic acid that has been codon-optimized for expression primarily in felines; given as DNA sequence SEQ ID NO:33 FeMoV "Lapön strain" H antigen translated amino acid sequence SEQ ID NO:34 FeMoV "Lapön strain" M antigen "wild-type" nucleic acid; given as DNA sequence SEQ ID NO:35 FeMoV "Lapön strain" M antigen nucleic acid that has been codon-optimized for expression primarily in felines; given as DNA sequence SEQ ID NO:36 FeMoV "Lapön strain" M antigen translated amino acid sequence SEQ ID NO:37 FeMoV "Lapön strain" F antigen "wild-type" nucleic acid; given as DNA sequence SEQ ID NO:38 FeMoV "Lapön strain" F antigen translated amino acid sequence SEQ ID NO:39 FeMoV "Lapön strain" N antigen "wild-type" nucleic acid; given as DNA sequence SEQ ID NO:40 FeMoV "Lapön strain" N antigen translated amino acid sequence SEQ ID NO:41 FeMoV "Lapön strain" P antigen "wild-type" nucleic acid; given as DNA sequence SEQ ID NO:42 FeMoV "Lapön strain" P antigen translated amino acid sequence SEQ ID NO:43 FeMoV "Lapön strain" L antigen "wild-type" nucleic acid; given as DNA sequence SEQ ID NO:44 FeMoV "Lapön strain" L antigen translated amino acid sequence SEQ ID NO:45 ALVAC insertion locus C3 flanking region left arm; given as DNA sequence SEQ ID NO:46 ALVAC insertion locus C3 flanking region right arm; given as DNA sequence SEQ ID NO:47 ALVAC insertion locus C5 flanking region left arm; given as DNA sequence SEQ ID NO:48 ALVAC insertion locus C5 flanking region right arm; given as DNA sequence SEQ ID NO:49 passage 3 C5 insertion locus of vCP3025 including C5 flanking region right arm, H6 vaccinia promoter, codon-optimized Gordon H antigen, C5 flanking region left arm, i.e. base pairs 304,701 to 308,870

SEQ ID NO:50 passage 3 C5 insertion locus of vCP3029 including C5 flanking region right arm, H6 vaccinia promoter, codon-optimized Gordon H antigen, C5 flanking region left arm, i.e. base pairs 304,166 to 308,380

SEQ ID NO:51 passage 3 C3 insertion locus of vCP3029 including C3 flanking region right arm, 42 k (long) poxviral promoter, codon-optimized Gordon M antigen, C3 flanking region left arm, i.e. base pairs 38,608 to 42,807

SEQ ID NO:52 PCR Primer "Gordon_M_probe_F"
SEQ ID NO:53 PCR Primer "Gordon_M_probe_R"
SEQ ID NO:54 PCR Primer "C3F"
SEQ ID NO:55 PCR Primer "C3R"
SEQ ID NO:56 PCR Primer "7520"
SEQ ID NO:57 PCR Primer "7521"
SEQ ID NO:58 PCR Primer "C3-PCR-F"
SEQ ID NO:59 PCR Primer "C3-PCR-R"
SEQ ID NO:60 PCR Primer "C3-R1"
SEQ ID NO:61 PCR Primer "C3-R2"
SEQ ID NO:62 PCR Primer "C3-R3"
SEQ ID NO:63 PCR Primer "C3-R4"
SEQ ID NO:64 PCR Primer "C3-R5"
SEQ ID NO:65 PCR Primer "C3-R6"
SEQ ID NO:66 PCR Primer "C3-R7"
SEQ ID NO:67 PCR Primer "C3-R8"
SEQ ID NO:68 PCR Primer "C3-R9"
SEQ ID NO:69 PCR Primer "Gordon_M_1F"
SEQ ID NO:70 PCR Primer "Gordon_M_2F"
SEQ ID NO:71 PCR Primer "Gordon_M_3F"
SEQ ID NO:72 PCR Primer "Gordon_M_1R"
SEQ ID NO:73 PCR Primer "C3-F5"
SEQ ID NO:74 PCR Primer "C3-F7"
SEQ ID NO:75 PCR Primer "7931"
SEQ ID NO:76 PCR Primer "7932"
SEQ ID NO:77 PCR Primer "7927.DC"
SEQ ID NO:78 PCR Primer "7696.CXL"
SEQ ID NO:79 PCR Primer "7697.CXL"
SEQ ID NO:80 PCR Primer "7925.DC"
SEQ ID NO:81 PCR Primer "7792.SL"
SEQ ID NO:82 PCR Primer "7793SL"
SEQ ID NO:83 PCR Primer "7928.DC"
SEQ ID NO:84 PCR Primer "7929.DC"
SEQ ID NO:85 PCR Primer "7926.DC"
SEQ ID NO:86 PCR Primer "Gordon_H_1R"
SEQ ID NO:87 PCR Primer "Gordon_H_2F"
SEQ ID NO:88 PCR Primer "Gordon_H_probe_R"
SEQ ID NO:89 PCR Primer "Gordon_H_probe_F"
SEQ ID NO:90 PCR Primer "Gordon_H_1F"
SEQ ID NO:91 PCR Primer "Gordon_H_3F"
SEQ ID NO:92 PCR Primer "Gordon_H_4F"
SEQ ID NO:93 PCR Primer "Gordon_H_5F"

SEQ ID NO:94 FeMoV "Lapön strain" H antigen "wild-type"—without BamH1 restriction enzyme site—nucleic acid; given as DNA sequence SEQ ID NO:95 vCP3041 cloned insertion locus C3 and its theoretical nucleotide sequence from base pair 38,619 to 43,588 including right flanking sequence of the insertion locus C3, 42 k (long) promoter, Lapön H (wt; no BamH I restriction enzyme site) and left flanking sequence of the insertion locus C3

This application additionally comprises the following clauses:

1. A viral vector comprising at least one exogenous antigen encoding sequence relating to at least one pathogen infecting felines, wherein the at least one pathogen infecting felines is feline paramyxovirus.

2. The viral vector according to clause 1, wherein the viral vector is selected from the group consisting of: avipox virus viral vector, canine morbillivirus viral vector, herpes virus viral vector, varicella virus viral vector.

3. The viral vector according to any one of clauses 1 to 2, wherein the at least one pathogen infecting felines being feline paramyxovirus is selected from the group consisting of:
(a) a feline paramyxovirus type 2 (FPaV-2);
(b) a feline paramyxovirus type 2 (FPaV-2), the genome of which comprises a ribonucleic acid complementary to the nucleic acid sequence selected from the group consisting of:
    (i) a nucleic acid sequence according to SEQ ID NO: 1,
    (ii) a nucleic acid sequence which is at least 70% identical to SEQ ID NO:1, at least 75% identical to SEQ ID NO:1, at least 80% identical to SEQ ID NO:1, at least 85% identical to SEQ ID NO:1, at least 90% identical to SEQ ID NO:1, at least 91% identical to SEQ ID NO:1, at least 92% identical to SEQ ID NO:1, at least 93% identical to SEQ ID NO:1, at least 94% identical to SEQ ID NO:1, at least 95% identical to SEQ ID NO:1, at least 96% identical to SEQ ID NO:1, at least 97% identical to SEQ ID NO:1, at least 98% identical to SEQ ID NO:1, at least 99% identical to SEQ ID NO:1;
(c) feline paramyxovirus type 2 (FPaV-2) as deposited at Collection Nationale de Culture de Microorganismes (CNCM) under accession number CNCM I-5123;
(d) a feline paramyxovirus type 2 (FPaV-2), the genome of which comprises a ribonucleic acid complementary to the nucleic acid sequence selected from the group consisting of:
    (i) a nucleic acid sequence according to SEQ ID NO: 2,
    (ii) a nucleic acid sequence which is at least 70% identical to SEQ ID NO:2, at least 75% identical to SEQ ID NO:2, at least 80% identical to SEQ ID NO:2, at least 85% identical to SEQ ID NO:2, at least 90% identical to SEQ ID NO:2, at least 91% identical to SEQ ID NO:2, at least 92% identical to SEQ ID NO:2, at least 93% identical to SEQ ID NO:2, at least 94% identical to SEQ ID NO:2, at least 95% identical to SEQ ID NO:2, at least 96% identical to SEQ ID NO:2, at least 97% identical to SEQ ID NO:2, at least 98% identical to SEQ ID NO:2, at least 99% identical to SEQ ID NO:2;
(e) a feline morbillivirus (FeMoV);
(f) a feline morbillivirus (FeMoV), the genome of which comprises a ribonucleic acid complementary to the nucleic acid sequence selected from the group consisting of:
    (i) a nucleic acid sequence according to SEQ ID NO: 3,
    (ii) a nucleic acid sequence which is at least 70% identical to SEQ ID NO:3, at least 75% identical to SEQ ID NO:3, at least 80% identical to SEQ ID NO:3, at least 85% identical to SEQ ID NO:3, at least 90% identical to SEQ ID NO:3, at least 91% identical to SEQ ID NO:3, at least 92% identical to SEQ ID NO:3, at least 93% identical to SEQ ID NO:3, at least 94% identical to SEQ ID NO:3, at least 95% identical to SEQ ID NO:3, at least 96% identical to SEQ ID NO:3, at least 97% identical to SEQ ID NO:3, at least 98% identical to SEQ ID NO:3, at least 99% identical to SEQ ID NO:3.

and preferably is selected from the group consisting of:
(b) a feline paramyxovirus type 2 (FPaV-2), the genome of which comprises a ribonucleic acid complementary to the nucleic acid sequence selected from the group consisting of:
    (i) a nucleic acid sequence according to SEQ ID NO: 1,
    (ii) a nucleic acid sequence which is at least 70% identical to SEQ ID NO:1, at least 75% identical to SEQ ID NO:1, at least 80% identical to SEQ ID NO:1, at least 85% identical to SEQ ID NO:1, at least 90% identical to SEQ ID NO:1, at least 91% identical to SEQ ID NO:1, at least 92% identical to SEQ ID NO:1, at least 93% identical to SEQ ID NO:1, at least 94% identical to SEQ ID NO:1, at least 95% identical to SEQ ID NO:1, at least 96% identical to SEQ ID NO:1, at least 97% identical to SEQ ID NO:1, at least 98% identical to SEQ ID NO:1, at least 99% identical to SEQ ID NO:1;
(c) feline paramyxovirus type 2 (FPaV-2) as deposited at Collection Nationale de Culture de Microorganismes (CNCM) under accession number CNCM I-5123;
(d) a feline paramyxovirus type 2 (FPaV-2), the genome of which comprises a ribonucleic acid complementary to the nucleic acid sequence selected from the group consisting of:
    (i) a nucleic acid sequence according to SEQ ID NO: 2,
    (ii) a nucleic acid sequence which is at least 70% identical to SEQ ID NO:2, at least 75% identical to SEQ ID NO:2, at least 80% identical to SEQ ID NO:2, at least 85% identical to SEQ ID NO:2, at least 90% identical to SEQ ID NO:2, at least 91% identical to SEQ ID NO:2, at least 92% identical to SEQ ID NO:2, at least 93% identical to SEQ ID NO:2, at least 94% identical to SEQ ID NO:2, at least 95% identical to SEQ ID NO:2, at least 96% identical to SEQ ID NO:2, at least 97% identical to SEQ ID NO:2, at least 98% identical to SEQ ID NO:2, at least 99% identical to SEQ ID NO:2.

4. The viral vector according to any one of clauses 1 to 3, wherein the viral vector is recombinant and/or non-naturally occurring.

5. The viral vector according to any one of clauses 1 to 4, wherein the viral vector is a canarypox vector, preferably an attenuated canarypox vector, more preferably ALVAC, even more preferably ALVAC-1 or ALVAC-2, most preferably ALVAC as deposited under the terms of the Budapest Treaty at the American Type Culture Collection (ATCC) under accession number VR-2547.

6. The viral vector according to any one of clauses 1 to 4, wherein the viral vector is a fowlpox vector, preferably an attenuated fowlpox vector, more preferably TROVAC, most preferably TROVAC as deposited under the terms of the Budapest Treaty at the American Type Culture Collection (ATCC) under accession number VR-2553.

7. The viral vector according to any one of clauses 1 to 5, wherein the viral vector is selected from the group consisting of: vCP3025, vCP3029, vCP3041.

8. The viral vector according to any one of clauses 1 to 7, wherein the at least one exogenous antigen encoding sequence is selected from the group consisting of: hemagglutinin protein ("H") encoding sequence, matrix protein ("M") encoding sequence, fusion protein ("F") encoding sequence, nucleocapsid protein ("N") encoding sequence, phosphoprotein ("P") encoding sequence, RNA-dependent RNA polymerase protein ("L") encoding sequence, and more preferably is a hemagglutinin protein ("H") encoding sequence and/or a matrix protein ("M") encoding sequence and/or a fusion protein ("F") encoding sequence.

9. The viral vector according to clause 8, wherein the at least one exogenous antigen encoding sequence is a hemagglutinin protein ("H") encoding sequence and the hemagglutinin protein ("H") encoding sequence comprises a nucleic acid sequence which is at least 70% identical to SEQ ID NO:4, at least 75% identical to SEQ ID NO:4, at least 80% identical to SEQ ID NO:4, at least 85% identical to SEQ ID NO:4, at least 90% identical to SEQ ID NO:4, at least 91% identical to SEQ ID NO:4, at least 92% identical to SEQ ID NO:4, at least 93% identical to SEQ ID NO:4, at least 94% identical to SEQ ID NO:4, at least 95% identical to SEQ ID NO:4, at least 96% identical to SEQ ID NO:4, at least 97% identical to SEQ ID NO:4, at least 98% identical to SEQ ID NO:4, at least 99% identical to SEQ ID NO:4, and preferably is selected from the group consisting of: SEQ ID NO:4, SEQ ID NO:5.

10. The viral vector according to clause 8, wherein the at least one exogenous antigen encoding sequence is a hemagglutinin protein ("H") encoding sequence and the hemagglutinin protein ("H") encoding sequence comprises a nucleic acid sequence encoding a polypeptide having an amino acid sequence which is at least 70% identical to SEQ ID NO:6, at least 75% identical to SEQ ID NO:6, at least 80% identical to SEQ ID NO:6, at least 85% identical to SEQ ID NO:6, at least 90% identical to SEQ ID NO:6, at least 91% identical to SEQ ID NO:6, at least 92% identical to SEQ ID NO:6, at least 93% identical to SEQ ID NO:6, at least 94% identical to SEQ ID NO:6, at least 95% identical to SEQ ID NO:6, at least 96% identical to SEQ ID NO:6, at least 97% identical to SEQ ID NO:6, at least 98% identical to SEQ ID NO:6, at least 99% identical to SEQ ID NO:6, and preferably is the amino acid sequence according to SEQ ID NO:6.

11. The viral vector according to clause 8, wherein the at least one exogenous antigen encoding sequence is a matrix protein ("M") encoding sequence and the matrix protein ("M") encoding sequence comprises a nucleic acid sequence which is at least 70% identical to SEQ ID NO:7, at least 75% identical to SEQ ID NO:7, at least 80% identical to SEQ ID NO:7, at least 85% identical to SEQ ID NO:7, at least 90% identical to SEQ ID NO:7, at least 91% identical to SEQ ID NO:7, at least 92% identical to SEQ ID NO:7, at least 93% identical to SEQ ID NO:7, at least 94% identical to SEQ ID NO:7, at least 95% identical to SEQ ID NO:7, at least 96% identical to SEQ ID NO:7, at least 97% identical to SEQ ID NO:7, at least 98% identical to SEQ ID NO:7, at least 99% identical to SEQ ID NO:7, and preferably is selected from the group consisting of: SEQ ID NO:7, SEQ ID NO:8.

12. The viral vector according to clause 8, wherein the at least one exogenous antigen encoding sequence is a matrix protein ("M") encoding sequence and the matrix protein ("M") encoding sequence comprises a nucleic acid sequence encoding a polypeptide having an amino acid sequence which is at least 70% identical to SEQ ID NO:9, at least 75% identical to SEQ ID NO:9, at least 80% identical to SEQ ID NO:9, at least 85% identical to SEQ ID NO:9, at least 90% identical to SEQ ID NO:9, at least 91% identical to SEQ ID NO:9, at least 92% identical to SEQ ID NO:9, at least 93% identical to SEQ ID NO:9, at least 94% identical to SEQ ID NO:9, at least 95% identical to SEQ ID NO:9, at least 96% identical to SEQ ID NO:9, at least 97% identical to SEQ ID NO:9, at least 98% identical to SEQ ID NO:9, at least 99% identical to SEQ ID NO:9, and preferably is the amino acid sequence according to SEQ ID NO:9.

13. The viral vector according to clause 8, wherein the at least one exogenous antigen encoding sequence is a fusion protein ("F") encoding sequence and the fusion protein ("F") encoding sequence comprises a nucleic acid sequence which is at least 70% identical to SEQ ID NO:10, at least 75% identical to SEQ ID NO:10, at least 80% identical to SEQ ID NO:10, at least 85% identical to SEQ ID NO:10, at least 90% identical to SEQ ID NO:10, at least 91% identical to SEQ ID NO:10, at least 92% identical to SEQ ID NO:10, at least 93% identical to SEQ ID NO:10, at least 94% identical to SEQ ID NO:10, at least 95% identical to SEQ ID NO:10, at least 96% identical to SEQ ID NO:10, at least 97% identical to SEQ ID NO:10, at least 98% identical to SEQ ID NO:10, at least 99% identical to SEQ ID NO:10, and preferably is selected from the group consisting of: SEQ ID NO:10, SEQ ID NO:11.

14. The viral vector according to clause 8, wherein the at least one exogenous antigen encoding sequence is a fusion protein ("F") encoding sequence and the fusion protein ("F") encoding sequence comprises a nucleic acid sequence encoding a polypeptide having an amino acid sequence which is at least 70% identical to SEQ ID NO:12, at least 75% identical to SEQ ID NO:12, at least 80% identical to SEQ ID NO:12, at least 85% identical to SEQ ID NO:12, at least 90% identical to SEQ ID NO:12, at least 91% identical to SEQ ID NO:12, at least 92% identical to SEQ ID NO:12, at least 93% identical to SEQ ID NO:12, at least 94% identical to SEQ ID NO:12, at least 95% identical to SEQ ID NO:12, at least 96% identical to SEQ ID NO:12, at least 97% identical to SEQ ID NO:12, at least 98% identical to SEQ ID NO:12, at least 99% identical to SEQ ID NO:12, and preferably is the amino acid sequence according to SEQ ID NO:12.

15. The viral vector according to clause 8, wherein the at least one exogenous antigen encoding sequence is a nucleocapsid protein ("N") encoding sequence and the nucleocapsid protein ("N") encoding sequence comprises a nucleic acid sequence which is at least 70% identical to SEQ ID NO:13, at least 75% identical to SEQ ID NO:13, at least 80% identical to SEQ ID NO:13, at least 85% identical to SEQ ID NO:13, at least 90% identical to SEQ ID NO:13, at least 91% identical to SEQ ID NO:13, at least 92% identical to SEQ ID NO:13, at least 93% identical to SEQ ID NO:13, at least 94% identical to SEQ ID NO:13, at least 95% identical to SEQ ID NO:13, at least 96% identical to SEQ ID NO:13, at least 97% identical to SEQ ID NO:13, at least 98% identical to SEQ ID NO:13, at least 99% identical to SEQ ID NO:13, and preferably is selected from the group consisting of: SEQ ID NO:13.

16. The viral vector according to clause 8, wherein the at least one exogenous antigen encoding sequence is a nucleocapsid protein ("N") encoding sequence and the nucleocapsid protein ("N") encoding sequence comprises a nucleic acid sequence encoding a polypeptide having an amino acid sequence which is at least 70% identical to SEQ ID NO:14, at least 75% identical to SEQ ID NO:14, at least 80% identical to SEQ ID NO:14, at least 85% identical to SEQ ID NO:14, at least 90% identical to SEQ ID NO:14, at least 91% identical to SEQ ID NO:14, at least 92% identical to SEQ ID NO:14, at least 93% identical to SEQ ID NO:14, at least 94% identical to SEQ ID NO:14, at least 95% identical to SEQ ID NO:14, at least 96% identical to SEQ ID NO:14, at least 97% identical to SEQ ID NO:14, at least 98% identical to SEQ ID NO:14, at least 99% identical to SEQ ID NO:14, and preferably is the amino acid sequence according to SEQ ID NO:14.

17. The viral vector according to clause 8, wherein the at least one exogenous antigen encoding sequence is a phosphoprotein ("P") encoding sequence and the phosphoprotein ("P") encoding sequence comprises a nucleic acid sequence which is at least 70% identical to SEQ ID NO:15, at least 75% identical to SEQ ID NO:15, at least 80% identical to SEQ ID NO:15, at least 85% identical to SEQ ID NO:15, at least 90% identical to SEQ ID NO:15, at least 91% identical to SEQ ID NO:15, at least 92% identical to SEQ ID NO:15, at least 93% identical to SEQ ID NO:15, at least 94% identical to SEQ ID NO:15, at least 95% identical to SEQ ID NO:15, at least 96% identical to SEQ ID NO:15, at least 97% identical to SEQ ID NO:15, at least 98% identical to SEQ ID NO:15, at least 99% identical to SEQ ID NO:15, and preferably is selected from the group consisting of: SEQ ID NO:15.

18. The viral vector according to clause 8, wherein the at least one exogenous antigen encoding sequence is a phosphoprotein ("P") encoding sequence and the phosphoprotein ("P") encoding sequence comprises a nucleic acid sequence encoding a polypeptide having an amino acid sequence which is at least 70% identical to SEQ ID NO:16, at least 75% identical to SEQ ID NO:16, at least 80% identical to SEQ ID NO:16, at least 85% identical to SEQ ID NO:16, at least 90% identical to SEQ ID NO:16, at least 91% identical to SEQ ID NO:16, at least 92% identical to SEQ ID NO:16, at least 93% identical to SEQ ID NO:16, at least 94% identical to SEQ ID NO:16, at least 95% identical to SEQ ID NO:16, at least 96% identical to SEQ ID NO:16, at least 97% identical to SEQ ID NO:16, at least 98% identical to SEQ ID NO:16, at least 99% identical to SEQ ID NO:16, and preferably is the amino acid sequence according to SEQ ID NO:16.

19. The viral vector according to clause 8, wherein the at least one exogenous antigen encoding sequence is a RNA-dependent RNA polymerase protein ("L") encoding sequence and the RNA-dependent RNA polymerase protein ("L") encoding sequence comprises a nucleic acid sequence which is at least 70% identical to SEQ ID NO:17, at least 75% identical to SEQ ID NO:17, at least 80% identical to SEQ ID NO:17, at least 85% identical to SEQ ID NO:17, at least 90% identical to SEQ ID NO:17, at least 91% identical to SEQ ID NO:17, at least 92% identical to SEQ ID NO:17, at least 93% identical to SEQ ID NO:17, at least 94% identical to SEQ ID NO:17, at least 95% identical to SEQ ID NO:17, at least 96% identical to SEQ ID NO:17, at least 97% identical to SEQ ID NO:17, at least 98% identical to SEQ ID NO:17, at least 99% identical to SEQ ID NO:17, and preferably is selected from the group consisting of: SEQ ID NO:17.

20. The viral vector according to clause 8, wherein the at least one exogenous antigen encoding sequence is a RNA-dependent RNA polymerase protein ("L") encoding sequence and the RNA-dependent RNA polymerase protein ("L") encoding sequence comprises a nucleic acid sequence encoding a polypeptide having an amino acid sequence which is at least 70% identical to SEQ ID NO:18, at least 75% identical to SEQ ID NO:18, at least 80% identical to SEQ ID NO:18, at least 85% identical to SEQ ID NO:18, at least 90% identical to SEQ ID NO:18, at least 91% identical to SEQ ID NO:18, at least 92% identical to SEQ ID NO:18, at least 93% identical to SEQ ID NO:18, at least 94% identical to SEQ ID NO:18, at least 95% identical to SEQ ID NO:18, at least 96% identical to SEQ ID NO:18, at least 97% identical to SEQ ID NO:18, at least 98% identical to SEQ ID NO:18, at least 99% identical to SEQ ID NO:18, and preferably is the amino acid sequence according to SEQ ID NO:18.

21. The viral vector according to clause 8, wherein the at least one exogenous antigen encoding sequence is a hemagglutinin protein ("H") encoding sequence and the hemagglutinin protein ("H") encoding sequence comprises a nucleic acid sequence which is at least 70% identical to SEQ ID NO:19, at least 75% identical to SEQ ID NO:19, at least 80% identical to SEQ ID NO:19, at least 85% identical to SEQ ID NO:19, at least 90% identical to SEQ ID NO:19, at least 91% identical to SEQ ID NO:19, at least 92% identical to SEQ ID NO:19, at least 93% identical to SEQ ID NO:19, at least 94% identical to SEQ ID NO:19, at least 95% identical to SEQ ID NO:19, at least 96% identical to SEQ ID NO:19, at least 97% identical to SEQ ID NO:19, at least 98% identical to SEQ ID NO:19, at least 99% identical to SEQ ID NO:19, and preferably is selected from the group consisting of: SEQ ID NO:19.

22. The viral vector according to clause 8, wherein the at least one exogenous antigen encoding sequence is a hemagglutinin protein ("H") encoding sequence and the hemagglutinin protein ("H") encoding sequence comprises a nucleic acid sequence encoding a polypeptide having an amino acid sequence which is at least 70% identical to SEQ ID NO:20, at least 75% identical to SEQ ID NO:20, at least 80% identical to SEQ ID NO:20, at least 85% identical to SEQ ID NO:20, at least 90% identical to SEQ ID NO:20, at least 91% identical to SEQ ID NO:20, at least 92% identical to SEQ ID NO:20, at least 93% identical to SEQ ID NO:20, at least 94% identical to SEQ ID NO:20, at least 95% identical to SEQ ID NO:20, at least 96% identical to SEQ ID NO:20, at least 97% identical to SEQ ID NO:20, at least 98% identical to SEQ ID NO:20, at least 99% identical to SEQ ID NO:20, and preferably is the amino acid sequence according to SEQ ID NO:20.

23. The viral vector according to clause 8, wherein the at least one exogenous antigen encoding sequence is a matrix protein ("M") encoding sequence and the matrix protein ("M") encoding sequence comprises a nucleic acid sequence which is at least 70% identical to SEQ ID NO:21, at least 75% identical to SEQ ID NO:21, at least 80% identical to SEQ ID NO:21, at least 85% identical to SEQ ID NO:21, at least 90% identical to SEQ ID NO:21, at least 91% identical to SEQ ID NO:21, at least 92% identical to SEQ ID NO:21, at least 93% identical to SEQ ID NO:21, at least 94% identical to SEQ ID NO:21, at least 95% identical to SEQ ID NO:21, at least 96% identical to SEQ ID NO:21, at least 97% identical to SEQ ID NO:21, at least 98% identical to SEQ ID NO:21, at least 99% identical to SEQ ID NO:21, and preferably is selected from the group consisting of: SEQ ID NO:21.

24. The viral vector according to clause 8, wherein the at least one exogenous antigen encoding sequence is a matrix protein ("M") encoding sequence and the matrix protein ("M") encoding sequence comprises a nucleic acid sequence encoding a polypeptide having an amino acid sequence which is at least 70% identical to SEQ ID NO:22, at least 75% identical to SEQ ID NO:22, at least 80% identical to SEQ ID NO:22, at least 85% identical to SEQ ID NO:22, at least 90% identical to SEQ ID NO:22, at least 91% identical to SEQ ID NO:22, at least 92% identical to SEQ ID NO:22, at least 93% identical to SEQ ID NO:22, at least 94% identical to SEQ ID NO:22, at least 95% identical to SEQ ID NO:22, at least 96% identical to SEQ ID NO:22, at least 97% identical to SEQ ID NO:22, at least 98% identical to SEQ ID NO:22, at least 99% identical to SEQ ID NO:22, and preferably is the amino acid sequence according to SEQ ID NO:22.

25. The viral vector according to clause 8, wherein the at least one exogenous antigen encoding sequence is a fusion protein ("F") encoding sequence and the fusion protein ("F") encoding sequence comprises a nucleic acid sequence which is at least 70% identical to SEQ ID NO:23, at least 75% identical to SEQ ID NO:23, at least 80% identical to SEQ ID NO:23, at least 85% identical to SEQ ID NO:23, at least 90% identical to SEQ ID NO:23, at least 91% identical to SEQ ID NO:23, at least 92% identical to SEQ ID NO:23, at least 93% identical to SEQ ID NO:23, at least 94% identical to SEQ ID NO:23, at least 95% identical to SEQ ID NO:23, at least 96% identical to SEQ ID NO:23, at least 97% identical to SEQ ID NO:23, at least 98% identical to SEQ ID NO:23, at least 99% identical to SEQ ID NO:23, and preferably is selected from the group consisting of: SEQ ID NO:23.

26. The viral vector according to clause 8, wherein the at least one exogenous antigen encoding sequence is a fusion protein ("F") encoding sequence and the fusion protein ("F") encoding sequence comprises a nucleic acid sequence encoding a polypeptide having an amino acid sequence which is at least 70% identical to SEQ ID NO:24, at least 75% identical to SEQ ID NO:24, at least 80% identical to SEQ ID NO:24, at least 85% identical to SEQ ID NO:24, at least 90% identical to SEQ ID NO:24, at least 91% identical to SEQ ID NO:24, at least 92% identical to SEQ ID NO:24, at least 93% identical to SEQ ID NO:24, at least 94% identical to SEQ ID NO:24, at least 95% identical to SEQ ID NO:24, at least 96% identical to SEQ ID NO:24, at least 97% identical to SEQ ID NO:24, at least 98% identical to SEQ ID NO:24, at least 99% identical to SEQ ID NO:24, and preferably is the amino acid sequence according to SEQ ID NO:24.

27. The viral vector according to clause 8, wherein the at least one exogenous antigen encoding sequence is a nucleocapsid protein ("N") encoding sequence and the nucleocapsid protein ("N") encoding sequence comprises a nucleic acid sequence which is at least 70% identical to SEQ ID NO:25, at least 75% identical to SEQ ID NO:25, at least 80% identical to SEQ ID NO:25, at least 85% identical to SEQ ID NO:25, at least 90% identical to SEQ ID NO:25, at least 91% identical to SEQ ID NO:25, at least 92% identical to SEQ ID NO:25, at least 93% identical to SEQ ID NO:25, at least 94% identical to SEQ ID NO:25, at least 95% identical to SEQ ID NO:25, at least 96% identical to SEQ ID NO:25, at least 97% identical to SEQ ID NO:25, at least 98% identical to SEQ ID NO:25, at least 99% identical to SEQ ID NO:25, and preferably is selected from the group consisting of: SEQ ID NO:25.

28. The viral vector according to clause 8, wherein the at least one exogenous antigen encoding sequence is a nucleocapsid protein ("N") encoding sequence and the nucleocapsid protein ("N") encoding sequence comprises a nucleic acid sequence encoding a polypeptide having an amino acid sequence which is at least 70% identical to SEQ ID NO:26, at least 75% identical to SEQ ID NO:26, at least 80% identical to SEQ ID NO:26, at least 85% identical to SEQ ID NO:26, at least 90% identical to SEQ ID NO:26, at least 91% identical to SEQ ID NO:26, at least 92% identical to SEQ ID NO:26, at least 93% identical to SEQ ID NO:26, at least 94% identical to SEQ ID NO:26, at least 95% identical to SEQ ID NO:26, at least 96% identical to SEQ ID NO:26, at least 97% identical to SEQ ID NO:26, at least 98% identical to SEQ ID NO:26, at least 99% identical to SEQ ID NO:26, and preferably is the amino acid sequence according to SEQ ID NO:26.

29. The viral vector according to clause 8, wherein the at least one exogenous antigen encoding sequence is a phosphoprotein ("P") encoding sequence and the phosphoprotein ("P") encoding sequence comprises a nucleic acid sequence which is at least 70% identical to SEQ ID NO:27, at least 75% identical to SEQ ID NO:27, at least 80% identical to SEQ ID NO:27, at least 85% identical to SEQ ID NO:27, at least 90% identical to SEQ ID NO:27, at least 91% identical to SEQ ID NO:27, at least 92% identical to SEQ ID NO:27, at least 93% identical to SEQ ID NO:27, at least 94% identical to SEQ ID NO:27, at least 95% identical to SEQ ID NO:27, at least 96% identical to SEQ ID NO:27, at least 97% identical to SEQ ID NO:27, at least 98% identical to SEQ ID NO:27, at least 99% identical to SEQ ID NO:27, and preferably is selected from the group consisting of: SEQ ID NO:27.

30. The viral vector according to clause 8, wherein the at least one exogenous antigen encoding sequence is a phosphoprotein ("P") encoding sequence and the phosphoprotein ("P") encoding sequence comprises a nucleic acid sequence encoding a polypeptide having an amino acid sequence which is at least 70% identical to SEQ ID NO:28, at least 75% identical to SEQ ID NO:28, at least 80% identical to SEQ ID NO:28, at least 85% identical to SEQ ID NO:28, at least 90% identical to SEQ ID NO:28, at least 91% identical to SEQ ID NO:28, at least 92% identical to SEQ ID NO:28, at least 93% identical to SEQ ID NO:28, at least 94% identical to SEQ ID NO:28, at least 95% identical to SEQ ID NO:28, at least 96% identical to SEQ ID NO:28, at least 97% identical to SEQ ID NO:28, at least 98% identical to SEQ ID NO:28, at least 99% identical to SEQ ID NO:28, and preferably is the amino acid sequence according to SEQ ID NO:28.

31. The viral vector according to clause 8, wherein the at least one exogenous antigen encoding sequence is a RNA-dependent RNA polymerase protein ("L") encoding sequence and the RNA-dependent RNA polymerase protein ("L") encoding sequence comprises a nucleic acid sequence which is at least 70% identical to SEQ ID NO:29, at least 75% identical to SEQ ID NO:29, at least 80% identical to SEQ ID NO:29, at least 85% identical to SEQ ID NO:29, at least 90% identical to SEQ ID NO:29, at least 91% identical to SEQ ID NO:29, at least 92% identical to SEQ ID NO:29, at least 93% identical to SEQ ID NO:29, at least 94% identical to SEQ ID NO:29, at least 95% identical to SEQ ID NO:29, at least 96% identical to SEQ ID NO:29, at least 97% identical to SEQ ID NO:29, at least 98% identical to SEQ ID NO:29, at least 99% identical to SEQ ID NO:29, and preferably is selected from the group consisting of: SEQ ID NO:29.

32. The viral vector according to clause 8, wherein the at least one exogenous antigen encoding sequence is a RNA-dependent RNA polymerase protein ("L") encoding sequence and the RNA-dependent RNA polymerase protein ("L") encoding sequence comprises a nucleic acid sequence encoding a polypeptide having an amino acid sequence which is at least 70% identical to SEQ ID NO:30, at least 75% identical to SEQ ID NO:30, at least 80% identical to SEQ ID NO:30, at least 85% identical to SEQ ID NO:30, at least 90% identical to SEQ ID NO:30, at least 91% identical to SEQ ID NO:30, at least 92% identical to SEQ ID NO:30, at least 93% identical to SEQ ID NO:30, at least 94% identical to SEQ ID NO:30, at least 95% identical to SEQ ID NO:30, at least 96% identical to SEQ ID NO:30, at least 97% identical to SEQ ID NO:30, at least 98% identical to SEQ ID NO:30, at least 99% identical to SEQ ID NO:30, and preferably is the amino acid sequence according to SEQ ID NO:30.

33. The viral vector according to clause 8, wherein the at least one exogenous antigen encoding sequence is a hemagglutinin protein ("H") encoding sequence and the hemagglutinin protein ("H") encoding sequence comprises a nucleic acid sequence which is at least 70% identical to SEQ ID NO:31, at least 75% identical to SEQ ID NO:31, at least 80% identical to SEQ ID NO:31, at least 85% identical to SEQ ID NO:31, at least 90% identical to SEQ ID NO:31, at least 91% identical to SEQ ID NO:31, at least 92% identical to SEQ ID NO:31, at least 93% identical to SEQ ID NO:31, at least 94% identical to SEQ ID NO:31, at least 95% identical to SEQ ID NO:31, at least 96% identical to SEQ ID NO:31, at least 97% identical to SEQ ID NO:31, at least 98% identical to SEQ ID NO:31, at least 99% identical to SEQ ID NO:31, and preferably is selected from the group consisting of: SEQ ID NO:31, SEQ ID NO:32.

34. The viral vector according to clause 8, wherein the at least one exogenous antigen encoding sequence is a hemagglutinin protein ("H") encoding sequence and the hemagglutinin protein ("H") encoding sequence comprises a nucleic acid sequence encoding a polypeptide having an amino acid sequence which is at least 70% identical to SEQ ID NO:33, at least 75% identical to SEQ ID NO:33, at least 80% identical to SEQ ID NO:33, at least 85% identical to SEQ ID NO:33, at least 90% identical to SEQ ID NO:33, at least 91% identical to SEQ ID NO:33, at least 92% identical to SEQ ID NO:33, at least 93% identical to SEQ ID NO:33, at least 94% identical to SEQ ID NO:33, at least 95% identical to SEQ ID NO:33, at least 96% identical to SEQ ID NO:33, at least 97% identical to SEQ ID NO:33, at least 98% identical to SEQ ID NO:33, at least 99% identical to SEQ ID NO:33, and preferably is the amino acid sequence according to SEQ ID NO:33.

35. The viral vector according to clause 8, wherein the at least one exogenous antigen encoding sequence is a matrix protein ("M") encoding sequence and the matrix protein ("M") encoding sequence comprises a nucleic acid sequence which is at least 70% identical to SEQ ID NO:34, at least 75% identical to SEQ ID NO:34, at least 80% identical to SEQ ID NO:34, at least 85% identical to SEQ ID NO:34, at least 90% identical to SEQ ID NO:34, at least 91% identical to SEQ ID NO:34, at least 92% identical to SEQ ID NO:34, at least 93% identical to SEQ ID NO:34, at least 94% identical to SEQ ID NO:34, at least 95% identical to SEQ ID NO:34, at least 96% identical to SEQ ID NO:34, at least 97% identical to SEQ ID NO:34, at least 98% identical to SEQ ID NO:34, at least 99% identical to SEQ ID NO:34, and preferably is selected from the group consisting of: SEQ ID NO:34, SEQ ID NO:35.

36. The viral vector according to clause 8, wherein the at least one exogenous antigen encoding sequence is a matrix protein ("M") encoding sequence and the matrix protein ("M") encoding sequence comprises a nucleic acid sequence encoding a polypeptide having an amino acid sequence which is at least 70% identical to SEQ ID NO:36, at least 75% identical to SEQ ID NO:36, at least 80% identical to SEQ ID NO:36, at least 85% identical to SEQ ID NO:36, at least 90% identical to SEQ ID NO:36, at least 91% identical to SEQ ID NO:36, at least 92% identical to SEQ ID NO:36, at least 93% identical to SEQ ID NO:36, at least 94% identical to SEQ ID NO:36, at least 95% identical to SEQ ID NO:36, at least 96% identical to SEQ ID NO:36, at least 97% identical to SEQ ID NO:36, at least 98% identical to SEQ ID NO:36, at least 99% identical to SEQ ID NO:36, and preferably is the amino acid sequence according to SEQ ID NO:36.

37. The viral vector according to clause 8, wherein the at least one exogenous antigen encoding sequence is a fusion protein ("F") encoding sequence and the fusion protein ("F") encoding sequence comprises a nucleic acid sequence which is at least 70% identical to SEQ ID NO:37, at least 75% identical to SEQ ID NO:37, at least 80% identical to SEQ ID NO:37, at least 85% identical to SEQ ID NO:37, at least 90% identical to SEQ ID NO:37, at least 91% identical to SEQ ID NO:37, at least 92% identical to SEQ ID NO:37, at least 93% identical to SEQ ID NO:37, at least 94% identical to SEQ ID NO:37, at least 95% identical to SEQ ID NO:37, at least 96% identical to SEQ ID NO:37, at least 97% identical to SEQ ID NO:37, at least 98% identical to SEQ ID NO:37, at least 99% identical to SEQ ID NO:37, and preferably is selected from the group consisting of: SEQ ID NO:37.

38. The viral vector according to clause 8, wherein the at least one exogenous antigen encoding sequence is a fusion protein ("F") encoding sequence and the fusion protein ("F") encoding sequence comprises a nucleic acid sequence encoding a polypeptide having an amino acid sequence which is at least 70% identical to SEQ ID NO:38, at least 75% identical to SEQ ID NO:38, at least 80% identical to SEQ ID NO:38, at least 85% identical to SEQ ID NO:38, at least 90% identical to SEQ ID NO:38, at least 91% identical to SEQ ID NO:38, at least 92% identical to SEQ ID NO:38, at least 93% identical to SEQ ID NO:38, at least 94% identical to SEQ ID NO:38, at least 95% identical to SEQ ID NO:38, at least 96% identical to SEQ ID NO:38, at least 97% identical to SEQ ID NO:38, at least 98% identical to SEQ ID NO:38, at least 99% identical to SEQ ID NO:38, and preferably is the amino acid sequence according to SEQ ID NO:38.

39. The viral vector according to clause 8, wherein the at least one exogenous antigen encoding sequence is a nucleocapsid protein ("N") encoding sequence and the nucleocapsid protein ("N") encoding sequence comprises a nucleic acid sequence which is at least 70% identical to SEQ ID NO:39, at least 75% identical to SEQ ID NO:39, at least 80% identical to SEQ ID NO:39, at least 85% identical to SEQ ID NO:39, at least 90% identical to SEQ ID NO:39, at least 91% identical to SEQ ID NO:39, at least 92% identical to SEQ ID NO:39, at least 93% identical to SEQ ID NO:39, at least 94% identical to SEQ ID NO:39, at least 95% identical to SEQ ID NO:39, at least 96% identical to SEQ ID NO:39, at least 97% identical to SEQ ID NO:39, at least 98% identical to SEQ ID NO:39, at least 99% identical to SEQ ID NO:39, and preferably is selected from the group consisting of: SEQ ID NO:39.

40. The viral vector according to clause 8, wherein the at least one exogenous antigen encoding sequence is a nucleocapsid protein ("N") encoding sequence and the nucleocapsid protein ("N") encoding sequence comprises a nucleic acid sequence encoding a polypeptide having an amino acid sequence which is at least 70% identical to SEQ ID NO:40, at least 75% identical to SEQ ID NO:40, at least 80% identical to SEQ ID NO:40, at least 85% identical to SEQ ID NO:40, at least 90% identical to SEQ ID NO:40, at least 91% identical to SEQ ID NO:40, at least 92% identical to SEQ ID NO:40, at least 93% identical to SEQ ID NO:40, at least 94% identical to SEQ ID NO:40, at least 95% identical to SEQ ID NO:40, at least 96% identical to SEQ ID NO:40, at least 97% identical to SEQ ID NO:40, at least 98% identical to SEQ ID NO:40, at least 99% identical to SEQ ID NO:40, and preferably is the amino acid sequence according to SEQ ID NO:40.

41. The viral vector according to clause 8, wherein the at least one exogenous antigen encoding sequence is a phosphoprotein ("P") encoding sequence and the phosphoprotein ("P") encoding sequence comprises a nucleic acid sequence which is at least 70% identical to SEQ ID NO:41, at least 75% identical to SEQ ID NO:41, at least 80% identical to SEQ ID NO:41, at least 85% identical to SEQ ID NO:41, at least 90% identical to SEQ ID NO:41, at least 91% identical to SEQ ID NO:41, at least 92% identical to SEQ ID NO:41, at least 93% identical to SEQ ID NO:41, at least 94% identical to SEQ ID NO:41, at least 95% identical to SEQ ID NO:41, at least 96% identical to SEQ ID NO:41, at least 97% identical to SEQ ID NO:41, at least 98% identical to SEQ ID NO:41, at least 99% identical to SEQ ID NO:41, and preferably is selected from the group consisting of: SEQ ID NO:41.

42. The viral vector according to clause 8, wherein the at least one exogenous antigen encoding sequence is a phosphoprotein ("P") encoding sequence and the phosphoprotein ("P") encoding sequence comprises a nucleic acid sequence encoding a polypeptide having an amino acid sequence which is at least 70% identical to SEQ ID NO:42, at least 75% identical to SEQ ID NO:42, at least 80% identical to SEQ ID NO:42, at least 85% identical to SEQ ID NO:42, at least 90% identical to SEQ ID NO:42, at least 91% identical to SEQ ID NO:42, at least 92% identical to SEQ ID NO:42, at least 93% identical to SEQ ID NO:42, at least 94% identical to SEQ ID NO:42, at least 95% identical to SEQ ID NO:42, at least 96% identical to SEQ ID NO:42, at least 97% identical to SEQ ID NO:42, at least 98% identical to SEQ ID NO:42, at least 99% identical to SEQ ID NO:42, and preferably is the amino acid sequence according to SEQ ID NO:42.

43. The viral vector according to clause 8, wherein the at least one exogenous antigen encoding sequence is a RNA-dependent RNA polymerase protein ("L") encoding sequence and the RNA-dependent RNA polymerase protein ("L") encoding sequence comprises a nucleic acid sequence which is at least 70% identical to SEQ ID NO:43, at least 75% identical to SEQ ID NO:43, at least 80% identical to SEQ ID NO:43, at least 85% identical to SEQ ID NO:43, at least 90% identical to SEQ ID NO:43, at least 91% identical to SEQ ID NO:43, at least 92% identical to SEQ ID NO:43, at least 93% identical to SEQ ID NO:43, at least 94% identical to SEQ ID NO:43, at least 95% identical to SEQ ID NO:43, at least 96% identical to SEQ ID NO:43, at least 97% identical to SEQ ID NO:43, at least 98% identical to SEQ ID NO:43, at least 99% identical to SEQ ID NO:43, and preferably is selected from the group consisting of: SEQ ID NO:43.

44. The viral vector according to clause 8, wherein the at least one exogenous antigen encoding sequence is a RNA-dependent RNA polymerase protein ("L") encoding sequence and the RNA-dependent RNA polymerase protein ("L") encoding sequence comprises a nucleic acid sequence encoding a polypeptide having an amino acid sequence which is at least 70% identical to SEQ ID NO:44, at least 75% identical to SEQ ID NO:44, at least 80% identical to SEQ ID NO:44, at least 85% identical to SEQ ID NO:44, at least 90% identical to SEQ ID NO:44, at least 91% identical to SEQ ID NO:44, at least 92% identical to SEQ ID NO:44, at least 93% identical to SEQ ID NO:44, at least 94% identical to SEQ ID NO:44, at least 95% identical to SEQ ID NO:44, at least 96% identical to SEQ ID NO:44, at least 97% identical to SEQ ID NO:44, at least 98% identical to SEQ ID NO:44, at least 99% identical to SEQ ID NO:44, and preferably is the amino acid sequence according to SEQ ID NO:44.

45. The viral vector according to any one of clauses 1 to 44, wherein the viral vector comprises two or more exogenous antigen encoding sequences, preferably a hemagglutinin protein ("H") encoding sequence and a matrix protein ("M") encoding sequence, or a hemagglutinin protein ("H") encoding sequence and a fusion protein ("F") encoding sequence, or a matrix protein ("M") encoding sequence and a fusion protein ("F") encoding sequence, or a hemagglutinin protein ("H") encoding sequence and a matrix protein ("M") encoding sequence and a fusion protein ("F") encoding sequence; or preferably the same two exogenous antigen coding sequences (i.e. H+H, F+F, M+M, P+P, L+L, N+N), but from two different strains, such as one exogenous antigen coding sequence from a feline paramyxovirus type 2 (FPaV-2) strain, more preferably the "Gordon strain" or the "TV25 strain", and the other one exogenous antigen coding sequence from a feline morbillivirus strain, more preferably the "Lapön strain"—for instance, a hemagglutinin protein ("H") encoding sequence of one strain and a hemagglutinin protein ("H") encoding sequence of another strain; more preferably, the one strain of "the hemagglutinin protein ("H") encoding sequence of one strain" is a feline paramyxovirus type 2 (FPaV-2) strain, even more preferably the "Gordon strain" or the "TV25 strain", and the another strain of the "hemagglutinin protein ("H") encoding sequence of another strain" is a feline morbillivirus strain, even more preferably the "Lapön strain"; most preferably, the one strain of "the hemagglutinin protein ("H") encoding sequence of one strain" is a hemagglutinin protein ("H") encoding sequence and the hemagglutinin protein ("H") encoding sequence comprises a nucleic acid sequence which is at least 70% identical to SEQ ID NO:4 or 19, at least 75% identical to SEQ ID NO:4 or 19, at least 80% identical to SEQ ID NO:4 or 19, at least 85% identical to SEQ ID NO:4 or 19, at least 90% identical to SEQ ID NO:4 or 19, at least 91% identical to SEQ ID NO:4 or 19, at least 92% identical to SEQ ID NO:4 or 19, at least 93% identical to SEQ ID NO:4 or 19, at least 94% identical to SEQ ID NO:4 or 19, at least 95% identical to SEQ ID NO:4 or 19, at least 96% identical to SEQ ID NO:4 or 19, at least 97% identical to SEQ ID NO:4 or 19, at least 98% identical to SEQ ID NO:4 or 19, at least 99% identical to SEQ ID NO:4 or 19, and preferably is selected from the group consisting of: SEQ ID NO:4, SEQ ID NO:5, SEQ ID NO:19; and the another strain of the "hemagglutinin protein ("H") encoding sequence of another strain" is a hemagglutinin protein ("H") encoding sequence and the hemagglutinin protein ("H") encoding sequence comprises a nucleic acid sequence which is at least 70% identical to SEQ ID NO:31 or 94, at least 75% identical to SEQ ID NO:31 or 94, at least 80% identical to SEQ ID NO:31 or 94, at least 85% identical to SEQ ID NO:31 or 94, at least 90% identical to SEQ ID NO:31 or 94, at least 91% identical to SEQ ID NO:31 or 94, at least 92% identical to SEQ ID NO:31 or 94, at least 93% identical to SEQ ID NO:31 or 94, at least 94% identical to SEQ ID NO:31 or 94, at least 95% identical to SEQ ID NO:31 or 94, at least 96% identical to SEQ ID NO:31 or 94, at least 97% identical to SEQ ID NO:31 or 94, at least 98% identical to SEQ ID NO:31 or 94, at least 99% identical to SEQ ID NO:31 or 94, and preferably is selected from the group consisting of: SEQ ID NO:31, SEQ ID NO:32, SEQ ID NO:94.

46. The viral vector according to any one of clauses 1 to 45, wherein the at least one exogenous antigen encoding sequence is inserted in at least one insertion locus, preferably in a non-essential region of the viral vector genome.

47. The viral vector according to clause 46, wherein the at least one exogenous antigen encoding sequence is inserted in two or more insertion loci.

48. The viral vector according to any one of clauses 46 to 47, wherein the at least one insertion locus is insertion locus C3.

49. The viral vector according to any one of clauses 46 to 48, wherein the viral vector comprises flanking sequences of the insertion locus C3, preferably according to SEQ ID NO:45 (C3 flanking region left arm) and SEQ ID NO:46 (C3 flanking region right arm).

50. The viral vector according to any one of clauses 46 to 49, wherein the at least one insertion locus is insertion locus C5.

51. The viral vector according to any one of clauses 46 to 50, wherein the viral vector comprises flanking sequences of the insertion locus C5, preferably according to SEQ ID NO:47 (C5 flanking region left arm) and SEQ ID NO:48 (C5 flanking region right arm).

52. The viral vector according to clauses 46 to 51, wherein the at least one insertion locus is insertion locus C6.

53. The viral vector according to any one of clauses 1 to 46, wherein the at least one exogenous antigen encoding sequence is operably linked to at least one promoter sequence, preferably a weak promoter sequence.

54. The viral vector according to clause 53, wherein the at least one promoter sequence is H6 vaccinia promoter.

55. The viral vector according to any one of clauses 53 to 54, wherein the at least one promoter sequence is I3L vaccinia promoter.

56. The viral vector according to any one of clauses 53 to 55, wherein the at least one promoter sequence is 42 k (long) poxviral promoter.

57. The viral vector according to any one of clauses 53 to 56, wherein the at least one promoter sequence is 7.5 k vaccinia promoter.

58. The viral vector according to any one of clauses 53 to 57, wherein the at least one promoter sequence is Pi vaccinia promoter.

59. The viral vector according to any one of clauses 1 to 58, wherein the viral vector further comprises additional regulatory sequences, such as a termination signal and/or polyadenylation sequence.

60. The viral vector according to any one of clauses 1 to 59, wherein the viral vector comprises a nucleic acid sequence which is at least 70%, 75%, 80%, 85%, 90%, 91%, 92%, 93%, 94%, 95%, 96%, 97%, 98%, 99% identical to the nucleic acid sequence selected from the group consisting of SEQ ID NO:49, SEQ ID NO:50, SEQ ID NO:51, SEQ ID NO:95, and preferably is the nucleic acid sequence selected from the group consisting of: SEQ ID NO:49, SEQ ID NO:50, SEQ ID NO:51, SEQ ID NO:95.

61. The viral vector according to any one of clauses 1 to 60, wherein the feline is a cat, preferably a domestic cat.

62. A mammalian host cell characterized in that it comprises the viral vector according to any one of clauses 1 to 61.

63. Use of the viral vector according to any one of clauses 1 to 61 or the mammalian host cell according to clause 62 for the manufacture of an immunogenic composition or vaccine.

64. An immunogenic composition comprising
(a) the viral vector according to any one of clauses 1 to 61 or the mammalian host cell according to clause 62, and/or
(b) a polypeptide encoded by the viral vector according to any one of clauses 1 to 61, such as a virus, a modified live virus, a virus like particle (VLP) or the like, and
(c) optionally a pharmaceutical- or veterinary-acceptable carrier or excipient, preferably said carrier being suitable for oral, intradermal, intramuscular or intranasal application;

wherein preferably said immunogenic composition comprises a virus, such as an infectious virus.

65. A vaccine or pharmaceutical composition comprising
(a) the viral vector according to any one of clauses 1 to 61 or the mammalian host cell according to clause 62, and/or
(b) a polypeptide encoded by the viral vector according to any one of clauses 1 to 61, such as a virus, a modified live virus, a virus like particle (VLP) or the like, and
(c) a pharmaceutical- or veterinary-acceptable carrier or excipient, preferably said carrier being suitable for oral, intradermal, intramuscular or intranasal application,
(d) optionally said vaccine or pharmaceutical composition further comprising an adjuvant.

66. A method for the preparation of an immunogenic composition or a vaccine for reducing the incidence and/or the severity of one or more clinical signs associated with or caused by an infection with at least one pathogenic paramyxovirus, comprising the following steps:
(a) infecting the mammalian host cell according to clause 62 with the viral vector according to any one of clauses 1 to 61,
(b) cultivating the infected cells under suitable conditions,
(c) collecting infected cell cultures,
(d) optionally purifying the collected infected cell cultures of step (c),
(e) optionally mixing said collected infected cell culture with a pharmaceutically acceptable carrier.

67. The immunogenic composition according to clause 64 or the vaccine according to clause 65 for use in a method of reducing or preventing the clinical signs or disease caused by an infection with at least one pathogenic paramyxovirus or for use in a method of treating and/or preventing an infection with at least one pathogenic paramyxovirus, wherein preferably said feline is a cat, more preferably a domestic cat, wherein preferably the at least one pathogenic paramyxovirus is at least one feline paramyxovirus, wherein preferably said clinical signs or disease caused by an infection with at least one pathogenic paramyxovirus or said infection with at least one pathogenic paramyxovirus are selected from the group consisting of: viremia, fever, virus shedding in the environment, infections of the urogenital system, infections of the urinary system, kidney disease, chronic kidney disease (CKD), inflammation of the renal tubules and renal interstitial tissue, idiopathic tubulointerstitial nephritis (TIN).

68. A method of immunizing a feline, such as a cat, more preferably a domestic cat, against a clinical disease caused by at least one pathogenic paramyxovirus in said feline, said method comprising the step of administering to the feline the immunogenic composition according to clause 64 or the vaccine according to clause 65, wherein said immunogenic composition or vaccine fails to cause clinical signs of infection but is capable of inducing an immune response that immunizes the feline against pathogenic forms of said at least one paramyxovirus, wherein preferably the at least one pathogenic paramyxovirus is at least one feline paramyxovirus, wherein preferably said clinical disease or said clinical signs of infection are selected from the group consisting of: viremia, fever, virus shedding in the environment, infections of the urogenital system, infections of the urinary system, kidney disease, chronic kidney disease (CKD), inflammation of the renal tubules and renal interstitial tissue, idiopathic tubulointerstitial nephritis (TIN).

69. A kit for vaccinating a feline, preferably a cat, more preferably a domestic cat, against a disease associated with and/or reducing the incidence or the severity of one or more clinical signs associated with or caused by at least one pathogenic paramyxovirus in a feline comprising:
(a) a dispenser capable of administering a vaccine to said feline; and
(b) the immunogenic composition according to clause 64 or the vaccine according to clause 65, and
(c) optionally an instruction leaflet;

wherein preferably the at least one pathogenic paramyxovirus is at least one feline paramyxovirus, wherein preferably said disease or said clinical signs are selected from the group consisting of: viremia, fever, virus shedding in the environment, infections of the urogenital system, infections of the urinary system, kidney disease, chronic kidney disease (CKD), inflammation of the renal tubules and renal interstitial tissue, idiopathic tubulointerstitial nephritis (TIN).

EXAMPLES

Example 1: Construction of vCP3025: ALVAC C5/H6p Synthetic Gordon H and vCP3029: ALVAC C3/42 k Long Synthetic Gordon M+C5/H6p Synthetic Gordon H (comprising SEQ ID NOS: 49, 50 and 51; FIGS. 2, 3 and 4)

Purpose: To generate two ALVAC constructs: one with a single insert and one with a double insert. The single construct expresses codon optimized Gordon H in the C5 insertion locus under an H6 promoter. The double construct expresses both codon optimized Gordon H in the C5 insertion locus under an H6 promoter and codon optimized Gordon M in the C3 insertion locus under a 42 k long promoter.

Genes: Synthetic Gordon H; Synthetic Gordon M

General information of recombinant:

A. Parental virus: later passage derived ALVAC, essentially the same virus as parental ALVAC ATCC VR-2547, except the passage level; Titer=1.5×10^10 pfu/mL
B. Donor plasmids: pC5 H6p Gordon H (opt); pC3 42 K Gordon M (opt)
C. Insertion locus: single=C5; double=C3 and C5
D. Promoters: C5 site/insertion locus=H6 promoter; C3 site/insertion locus=42 k Long promoter
E. Cells for in vitro recombination: Primary chicken embryo fibroblast cells (1° CEF)
F. Methods for recombinant selection: Plaque hybridization by Gordon H and Gordon M specific probes Detailed Description of Recombinant Generation.

The in vitro recombination (IVR) is performed by transfection of 1° CEF cells with Not I-linearized donor plasmids. A single IVR is performed using 20 μg of each donor plasmids [pC5 H6p Gordon H (opt) and pC3 42 K Gordon M (opt)]. Fugene HD (Promega Cat #E2311) is the transfection reagent. The transfected cells are subsequently infected with parental ALVAC as rescue virus at MOI of 10. After 24 hours, the transfected-infected cells are harvested, sonicated and used for recombinant virus screening.

Recombinant plaques are screened based on the plaque lift hybridization method. Infected monolayers are lifted onto positively charged nylon transfer membranes (GE Healthcare Cat #RPN82B) and copies of those lifts are made by pressing additional nylon membranes against the original lifts in the presence of lifting buffer. The copies are probed with either a biotin labeled Gordon H-specific probe or a biotin labeled Gordon M-specific probe. In rounds 3 and 4, a third set of lifts are made and probed with ALVAC specific parental probes (C3 probe in round 3; C5 probe in round 4). The ALVAC parental probes bind to regions of the ORFs which are deleted during recombination. Probes are labeled using Thermo Scientific DecaLabel DNA Labeling Kit; product #10622. Probed lifts are developed using Thermo Scientific Chemiluminescent Nucleic Acid Detection Module Kit; product #89880. Recombinant plaques are selected, cut from the original membrane, and used for infection in the next round of purification. In the third sequential round of plaque purification, a recombinant designated as vCP3029.2.2.1 is picked. Based on film results, this plaque is expected to produce double insert virus in the next round of screening. However, plating of this picked plaque in the fourth round of screening produces both single insert [Gordon H (opt) in the C5 site] and double insert [Gordon H (opt) in the C5 site and Gordon M (opt) in the C3 site] plaques. The double insert plaque is picked and labeled vCP3029.2.2.1.2. The single insert plaque is picked and labeled vCP3025.2.2.1.1.

A fifth and final round of plaque purification is performed for vCP3025.2.2.1.1 and for vCP3029.2.2.1.2. Two agarose punches of individual plaques are taken from the undiluted plate of vCP3025.2.2.1.1 (vCP3025.2.2.1.1.1 and vCP3025.2.2.1.1.2). Similarly, three agarose punches of individual plaques are taken from the undiluted plate of vCP3029.2.2.1.2. (vCP3029.2.2.1.2.3, vCP3029.2.2.1.2.4, and vCP3029.2.2.1.2.5). These punches are expanded to obtain P1s (passage 1) (T-25 flask). PCR testing confirms that vCP3025.2.2.1.1.2 contains the Gordon H (opt) insert in the C5 site and that it does not contain Gordon M (opt) insert in the C3 site. Similarly, PCR testing confirms that vCP3029.2.2.1.2.3 contains the Gordon H (opt) insert in the C5 site and the Gordon M (opt) insert in the C3 site. vCP3025.2.2.1.1.2 (single insert) and vCP3029.2.2.1.2.3 (double insert) are expanded to P2 (passage 2) (two T-150 flasks for each construct). These P2 stocks are referred to as vCP3025 P2 and vCP3029 P2.

vCP3025 P2 and vCP3029 P2 are scaled up to P3 (passage 3) (four roller bottles per construct). The P3 materials are concentrated and purified via sucrose pellet. These P3 stocks are referred to as vCP3025 and vCP3029.

Analysis of recombinant: The following analyses are performed on the P3 stocks

Sterility: Sterility testing is performed on the P3 stocks of vCP3025 and vCP3029. For each construct, 50 μL aliquots are plated onto each of two Sabouraud Dextrose Agar (SDA) plates and onto each of two Trypticase Soy Agar with 5% Sheep's Blood (TSA II 5% SB) plates (BBL Catalogue #221180 and #221239, respectively). For each construct, one SDA plate and one TSA II 5% SB plate are incubated at 37° C. for 10 days, and the other set of plates are incubated at room temperature for 10 days. At the end of 10 days, none of the plates shows any signs of bacterial or fungal growth.

Confirmation of Genetic Purity:

Purity of the P3 stocks are confirmed via several separate PCR reactions. The first PCR reaction uses primers located at either end of the C5 arms (primers 7931 and 7932). These primers produce a 2,470 bp band for wild type ALVAC and a 4240 bp band for recombinants containing Gordon H (opt) in the C5 site. Although primers exist that would amplify the entire C3 region, those primers would produce a 4539 bp band for wild type ALVAC and a 4289 bp band recombinants containing Gordon M (opt) in the C3 site. This size difference is hard to detect on a gel. For that reason, two other PCRs are performed to analyze the C3 site. In the first reaction, primers used to make the Gordon M probe (Gordon_M_probe_F and Gordon_M_probe_R) are used to amplify the samples. These primers produce a 621 bp band for recombinants containing Gordon M (opt) in the C3 site and produce no band for wild type ALVAC. In the second reaction, primers used to make the wild type C3 probe (C3F and C3R) are used to amplify the samples. These primers are located in a region that is deleted during recombination and produce a 1007 bp band for wild type ALVAC and no band for recombinants containing Gordon M (opt) in the C3 site.

Sequence analysis: More detailed sequence analyses of the P3 stocks are performed by PCR amplification and sequence analysis of the C5 site for vCP3025 and of the C3 and C5 sites for vCP3029. The C5 sites are amplified using primers 7931 and 7932, which are located just outside the C5 recombination arms. The C3 site is amplified using primers C3-PCR-F and C3-PCR-R, which are located just outside the C3 recombination arms. In all cases, the PCR produces a single band of the expected size and sequencing demonstrates the expected results for the recombined arm.

Methods, Reagents, and Primers

Primers for amplifying the Gordon H (opt) probe:

| | | |
|---|---|---|
| Gordon H probe F | GTTCGCCACCGTGAACATCC | (SEQ ID NO: 89) |
| Gordon H probe R | CACTGCCTTCACGGTCACG | (SEQ ID NO: 88) |

Primers for amplifying the Gordon M (opt) probe:

| | | |
|---|---|---|
| Gordon M probe F | GGAGATCCTGACTCTGAACATCG | (SEQ ID NO: 52) |
| Gordon M probe R | CTCCACAGAGTTTTATTCAGCCC | (SEQ ID NO: 53) |

Primers for amplifying ALVAC Parental probe (C3 site):

| | | |
|---|---|---|
| C3F | CGTAGAGTTTTTTGTCTAGTTCTAT | (SEQ ID NO: 54) |
| C3R | GTTGTTTTATGCGGTAAAGAATAAT | (SEQ ID NO: 55) |

Primers for amplifying ALVAC Parental probe (C5 site):

| | | |
|---|---|---|
| 7520 | TCTTGCTTCGCAGTCATCGTTCTG | (SEQ ID NO: 56) |
| 7521 | TCTAAAATGCATAATTTCTAA | (SEQ ID NO: 57) |

Primers for PCR amplification of the C3 site for sequencing:

| | | |
|---|---|---|
| C3-PCR-F | GCTAACACAAGTTAGAGGCGTATTAC | (SEQ ID NO: 58) |
| C3-PCR-R | CATTAATTATGTGATGAGGCATCCAAC | (SEQ ID NO: 59) |

Primers for PCR amplification of the C5 site for sequencing:

| | | |
|---|---|---|
| 7931 | GAATCTGTTAGTTAGTTACTTGGAT | (SEQ ID NO: 75) |
| 7932 | TGATTATAGCTATTATCACAGACTC | (SEQ ID NO: 76) |

Primers for sequencing the C3 Site:

| | | |
|---|---|---|
| C3-PCR-F | GCTAACACAAGTTAGAGGCGTATTAC | (SEQ ID NO: 58) |
| C3-PCR-R | CATTAATTATGTGATGAGGCATCCAAC | (SEQ ID NO: 59) |
| C3-R1 | TTTATAGGTAAATCCAGGAA | (SEQ ID NO: 60) |
| C3-R2 | GCCTACTAAGAAAACTAGAAGATAC | (SEQ ID NO: 61) |
| C3-R3 | AGATTGATATAAATGAATATGTAA | (SEQ ID NO: 62) |
| C3-R4 | CGACGTTAGGTTAGATACTG | (SEQ ID NO: 63) |
| C3-R5 | ATGCGGTACCCTGTTCGAAG | (SEQ ID NO: 64) |
| C3-R6 | CAGAAATGAGTAATGGAAGA | (SEQ ID NO: 65) |
| C3-R7 | CTGGAAATAGTCCGTTATAT | (SEQ ID NO: 66) |
| C3-R8 | CAGTATCTCATAAAGGCACTTA | (SEQ ID NO: 67) |
| C3-R9 | CCGTTCTAAATATAGCTGTTGCAT | (SEQ ID NO: 68) |
| Gordon M 1F | ATGACTGAGATCTTCAACCTGG | (SEQ ID NO: 69) |
| Gordon M 2F | TGAGCATGGGGACCATCCTG | (SEQ ID NO: 70) |
| Gordon M 3F | GGGCTGAATAAAACTCTGTGGAG | (SEQ ID NO: 71) |
| Gordon M probe F | GGAGATCCTGACTCTGAACATCG | (SEQ ID NO: 52) |
| Gordon M 1R | CGATGTTCAGAGTCAGGATCTCC | (SEQ ID NO: 72) |
| C3-F5 | CACGGATTATCTACTGTGAT | (SEQ ID NO: 73) |
| C3-F7 | GCAACAGTAGTTATACGATGAG | (SEQ ID NO: 74) |

Primers for sequencing the C5 Site:

| | | |
|---|---|---|
| 7931 | GAATCTGTTAGTTAGTTACTTGGAT | (SEQ ID NO: 75) |
| 7932 | TGATTATAGCTATTATCACAGACTC | (SEQ ID NO: 76) |
| 7927.DC | CTCTTGCATATTCGTAATAGTAATTG | (SEQ ID NO: 77) |
| 7696.CXL | ATTCTATCGGAAGATAGGATACCAG | (SEQ ID NO: 78) |
| 7697.CXL | ATGCACAACTTCTTGTCTGCATGATG | (SEQ ID NO: 79) |
| 7925.DC | TACGGCTATATGTAGAGGAGTTAACC | (SEQ ID NO: 80) |
| 7792.SL | CTCTGAGACACAAAAGAGGTAGCTG | (SEQ ID NO: 81) |

-continued

```
                                     (SEQ ID NO: 82)
7793SL            CATAGAACGGTATAGAGCGTTAATC (SEQ ID NO: 83)
7928.DC           CATCATGAGCAACGCGTTAGTATAT (SEQ ID NO: 84)
7929.DC           GGAGATACCTTTAGATATGGATCTG (SEQ ID NO: 85)
7926.DC           TCAACAACCGCTCGTGAACAGCTTC (SEQ ID NO: 86)
Gordon H 1R       GCTCGGTGCTCATTGCGTTG (SEQ ID NO: 87)
Gordon H 2F       CAACGCAATGAGCACCGAGC (SEQ ID NO: 88)
Gordon H probe R  CACTGCCTTCACGGTCACG (SEQ ID NO: 89)
Gordon H probe F  GTTCGCCACCGTGAACATCC (SEQ ID NO: 90)
Gordon H 1F       TCGCGATATCCGTTAAGTTTGTA (SEQ ID NO: 91)
Gordon H 3F       GAATATCCCCACCAGGTCTATCTAC (SEQ ID NO: 92)
Gordon H 4F       TACCGACGATGTGCCCATCC (SEQ ID NO: 93)
Gordon H 5F       ATCTCCGACGGCCTGATCAT
```

Cells for in vitro recombination: Primary chicken embryo fibroblast cells (1° CEF) are grown in 10% FBS (Hyclone Cat #SH30071.03) DMEM (Gibco Cat #11960) supplemented with 4 mM Glutamine (Gibco Cat #25030) and 1 mM Sodium Pyruvate (Gibco #11360) in the presence of 1× antibiotics/antimycotics (P/S/A/A, Gibco Cat #15240). Fugene transfection reagent (Promega Cat #E2311).

Final virus concentrate is re-suspended in 1 mM Tris, pH9.0 vCP3025 titer=2.3×10^9 pfu/mL
vCP3029 titer=1.9×10^9 pfu/mL

Example 2: Vaccination Example (vCP3025—Gordon H; Comprising SEQ ID NO: 49; FIG. 2)

On SD0 and SD21, a total dose of 1 mL of the ALVAC-Gordon H vector vaccine with a titer of approximately $1 \times 10^8$ TCID$_{50}$/mL is administered to the group of 8 cats (group 1). This dose is expected to deliver sufficient amounts of vaccine virus in order to facilitate immune response towards the selected antigen (FaPV-2 hemagglutinin). The negative control (group 3) is vaccinated with an irrelevant ALVAC vector construct (i.e. ALVAC rabies). The animals are blood sampled on SD0, SD21 and SD 42 and humoral immune response is measured by specific ELISA, immunofluorescence assay (IFA) and/or virus/serum neutralization test (VNT/SNT) (Example 4). On SD42 the animals of the respective groups are intravenously (IV) inoculated with the challenge virus as described below (Example 5) and given infection parameters are measured in addition (viremia, shedding, virus distribution).

Example 3: Vaccination Example (vCP3029—Gordon H+Gordon M; Comprising SEQ ID NOS: 50+51; FIGS. 3+4)

On SD0 and SD21, a total dose of 1 mL of the ALVAC-Gordon H+M vector vaccine with a titer of approximately $1 \times 10^8$ TCID$_{50}$/mL is administered to the group of 8 cats (group 2). This dose is expected to deliver sufficient amounts of vaccine virus in order to facilitate immune response towards the selected antigens (FaPV-2 hemagglutinin and matrix protein). The negative control (group 3) is vaccinated with an irrelevant ALVAC vector construct (i.e. ALVAC rabies). The animals are blood sampled on SD0, SD21 and SD 42 and humoral immune response is measured by specific ELISA, immunofluorescence assay (IFA) and/or virus/serum neutralization test (VNT/SNT) (Example 4). On SD42 the animals of the respective groups are intravenously (IV) inoculated with the challenge virus as described below (Example 5) and given infection parameters are measured (viremia, shedding, virus distribution).

Example 4: Virus Neutralization Test (VNT)/Serum Neutralization Test (SNT)

To detect neutralizing antibodies against feline paramyxovirus, such as FPaV-2, a virus/serum neutralization assay (VNT/SNT) is performed. Therefore, cat serum samples are treated at 56° C. for 30 minutes to inactivate complement factors. 50 µl of these heat inactivated serum samples are mixed with 50 µl DMEM containing 100 fluorescence forming units (FFU) of feline paramyxovirus, such as FPaV-2 (isolate 'Gordon'), and are then incubated for one hour at 4° C. The mixture is used to infect LLC-MK2-cells in a 96-well cell culture plate for two hours at 37° C. Then the serum/virus-mixture is removed and replaced by DMEM containing 2% (v/v) heat inactivated FBS, sodium pyruvate, non-essential amino acids, penicillin and streptomycin. The cells are incubated for five days at 37° C., 5% $CO_2$ and 90% humidity followed by immunofluorescence staining as described below. The neutralization titer of the test serum sample is defined as the reciprocal of the highest test serum dilution for which the virus infectivity is reduced by 50% when compared to the virus control without serum incubation.

To detect feline paramyxovirus infections, such as FPaV-2 infections, LLC-MK2 cells are infected as described below and stained with a feline paramyxovirus-specific antibody using immunofluorescence techniques. For this purpose adherent cells are washed with PBS after an infection period of 5 days and subsequently fixed with 80% of acetone at −20° C. for 10 minutes. Cells are washed twice with PBS and unspecific binding is blocked by incubation with 5% BSA in PBS at 37° C. for one hour. This is followed by an incubation step with anti-feline paramyxovirus antibody (e.g. anti-FPaV-2 nucleocapsid, polyclonal, rabbit) at a final concentration of 1 µg/ml in 1% BSA in PBS for one hour at 37° C. Cells are washed three time with PBS followed by the application of 'Goat anti-Rabbit IgG (H+L) Secondary Antibody, Alexa Fluor® 488 conjugate' (Thermo Fisher Scientific) at a final dilution of 1:1000 in 1% BSA in PBS. After an incubation time of one hour at 37° C. cells are washed twice with PBS and cells are screened for the presence of FPaV-2 using a fluorescence microscope.

For virus cultivation LLC-MK2 and CrFK cells are seeded in 75 cm$^2$ cell culture flasks in DMEM (with sodium pyruvate and non-essential amino acids) with 5% of FBS in an atmosphere including 5% carbon dioxide at 37° C. and 90% humidity. At 70-80% confluence cells are infected with a mixture of one milliliter urine and 5 ml DMEM (with penicillin and streptomycin) over night at 37° C., 5% $CO_2$ and 90% humidity. After 24 hours the infection medium is replaced by 8 ml of cultivation medium (DMEM, sodium pyruvate, non-essential amino acids, 5% FBS, penicillin and streptomycin) and cultivated for further 6 days at the indicated conditions. The cell culture supernatant from this infection is passaged for further three times. Afterwards 600 μl of the cell culture supernatant are tested for the presence of feline paramyxoviruses.

Example 5: Challenge Model

A challenge model clinical study to investigate on early stages of infection and disease expression is employed. An intravenous (IV) challenge at a dose as close as possible to a challenge dose of $1 \times 10^5$ $TCID_{50}$/mL with the FPaV-2 "Gordon strain" is performed with a follow-up of 56 days post challenge. As no clinical signs of CKD are expected, the main objectives of the challenge model clinical study are to monitor primo infection, possible effect of infection on renal function, immune response to the infection, to evaluate a potential spreading and to confirm the virus settlement in kidney by immunohistochemistry (IHC) and possibly other organs.

Expected symptoms at early stages of the disease are associated with viremia (apathy, hyperthermia, weight loss). Expected symptoms at late stages are possibly related to chronic renal failure (bodyweight loss, uremia, mucosal lesions). Virus stock of FPaV-2 "Gordon strain" (with the titer $1\times10^5$ $TCID_{50}$/ml) is prepared on primary cat peripheral blood mononuclear cells (PBMCs) or on other cells like LLC-MK2 cell line. The stock has been tested negative for the presence of common feline pathogens (including feline panleucopenia virus, feline immunodeficiency virus, feline leukemia virus and feline coronavirus, respectively). Cats, mixed breed are inoculated with 1 ml ($1\times10^5$ TCID50/ml) of virus stock intravenously (IV).

Experimental plan and follow-up: for a graphical overview, refer to FIG. 5.

Below cat groups A1, A2, B1, B2, C1, and C2 represent different timings of necropsy: A1 and A2 at D14, B1 and B2 at D28, C1 and C2 at D56. The subdivision is motivated by avoiding the sampling of all the cats every day in order to avoid too much stress for the animals Clinical examination and rectal temperature on a daily basis from D0 to D14 (except week ends) and twice a week from D15 to D56

Weighing twice a week from D0 to D56

Blood sampling for viremia monitoring by PCR

| Viremia | D-7 | D1 | D2 | D3 | D4 | D5 | D6 | D7 | D8 | D9 | D10 | D11 | D12 | D14 | D21 | D28 | D35 | D42 | D49 | D56 |
|---|---|---|---|---|---|---|---|---|---|---|---|---|---|---|---|---|---|---|---|---|
| A1 | X | X | | | | | | X | | | | | | X | | | | | | |
| A2 | X | | X | | | | | | X | | | | | X | | | | | | |
| B1 | X | | | X | | | | | | X | | | | | X | X | | | | |
| B2 | X | | | | X | | | | | | X | | | | | X | | | | |
| C1 | X | | | | | X | | | | | | X | | | | | X | | X | X |
| C2 | X | | | | | | X | | | | | | x | | | | | X | | X |

Urine sampling for viremia monitoring by PCR and lipiduria

| Urine | D7 | D14 | D21 | D28 | D35 | D42 | D49 | D56 |
|---|---|---|---|---|---|---|---|---|
| A1 | C | PM | | | | | | |
| A2 | | PM | | | | | | |
| B1 | | | C | PM | | | | |
| B2 | | | | PM | | | | |
| C1 | | | | | C | | C | PM |
| C2 | | | | | | C | | PM |

(C = cystocenthesis; PM = post mortem)

Oro-nasal swabs for viremia monitoring by PCR

| Swabs | D-7 | D1 | D2 | D3 | D4 | D5 | D6 | D7 | D8 | D9 | D10 | D11 | D12 | D14 | D21 | D28 | D35 | D42 | D49 | D56 |
|---|---|---|---|---|---|---|---|---|---|---|---|---|---|---|---|---|---|---|---|---|
| A1 | X | X | | | | | | X | | | | | | X | | | | | | |
| A2 | X | | X | | | | | | X | | | | | X | | | | | | |
| B1 | X | | | X | | | | | | X | | | | | X | X | | | | |
| B2 | X | | | | X | | | | | | X | | | | | X | | | | |
| C1 | X | | | | | X | | | | | | X | | | | | X | | X | X |
| C2 | X | | | | | | X | | | | | | x | | | | | X | | X |

Blood biochemistry and cell count

| | D-7 | D14 | D21 | D28 | D35 | D42 | D49 | D56 |
|---|---|---|---|---|---|---|---|---|
| A1 | X | X | | | | | | |
| A2 | X | X | | | | | | |
| B1 | X | | X | X | | | | |
| B2 | X | | | X | | | | |
| C1 | X | | | | X | | X | X |
| C2 | X | | | | | X | | X |

Sera sampling for serology

| Serology | D-7 | D7 or D8 | D14 | D28 | D56 |
|---|---|---|---|---|---|
| A1 | X | X | X | | |
| A2 | X | X | X | | |
| B1 | X | | | X | |
| B2 | X | | | X | |
| C1 | X | | | | X |
| C2 | X | | | | X |

Necropsy and histology Full necropsy is performed for each animal with sampling of kidney, spleen, liver, bladder and lung. Organs are sampled for histology and viral detection by PCR.

The challenge model clinical study tests the hypothesis that the viral vector based vaccines according to the present invention are able to prevent and/or reduce the intensity and/or duration of feline paramyxovirus viremia upon challenge in cats. In addition, the vaccination of cats with the viral vectors of the underlying invention induces antibodies against e.g. feline paramyxovirus hemagglutinin antigen.

Example 6: Construction of vCP3041: ALVAC C5/H6p Synthetic Gordon H+C3/42 k Long Wild Type Lapön H (Comprising SEQ ID NOS: 49+95)

Figure 6:
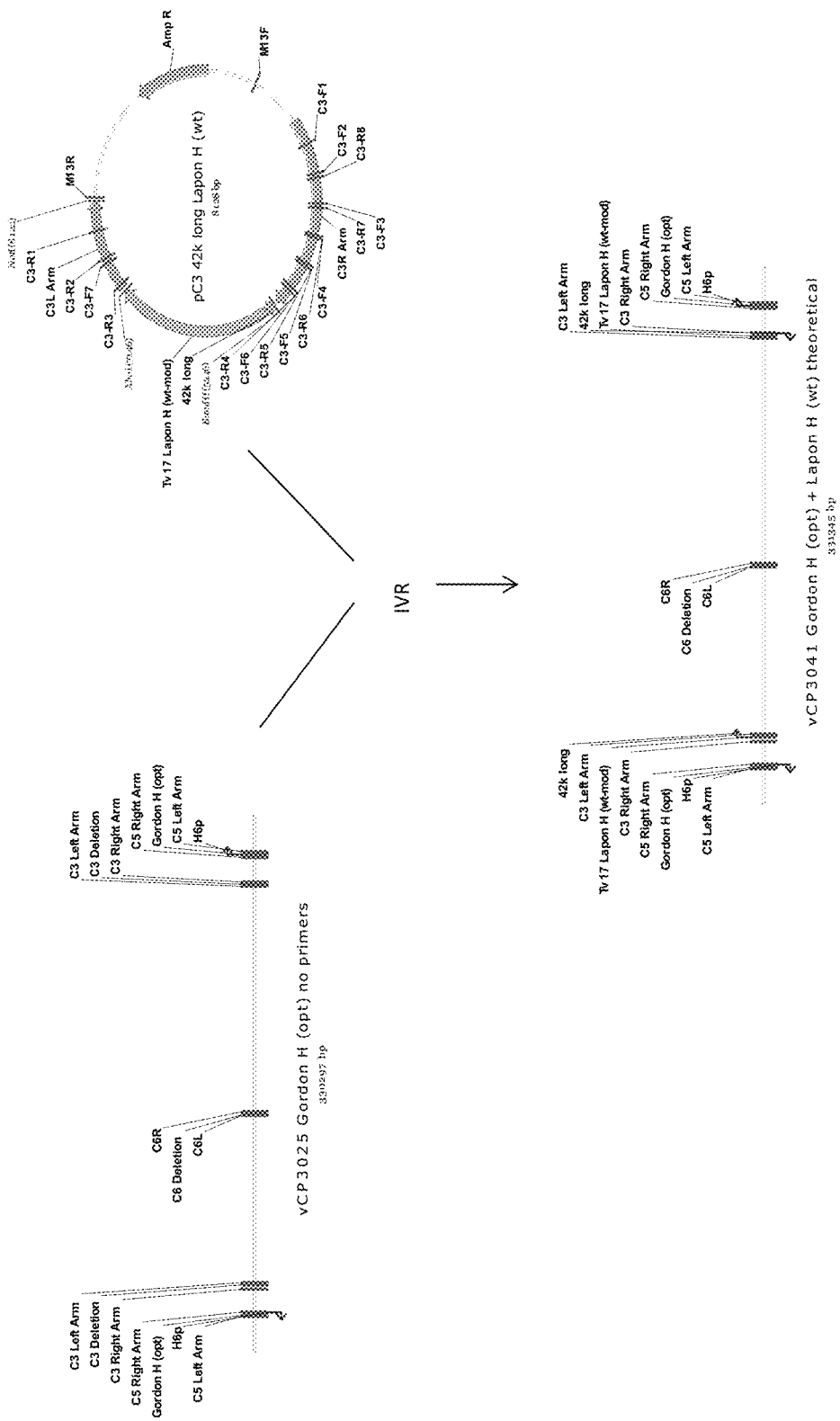
FIG. 6 depicts the schematic overview about the in vitro recombination (IVR) with the parent ALVAC vector vCP3025 and donor plasmid pC3 42 k long Lapön H (wt—without BamH1 restriction enzyme site) and the resulting construct vCP3041.

Purpose: To generate an ALVAC construct with a double insert. The construct expresses codon optimized Gordon H in the C5 insertion locus under an H6 promoter (used as a parent) and wild type Lapön H (without BamH1 restriction enzyme site; SEQ ID NO: 94) in the C3 insertion locus under a 42 k long promoter (new insert) (FIGS. 6 and 7).

Genes: Synthetic Gordon H; Wild Type Lapön H
General information of recombinant:
A. Parental virus: vCP3025: ALVAC C5/H6p Synthetic Gordon H; Titer=2.3×10^9 pfu/mL
B. Donor plasmids: pC3 42 k long Lapön H (wt—without BamH1 restriction enzyme site)
C. Insertion locus: C3
D. Promoters: 42 k Long promoter
E. Cells for in vitro recombination: Primary chicken embryo fibroblast cells (1° CEF)
F. Methods for recombinant selection: Plaque hybridization by Gordon H (opt) and Lapön H (wt) specific probes Detailed Description of Recombinant Generation.
G. The in vitro recombination (IVR) is performed by transfection of 1° CEF cells with 20 µg of Not I-linearized donor plasmid [pC3 42 k long Lapön H (wt—without BamH1 restriction enzyme site)]. Fugene HD (Promega Cat #E2311) is the transfection reagent. The transfected cells are subsequently infected with vCP3025 as rescue virus at MOI of 10. After 24 hours, the transfected-infected cells are harvested, sonicated and used for recombinant virus screening.

Recombinant plaques are screened based on the plaque lift hybridization method. Infected monolayers are lifted onto positively charged nylon transfer membranes (GE Healthcare Cat #RPN82B) and copies of those lifts made by pressing additional nylon membranes against the original lifts in the presence of lifting buffer. The copies are probed with a biotin labeled Lapön H (wt—without BamH1 restriction enzyme site)-specific probe or a biotin labeled ALVAC parental C3 probe. The ALVAC parental probe binds to a region of the ORF which is deleted during recombination. Probes are labeled using Thermo Scientific DecaLabel DNA Labeling Kit; product #10622. Probed lifts are developed using Thermo Scientific Chemiluminescent Nucleic Acid Detection Module Kit; product #89880. Recombinant plaques are selected, cut from the original membrane, and used for infection in the next round of purification. Following three or four rounds of sequential plaque purification, recombinants containing the Lapön H (wt—without BamH1 restriction enzyme site) gene in the C3 locus is isolated.

In a final round of purification, several agarose punches are taken of single, isolated plaques. These punches are expanded to obtain P1s (passage 1) (T-25 flask). PCR testing is performed to confirm which P1s contain both the Gordon H (opt) insert in the C5 sites and the Lapön H (wt—without BamH1 restriction enzyme site) inserts in the C3 sites. Two acceptable candidates are expanded to P2 (passage 2) (two T-150 flasks for each construct).

A single P2 is scaled up to P3 (passage 3) (four roller bottles). The P3 material is concentrated and purified via sucrose pellet and referred to as vCP3041.

Analysis of recombinant: The following analyses is performed on the P3 stocks

Sterility: Sterility testing is performed on the P3 stocks of vCP3041. 50 µL aliquots are plated onto each of two Sabouraud Dextrose Agar (SDA) plates and onto each of two Trypticase Soy Agar with 5% Sheep's Blood (TSA II 5% SB) plates (BBL Catalogue #221180 and #221239, respectively). For each construct, one SDA plate and one TSA II 5% SB plate are incubated at 37° C. for 10 days, and the other set of plates is incubated at room temperature for 10 days. If after 10 days, no bacterial or fungal growth is visible on any of the plates the construct have passed sterility testing.

Confirmation of Genetic Purity:

Purity of the P3 stocks are confirmed via PCR. Primers located at either end of the C3 arms (C3-PCR-F and C3-PCR-R) are used to amplify samples. These primers produce a 4539 bp band for ALVAC viruses containing wild type sequence at the C3 site and a 5063 bp band for recombinants containing Lapön H (wt—without BamH1 restriction enzyme site) in the C3 site. A second PCR may be useful should it be difficult to distinguish between the ~4.5 Kb and ~5 Kb bands in the first PCR. The second PCR includes primers used to make the wild type C3 probe (C3F and C3R). These primers are located in a region that is deleted during recombination of the C3 site and produce a 1007 bp band for wild type ALVAC sequence and no band for recombinants. This second PCR confirms that no parental virus remains in the P3 sample.

Sequence analysis: More detailed sequence analyses of the P3 stocks is performed by PCR amplification and sequence analysis of the C3 and C5 sites for vCP3041. The C5 sites are amplified using primers 7931 and 7932 which are located just outside the C5 recombination arms. The C3 site are amplified using primers C3-PCR-F and C3-PCR-R which are located just outside the C3 recombination arms. Amplified regions are sequenced to confirm the integrity of promoters and genes.

Primers

Primers for amplifying ALVAC Parental probe (C3 site):

```
                                     (SEQ ID NO: 54)
C3F         CGTAGAGTTTTTTGTCTAGTTCTAT (SEQ ID NO: 55)
C3R         GTTGTTTTATGCGGTAAAGAATAAT
```

Primers for amplifying the C3 Site:

```
                                     (SEQ ID NO: 58)
C3-PCR-F    GCTAACACAAGTTAGAGGCGTATTAC (SEQ ID NO: 59)
C3-PCR-R    CATTAATTATGTGATGAGGCATCCAAC
```

Primers for amplifying the C5 Site:

```
                                         (SEQ ID NO: 75)
7931         GAATCTGTTAGTTAGTTACTTGGAT (SEQ ID NO: 76)
7932         TGATTATAGCTATTATCACAGACTC
```

Example 7: Vaccination Example
(vCP3025—Gordon H; Comprising SEQ ID NO: 49; FIG. 2)

On SD0 and SD21, a total dose of 1 mL of the ALVAC-Gordon H vector vaccine with a titer of approximately $1\times10^{7.7}$ TCID$_{50}$/dose is administered to the group of 7 cats (group A). This dose is expected to deliver sufficient amounts of vaccine virus in order to facilitate immune response towards the selected antigen (FaPV-2 hemagglutinin). The negative control (group C) is not vaccinated. The animals are blood sampled on SD0, SD21 and SD 35 and humoral immune response is measured by specific ELISA, immunofluorescence assay (IFA) and/or virus/serum neutralization test (VNT/SNT) (Example 9). On SD49 the animals of the respective groups are intravenously (IV) inoculated with the challenge virus as described below (Example 10) and given infection parameters are measured in addition (viremia, shedding, virus distribution).

Example 8: Vaccination Example (vCP3029—Gordon H+Gordon M; Comprising SEQ ID NOS: 50+51; FIGS. 3+4)

On SD0 and SD21, a total dose of 1 mL of the ALVAC-Gordon H+M vector vaccine with a titer of approximately $1\times10^{7.7}$ $TCID_{50}$/dose is administered to the group of 7 cats (group B). This dose is expected to deliver sufficient amounts of vaccine virus in order to facilitate immune response towards the selected antigens (FaPV-2 hemagglutinin and matrix protein). The negative control (group C) is not vaccinated. The animals are blood sampled on SD0, SD21 and SD 35 and humoral immune response is measured by specific ELISA, immunofluorescence assay (IFA) and/or virus/serum neutralization test (VNT/SNT) (Example 9). On SD42 the animals of the respective groups are intravenously (IV) inoculated with the challenge virus as described below (Example 10) and given infection parameters are measured (viremia, shedding, virus distribution).

Example 9: Virus Neutralization Test (VNT)/Serum Neutralization Test (SNT)

To detect neutralizing antibodies against feline paramyxovirus, such as FPaV-2, a virus/serum neutralization assay (VNT/SNT) is performed. Therefore, cat serum samples are treated at 56° C. for 30 minutes to inactivate complement factors. 50 µl of these heat inactivated serum samples are mixed with 50 µl DMEM containing 100 TCID50 fluorescence forming units (FFU) of feline paramyxovirus, such as FPaV-2 (isolate 'Gordon'), and are then incubated for one hour at 37° C. The mixture is used to infect LLC-MK2-cells in a 96-well cell culture plate for two hours at 37° C. The cells are incubated for five days at 37° C., 5% $CO_2$ and 90% humidity followed by immunofluorescence staining as described below. The neutralization titer of the test serum sample is defined as the reciprocal of the highest test serum dilution for which the virus infectivity is reduced by 50% when compared to the virus control without serum incubation.

To detect feline paramyxovirus infections, such as FPaV-2 infections, LLC-MK2 cells are infected as described below and stained with a feline paramyxovirus-specific antibody using immunofluorescence techniques. For this purpose adherent cells are washed with PBS after an infection period of 5 days and subsequently fixed with 80% of acetone at −20° C. for 10 minutes. Cells are washed twice with PBS and unspecific binding is blocked by incubation with 5% BSA in PBS at 37° C. for one hour. This is followed by an incubation step with anti-feline paramyxovirus antibody (e.g. anti-FPaV-2 nucleocapsid, polyclonal, rabbit) at a final concentration of 1 µg/ml in 1% BSA in PBS for one hour at 37° C. Cells are washed three times with PBS followed by the application of 'Goat anti-Rabbit IgG (H+L) Secondary Antibody, Alexa Fluor® 488 conjugate' (Thermo Fisher Scientific) at a final dilution of 1:1000 in 1% BSA in PBS. After an incubation time of one hour at 37° C. cells are washed twice with PBS and cells are screened for the presence of FPaV-2 using a fluorescence microscope.

For virus isolation from the clinical samples LLC-MK2 and CRFK cells are seeded in 75 $cm^2$ cell culture flasks in DMEM (with sodium pyruvate and non-essential amino acids) with 5% of FBS in an atmosphere including 5% carbon dioxide at 37° C. and 90% humidity. At 70-80% confluence cells are infected with a mixture of one milliliter urine and 5 ml DMEM (with penicillin and streptomycin) over night at 37° C., 5% $CO_2$ and 90% humidity. After 24 hours the infection medium is replaced by 8 ml of cultivation medium (DMEM, sodium pyruvate, non-essential amino acids, 5% FBS, penicillin and streptomycin) and cultivated for further 6 days at the indicated conditions. The cell culture supernatant from this infection is passaged for further three times. Afterwards 600 µl of the cell culture supernatant are tested for the presence of feline paramyxoviruses.

Example 10: Challenge Model

A challenge model clinical study to investigate on early stages of infection and disease expression is employed. An intravenous (IV) challenge at a dose as close as possible to a challenge dose of $1\times10^5$ $TCID_{50}$/mL with the FPaV-2 "Gordon strain" is performed with a follow-up of 56 days post challenge. As no clinical signs of CKD are expected, the main objectives of the challenge model clinical study are to monitor primo infection, possible effect of infection on renal function, immune response to the infection, to evaluate a potential spreading and to confirm the virus settlement in kidney by immunohistochemistry (IHC) and possibly other organs.

Expected symptoms at early stages of the disease are associated with viremia (apathy, hyperthermia, weight loss). Expected symptoms at late stages are possibly related to chronic renal failure (bodyweight loss, uremia, mucosal lesions). Virus stock of FPaV-2 "Gordon strain" (with the titer $1\times10^5$ $TCID_{50}$/ml) is prepared on primary cat peripheral blood mononuclear cells (PBMCs) or on other cells like LLC-MK2 cell line. The stock has been tested negative for the presence of common feline pathogens (including feline panleucopenia virus, feline immunodeficiency virus, feline leukemia virus and feline coronavirus, respectively). Cats, mixed breed are inoculated with 1 ml ($1\times10^5$ TCID50/ml) of virus stock intravenously (IV).

Experimental Plan and Follow-Up:

Below cat groups A1, A2, B1, B2, C1, and C2 represent different timings of necropsy: A1 and A2 at D14, B1 and B2 at D28, C1 and C2 at D56. The subdivision is motivated by avoiding the sampling of all the cats every day in order to avoid too much stress for the animals

- Clinical examination and rectal temperature on a daily basis from D0 to D14 (except week ends) and twice a week from D15 to D56
- Weighing twice a week from D0 to D56
- Blood sampling for viremia monitoring by PCR

| Viremia | D-11 | D1 | D2 | D3 | D4 | D5 | D6 | D7 | D8 | D9 | D10 | D11 | D12 | D14 | D21 | D28 | D35 | D42 | D49 | D56 |
|---|---|---|---|---|---|---|---|---|---|---|---|---|---|---|---|---|---|---|---|---|
| A1 | X | X |   |   |   |   |   | X |   |   |   |   |   | X |   |   |   |   |   |   |
| A2 | X |   | X |   |   |   |   |   | X |   |   |   |   | X |   |   |   |   |   |   |
| B1 | X |   |   | X |   |   |   |   |   | X |   |   |   |   | X | X |   |   |   |   |
| B2 | X |   |   |   | X |   |   |   |   |   | X |   |   | X |   |   |   |   |   |   |
| C1 | X |   |   |   |   | X |   |   |   |   |   | X |   |   |   | X |   | X | X |   |
| C2 | X |   |   |   |   |   | X |   |   |   |   |   | x |   |   | X |   |   | X | X |

Urine sampling for viremia monitoring by PCR and lipiduria

| Urine | D7 | D14 | D20 | D24 | D35 | D42 | D49 | D56 |
|---|---|---|---|---|---|---|---|---|
| A1 | C | PM |   |   |   |   |   |   |
| A2 |   | PM |   |   |   |   |   |   |
| B1 |   |   | C | PM |   |   |   |   |
| B2 |   |   |   | PM |   |   |   |   |
| C1 |   |   |   |   | C |   | C | PM |
| C2 |   |   |   |   |   | C |   | PM |

(C = cystocenthesis; PM = post mortem)

Oro-nasal swabs for viremia monitoring by PCR

| Swabs | D-11 | D1 | D2 | D3 | D4 | D5 | D6 | D7 | D8 | D9 | D10 | D11 | D12 | D14 | D20 | D28 | D35 | D42 | D49 | D56 |
|---|---|---|---|---|---|---|---|---|---|---|---|---|---|---|---|---|---|---|---|---|
| A1 | X | X |   |   |   |   |   | X |   |   |   |   |   | X |   |   |   |   |   |   |
| A2 | X |   | X |   |   |   |   |   | X |   |   |   |   | X |   |   |   |   |   |   |
| B1 | X |   |   | X |   |   |   |   |   | X |   |   |   |   | X | X |   |   |   |   |
| B2 | X |   |   |   | X |   |   |   |   |   | X |   |   | X |   |   |   |   |   |   |
| C1 | X |   |   |   |   | X |   |   |   |   |   | X |   |   |   | X |   | X | X |   |
| C2 | X |   |   |   |   |   | X |   |   |   |   |   | x |   |   | X |   |   | X | X |

Blood biochemistry and cell count

|  | D-7 | D14 | D21 | D28 | D35 | D42 | D49 | D56 |
|---|---|---|---|---|---|---|---|---|
| A1 | X | X |   |   |   |   |   |   |
| A2 | X | X |   |   |   |   |   |   |
| B1 | X |   | X | X |   |   |   |   |
| B2 | X |   |   | X |   |   |   |   |
| C1 | X |   |   |   | X |   | X | X |
| C2 | X |   |   |   |   | X |   | X |

| Serology | D-11 | D7 or D8 | D14 | D24 | D56 |
|---|---|---|---|---|---|
| A1 | X | X | X |   |   |
| A2 | X | X | X |   |   |
| B1 | X |   |   | X |   |
| B2 | X |   |   | X |   |
| C1 | X |   |   |   | X |
| C2 | X |   |   |   | X |

Sera sampling for serology
Necropsy and histology

Full necropsy is performed for each animal with sampling of kidney, spleen, liver, bladder and lung. Organs are sampled for histology and viral detection by PCR.

The challenge model clinical study tests the hypothesis that the viral vector based vaccines according to the present invention are able to prevent and/or reduce the intensity and/or duration of feline paramyxovirus viremia upon challenge in cats. In addition, the vaccination of cats with the viral vectors of the underlying invention induces antibodies against e.g. feline paramyxovirus hemagglutinin antigen.

Example 11: Serological Examination of Cat Sera

Serological examination of cat sera is performed using the virus neutralization test (VNT) (Example 9). Cats were divided in three groups: A) Vaccination with recombinant ALVAC vector expressing hemagglutinin (H) protein of feline paramyxovirus type-2 "Gordon" strain (vCP3025); B) Vaccination with recombinant ALVAC vector expressing hemagglutinin (H) and matrix (M) proteins of feline paramyxovirus type-2 "Gordon" strain (vCP3029); C) Cats are not vaccinated (challenge control group).

Serum samples are taken from cats on day 0 (at the day of first vaccination), at day 21 (21 days after first vaccination), at day 35 (14 days after second vaccination) and day 49.

By using VNT methodology, it is clearly detected that all animals shown to be VNT-negative before vaccination at day 0 (titer <1:10). Furthermore, non-vaccinated cats remain VNT negative at all time-points before challenge, which is the requirement for the valid animal study.

At 21 days (D21) after initial vaccination, one vaccine cat from group A shows to be positive, with the VNT titer of 1:20 and one cat from group B with titer 1:10. On day 35 (D35) (14 days after second vaccination), all cats in vaccine group A (6/6) have significant neutralization titers (group median titer 1:160), while in group B, 5 out of 6 cats have significant neutralization titers against feline paramyxovirus type-2 (group median titer 1:160). Finally on day 49 (D49), all the cats are VNT positive (6/6) with the group VNT titer in the group A further increased (median group titer 1:693, 33). In group B, all cats are positive to feline paramyxovirus type-2 (6/6) with the median group titer of 1:403,33.

In conclusion, all cats vaccinated with either recombined ALVAC vectors expressing H or H+M proteins of feline paramyxovirus type-2 "Gordon" strain strongly react and seroconvert upon vaccination. Also, significant values of virus neutralization titers against challenge virus are detected on D35 and D49. Group A median titer is 1:160 on day 35 and 1:693,33 on day 49. Group B media titers are 1:160 on day 35, while 1:403,33 on day 49. Those days correspond to 14 and 28 days post second vaccination respectively. Such strong feline paramyxovirus type-2 neutralization titers indicate very strong vaccination response against feline paramyxovirus type-2.

Example 12: Prevention or Reduction of Viremia Upon Challenge

Cats are divided in three groups: A) Vaccination with recombinant ALVAC vector expressing hemagglutinin (H) protein of feline paramyxovirus type-2 "Gordon" strain (vCP3025); B) Vaccination with recombinant ALVAC vector expressing hemagglutinin (H) and matrix (M) proteins of feline paramyxovirus type-2 "Gordon" strain (vCP3029); C) Cats are not vaccinated (challenge control group).

On the day of challenge (D49), cats are intravenously (IV) infected with 1 ml of feline paramyxovirus type-2 "Gordon" strain with the infectious titer of $1\times10^{5.1}$ TCID50/ml. Plasma samples are taken from cats on day 3 post virus inoculation (D52) and day 7 post virus inoculation (D56). RNA is extracted from plasma, and feline paramyxovirus type-2 specific real-time qPCR is performed. Sensitivity of the qPCR is 2.9 log 10 RNA copy number/mL, which is used as a cutoff for calculation.

Group C—non-vaccinated cats (challenge control): on day 3 (D52) post virus inoculation, five out of 6 cats in the non-vaccinated control group become viremic, with the mean RNA copy number of 3.67 $\log_{10}$/ml, while on day 7 (D56), all the samples from non-vaccinated cats are positive, with the mean feline paramyxovirus type-2 RNA copy number of 5.97 $\log_{10}$/ml.

Group A—ALVAC Gordon H vaccine: cats vaccinated with ALVAC-Gordon-H vaccine remain fully negative on both day 3 and day 7 post challenge.

Group B—ALVAC Gordon H+M vaccine: in the group of cats vaccinated with ALVAC-Gordon-H+M vaccine four cats on both days remain negative, while two cats on day 3 (D52) and day 7 (D56) post challenge are positive, but have reduced feline paramyxovirus type-2 RNA copy numbers (3.72 $\log_{10}$/ml and 3.33 $\log_{10}$/ml respectively).

In conclusion, all cats vaccinated with recombined ALVAC vector expressing H protein of feline paramyxovirus type-2 remain fully protected and have no detectable viremia post inoculation of feline paramyxovirus type-2 challenge virus. Cats vaccinated with ALVAC vector expressing H and M proteins of feline paramyxovirus type-2 are protected, with 4 cats remaining completely negative and 2 cats on both days having reduced feline paramyxovirus type-2 RNA copy numbers as a result of vaccination.

All of the compositions and methods disclosed and claimed herein can be made and executed without undue experimentation in light of the present disclosure. While the compositions and methods of this invention have been described in terms of specific aspects, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the following claims.

REFERENCES

The following references, to the extent that they provide exemplary procedural or other details supplementary to those set forth herein, are specifically incorporated herein by reference.

(1) De Vries P et al., J. Gen. Virol. 1988, 69: 2071-2083
(2) Furuya et al., Archives of virology 2014, 159(2): 371-373
(3) JP 2015 198654 A
(4) Lorusso et al., Vet Ital. 2013, 51(3): 235-237
(5) Lulich J P et al., Compendium on continuing education for the practicing veterinarian 1992; 14(2): 127-152
(6) Marcacci M et al., Journal of Virological Methods 2016, 234: 160-163
(7) Marciani D J et al., Vaccine 1991, 9(2): 89-96
(8) McEachern J A et al., Vaccine 2008, 26(31): 3842-3852
(9) Sakaguchi et al., General Virology 2014, 95(7): 1464-1468
(10) Sharp et al., Emerging Infectious Diseases 2016, 22(4): 760
(11) Sieg et al., Virus Genes 2015, 51(2): 294-297
(12) Tartaglia J et al., J Virology 1993, 67(4): 2370-2375.
(13) Taylor J et al., Vaccine 1991, 9(3): 190-193
(14) Taylor J et al., Virology 1992, 187(1): 321-328
(15) Taylor J et al., Dev Biol Stand 1994, 82: 131-135
(16) U.S. Pat. No. 4,769,330
(17) U.S. Pat. No. 4,722,848
(18) U.S. Pat. No. 4,603,112
(19) U.S. Pat. No. 5,110,587
(20) U.S. Pat. No. 5,174,993
(21) U.S. Pat. No. 5,494,807
(22) U.S. Pat. No. 5,505,941
(23) U.S. Pat. No. 5,756,103
(24) U.S. Pat. No. 5,766,599
(25) US 2013/0230529
(26) Weli S C et al., Virology J. 2011, 8 (1): 49
(27) WO 2005/013918
(28) WO 2006/073431
(29) WO 2006/115843
(30) WO 2013/107290
(31) WO 2013/123242
(32) Woo et al., Proc. Nat. Acad. Sci. 2012; 109(14): 5435-5440

The invention claimed is:

1. A viral vector, comprising at least one exogenous antigen encoding sequence relating to/of at least one pathogen infecting felines, wherein the at least one pathogen infecting felines is feline paramyxovirus is selected from the group consisting of:

(a) a feline paramyxovirus type 2 (FPaV-2), the genome of which comprises a ribonucleic acid complementary to the nucleic acid sequence selected from the group consisting of:
  (i) a nucleic acid sequence according to SEQ ID NO: 1,
  (ii) a nucleic acid sequence which is at least 85% identical to SEQ ID NO:1 over the whole length of SEQ ID NO:1;

(b) feline paramyxovirus type 2 (FPaV-2) as deposited at Collection Nationale de Culture de Microorganismes (CNCM) under accession number CNCM I-5123;

(c) a feline paramyxovirus type 2 (FPaV-2), the genome of which comprises a ribonucleic acid complementary to the nucleic acid sequence selected from the group consisting of:
  (i) a nucleic acid sequence according to SEQ ID NO: 2,
  (ii) a nucleic acid sequence which is at least 85% identical to SEQ ID NO:2 over the whole length of SEQ ID NO:2;

(d) a feline morbillivirus (FeMoV), the genome of which comprises a ribonucleic acid complementary to the nucleic acid sequence selected from the group consisting of:
  (i) a nucleic acid sequence according to SEQ ID NO: 3,
  (ii) a nucleic acid sequence which is at least 94% identical to SEQ ID NO:3 over the whole length of SEQ ID NO:3.

2. The viral vector according to claim 1, wherein the viral vector is selected from the group consisting of: avipox virus viral vector, canine morbillivirus viral vector, herpes virus viral vector.

3. The viral vector according to claim 1, wherein the viral vector is an attenuated canarypox vector.

4. The viral vector according to claim 1, wherein the at least one exogenous antigen encoding sequence is selected from the group consisting of: hemagglutinin protein (H) encoding sequence, matrix protein (M) encoding sequence, fusion protein (F) encoding sequence, nucleocapsid protein (N) encoding sequence, phosphoprotein (P) encoding sequence, RNA-dependent RNA polymerase protein (L) encoding sequence.

5. The viral vector according to claim 4, wherein the at least one exogenous antigen encoding sequence is a hemagglutinin protein (H) encoding sequence and the hemagglutinin protein (H) encoding sequence comprises a nucleic acid sequence which is at least 70% identical to SEQ ID NO:4, or SEQ ID NO: 5; or wherein the at least one exogenous antigen encoding sequence is a hemagglutinin protein (H) encoding sequence and the hemagglutinin protein (H) encoding sequence comprises a nucleic acid sequence encoding a polypeptide having an amino acid sequence which is at least 85% identical to SEQ ID NO:6.

6. The viral vector according to claim 4, wherein the at least one exogenous antigen encoding sequence is a matrix protein (M) encoding sequence and the matrix protein (M) encoding sequence comprises a nucleic acid sequence which is at least 70% identical to SEQ ID NO:7 or SEQ ID NO:8, or wherein the at least one exogenous antigen encoding sequence is a matrix protein (M) encoding sequence and the matrix protein (M) encoding sequence comprises a nucleic acid sequence encoding a polypeptide having an amino acid sequence which is at least 85% identical to SEQ ID NO:9.

7. The viral vector according to claim 4, wherein the at least one exogenous antigen encoding sequence is a fusion protein (F) encoding sequence and the fusion protein F) encoding sequence comprises a nucleic acid sequence which is at least 70% identical to SEQ ID NO:10 or SEQ ID NO:11, or wherein the at least one exogenous antigen encoding sequence is a fusion protein (F) encoding sequence and the fusion protein (F) encoding sequence comprises a nucleic acid sequence encoding a polypeptide having an amino acid sequence which is at least 85% identical to SEQ ID NO:12.

8. The viral vector according to claim 1, wherein the viral vector comprises two or more exogenous antigen encoding sequences, a hemagglutinin protein (H) encoding sequence and a matrix protein (M) encoding sequence, or a hemagglutinin protein (H) encoding sequence and a fusion protein (F) encoding sequence, or a matrix protein (M) encoding sequence and a fusion protein (F) encoding sequence, or a hemagglutinin protein (H) encoding sequence and a matrix protein (M) encoding sequence and a fusion protein (F) encoding sequence.

9. The viral vector according to claim 1, wherein the viral vector comprises two exogenous antigens, wherein said exogenous antigens encode for the same protein derived from two distinct viral species, wherein the first exogenous antigen is derived from the feline paramyxovirus type 2 (FPaV-2), and wherein the second exogenous antigen is derived from the feline morbillivirus.

10. The viral vector according to claim 1, wherein the viral vector is an ALVAC vector and wherein the at least one exogenous antigen encoding sequence is inserted in at least one insertion locus, in a non-essential region of the viral vector genome; or wherein the at least one exogenous antigen encoding sequence is inserted in two or more insertion loci; and/or wherein the at least one insertion locus is insertion locus C3; and/or wherein the viral vector comprises flanking sequences of the insertion locus C3, wherein the flanking sequences are selected from the group comprising SEQ ID NO:45 (C3 flanking region left arm) and SEQ ID NO:46 (C3 flanking region right arm); or wherein the at least one insertion locus is insertion locus C5; and/or wherein the viral vector comprises flanking sequences of the insertion locus C5, wherein the flanking sequences are selected from the group comprising SEQ ID NO:47 (C5 flanking region left arm) and SEQ ID NO:48 (C5 flanking region right arm).

11. The viral vector according to claim 1, wherein the viral vector comprises a nucleic acid sequence which is at least 70% identical to the nucleic acid sequence selected from the group consisting of SEQ ID NO:49, SEQ ID NO:50, SEQ ID NO:51, SEQ ID NO:95, or is the nucleic acid sequence selected from the group consisting of: SEQ ID NO:49, SEQ ID NO:50, SEQ ID NO:51, SEQ ID NO:95.

12. The viral vector according to claim 1, wherein the feline is a cat.

13. An isolated mammalian host cell characterized in that it comprises the viral vector according to claim 1.

14. An immunogenic composition comprising
(a) the viral vector according to claim 1, and
(b) optionally a pharmaceutical- or veterinary-acceptable carrier or excipient.

15. A vaccine or pharmaceutical composition comprising
(a) the viral vector according to claim 1, and
(b) a pharmaceutical- or veterinary-acceptable carrier or excipient,
(c) optionally said vaccine or pharmaceutical composition further comprising an adjuvant.

16. A method for the preparation of an immunogenic composition or a vaccine for reducing the incidence and/or the severity of one or more clinical signs associated with or caused by an infection with at least one pathogenic paramyxovirus, comprising the following steps:
(a) infecting an isolated mammalian host cell with the viral vector according to claim 1,
(b) cultivating the infected cells under suitable conditions,
(c) collecting infected cell cultures,
(d) optionally purifying the collected infected cell cultures of step (c),
(e) optionally mixing said collected infected cell culture with a pharmaceutically acceptable carrier.

17. A method of treating, and/or inhibiting infection, and/or reducing or preventing the clinical signs or disease caused by an infection with at least one pathogenic paramyxovirus in a feline, comprising administering to the feline an effective amount of the immunogenic composition according to claim 16 or the vaccine or pharmaceutical composition according to claim 15, wherein the at least one pathogenic paramyxovirus is a feline paramyxovirus, and wherein said clinical signs or disease caused by an infection with at least one pathogenic paramyxovirus or said infection are selected from the group consisting of: viremia, fever, virus shedding in the environment, infections and diseases of the urogenital system.

18. A method of immunizing a feline against a clinical disease caused by at least one pathogenic paramyxovirus in said feline, said method comprising the step of administering to the feline the immunogenic composition according to claim 16 or the vaccine or pharmaceutical composition according to claim 15, wherein said immunogenic composition or vaccine fails to cause clinical signs of infection but is capable of inducing an immune response that immunizes the feline against pathogenic forms of said at least one paramyxovirus, wherein said clinical disease or said clinical signs of infection are selected from the group comprising of: viremia, fever, virus shedding in the environment, infections of the urogenital system, infections of the urinary system, kidney disease, chronic kidney disease (CKD), inflammation of the renal tubules and renal interstitial tissue, idiopathic tubulointerstitial nephritis (TIN).

19. The viral vector according to claim 9, wherein the one strain of "the hemagglutinin protein (H) encoding sequence of one strain" is a hemagglutinin protein (H) encoding sequence and the hemagglutinin protein (H) encoding sequence comprises a nucleic acid sequence which is at least 70% identical to SEQ ID NO:4 or 19 or is selected from the group consisting of: SEQ ID NO:4, SEQ ID NO:5, SEQ ID NO:19; and the another strain of the "hemagglutinin protein (H) encoding sequence of another strain" is a hemagglutinin protein (H) encoding sequence and the hemagglutinin protein (H) encoding sequence comprises a nucleic acid sequence which is at least 70% identical to SEQ ID NO:31 or 94 or is selected from the group consisting of: SEQ ID NO:31, SEQ ID NO:32, SEQ ID NO:94.

20. The method of claim 17, wherein the infections and disease of the urogenital system are selected from the group comprising, infections of the urinary system, kidney disease, chronic kidney disease (CKD), inflammation of the renal tubules and renal interstitial tissue, and idiopathic tubulointerstitial nephritis (TIN).

21. The viral vector according to claim 1, wherein the viral vector is an attenuated fowlpox vector.

22. The viral vector according to claim 3, wherein the attenuated canarypox vector is ALVAC.

23. The viral vector according to claim 22, wherein the ALVAC is selected from the group comprising ALVAC-1 or ALVAC-2, and ALVAC as deposited under the terms of the Budapest Treaty at the American Type Culture Collection (ATCC) under accession number VR-2547.

24. The viral vector according to claim 21, wherein the attenuated fowlpox vector is TROVAC.

25. The viral vector according to claim 24, wherein the TROVAC is TROVAC as deposited under the terms of the Budapest Treaty at the American Type Culture Collection (ATCC) under accession number VR-2553.

26. The viral vector according to claim 9, wherein the first exogenous antigen is derived from the feline paramyxovirus type 2 (FPaV-2) Gordon strain or the FPaV-2 TV25 strain.

27. The viral vector according to claim 9, wherein the second exogenous antigen is derived from the feline morbillivirus Lapön strain.

\* \* \* \* \*

SEQUENCE LISTING

```
<160> NUMBER OF SEQ ID NOS: 95

<210> SEQ ID NO 1
<211> LENGTH: 16047
<212> TYPE: DNA
<213> ORGANISM: Feline paramyxovirus type 2
<220> FEATURE:
```

<221> NAME/KEY: misc_feature
<223> OTHER INFORMATION: FPaV-2 "Gordon strain" full genome sequence;
     given as a DNA sequence that correspond to the positive RNA-strand
     into which the negative RNA strand viral genome is transcribed,
     i.e. it comprises the ORFs in 5' to 3' direction like an mRNA

<400> SEQUENCE: 1

```
accagacaaa gatgtctgtg acctattcta acggttagat tattacttga tatttaggaa      60
taacgattcc attagtcagg taagggagag gaatcagtta ttctataatg gctagtttac     120
tcaggtcact tgcggcattc aagaaacaca gagaacaacc aactgttcct tctgggtcag     180
gagggacgat caaaggatta aaaaatacaa ttattgtgcc tgttcctgga gatacagtca     240
tcactaccag atcgaactta ctgttcagat tagtctacat aattggtaat ccagatacac     300
ctttaagcac ttcaacaggg gcaataatat cattgttgac attatttgtt gaatctccag     360
gtcaattaat tcaaagaatc gctgatgatc ctgatgctgt ttttaaatta gtagaggtgg     420
ttcctgaggt tggtaatcct ggagaattaa cttttgcatc tagaggaatt aacttggata     480
aacaagctca acaatacttt agattggctg agaaaaatga tcaaggatat tatgtaagtt     540 tgggggtttga aaatccacca aatgatgatg atataacgtc aagtcctgaa atctttaatt     600
atattttagc atctgtactt gcacagatct ggattctcct agctaaggct gtaactgctc     660
cagacacagc tgctgaggct gaaaaccgta ggtggattaa attgatgcaa caacgcagag     720
tggatggtga gcttagatta agtaaaggat ggttggactt agtgaggaat aaaatcgcat     780
cggatatcac aattagaagg tttatggtag cattagttct tgacattaaa cgttctcctg     840
gaacaagacc aagaattgct gaaatgattt gtgatataga caattatatt gtggaggccg     900
gactggcaag ttttctgtta actatcaaat ttggtataga aacacgttac ccggcattag     960
cgttacatga gttttcgggg gaattagcca ctattgaagg actcatgaaa ttgtaccagt    1020
ctatgggaga aatggcacca tacatggtca ttctagagaa ttcgatccag actaggttta    1080
gtgctgggtc ttatccgtta ctctggagct atgctatggg tgttggtgta gaacttgaaa    1140
gatcaatgag tggattaaac ttcacaagaa gtttctttga tcctacgtac ttcaggttgg    1200
gtcaggagat ggtaagaagg tcttcaggaa tggttaatag ctcatttgcc aaagaacttg    1260
gactatctga acatgaaaca caacttgtta gccagatcat taactcaggt ggtgagtcag    1320
gtataccgaa atttgatgga tttagagcaa acccaacaac atttctaggg gctaaggaca    1380
acatcactga taggagtgaa gatccattga ttgcaattcc agggtcatca ggacaaccat    1440
tgccaggtta tgaccccaat atctcaggtg actcatatag aattgatagt agcactaaag    1500
acacaaacaa tatatcagat ggaggaacaa atccaagtca tgatgtttcc aattctgcta    1560
tggaagagct gagaagattg gtagagtcta ccaacaagat tgatacaaag aaatctgaaa    1620
gcccaggcat cgttaatcat tacaacgata ctgaccttct gagataataa ggatatattc    1680
aggtagatct ttacagaatt taaattaaga aaaacttagg acctcaaggt tcacactcct    1740 ctggcccttta tcagaattcg gccaattcct cactcactcc atgtcagcag aacaaatcca    1800
acaagttaga catggccttg aatccttgca agagatcaaa acaacccctc caccctctca    1860
agatgtcaat cttgccaggg aaatttacga atccattaaa caaacaggaa cacctttcaac    1920 acaaggaggg accattacag gaaataatac tgcgtcaggg tgtgacaatt actcaatgca    1980
tagccaggga tcaggtcctt ctgttttcagg tgctgacaag aatatcgaga gacttactgg    2040
acccgattat tcagaattat gggatccaga aggtaacctc tgcatgctat tcgaaagcga    2100
tgatgatgac aacaattatt cagagattaa tggccggtct accgctatcg aaggattgga    2160
```

```
tgaacagaat aataaggacc caggtattaa acaatcagga gatcagtgtt ctgaaggagt    2220
gtctaagatt aattcatctt ctagtcccca agaagctaca ttatcttctg ggagatctga    2280
tatatctggg acaggagtat ctccctgtgc ctctttggat ataactgtta atgaattaga    2340
agatgcaact gttaagaata gtaataatat gaaaggaaat tggccaatcc caaagttgct    2400
tgtcaaacca ccaccaagaa tgaaatcact ttctgactct gttacaccat taaaaggggc    2460
caccgacggg aaatcagtct tacctgggat ggagattaca ttgtccggga agaatggtgc    2520
aaccctacct gtacacccat ttacacaacc tataaaagac tcaaatgcag atgtaagcaa    2580
tgtccgtcaa catgtcccaa gtgtgactga tggtcatagt gatgataatg aggaagtacc    2640
cggtttgcat aaagaaacta tagacaaagc tgatctatct atgcaggaca tatacaattt    2700
aattcttgga tttaaggatg attacaggaa actatcaaat aaattggata tgatactaga    2760
gatgaaacaa gatattgata atcttaaaaa gagtagtgca aaaatacaac ttgcattatc    2820
aacaattgaa ggacatctgt ccagtgttat gattgctatt ccaggttcag gtattgatat    2880
aaatcaagat gagaagaagg atcaattaaa ctctgactta aagccattac tagggaggga    2940
ccattgccgt gcatttcgtg aagtcactaa tcctttagat gaaacgtcat tgaccaacgc    3000
tccgaccaaa catgttgcta agatcaacaa aaattgcact cttcagaaaa tcaataacaa    3060
tgagacatct gcaattaagt ttgtacctaa tgatagccat gcaagtatct cgactatcaa    3120
gtctattgtc aaatcctcaa accttaatca agagcttaaa gtcaagttac tgacaattct    3180
atctcaaatt aaaggggtag acaatattaa ggagttttat gagaaagtta tgatattgat    3240
caagaataat aactgatctt gactaatcaa tagatactac ttatcaaatc tcgctctgac    3300
atcaagtgaa ttcatcttta ttaacaagta ttaatcttaa ataattataa aaaacttagg    3360
agttcaggat tagtgggtca tatacaatat gactgagata ttcaatctgg atgaaagttc    3420
atggtcagtc aagggaacac tggacccatt gacgcctgat acttatcctg atgggcgcct    3480
agtacccaag attcgggtta ttgatcccgg tctaggtgat cgtaaaagtg gaggatatat    3540
gtacttactc cttcacggtg tcatcgagga cagtgagacc gtcataaatc cgaaagggag    3600
agcatttgga gctttccctt taggcgtagg gcaatcaacc gagaacccag aagacttatt    3660
taaggaaata ttaaccctca acattgttac tcgcaggact gctggcttca atgaaaaatt    3720
ggtgtattat aatactacac ctctaaatct actaaccct tggaaaaaag tactagcata    3780
tggaagtatc tttactgcta atcaggtctg caataataca agttctatcc ctatagacat    3840
tcctcagaaa tttcgacctg tctatttaac tgttaccaag ttatcggatg atggatatta    3900
tcagatacct aaaatgatac aggatttcaa atcatcaaac tctgttgcat taacatcct    3960 tgtgcatcta tcaatgggaa caattttact tgactcatct aaaggctctc gagtaggaaa    4020
ccctgcagaa aatttgatca cattcatgat tcatattggg aatttcaaac ggaagaataa    4080
taaagcttat tctcccgaat attgtaagag gaaaataatg aggcttggat taattttctc    4140
actaggagcc attggtggaa caagtttgca tattcgatgc acaggcaaaa tgagtaagag    4200
attacaagcc tacttagggt ttaaaagaac tttatgttat cctctgatgt atgtcaatga    4260
gggtctaaat aaaaccttat ggagaaatga atgcaaaatt gagaaggttc aagcagtatt    4320
acagccatca gttccgaatg aatttaagat ttatgatgat ataatcattg ataacacgaa    4380
tggcctcttt aaggttaagt aagctgtgac tagtatcagg agttactagt caaaatcatg    4440
tgttgatatc cgaattaata gctttaagtt gaatatatta aacctgtgat aatttaaatt    4500
```

```
tgaaacataa ttagtatgta gtattgtatt aatcagttta taatcttgtt tgaggatcca   4560
aattataacc ctattaggta ttgccactcc agtcttacag gtaaatctaa gcgaatatac   4620
aaataattga tattcgggat taaacaatac ttgtatatta atccataggt atattagatt   4680
ttactatatt caattattat aatgtttatt gagttaagct ctcatgatta taaaaaacta   4740
aggattccac ataatcacag tttgattgcc aattgatgtg tttagtatta gttgtgtgaa   4800
atattgatat taataaggtt aatcaacttt tgtacagaag tgaaagtgta attagataga   4860
aatagattaa tccttagtag ccgttttgat aattgaattg attcttgttt taattctgaa   4920
ttgagattat taatcaccag ctcggcataa tgtataagat taaggttgta atcatgggtt   4980
ttttactgtt atcagatatt acatttgcac aggtaggttg ggataattta acctcaattg   5040
gagttataag tactaaacaa tataactata agataactac tttgaatact aatcaactca   5100
tggtgatcaa aatggtaccc aatatatcat caattattaa ctgtactaaa cttgaattag   5160
caaaatatag ggaactgatt acaggaatac tgagaccaat taatgaatca ttagaattga   5220
tgaattcata tatcaacatg agaacaggtt cagagagatt catagggggct gttatagcag   5280 gagtagctct aggggttgca actgcggcgc agataacatc gggaattgcc ttacataatt   5340
cgattatgaa taaaaaacag atacaggaat taaggaaagc ccttagtact acaaataagg   5400
caattgatga gataaggatt gcaggtgaaa gaactctgat agctgtccaa ggtgtgcaag   5460
attacattaa caatgttatt atccctatgc aagagaaact ccagtgcgat attttagcct   5520
cacagctatc tattgcccta ctcagatact atactaatat actgactgtt tttggaccaa   5580
gtataagaga tcctattact agtacaattt ctatacaagc tctcagtcaa gcattcaatg   5640
gtaatctaca ggcattgctt gatggattag ggtatactgg acaagactta catgatctca   5700
tagaaagtag atctatcact ggtcaaatta ttcacgctga tatgactgat ttattccttg   5760
tattgagaat caattatcca tctattacgg atatgcaagg agtggtaata tatgagctga   5820
attctatcac atatcatatt ggacctgaag agtggtacac tattatgcct aatttcatag   5880
ctgttcaggg atttctggta tctaatttcg atgaacgtaa atgttcaatt actaaaacaa   5940
gtatactgtg tcaacagaat tcaatttatc ctatgtcaac cgaaatgcaa agatgtataa   6000
aaggtgagat taaattctgt ccaaggtcca aagcaattgg gacattagtt aatcgattta   6060
tattaattaa tgggaatcta atggccaatt gtttgggtat tatctgtaga tgttataccT   6120
caggtcaaat tataacgcaa gacccaaata aattaatcac aattatatca caagaagaat   6180
gtagagaggt tggtgttgat gggattcgta taatggtggg gcctaaaaaa ttaccggatg   6240
ttatctttaa tgccagacta gaaataggtg tacctatctc attaagcaag ctggatgttg   6300
ggaccgactt ggcaattgct tcagctaaac tcaataactc taaggcactt ttggagcagt   6360
ctgataaaat cttaaattct atgtctaagt tggattcttt aaattcacgt atcttaggat   6420
ctgtctttat aattatgata atcttcgtga ctgtaattgt gattatttgg attatttgta   6480
aaaagtgtag aaataagagg aacaaattaa gtgcttctat tgaacccctc tacatacctc   6540
cctcttataa ttcaccccat agcatagtta atctatttg aaatataagt gtataatctg   6600
atataacaga tgcagtagaa ttattaatca atgataatat tattatgata atgattcagt   6660
tagatgttca ttgtatctca taacttaata ttgacaaatt tcaattagtt aaatttattc   6720
tcttcataat atgtatttgt ttaattatcc tagattcatg tactgttatt aaattggtca   6780
tctttaataa ctaactcagc aatactatcc tatacacatg tattagctaa taacgatgta   6840
atattgccat ttaataataa gtacctagta gaatgggaag cattagctgt agtcaatgaa   6900
```

```
ccattacctg ctcaattaga aaaaacttag gaatccatgt taatgggagc tggccatcat    6960
ggaatctaat aacaacaagt actataaaga ttcaaaccgg tattttagca agatactaga    7020
tgagaacaag acggtaaata atcatctgta tagtcttagt ataaggataa ttaccgttat    7080
agctattgtt gtgagtctaa ttgcaacaac aataaccatc attaatgcta taagcggaag    7140
gactactctt aataataata tggacatgct actcaaccaa caagacaaga ttaataatat    7200
caaggaaatg atatttgatc gtatctatcc cctgataaat gccatgagta cagagcttgg    7260
tcttcacatt ccaactttat tggatgagct gactaaatca attgatcaaa aaatcaagat    7320
aatgactcca ccacttgaaa ctacaacatc taatctcaat tggtgtatca accccccaaa    7380
tggcattatt gtagatccta aaggttattg tgaaggcttg gaactgtcaa aaacttataa    7440
gttattactt gatcaattag atatgttaag aaagaaatca cttattatta ataagaaaag    7500
tattaatcag tgtagacttg ttgatagttc gaatatcgtc tttgcaacag ttaatataca    7560
atctacaccg agattcttaa atcttggtca cacagttagt aaccaacgta taacattcgg    7620
tcaaggaaca tatagtagca cttatattat aactatacaa gaggatggat taactgatgt    7680
tcagtaccga gtatttgaaa taggatatat ctcagatcaa tttggaacct tcccttctct    7740
aatcgtttcc agagtactac ctgtgcgaat ggtacttgga atggaatctt gtacactgac    7800
cagtgacaag tttggggggtt attttttatg catgaacatt ccgacacgct ctatatgat    7860 ttatgtcaac ataagagact taaagtcact atacgtcaca atccctcatt atggcaaaat    7920
taattacact tactttaatt ttgggaaagt cagaagccca catgaaattg ataagatttg    7980
gcttacatca gaaaggggac agatgatttc aggttacttt gcagcatttg ttacgattac    8040
aattagaaat tataacaatt atccctataa atgcttacat aacccgtgtc ttgaaagatc    8100
tgagagttat tgcaaaggat ggtacaaaaa tattacaggt actgatgatg ttccaatatt    8160
agcatatcta ttagttgaaa tgaatgatga ggaaggaccc ttaattacat tggttgagat    8220
accaccttac aattatacgg ctccttctca taattccctt tactatgatg ataaaattaa    8280
caaattaata atgacaacat ctcatatagg atacattcaa atcaatgaag tgcatgaagt    8340
cattgtcggg gataatctta aggctattct cttaaacaga ttatctgatg aacaccctac    8400
tcttactgct tgtagattta atcaggaaat taaagagcga catatatctg atggattaat    8460
aatatctaac tctgctctta ttgatataca agaacgtatg tatgttacag ttaaggctgt    8520
tccacccata ggaaattata acttcacggt agagttgcat tcacggtcaa atacatctta    8580
cgtagggttg ccaaggcagt tcaatgctag gtatgacaaa ctgcatctcg aatgctttgc    8640
ctgggatagg tcttggtggt gcgctttgat acctcaattt tcattaagtt ggaatgaatc    8700
tctttcagta gatactgcca ttttcaactt aataaactgt aattaagttt gtggcttgtt    8760
ctagattgat catttgaata acagttgatt aagccaaagt tagtaaatac atacattaac    8820
ctgttcttga ccaagtatat atcccaatcc aattataaaa aacttaggac tcaaggtgtt    8880
gatggcaatg gagcaatcag attatcaaga tattttatat ccagaggtac atctcaacag    8940
tcctatagtt atctctaaat tagtgggtat tttggagtat tctaaggttg ttcacaatca    9000
gcagttatct gatcacacaa tagtcaagaa tatacaattt agattgagaa atggattcaa    9060
tagtccaaga atacaaacac tgttagttat gggtgaaatt atcaataaaa tcaaaaataa    9120
atacccaaat tatttgcaca taccttatcc tgaatgtaat caaaagttat ttaggatagc    9180
tgacccggag ttaacatcta aactagaagc cctcttggac aaaggtgaca cattatatct    9240
```

```
taagattaag acagagatca tagcttgttt cgataagtta aaaactaaaa tgagcataac    9300
caatgatctg attagtgaca ataggcagct aatttcagat ctacctataa ttgtcaaggg    9360
atctcaatgg ttttttcccctt ttttgctctg gttctctgtt aaaactgaga ctaggaactg   9420
tattcgacaa aatcaaaaaa ctcgtgttag gtcacaatac cgacctcatt tgtcagaaac    9480
taaaagaatt acgctggtcg ttactcatga cttgatcaca atatttgacc acgtcaacaa    9540
atgtatatat catctgactt tgagatgtt gttgatgtat tgtgatgtag tagaagggag     9600
gttaatgacc gaagcatcta tgagtctaga tcacagattt attaacctat tgtcgagggt    9660
ccagtatatg tgggatctat tagatgggat gtttgagagt ctaggaaatc agctatattc    9720
aatcattgca ctcttagaac ctctctctct tgcctatcta cagttgatgg atgcagaccc    9780
acagatacgg ggtacatttt tacaccattg cctttcagag ttggaagaac tcttatttag    9840
taaattccct tttgatcctg taatttatga aaatctaatt agtggacttg attacatcta    9900
tttaacagac gatattcatt taactgctga gatattttct ttctttagaa gttttggtca    9960
tccttattta gaagcacaaa atgcagctag caatgttagg aaatatatga atcaacctaa   10020
agttatctca taccagactc taatgcaagg acatgcaatt ttttgtggca ttataataaa   10080
tgggttcaga gatcgtcacg gagggacatg gccacccgta gagctaccac atcatgcatc   10140
cgctgtaatt agaaatgctc agttatctgg agaaggatta acacctgagc agtgtgctca   10200
atactggagg tcattttgtg gatttaaatt taaatgtttt atgccattaa gtttagatag   10260
cgacctcacc atgtacctta gagacaaggc attatcacct attaagaatg agtgggactc   10320
tgtgtatgct aaagagtatt taagatacaa ccctggctta ccgactagct ctcgaagatt   10380
agtcaatgta tttcttgaag atgataaatt tgatccgtac gaaatgatta tgtacgtaat   10440
aaacggtgat tatttaaggg ataatgagtt caatctctca tatagtctta aagaaaagga   10500
gatcaaggag gtaggccgat tgttcgctaa aatgacttat aaaatgagag cttgtcaggt   10560
aatagcagaa aatttaattg caatggagt tgggaaattt tttaaagaca atgggatggc    10620
gaaggatgaa cataaattaa ccaaaacatt acataagctg gccatttctg gtgtacctaa   10680
agataatttt caactctatt taagtgaatg ttgggaacaa gtggtagaac aatgcgtaac   10740
cagtacgcaa acaaaaaatc aaattatcag ttcacactca agaaaatcag ttgcatcaaa   10800
gtttccaaga tcaaatccca atgatagggg tattctaaat agtggcagac atttgaataa   10860
acatccaaaa catccttcaa acaccgaata ctatgaaact gtcagtagtt ttataactac   10920
tgatctcaag aaatattgcc tcaactggcg ctatgaatca agtagtgtgt ttgcagaaag   10980
actcaatgag atttatgggt taccaggatt ttttcattgg cttcatagaa ttttggagaa   11040
atctgtatta tatgttagtg atccatccag tccacctgat tttgatcaac atgttgatat   11100
tgattcagtt ccaaatgatc atattttat caaatacccca atgggtggga tagaaggatt    11160
ttgtcaaaaa ttatggacaa tcagcacaat cccattttta tatttagcag cttttgatac   11220
aggggttaga atatcttcgt tggttcaagg tgataatcaa gcaattgcag tgaccaaaag   11280
agttccatcg tcctggagtt attcgagaaa aaaagaggag tcaactaaag ttacaacaca   11340
atatttttta aacttaagac aacgcttaca tgatataggt catgagttaa aggcaaatga   11400
gactattata tcttcacact ttttgtttta ctctaagggt atttattatg atggtatact   11460
tctttcacaa tcccttaaaa gtattgcaag atgtgttttt tggtccgaga caattgtcga   11520
tgagactagg tcagcttgca gcaatatatc cactaccctt gctaaagcta ttgaacgggc   11580
ttatgataaa ttcgtggcat acgctattaa tatatataag actatacacc aggtcttaat   11640
```

```
tgcattatct tttactatta atcccactat gactccggac ataacagaac cttttttataa   11700 aagtttagat ttacttaaaa acctcattct gataccagca ccattgggtg ggatgaatta    11760
catgaatatg agcagattat ttgttagaaa cataggtgat cccattacag cttcatttgc    11820
tgacatcaag cgtatgatcg aatgcgggtt attagggcac aatgttctct cacaaataat    11880
gtatcagaaa tgtggtacct cgaaatactt agattgggct agtgacccct attccataaa    11940
tcttccttat agtcaaagca tgaccaaagt attaaaaaat ataaccgcga gatatgttct    12000
catgcacagt cctaacccta tgctaaaaga tttattccat gagaagtcac aagaagaaga    12060
tgagattctt gctgaatttt tgctggatcg tcagttaata atccctagag ctgcacatga    12120
aattttatcg aattcagtaa caggagctag agagtcgatt gcaggatgc ttgatactac     12180 taaaggactt attcgagcca gtatgtcaag aggtggtctg acatcttcac ttgtgttgaa    12240
attgtcaaca tatgattatc aacaatttag aacatgcctt gaatggcttt atgccctac     12300 cacaggaata gcagtaagtg ctgattcttg ttcagttttt ttagccagag ctattcgaaa    12360
aaggatgtgg gttcacctga ctaaaggaag agaaatttat ggcctagaag tgcctgatat    12420
attagaatgt atgcagagca atgtaattgt tgatcatgaa gattgttatt catgtattca    12480
aggatcaaga tactacacat ggttttttgt accttctaat tgtcagcttg atcagattaa    12540
caagtctaca aattctctac gggttcctta cattggctct actacagagg aaagaagtga    12600
catgaaatta tcatacgtca gatcccctag taggccactt aaggcagcag tccgaattgc    12660
agcagtctac acatgggcat acggtgatga cgatctgtct tggcgtgagg cttggtactt    12720
ggcaaggact agggcaaatg ttactttcga tgagcttaaa ttagtaacac ccatagctac    12780
ctctacgaac ttggcacata gattaaggga caggagtact caagttaagt attcaggaac    12840
ttcattagta agagtggcac gctatacaac aatatccaat gataatatgt catttgtcat    12900
taatgacaaa aagtagata ctaattttgt ctatcaacag ggcatgttat tgggtttgag     12960
tatcctagaa tatatattta gatactgtaa aagtactggt caatcaaata ctgtagttca    13020
cttgcatgca gatgttaatt gttgcataat ccaaatgaca gatcaacctt atactccaag    13080
cttaacgaaa aaattacctg agattaaacc tattaataat aagttgattt atgatccagc    13140
tcctataatt gatactgatg cagctaggtt atattctcag aagtacttat cacacctgat    13200
agattttcca aattggtcaa tgaatcagct aaatgtagtt ttagcaaaag tagttgcaat    13260
atctattgtg gacttgataa ctaaagcgag taaagatcat ctcaatgaaa ttatggcagt    13320
tgttggagat gatgacatta atagcttat aacagaattt ttgctagttg atccgaggct     13380
atttacattg tacttaggtc aatacacgtc acttcaatgg gcatatgaaa ttcattatca    13440
ccgacccgta ggcaaatacc agatggcaga agtgttacac actttactgt caagagcaag    13500
taaaggtata tttaatatat taactaatgc ttttagtcat cctagagttt acaaaagatt    13560
ttgggaatgt ggattactgg agcctatta tggaccatac ataggagcc aaaatttata      13620 tagtacagta attgattacc tttacaatgc ttatataact tatttagatg cttatctatc    13680
tgatcatatc gaagatgcag acatagtaat atgtgagaca gaagaaactt gtctagctaa    13740
taggattgat aactatcaag gtaggcatct agccgtactt attgatcttt attgtgattc    13800
tactaggtgt cctaatataa aagggtcaga cacaatcatg cgaaactcaa ttctcaaatc    13860
ttttattgat aatgagagaa ggacaagtcc attaggtcta acatggaatc ttgatccatt    13920
actcatagat catttcagtt gttcaattac ttatctgagg agaggtatta ttaaacagat    13980
```

```
taggctaagg tttgatccaa acatatctat tgagttggtt aaattggcaa aacctgaagt  14040
gattcatcaa ggaccaaaaa taccgtcttc ttgggccctt atagatatta atcctgaggt  14100
caatgatctt aatacagttt tcggagaatt aaatagtaaa tggaaagata ttcctattgg  14160
acaaattaga attcaaaatt atgagatcca tgcttaccga agaattggag ttaattcaac  14220
tgcatgttat aaagcattgg aaatgctatc tgtactaacc cggtttatgt ctaacccagc  14280
aggagctttg tttttaggag agggtgcagg gtcaatgtta gttacctatc gtgcgtttat  14340
cccgttcaag agaatttatt ataatagtgg aatttctata caaaatattc aaagccaaag  14400
agaactaagt ctatacccat ctgaagtagc cttggttgat aataaaaatc gtttgaccag  14460
tgatcctgat atcaaagtct tatttaatgg caagccagaa tccacgtggg ttgggaatat  14520
agactgcttt gcttatattc tgagtcatat tgaaacttct agtttaacat taatccacag  14580
tgatattgaa tctagcttga gtaaaacaaa gaataagatt cttgaggagc tttgccatat  14640
tctatcaatg gcactgattt taggaaagat tggatctgta ttagttatta agctgttacc  14700
acgggttggt gactacacat attcattttg caagtatgcg tcagaattct accaacagaa  14760
ttttttattt ttacctagat ttagcaacat gtcatcatct gaaatttact acgttggagt  14820
tcatttaaat accaatagac tggttgatcc agataggatt gtgcaatata taatcaggaa  14880
tctccaatct actccagtta ctttcttatc ttacattttg gaaactaaat atagaaataa  14940
tatggttaca aattatgggc tctgcttgtc tgatggacat aaaagcgatt acttgtcatc  15000
aatcaccaag atagaaaatg ttcttttatc atgtggattg gaattgaatg gacctaagat  15060
tatacagcaa ttatctggac atgactacgc caatggagag attagcttag aatcaagtat  15120
aatggtactg gttagagaat atctaaatgc aactatccaa ggtcgggaaa cactaggtct  15180
tttttcacct taccctgtgt tacatgagag tcagttaaga gaaattaaca ggtgcattgc  15240
attgaagtat gttgtatatt tacttttta ctcaacctct gtaggatcta gtagacaaat  15300
catgagcaat ctcagaaaag gagtattaat gtatgactta agagatgagt tttcatgga  15360
aaggttatca acaaatttca agaaaaaaat aatgtcacaa gaggttaaaa ctacatggat  15420
ctttaatatt gatgtaccaa caagaaaagc tctgtataaa ttagttggtt attcacttat  15480
cattaatcac gtataacaag tgtattgagt tggtaatatt ctagatgaac aagtataggt  15540
ttatgtacag taagtgatta aatattagat tcaggtagat aaacttccta atagtgtatc  15600
ctatagataa cctaaggcta tttaatgtta gattaattag aaaaaacttc ttgaattatg  15660
atagacttca acccctggct aagacttatc atttaaaatt ataaccaagt tgtcctgata  15720
atatcagatc tcattaatta cttgatagcg taatataaca ggtgcatgat gatcctttat  15780
tactcatata cctgttatta agctcctgtt caaattatcc cctatttaag ttgcctttta  15840
aattacctaa tatgttttgt aatgagaaac attgatacat acaaagctaa agaagcctga  15900
ttttatctaa ggttgtatct aattgttgtc aatttataat tcggaatatc tgggccctaa  15960
acctcctcca aatatactaa aaggttttaa aaaaacaaaa aaggtttctt acttattgta  16020
cggacctata gctttctttt gtctggt                                      16047
```

```

<210> SEQ ID NO 2
<211> LENGTH: 16045
<212> TYPE: DNA
<213> ORGANISM: Feline paramyxovirus type 2
<220> FEATURE:
<221> NAME/KEY: misc_feature
<223> OTHER INFORMATION: FPaV-2 “TV25 strain” full genome sequence;
      given as a DNA sequence that correspond to the positive RNA-strand
``` into which the negative RNA strand viral genome is transcribed,
i.e. it comprises the ORFs in 5' to 3' direction like an mRNA

<400> SEQUENCE: 2

```
accagacaaa gatgtctgtg acctattcta acggttagat tattacttga tatttaggaa      60
taacgattcc attagtcagg taagggagag gaatcagtta ttctataatg gctagtttac     120
tcaggtcact tgcggcattc aagaaacaca gagaacaacc aactgttcct tctgggtcag     180
gagggacgat caaaggatta aaaaatacaa ttattgtgcc tgttcctgga gatacagtca     240
tcactaccag atcgaactta ctgttcagat tagtctacat aattggtaat ccagatacac     300
ctttaagcac ttcaacaggg gcaataatat cattgttgac attatttgtt gaatctccag     360
gtcaattaat tcaaagaatc gctgatgatc ctgatgctgt ttttaaatta gtagaggtgg     420
ttcctgaggt tggtaatcct ggagaattaa cttttgcatc tagaggaatt aacttggata     480
aacaagctca acaatacttt agattggctg agaaaaatga tcaaggatat tatgtaagtt     540
tggggtttga aaatccacca aatgatgatg atataacgtc aagtcctgaa atcttaaatt     600
atatttagc atctgtactt gcacagatct ggattctcct agctaaggct gtaactgctc     660
cagacacagg tggtgaggct gaaaatcgta ggtggattaa attgatgcaa caacgcagag     720
tggatggtga gcttagatta agtaaaggat ggttggactt agtgaggaat aaaatcgcat     780
cggatatcac aattagaagg tttatggtag cattagttct tgacattaaa cgttctcctg     840
gaacaagacc aagaattgct gaaatgattt gtgatataga caattatatt gtggaggccg     900
gactggcaag ttttctgtta actatcaaat ttggtataga aacacgttac ccagcattgg     960
cgttacatga gttttcgggg gaattagcca ctattgaagg actcatgaaa ttgtaccagt    1020
ctatgggaga aatggcacca tacatggtca ttctagagaa ttcgatccag actaggttta    1080
gtgctgggtc ttatccgtta ctctggagct atgctatggg tgttggtgta gaacttgaga    1140
gatcaatgag tggattaaac ttcacaagaa gtttctttga tcctacgtac ttcaggttgg    1200
gtcaggagat ggtaagaagg tcttcaggaa tggttaatag ctcatttgct aaagaacttg    1260
gactatctga acatgaaaca caacttgtta gccagatcat taactctggt ggtgaatcag    1320
gtataccgaa atttgatgga tttagagcaa acccaacaac atttctaggg gctaaggaca    1380
acatcactga taggagtgaa gatccattga ttgcaattcc agggtcatca ggacaaccat    1440
tgccaggtca tgacccccaat atctcaggtg actcatatag aattgatagt agcactaaag    1500
acacgaacaa tatatcagat ggaggaacaa atccaagtca tgatgtttcc aattctgcta    1560
tggaagagct gagaagattg gtagagtcta ccaacaagat tgatacaaag aaatctgaaa    1620
gcccaggcat tgttaatcat acaacgata ctgaccttct gagataataa ggatatattc    1680
aggtagatct ttacagaatt taaattaaga aaaacttagg acctcaaggt tcacactcct    1740
ctggccttca tcagaactcg gccaattcct cactcactcc atgtcagcag aacaaatcca    1800
acaagttaga catggccttg aatccttgca agagatcaaa acaaccctc caccctctca    1860
agatgtcaat cttgccaggg aaatttacga atccattaaa caaacaggaa caccttcaac    1920
acaaggaggg accattacag gaaataatac tacgtcaggg tgtgacaatt actcaatgca    1980
tagccaggga tcaggtccctt ctgtttcagg tgctgacaag aatatcgaga gacttactgg    2040
acccgattat tcagaattat gggatccaga aggtaacctc tgcatgctat tcgaaagcga    2100
tgatgatgac aacaattatt cagagattaa tggccggtct accgctatcg aaggattgga    2160
tgaacagaat aataaggacc caggtattaa acaatcagga gatcagtgtt ctgaaggagt    2220
```

```
gtctaagatt aattcatctt ctagtcccca agaagctaca ttatcttctg ggagatctga    2280
tatatctggg acaggagtat ctccctgtgc ctctttggat ataactgtta atgaattaga    2340
agatgcaact gttaagaata gtaataatat gaaaggaaat tggccaatcc caaagttgct    2400
tgtcaaacca ccaccaagaa tgaaatcact ttctgactct gttacaccat taaaaggggc    2460
caccgacggg aaatcagtct tacctgggat ggagattaca ttgtccggga agaatggtgc    2520
aaccctacct gtacacccat ttacacaacc tgtaaaagac tcaaatgcag atgtaagcaa    2580
tgtccgtcaa catgtcccaa gtgtgactga tggttatagt gatgataatg aggaagtacc    2640
cggtttgcat aaagaaacta tagacaaagc tgatctatct atgcaggaca tatacaattt    2700
aattcttgga tttaaggatg attacaggaa actatcaaat aaattggata tgatactaga    2760
gatgaaacaa gatattgata atcttaaaaa gagtagtgca aaaatacaac ttgcattatc    2820
aacaattgaa ggacatctgt ccagtgttat gattgctatt ccaggttcag gtattgatat    2880
gaatcaagat gagaagaagg atcaattaaa ctctgactta aagccattac tagggaggga    2940
ccattgccgt gcatttcgtg aagtcactaa tcctttagat gaaacgtcat tgaccaacgc    3000
tccgaccaaa catgttgcta agatcaacaa aaattgcact cttcagaaaa tcaataagaa    3060
tgagacatct gcaattaagt ttgtacctaa tgatagctat gcaagtatct cgactatcaa    3120
gtctattgtc aaatcctcaa accttaatca agagcttaaa gtcaagttac tgacaattct    3180
atctcaaatt aaagggggtag acaatattaa ggagttttat gagaaagtta tgatattgat    3240
caagaataat aactgatctt gactaatcaa tagatactac ttatcaaatc tagctctgac    3300
atcaagtgaa ttcatctttta ttaacaagta ttaatcttaa ataattataa aaaacttagg    3360
agttcaggat cagtgggtca tatacaatat gactgagata ttcaatctgg atgaaagttc    3420
atggtcagtc aagggaacac tggacccatt gacgcctgat acttatcctg atgggcgcct    3480
agtacccaag attcgggtta ttgatcccgg tctaggtgat cgtaaaagtg gaggatatat    3540
gtacttactc cttcacggtg tcatcgagga cagtgagacc gtcataaatc cgaaagggag    3600
agcatttgga gctttccctt aggtgtaggg gcaatcaacc gagaacccag aagacttatt    3660
taaggaaata ttaaccctca acattgttac tcgcaggact gctggcttca atgaaaaatt    3720
ggtgtattat aatactacac ctctaaatct actaaccct tggaaaaaag tactagcata    3780
tggaagtatc tttactgcta atcaggtctg caataataca agttctatcc ctatagacat    3840
tcctcagaaa tttcgacctg tctatttaac tgttaccaag ttatcggatg atggatatta    3900
tcagataccc aaaatgatac aggatttcaa atcatcaaac tctgttgcat ttaacatcct    3960
tgtgcatcta tcaatgggaa caattttact tgactcatct aaaggctctc gagtaggaaa    4020
tcctgcagaa aatttgatca cattcatgat tcatattggg aatttcaaac ggaagaataa    4080
taaagcttat tctcccgaat attgtaagag gaaaataatg aggcttggat taatcttctc    4140
actaggagcc attggtggaa caagtttgca tattcgatgc acaggcaaaa tgagtaagcg    4200
attacaagcc tacttagggt ttaaaagaac tttatgttat cctctgatgt atgtcaatga    4260
gggtctaaac aaaaccttat ggagaaatga atgcagaatt gagaaggttc aagcagtatt    4320
acagccatca gttccgaatg aatttaagat ttatgatgat ataatcattg ataacacgaa    4380
tggcctcttt aaggttaagt aagctgtgac tagtatcagg agttactagt caaaatcatg    4440
tgttgatatc cgaattaata gctttaagtt gaatatatta aacctgtgat aattcaaatt    4500
tgaaacataa ttagtatgta gtattgtatt aatcagtttg taatcttgtt tgaggatcca    4560
aattataacc tattaggtat tgccactcca gcttacaggt aaatctaagc gaatatacaa    4620
```

```
ataattgata ttcgggatta aacaatactt gcatattaat ccataggtat attagatttt    4680
actatattca attattataa tgtttattga gttaagctct catgattata aaaaacttag    4740
gattccacat aatcacagtt tgattgccaa ttgatgtgtt tagtattagt tgtgtgaaat    4800
attgatatta ataaggttaa tcaactttg tacagaagtg aaggtgtaat tagatagaaa    4860
tagattaatc cttagtagcc gttttgataa ttgaattgat tcttgtttta attctgaatt    4920
gagattatta atcaccagct cggcataatg tataagatta aggttgtaat catgggtttt    4980
ttactgttat cagatattac atttgcacag gtaggttggg ataatttaac ctcaattgga    5040
gttataagta ctaaacaata taactataag ataactactt tgaatactaa tcaactcatg    5100
gtgattaaaa tggtacccaa tatatcatca attattaact gtactaaact tgaattagca    5160
aaatataggg aactgattac aggaatactg agaccaatta atgaatcatt agaattgatg    5220
aattcatata tcaacatgag aacaggttca gagagattca tagggctgt tatagcagga     5280 gtagctctag gggttgcaac tgcggcgcag ataacatcgg gaattgcctt acataattcg    5340
attatgaata aaaaacagat acaggaatta aggaaagccc ttagtactac aaataaggca    5400
attgatgaga taaggattgc aggtgaaaga actctgatag ctgtccaagg tgtgcaagat    5460
tacattaaca atgttattat ccctatgcaa gagaaactcc agtgcgatat tttagcctca    5520
cagctatcta ttgccctact cagatactat actaatatac tgactgtttt tggaccaagt    5580
ataagagatc ctattactag tacaatttct atacaagctc tcagtcaagc attcaatggt    5640
aatctacagg cattgcttga tggattaggg tatactggac aagacttaca tgatctcata    5700
gaaagtagat ctatcactgg tcaaataatt cacgctgata tgactgattt attccttata    5760
ttgagaatca attatccatc tattacggat atgcaaggag tggtaatata tgagctgaat    5820
tctatcacat atcatattgg acctgaagag tggtacacta ttatgcctaa tttcatagct    5880
gttcagggat ttctggtatc taatttcgat gaacgtaaat gttcaattac taaaacaagt    5940
atactgtgtc aacagaattc aatttatcct atgtcaaccg aaatgcaaag atgtataaaa    6000
ggtgagatta aattctgtcc aaggtccaaa gcaattggga cattagttaa tcgatttata    6060
ttaattaatg ggaatctaat ggccaattgt ttgggtatta tttgtagatg ttatacctca    6120
ggtcaaatta taacgcaaga cccaaataaa ttaatcacaa ttatatcaca agaagaatgt    6180
agagaggttg gtgttgatgg gattcgtata atggtgggac taaaaaatt accggatgtt    6240 atctttaatg ccagactaga aataggtgta cctatctcat taagcaagct ggatgttggg    6300
accgatttgg caattgcttc agctaaactc aataactcta aggcactttt ggagcagtct    6360
gataaaatct taattctat gtctaagttg gattctttaa attcacgtat cttaggatct    6420
gtctttataa tgatgataat ctttgtgatt gtaattgtga ttatttggat tattgtaag    6480 aagtgtagaa ataagaggaa caaattaagt gcttctattg aacccctcta catacctccc    6540
tcttataatt cacccatag catagttaaa tctatttgaa ataaagtgt ataatctgat     6600 ataacagatg cagtagaatt attaatcaat gataatatta ttatgataat gattcagtta    6660
gatgttcatt atatctcata acttaatatt gacaaatttc aattagttaa atttattctc    6720
ttcataatat gtatttgttt aattatccta gattaatgta ttgttattaa actggtcatc    6780 tttaataacct aactcagcaa tactatccta tacacatgta ttagctaata acgatgtaat    6840
attgccattt aataataagt acctagtaga atgggaagca ttagctgtag tcaatgaatc    6900
attatctgct caattagaaa aaayttagga atccatgtta atgggagttg gccatcatgg    6960
```

```
agtctaataa caacaagtac tataaagatt caaaccggta ttttagcaag atactagatg    7020
agaacaagac ggtaaataat catctgtata gtcttagtat aaggataatt accgttatag    7080
ctattgttgt gagtctaatt gcaacaacaa taaccatcat taatgctata agcggaagga    7140
ctactcttaa taataatatg gacatgctac tcaaccaaca agacaagatt aataatatca    7200
aggaaatgat atttgatcgt atctatcccc tgataaatgc catgagtaca gagcttggtc    7260
ttcacattcc aactttattg gatgagctga ctaaatcaat tgatcaaaaa atcaagataa    7320
tgactccacc acttgaaact acgacatcta atctcaattg gtgtatcaac cccccaaatg    7380
gcattattgt agatcctaaa ggttactgtg aaggcttgga actgtcaaaa acttataagt    7440
tattacttga tcaattagat atgttaagaa agaaatcact tattattaat aagaaaagta    7500
ttaatcagtg tagacttgtt gatagctcga atatcatctt tgcaacagtt aatatacaat    7560
ctacaccgag attcttaaat cttggtcaca cagttagtaa ccaacgtata acattcggtc    7620
aaggaacata tagtagcact tatattataa ctatacaaga ggatggatta actgatgttc    7680
agtaccgagt atttgaaata ggatatatct cagatcaatt tggaaccttc ccttctctaa    7740
tcgtttctag agtactacct gtgcgaatgg tacttggaat ggaatcttgt acactgacca    7800
gtgacaagtt cggggttat tttttatgca tgaacattcc gacacgctct atatatgatt     7860
atgtcaacat aagagactta aagtcactat acgtcacaat ccctcattat ggcaaaatta    7920
attacactta ctttaatttt ggaaaagtca gaagcccaca tgaaattgat aagatttggc    7980
ttacatcaga aaggggacag atgatttcag gttactttgc agcatttgtt acgattacaa    8040
ttagaaatta taacaattat ccctataaat gcttacataa cccgtgtctt gaaagatctg    8100
agagttattg caaaggatgg tacaaaaata ttacaggtac tgatgatgtt ccaatattag    8160
catatctatt agttgaaatg aaggatgagg aaggaccttt aattacactg gttgaaatac    8220
caccttacaa ttatacggct ccttctcata attcccttta ctatgatgat aaaattaaca    8280
aattaataat gacaacatct catataggat acattcaaat caatgaagtg catgaagtca    8340
ttgtcgggga taatcttaag gctattctct aaacagatt atctgatgaa cacctactc     8400 ttactgcttg tagatttaat caggaaatta aagagcgaca tatatctgat gggttaataa    8460
tatctaactc tgctcttatt gatatacaag aacgtatgta tattacagtt aaggctgttc    8520
cacccatagg aaattataac ttcacggtag agttgcattc acggtcaaat acatcttacg    8580
tagggttgcc aaggcagttc aatgctaggt atgacaaact gcatctcgaa tgcttttgcct   8640 gggataggtc ttggtggtgc gctttgatac ctcaattttc attaagttgg aatgaatctc    8700
tttcagtaga tactgccatt tcaacttaa taaactgtaa ttaagtttgt ggcttgttct     8760
agattgatca tttgaataac agttgattaa gccgaagtta gtaaatacat acattaacct    8820
gttcttgacc aagtatgtat cctaatccaa ttataaaaaa cttaggactc aaggtgttga    8880
tggcaatgga gcaatcagat tatcaagata ttttatatcc agaggtacat ctcaacagtc    8940
ctatagttat ctctaaatta gtgggtattt tggagtattc taaggttgtt cacaatcagc    9000
agttatctga tcacacaata gtcaagaata tacaatttag attgagaaat ggattcaata    9060
gtccaagagt acaaacactg ttagttatgg gtgaaattat caataaaatc aaaaataaat    9120
acccaaatta tttgcacata ccttatcctg aatgtaatca aaagttattt aggatggctg    9180
acccggagtt aacatctaaa ctagaagccc tcttggacaa aggtgacaca ttatatctta    9240
agattaagac agagatcata gcttgttttcg ataagttaaa aactaaaatg agcataacca    9300
atgatctgat tagtgacaat aggcagctaa tttcagatct acctctaatt gtcaagggat    9360
```

```
ctcaatggtt tttcccttt  ttgctctggt tttctgttaa aactgagact aggaactgta   9420
ttcgacaaaa tcaaaaaact cgtgttaggt cacaataccg acctcatttg tcagaaacta   9480
aaagaattac gctggtcgtt acccctgact tgatcacaat atttgaccac gtcaacaaat   9540
gtatatatca tctgactttt gagatgttgt tgatgtattg tgatgtagta aagggaggt    9600
taatgaccga agcatctatg agtctagatc acagatttat taacctattg tcgagggtcc   9660
agtatatgtg ggatctatta gatgggatgt ttgagagtct aggaaatcag ctatattcaa   9720
tcattgcact cttagaacct ctctctcttg cctatctaca gttgatggat gcagacccac   9780
agatacgggg tacattttta caccattgcc tttcagagtt ggaagaactc ttatttagta   9840
aatcccctt  tgatcctgtg atttatgaaa atctaattag tggacttgat tacatctatt   9900
taacagacga tattcattta actgctgaga tattttcttt ctttagaagt tttggtcatc   9960
cttatttaga agcacaaaat gcagctagca atgttaggaa atatatgaat caacctaaag   10020
ttatctcata ccagactcta atgcaaggac atgcaatttt ttgtggcatt ataataaatg   10080
ggttcagaga tcgtcacgga gggacatggc cacctgtaga gctaccacat catgcatccg   10140
ctgtaattag aaatgctcag ttatctggag aaggattaac acctgagcag tgtgctcaat   10200
actggaggtc atttttgtgga tttaaattta aatgttttat gccattaagt ctagatagcg   10260
acctcaccat gtaccttaga gataaggcat tatcacctat taagaatgag tgggattctg   10320
tgtatgctaa agagtattta agatacaacc ctggcttacc gactagctct cgaagattag   10380
tcaatgtatt tctagaagat gataaatttg atccgtacga aatgattatg tacgtaataa   10440
acggtgatta tttaagggat aatgagttca atctctcata tagtcttaaa gaaaaggaga   10500
tcaaggaggt aggccgattg ttcgctaaaa tgacttataa gatgagagct tgtcaggtaa   10560
tagcagaaaa tttaattgca aatggagttg ggaaatttt taaagacaat gggatggcga   10620
aggatgaaca taaattaacc aaaacattac ataagctggc tatttctggt gtacctaaag   10680
ataattctca actctatttta agtgaatgtt gggaacaagt ggtagaacaa tgcgtaacca   10740
gtacgcaaac aaaaatcaa attatcagtt cacactcagg aaaatcagtt gcatcaaagt   10800
tttcaagatc aaatcccaat gatagggta ttctaaatag tggtagacat ttgaataaac   10860
atccaaaaca tccatcaaac accgaatact atgaaactgt cagtagtttt ataactactg   10920
atctcaagaa atattgcctc aactggcgct atgaatcaag tagtgtgttt gcagaaagac   10980
tcaatgagat ttatgggtta ccaggatttt tccattggct tcatagaatt ttggagaaat   11040
ctgtattata tgttagtgat ccatccagtc cacctgattt tgatcaacat gtcgatattg   11100
attcagttcc aaatgatcat attttatca aatacccaat gggtgggata aaaggattt     11160
gtcaaaaatt atggacaatc agcacaatcc cattttata tttagcagcc tttgatcag    11220
gggttagaat atcttcgttg gttcaaggtg ataatcaagc aattgcagtg accaaaagag   11280
ttccatcatc ctggagttat tcgagaaaaa aagaggagtc aactaaagtt acaacacaat   11340
atttttaaa cttgagacaa cgcttacatg atataggtca tgagttaaag gcaaatgaga    11400
ctattatatc ttcacacttt tttgtttact ctaagggtat ttattatgat ggtatacttc   11460
tttcacaatc ccttaaaagt attgcaagat gtgttttttg gtccgagaca attgtcgatg   11520
agactaggtc agcttgcagc aatatatcca ctacccttgc taaagctatt gaacggggtt   11580
atgataaatt tgtagcatac gctattaata tatataagac tatacaccag gtcttaattg   11640
cattatcttt tactattaat cccactatga ctccggacat aacagaacct ttttataaaa   11700
```

```
gtttagattt acttaaaaac ctcattctga taccagcacc attgggtggg atgaattaca    11760
tgaatatgag cagattattt gttaggaaca taggtgatcc cattacagct tcatttgctg    11820
acatcaagcg tatgatcgaa tgcgggttat tagggcacaa tgttctctca caaataatgt    11880
atcagaaatg tggtacctcg aaatacttag attgggctag tgacccttat tccataaatc    11940
ttccttatag tcaaagcatg accaaagtat taaaaaatat aaccgcgaga tatgttctca    12000
tgcatagtcc taaccctatg ctaaaagatt tattccatga gaagtcacaa gaagaggatg    12060
agattcttgc tgaatttttg ctggatcgtc agttaataat ccctagagct gcacatgaaa    12120
ttttatcgaa ttcagtaaca ggagctagag agtcgattgc agggatgctt gatactacta    12180
aaggacttat tcgagccagt atgtcaagag gtggtctgac atcttcactt gttttgaaat    12240
tgtcaacata tgattatcaa caatttagaa catgccttga atggctttat gcccctacca    12300
caggaatagc agtaagtgct gattcttgtt cagttttttt agccagagct attcgaaaaa    12360
ggatgtgggt tcacctgact aaaggaagag aaatttatgg cctagaagtg cctgatatat    12420
tagaatgtat gcagagcaat gtaattgttg atcatgaaga ttgttattca tgtattcaag    12480
gatcaagata ctacacatgg ttttttgtac cttctaattg tcagcttgat cagattaaca    12540
agtctacaaa ttctctacgg gttccttaca ttggctctac tacagaggaa agaagtgaca    12600
tgaaattatc atacgtcaga tcccctagta ggccacttaa ggcagcagtc cgaattgcag    12660
cagtctacac atgggcatac ggtgatgacg atctgtcttg gcgtgaggct tggtacttgg    12720
caaggactag ggcaaatgtt actttcgatg agcttaaatt agtaacaccc atagctacct    12780
ctactaactt ggcacataga ttaagggaca ggagtactca agttaagtat tcaggaactt    12840
cattggtaag agtggcacgc tatacaacaa tatccaatga taatatgtca tttgttatta    12900
atgacaaaaa ggtagatact aattttgtct atcaacaggg catgttattg ggtttgagta    12960
tcctagaata tatatttaga tactgtaaaa gtactggtca atcaaatact gtagttcact    13020
tgcatgcaga tgttaattgt tgcataatcc aaatgacaga tcaaccttat actccaagct    13080
taacgaaaaa attacctgag attaaaccta ttaataataa attgatttat gatccagctc    13140
ctataattga tactgatgca gctaggttat attctcagaa gtacttatca cacctgatag    13200
attttccaaa ttggtcaatg aatcagctaa atgtagtttt agcaaaagta gttgcaatat    13260
ctattgtgga cttgataact aaagcgagta agatcatct caatgaaatt atggcagttg    13320
ttggagatga tgacattaat agctttataa cagaattttt gctagttgat ccgaggctat    13380
ttacattgta cttaggtcaa tacacgtcac ttcaatgggc atatgaaatt cattatcacc    13440
gacccgtagg caaataccag atggcagaag tgttacacac tttactgtca agagcaagta    13500
aaggtatatt taatatattg actaatgcct ttagtcatcc tagagtttac aaaagatttt    13560
gggaatgtgg attactggag cctatttatg gaccatacat agggagccaa aatttatata    13620
gtacagtaat tgattacctt tacaatgctt atataactta tttagatgct tatctatctg    13680
atcatatcga agatgcagac atagtaatat gtgagacaga agaaacttgt ctagctaata    13740
ggattgataa ctatcaaggt aggcatctcg ccgtacttat tgatctttat tgtgattcta    13800
ctaggtgtcc taatataaaa gggtcagaca caatcatgcg aaactcaatt ctcaaatctt    13860
ttattgataa tgagagaagg acaagtccat taggtctaac atggaatctt gatccattac    13920
tcatagatca tttcagttgt tcaattactt atctgaggag aggtattatt aaacagatta    13980
ggctaaggtt tgatccaaac atatctattg agttggtaa attggcaaaa cctgaagtga    14040
ttcatcaagg accaaaaata ccgtcttctt gggcccttat agatattaat cctgaggtca    14100
```

```
atgatcttaa tacagttttc ggagaattaa atagtaaatg gaaagatatt cctattggac    14160
aaattagaat tcaaaatttt gagatccatg cttaccgaag aattggagtt aattcaactg    14220
catgttataa agcattggaa atgctatctg tactaactcg gtttatgtct aacccagcag    14280
gagctttgtt tttaggagag ggtgcagggt caatgttagt tacctatcgt gcgtttatcc    14340
cgttcaagag aatttattat aatagtggag tttctataca aaatattcaa agccaaaggg    14400
aactaagtct atacccatct gaagtagcct tggtcgataa taaaaatcgt ttgaccagtg    14460
atcctgatat caaagtctta tttaatggca agccagaatc cacgtgggtt gggaatatag    14520
actgctttgc ttatattctg agtcatattg aaacttctag tttaacatta atccacagtg    14580
atattgaatc tagcttgagt aaaacaaaga ataagattct tgaggagctt tgccatattc    14640
tatcaatggc actgattcta ggaaagattg gatctgtatt agttattaag ctattaccac    14700
gggttggtga ctacacatat tcattttgca agtatgcgtc agaattctac caacagaatt    14760
tcttcatttt acctagattt agtaacatgt catcatctga aatttactac gttggagttc    14820
atttaaatac caatagactg gttgatccag ataggattgt gcaatatata atcaggaatc    14880
tccaatctac tccagtcact ttcttatctt acattttgga aactaaatat agaaataata    14940
tggttacaaa ttatgggctc tgtttgtctg atggacataa aagcgattac ttgtcatcaa    15000
tcaccaagat agaaaatgtt cttttatcat gtggattgga attgaatgga cctaagatta    15060
ttcagcaatt atctggacat gactacgcca atggagagat tagcttagaa tcaagtataa    15120
tggtactggt cagagaatat ctaaatgcaa ctatccaagg tcgagaaaca ctaggtcttt    15180
tttcacctta ccctgtgtta catgagagtc agttaagaga aattaacagg tgcattgcat    15240
tgaagtatgt tgtatattta ctttttttact caacctctgt aggatctagt agacagatca    15300
tgagcaatct cagaaaagga gtattaatgt atgacttaag agatgagttt ttcatggaaa    15360
ggttatcaac aaatttcaag aaaaaaataa tgtcacaaga ggttaaaact acatggatct    15420
ttaatattga tgtaccaaca agaaaagctc tgtataaatt agttggttat tcacttatca    15480
ttaatcacgt ataacaagtg tattgagttg gtaatattct agatgaacaa gtataggttt    15540
atgtacagta agtgattaaa tattagattc aggtagataa acttcctaat agtgtatcct    15600
atagataacc taaggctatt tgatgttaga ttaattagaa aaaacttctt gaattatgat    15660
agacttcaac ccctggctaa gacttatcat ttaaaattat aaccaagttg tcctgataat    15720
atcagatctc attaattact tgatagcgta atataacagg tgcatgatga tcctttatta    15780
ctcatatacc tgttattaag ctcctgttca cattatcccc tatttaagtt gccttttaaa    15840
ttacctaata tgtttagtaa tgagaaacat tgatacatac aaagctaaag aagcctgatt    15900
ttatctaagg ttgtatctaa ttgttgtcaa tttataattc ggaatatctg ggccctaaac    15960
ctcctccaaa tatactaaaa ggttttaaaa aaacaaaaaa ggtttcttac ttattgtacg    16020
gacctatagc tttcttttgt ctggt                                         16045
```

<210> SEQ ID NO 3
<211> LENGTH: 16050
<212> TYPE: DNA
<213> ORGANISM: Feline Morbillivirus
<220> FEATURE:
<221> NAME/KEY: misc_feature
<223> OTHER INFORMATION: FeMoV "Lapon strain" full genome sequence;
      given as a DNA sequence that correspond to the positive RNA-strand
      into which the negative RNA strand viral genome is transcribed,
      i.e. it comprises the ORFs in 5' to 3' direction like an mRNA -continued

```
<400> SEQUENCE: 3
accagacaaa gatgtctgtg acctattcta acgacaagac tattactaaa tatttaggaa      60
taacgattcc attggtgagg cgaggaggag gaatcagaca ttccacaatg tcgagtctac     120
taaggtcact tgctgcattt aaaagacata gggagcaacc aactgcaccg tcaggctcag     180
gtggtacaat taaaggattg aagaatacaa ttattgttcc agttccaggg gatacagtaa     240
ttactacgag gtctaacttg ttatttagat tagtttatat aataggcaat ccagatacac     300
ctttaagtac ctcaacggga gcaataatat cattgctgac cctatttgtt gaatccccg      360
gtcaattaat tcaaaggatt gctgatgatc ctgacgcagt ttttaaatta gtagaagtca     420
ttcctgaagt cggtaatcct ggagagctga cttttgcatc tcgaggaatt aatttggata     480
agcaagctca acaatatttc aaactggctg aaaaaaatga tcaggggtat tacgttagct     540
taggatttga gaacccacca aatgatgacg atataacatc tagtcctgag atatttaatt     600
atattctggc atctgtactt gcacaggttt ggattcttct ggcaaaagct gttactgccc     660
cagataccgc tgctgaggct gaaaaccgta gatggattaa gttgatgcag caacgtagag     720
tggatggtga actaagattg agcaaaggat ggctggatct ggtgaggaac aagattgcat     780
cagatattac aataagacga ttcatggtag cattagtcct tgatatcaaa cgttcccccg     840
gaacaagacc aagaatagct gagatgattt gtgatattga taattatatt gtagaagcag     900
ggcttgcaag cttttttgttg actatcaaat ttggcataga aacacgttac ccagcattgg     960
cattacatga attttctgga gaactagcta ccattgaggg gcttatgaaa ttgtaccaat    1020
ctatggggga aatggcacct tacatggtaa ttctggaaaa ttcaatccaa accaggttca    1080
gtgcagggtc ttatcctctg ttatggagtt atgctatggg tgttggcgta gagcttgaaa    1140
gatcaatggg tggacttaat tttactagga gtttctttga tcctacatat ttcagacttg    1200
gtcaggagat ggtgcgaaga tcttcaggga tggttaatag ttcatttgca agagaacttg    1260
ggttgtctga acatgagaca caacttgtca gccaaattgt caattctgga ggtgaatctg    1320
gtatacctaa gtttgatgga ttcagagcaa atcctacaac ttttctagga gccaaggaca    1380
acataaatga tggaggtgag gaccagtcaa attcagtatc aggattgcct ggaccaatat    1440
tgccaagtca tgacttgaat ctgtcaggtg attcatatgg gaatgatagt ggtatgaaaa    1500
atgtcaacga cagactaaat gaaggagtaa gtccagacca tgatgtttct agctctgcca    1560
tggaagaatt aaggagattg gttgagtcta ctaacagaat tgacactaaa aagccagagg    1620
ctccaggtgt tactaaccat tacaatgata ctgaccttct gaaataacat gggtatcatc    1680
tatttgatta ttatacaact taaattaaga aaaacttagg acctcaaggt tcacaactgt    1740
tgacagctca ccaggaaaca atcaactcct tacccaccac atgtcctctc accaaatcca    1800
acaggttaaa catggcctcg aatctttaca agagatcaaa aacaaccctc catcttccca    1860
agatgtcaat cttgccaggg agatttacga atccattaaa caaacaggaa cacttcagt    1920
gcaaggagga gccattacgg gagataatac tacgccaggg ggtaacaatt acacaatgta    1980
tagccaagga ccaagtcctt ctattccaag tgttaacaag aatatcgaag gacttactgg    2040
atccgatcat tcaggactat gggatccaga ggataacctc tgcatgttat tcgaaagcga    2100
tgatgatgaa aaccattatt cagagattaa tggccggcct tccactatcg aaagattgga    2160
tgaacaggat aatgagaacc caagtattaa acaaccagga aatcaatgta ctgaaggagt    2220
gtttaagact gattcatctt ctaattccca agaaactaca ctacctgttg ggagatctga    2280
tatacctggg acaggaatat caacctgtgc ctctttggat ataaccgtaa atgaactcga    2340
```

```
ggatgcaact gtaagaaata gcgacaatat gaagggaaac tggccaatac caaagttact    2400
tgttaagcca ccacccaggg caaaatcaag cgttgatcat agcaatccat taaaaggggc    2460
cacaggaggg aaattagtct tacctgggat ggagactaca ttgtccggga agagtggtgt    2520
aaccccatct gtgcacctat ctactcaacc tgtaaacgac ttcaatgtaa atgtaagcaa    2580
tgcccgtcaa cctgccccaa atgtgaataa tgatcacagt gacagtgggg taatagtgcc    2640
caacttacat aaagacattg aagataagtc tgaaatatcc attcaagata tatcaacttt    2700
aatacttggg tttaaggatg attatagaaa attgtctaat aaactggata tggtattaga    2760
gatgaaacaa gatattgaca atcttaaaaa gagtagtgct aaattacaat ggcattatc     2820 aactattgag ggacatctat ctagtgttat gatcgctatt ccagggtcag gtattgattc    2880
caccggggat gagaaaaagg atcagatgaa cactgactta aagccgttat tggggaggga    2940
tcattgcaga gcatttcgag aagttaccag tcctttagat gagatgtcat tagccaattc    3000
tcccacaaaa catgttgcta aaataaacaa aaactgcacc cttcagaaaa tcaataagaa    3060
tgaaacatct gcaatcaaat ttgtccccaa tgatagtcat gcaagcacat caaccatcag    3120
atcaatcatc agatcatcca atcttgatca ggatttgaaa acgaaactac tcacaattct    3180
atctcagatt cggggatag ataatattaa ggaattttat gaaaaagtca tgatactaat     3240
aaagaatagg aactaaacat caccattcta catgcactac tggttgtgat tatcctcaat    3300
agaatctggt acaattcatt tatatgctta ttgttttaaa acaattataa aaaacttagg    3360
agctaaaggt tattcagtcg gatacaacat gactgagata ttcaatcttg atgaaagctc    3420
atggtcagtc aaaggaacac ttgatccact aaccctgat acctatcctg atgggcgact     3480
tgtacctaaa gtccgggtaa tcgatccagg tttaggagat cgcaagagtg gagggtatat    3540
gtatctactt cttcatggtg tcatagaaga tagtgaaacc atggttagcc cgaaaggaag    3600
agcatttggg gcgttcccat taggagtagg tcagtcaact gaaaacccag aagatttgtt    3660
taaagaagta ttaaccctca acattgtaac tcgtaggact gctggcttta atgaaaaatt    3720
agtttattat aataccacgc ctctacactt attgactccc tggaagaaag tgttggcgta    3780
tgggagcatt ttcaatgcta atcaggtctg cagtgataca agttctatcc cgatagatat    3840
tccacaaaaa tttagacctg tatacttgac tattacaaaa ttatctgacg atggctatta    3900
tcagataccg aagatgatcc aagatttcaa atcatcaaat tctgttgcat ttaatatcct    3960
tgtgcattta tcaatgggca caactttaat tgaccaatcc aaagaccctc gattaagaag    4020
tgctccagaa actatgatca cattcatgat tcatattgga aatttcaaac ggaagagtaa    4080
caaatcttat tctcctgaat actgcaagag aaaaataata agacttggtt tgatattctc    4140
attaggtgca attggcggca caagcttaca tattagatgt acaggtaaga tgagcaaacg    4200
gctacaggct tatctaggat tcaaaaggac tctatgttac cccctgatgt atgggaatga    4260
agggttgaat aaaaactctgg ggagaaatga atgtaaaata gaaaaggttc aagcggttct   4320
acagccatca gttccaaatg aattcaagat atacgatgat gtcattattg acaataccaa    4380 tggtctttc aagattaagt aggctataat aatgataaac agttacaaaa tgatatcatg      4440
tttggaagtg catactgata attgtgaatt aaatatactg gattaattac aatgtatggt    4500
tggaatctag tcaatatgtg ggttaatagt taatcatcta ttagctttat ttgtcattct    4560 tatttttaaac tgtttaattt aaagatatca aaatgtaatg aattcagcat tactaaatca    4620
acatttagtt cttagaatcg aaatccatac gttgtcaaac ttacagttac attaaattct    4680
```

```
tttcaattaa acctctgtaa cattaattaa ttatcataca agcaattata aaaaactgag    4740
gacctaatgt aatagggatt cagatttcat ctagtaggct taggatcacc atactcaaac    4800
accaatttgc ctggtgtctg tccagctcaa accgaagatc acaactaaac tctcaacaag    4860
tgggcgaaac ctggataaat gttaagaatt gagatctcaa attgagttct cctgtaagtt    4920
agggtttctg taacacattg tcaatccaat atcatgggta aaattaaggt tataataatt    4980
agctctttac tactatcaac tattacgact gcacaagtag gttgggacaa tttaacttcg    5040
attggagtta taagtactaa gcaatatgat tataaaataa ccactttgaa tactaaccag    5100
ttgatggtta taaagatggt ccccaatata tcatcaatca tcaattgcac caagcctgag    5160
ttgattaaat atcgagagtt ggtcttaggg gttattagac caatcaatga atcgttagaa    5220
ttgatgaatt catacattaa catgaggaca ggttcagaga gattcatagg ggctgtaata    5280
gctggagttg cattgggtgt ggcaactgca gcgcaaataa catcaggaat tgcattacat    5340
aactcaatta tgaacaaaaa gcaaatacaa gaattgagga aggccctcag taccaccaat    5400
aaagcaattg atgaaataag gattgcaggt gagagaaaca taatagcagt ccaaggtgta    5460
caagattaca ttaataatat aattattcct atgcaggaca aacttcaatg tgatattttta   5520 tcatcacagc ttgctattgc cttactcagg tattatacaa atatattgac agttttttggg   5580 ccaagcatac gagatcctgt tactagtaca atctcaatac aagcacttag tcaggcgttt    5640
aatggtaatc tccaggcatt gcttgatgga ttaggatata ccgggagaga cttacgtgat    5700
cttttagaga gtagatctat tactggtcag ataattcatg cagatataac tgatttgttc    5760
cttgtcctca gaattaacta tccttctata actgaaatgc agggagtaac gatatatgaa    5820
cttaattcaa ttacatatca tattggaccct gaggaatggt atactattat gcctaatttt    5880
atagctgttc agggtttttt aacatccaat ttcgatgaaa ggaagtgctc aataactaaa    5940
tcaagtatac tgtgccaaca aaattcaatt tacccgatgt caacagaaat gcaaagatgt    6000
atcaagggtg agataagatt ctgtccaaga tccaaagcaa ttggaacatt agttaataag    6060
tttatcttga ctaaaggtaa tttaatggct aattgccttg gtattatatg caggtgttat    6120
acttcaggcc aaattataac acaagaccct agtaagttaa ttacaataat atcacaagag    6180
gaatgcaaag aagttggagt tgatggtatc cgtattatgg taggacctag gaaattacca    6240
gacattacct ttaacgctag gttagaggtt ggtgtgccga tatcattaag taaattagat    6300
gtaggaactg atttagcaat tgcttcagct aaacttaata attctaaggc actgttggaa    6360
caatcagata aaattctgga ctcaatgtct aaattggatt ctattaattc acgaatcaca    6420
gggttgatct tggcaatcat ggtaatcttt ataatcatcg ttactattgt ctggatcata    6480
tacaaaagat gcagaaataa agataataaa ttcagtactt caattgaacc gctttatata    6540
cctccttctt acaactcacc tcacagtgtg gttaagtcta tttgagtact aactgtatga    6600
tttactgtga taaattcagt gaaattaaca agtgatgata ttggtgtctc aataagtatt    6660
gatcatgtta catactctgt taaactaaat gctgataaca ggttatagat gattgtaatt    6720
gtttcaatga aattatatat taattctatt accttgcata atttttcatac aattgaatta    6780 tatgttatta attaataccct taatgggttt gccttatata cttagactaa tagacagata    6840
tgctatattg taatcaagaa tttaatactt aaaagacgga ataatttaac ttttttgctaa    6900 ttgatgattg tgtattcaat tagaaaaaac ttaggaatcc atgttaatac aagcttatta    6960
tcatggagtc caacaacatt aaatattaca aagactctaa tcggtatctt ggtaaaatat    7020
tagatgaaca caagacagtt aataatcaat tgtacaggtt gagtattaaa gtaattacca    7080
```

```
ttattgctat tattgtaagc ttaattgcaa caataataac tattattaat gccacaagtg    7140
gaagaactac cctaaacagt aatacagaca tactgcttag ccaaagagat gagattcata    7200
gtattcatga aatgatattt gaccgtattt atcctttgat aactgctatg agtacagagc    7260
taggacttca tattcctact ttattagatg aacttactaa agcaattgat caaaaaatta    7320
aaataatgaa tcctcccgtt gatactgtaa catctgatct taactggtgt atcaaacctc    7380
ctaatgggat tattatggat ccaaaaggtt attgcgaaag tatggaatta tctaaaactt    7440
acaaattatt gcttgatcag ttagatgtct caagaaagaa atcgctcatt ataaatagaa    7500
agaatatcaa ccagtgtcaa ttagttgatg actcaaagat cacttttgct actgttaata    7560
tacaatctac accaaggttt taaattttg gtcatacagt cagcaatcaa cgtataacat     7620
ttggtcaagg aacttatagt agtacttata ttataactat ccaagaagat ggaataaatg    7680
atgttcaata tcgagtgttt gaaattggat atatctctga tcagtttggt ttttteeeet    7740 cattaatagt atctagggta ttgcctatac gtatggtatt gggaatggaa tcctgtacct    7800
tgacgagtga tcgacaaggt gggtatttct tatgtatgaa tacattaaca cggtctatat    7860
atgattatgt caatataaga gatttgaaat cactatacat aacacttcct cattatggta    7920
aggttaatta tacttacttc aattttggga aaattaggag cccacatgag attgataaaa    7980
tttggctaac gtccgaaaga ggtcaaatta tttctggtta ttttgcagca tttgtcacaa    8040
ttacgattcg aaattataat aattatccct acaaatgttt gaataatcca tgttttgaca    8100
actctgagaa ttactgtagg ggatggtata agaacataac aggcaccgat gatgttccaa    8160
tactagcata cttactagtt gaaatgtatg atgaagaagg acctttaatt acacttgtag    8220
caataccacc ttacaattat acagctccat ctcataattc tctttactat gatgacaaaa    8280
ttaataagtt gataatgact acatctcaca ctgggtatat acagatcaat gaggtgcatg    8340
aggtgattgt tggtgatgat ttaaaggcta ttctcctgaa cagattatct gatgaacacc    8400
ctaatcttac agcctgtaga cttaatcaag gcattaaaga gcagtacaag tccgatggaa    8460
cgataatttc aaattctgca cttattgata tacaagaacg aatgtatatt acagtcaaag    8520
ctattccacc agtaggtaac tataacttta cagttgagtt gcactctaga tcaaacacat    8580
cttatatatt gttaccgaaa cagttcaatg ccaagtatga caaattacat cttgagtgct    8640
ttaattggga caagtcttgg tggtgtgctt tgatacctca attttcatta agttggaatg    8700
aatccctttc tgttgatact gctatttta atttaataaa ttgtaaatga atctatcagc     8760
taatagttaa tagttgttca aatgacagtt aattaaggta aaatgaatag agaagttgaa    8820
ttatcaacat ttgattaagt atatattcaa actagattac aaaaaactta ggagtcagaa    8880
acttcttcgc aatggagcag tcagactacc aagatattct atatccagag gtacatctta    8940
acagtcctat agtaatttct aaattggtag gcattttgga gtatgctcaa gttattcata    9000
atcaacaatt aacagatcat acaattatta agaatatcca atttagatta agaaatgggt    9060
ttaatagtcc caggatacag acactgtcaa ctatgggtga atcatcaac aaaattaaaa     9120 acaagtatcc taattatatt catataccett atcccgaatg caaccaaaaa ttgtttagga    9180
tagtagatcc agaactaaca tcaaaattag aatctcttct gaacaaaggt gatacactat    9240
ttctcaaaat tcggtcagat atcataaaat gtttcgataa actgaagatg aagatgaata    9300
taagtaatga tcttcttaat gacaaatagtc aattaatttt ggatcttcct ttaattatca    9360
aaggatctca atggtttttc ccgttttat tttggttttc tattaaaact gaaactagaa     9420
```

```
gctgtattcg ccaaaatcca aaagctcgtg ttagatcaca atatcgaccc cacttatcag    9480
agactaaaag aattacatta gttgttacat ctgatctgat tacaatattt gatcatatta    9540
ataaatgcac attttacctg acttttgaaa tgctattgat gtattgcgat gtgatagaag    9600
gtaggttaat gactgaaaca gctatgagcc tggattgtcg atttaccaat ctgttaccaa    9660
gagtgcaata tatgtgggat ttactagacg gaatgtttga aagtctaggt aatcagttat    9720
attcagttat tgcattatta gaacctcttt ctcttgctta tttgcaattg atagatgctg    9780
atccgcagat tcggggaaca ttcttgcatc actgtttctc agagttagaa gaaatcatat    9840
ttgacaaatc tccttttgac ccttttgtgt atgaaaatct tatcaacgga cttgattata    9900
tttatcttac agatgacatt catctaactg cagaagtttt ttcttttttt agaagttttg    9960
gtcatcctta cttagaagca caaaatgctg ccaacaatgt gaggaagtat atgaatcagc   10020
ctaaagtgat ctcataccag accttaatgc aaggacatgc aattttctgt ggaattataa   10080
taaatgggtt tagagatcgt catggaggaa catggcctcc tgtagaattg ccgagtcatg   10140
catctgctgt aatcagaaat gcccaactat ctggggaagg gttaacatct gaacaatgtg   10200
ctcaacattg gagatcgttt tgtgggttta aattcaaatg ttttatgcca ttaagtctag   10260
atagtgatct tacaatgtac cttcgagaca aagcattgtc acctgttaga agtgagtggg   10320
attctgtcta tgctaaagag tatttaagat ataatccagg attacctaca agttccagaa   10380
gattagtgaa tgtattttta gaagatgata agtttgaccc atatgaaatg attatgtacg   10440
tgataaatgg tgattaccta cgagataatg agttcaacct ttcatatagt cttaaagaaa   10500
aagagatcaa agaggttggt cgattgttcg ccaaaatgac ttataaaatg agggcttgtc   10560
magtaatagc tgaaaacttg attgctaatg gagtagggaa gttttttaaa gacaatggaa   10620
tggcaaaaga tgaacataaa ctaactaaga cattacacaa attagccatt tcaggtgtac   10680
ctaaagataa ttctcaactt tatctagatg aatgctggga gcaggtagtt cgacagtgtt   10740
caagtgatac acatcaaca aaaccgatta tgagttcgca accaaagagg ataattgaat   10800
caaagtcttc tagaccacct ctcaatcata gggatacttt taaaggtaag agagacccga   10860
atacacagtt aaagtaccct tcaaacaccg aatattatga gactatcagt agtttttataa   10920 ctactgacct caaaaagtac tgtcttaatt ggcgatatga atcaagtagt gtatttgcgg   10980
agagacttaa tgaaatttac ggattgcccg gattttccca gtggcttcat aaaattttgg   11040
aaaaatccgt tttgtatgtt agtgatccat ctagcccacc tgactttgat caacatgtcg   11100
atatagaatc agttccaaac gaccacatct ttattaaata tccaatgggt gggatagagg   11160
ggttctgtca gaaattatgg actattagta caatcccatt tctatactta gcagcctttg   11220
atacaggtgt tagaatcgca tcattggttc agggcgataa tcaagcgatc gcagtgacaa   11280
aaagagttcc gtcatcttgg agttactcga agaaaaagga agaatcaact aaaataacaa   11340
cacagtattt ccttaattta aggcaacgtc tgcatgatat aggtcatgaa ttgaaagcaa   11400
atgagactat catatcctct catttctttg tttactctaa aggtatttat tacgatggaa   11460
tacttctttc tcaggcactt aaaagtatgg caagatgtgt cttttggtct gaaacaattg   11520
ttgatgagac tagatcagct tgcagtaata tatccaccac acttgcgaag gcaattgaaa   11580
ggggttatga taaatttgtg gcatatgcca tcaatatttta taaaaccata catcaagttt   11640
tgattgcatt atctttttacc atcaatccta ctatgcacacc agatatcaca gaaccttttct   11700 acaaaagctt agatctactt aaaaacctag tcttaattcc tgcaccatta ggggatga   11760 actacatgaa catgagcagg ttgtttgtta gaaatatagg agatcccatt actgcttcat   11820
```

```
ttgctgatat aaagcgcatg attgaatgtg ggttgctggg atgtagtatc ttgtcacaga    11880
taatgtacca aaagtgtggt tcctctaagt atttagactg ggctagcgat ccttattcaa    11940
taaaccttcc gtatagccaa agtatgacca aggtattgaa gaatgtaacg gcaagatatg    12000
tgctcatgca tagccccaac cctatgctta aagatttgtt ccatgaaaag tcgcaagaag    12060
aggatgagat tcttgctgag tttttattag accgacattt ataattcct agggcagcac     12120 atgaaatttt atcaaattca gtaacaggtg ctagagaatc tattgcaggt atgcttgaca    12180
ctactaaggg tttgatccgt gctagtatgt cgagaggtgg tttgacatcg tcacttgttt    12240
taaaattatc aacatatgat tatcagcagt ttagaacgtg tcttgaatgg ctttatgctc    12300
ctaccacggg aattgctgtg agtgtcgatt tatgttctgt tttcttagct aagactatcc    12360
gaaaaagaat gtgggttcac ctaaccaaag aagggagatt ttacggggttg gaagtacctg    12420 acattttgga atgcatgcag aacaatataa ttatcgatca tgaagattgt tactcatgta    12480
ttcaaggatc gagatattat acatggtttt ttgtgccttc aaattgtcaa ctagatcaga    12540
taaataagtc aacaaattct ctccgagttc cttatgttgg atcaacaaca gaagaaagaa    12600
gtgatatgag gttatcatat gtgaggtcac caagtcgacc acttaaagcg gcagttagaa    12660
ttgcagctgt atatacatgg gcttatggtg atgatgattt atcttggcac gaggcttggt    12720
atttagcaag gaccagagca aatattacct ttgatgaact caaattaata acacctatag    12780
ccacatctac gaatttagca cacagattaa gagataggag tacccaggtt aaatattcag    12840
gaacttcttt agtaagagta gcgcgctaca caacaatctc caatgataat atgtcgttca    12900
ttattaacaa caagaaagta gatactaact ttgtctatca gcaaggcatg ttgttaggct    12960
tgagtatact agagtacata tttagatatt gtacaagcac tggacaatca aatactgtaa    13020
ttcacttaca tgcagacgtt aactgttgta tagtacagat gactgatcag ccctatacac    13080
ctagcttaac aaagaagcta cctgatatta aacctattaa taataaattg atatatgatc    13140
cggctcctat aattgatact gatgcagcta gattatattc tcaaaagtac ctatcacatc    13200
taatagattt cccaagctgg tcaactactc agcttaacac agtattggca aaagtggtgg    13260
cagtatctat tgtggaatta ataacaaagg caagtaaaga ccatcttaat gagataatag    13320
cagttgttgg tgatgatgat attaatagtt ttattacgga gtttctactt gttgatccac    13380
gtctgtttac actatactta ggccaatata catcattaca atgggcatat gaagttcatt    13440
accatagacc agtaggtaag taccagatgg ccgaagtgtt acataatcta ctgtcaaggg    13500
ctagtcgagg tatatttagc gtattgacta atgcctttag ccaccctagg gtatatagaa    13560
gattctggga atgtggttta ctagagccta tttatgggcc ctatataggg agtcagaatc    13620
tacatactgc agtgattgat tatatttata atgcatatat tacttatctg gatgcttatt    13680
tatctgatca ggtagatgat actgatatca taatatgcga aacagaggag acatgtctat    13740
caaataggat cgacaattat cagagcaggc atttagctat acttatagat ttgtattgtg    13800
attccactag atgccctaac ataaaggggt cagatacaat tatgcggaat tcaattctta    13860 gatctttttat agacaatgag agacgaacaa atccactcgg tttggcatgg aatcttgatc    13920
cgttacttgt ggatcacttt agctgttcta ttacatatct aagaagaggt attattaaac    13980 agatgagggtt aagatttgat ccaaacatat ctcttgagtt ggctaagatg atcaaacctg    14040
atgtaattta tcaagcacct aaagttccgt cttcgtgggc tctttatagat atcaatcctg    14100 aagtcaatga tcttaataca attttggag agctaaatag caaatggaaa gatattccta    14160
```

```
ttgggcaaat caggattcag aattatgaaa tacatgcata taggagaatt ggggttaatt    14220
caactgcatg ttataaggct ctagagatat tatctgtttt aaatcgattt atgtccaatc    14280
cattgggtgc actgttttta ggtgaaggag caggatcaat gctggtcaca taccgtgctt    14340
ttattccatt taagacaatc tattataata gtggtatttc tgtgcaaaat gtgcaaggtc    14400
agagagaact gagtctatat ccttctgaag tggcactggt tgacaacaaa aatcgtttgg    14460
ctaatgaccc taatatcaaa gtcttgttta acggtaagcc ggagtctacg tgggttggga    14520
atattgactg ttttgcctat attcttagcc atattgagac cgcaagcttg acattgatac    14580
atagtgatat cgagtccagt ttaagcaaga caaaaaataa gattcttgaa gagctatgcc    14640
acatcctatc aatggcactt atcttaggga gacttggatc cgtgttagtc attaaactac    14700
taccaagggt cggtgattat acctattcat tttgcaagta tgcatcagag ttctatcagc    14760
aaaactttct catattaccc agatttagta atatgtcgtc atctgaagtt tactacatag    14820
gagttcacct taatcaaaac agattgattg atcctgatag aatagtacaa tacataatta    14880
gaaatttgca acccaccoca gttacatttt tatcctatat ctttgagact aaatatagaa    14940
acaatatggt tacaaattat ggactatgct tgtcagatgg acacaaaagt gattacttat    15000
catcaattac caaaatagag aatgttcttc tgtcatgtga attagaattg gatggaccta    15060
agattatacc gccattatca ggacatgact atgcaaatgg ggagactagc ctggaatcaa    15120
gtataatgat attagttaga gaatatctta atgcaactat tcaaggccga gaaacattag    15180
gcttgttttc accttaccca gtattacatg agagtcagct aagagaaatt aataagtgta    15240
ttgcattgaa gtatattgtg tatttactct tttactcgaa ctctgtatca tctagtaaac    15300
agataatgag taatcttaga aaagggatat taatgtatga tttgagagac gaattttttca    15360 tatcaagatt atcagcaaat tacaagaaaa aagtaatgtc acaggaagtt aaaaccacat    15420
ggatatttaa tattgatacg ccaacaagaa aagcattata caagttagtg ggttattcat    15480
tgataattca tcacgtataa tgatcaactg tggttattca tctctagaaa agaaagataa    15540
gacctgatat attatagcta ctaaaacatt aactctgaat tgaaggattg ctcagttaca    15600
taattaataa gtaattgaga ttgtatttca aacagagcaa ttagaaaaaa cttcctctat    15660
taatcaagcc ctaattcatt ctatgttaat tttatttata atcttgagtt aaatctttgt    15720
ctaaaaacat cacaataata ctgatctatc aagggaacat aatcggtatt tggtattgag    15780
tttttatttg tgtaccttaa atcttatgcc tatcattatc aattgttatt taagtatcta    15840
attatagatg ttaatatgtt aaatgatgag aaccatcaat actgatattg ctggtaatta    15900
taggcactgt gtgaagcaat gtctaattct caccaaggta cagtctcaca tgtcggatcc    15960
ctcagcctcc cctcaatagg caagtggttt gaaaaaaaac aaaaaccaat cttgaatgat    16020
tgtacggacc tatagctttc tttgtctggt                                    16050
```

<210> SEQ ID NO 4
<211> LENGTH: 1788
<212> TYPE: DNA
<213> ORGANISM: Feline paramyxovirus type 2
<220> FEATURE:
<221> NAME/KEY: misc_feature
<223> OTHER INFORMATION: FPaV-2 "Gordon strain" H antigen "wild-type"
      nucleic acid; given as DNA sequence

<400> SEQUENCE: 4

```
atggaatcta ataacaacaa gtactataaa gattcaaacc ggtatttag caagatacta      60 gatgagaaca agacggtaaa taatcatctg tatagtctta gtataaggat aattaccgtt     120
```

-continued

```
atagctattg ttgtgagtct aattgcaaca acaataacca tcattaatgc tataagcgga      180
aggactactc ttaataataa tatggacatg ctactcaacc aacaagacaa gattaataat      240
atcaaggaaa tgatatttga tcgtatctat ccctgataa atgccatgag tacagagctt      300
ggtcttcaca ttccaacttt attggatgag ctgactaaat caattgatca aaaaatcaag      360
ataatgactc caccacttga aactacaaca tctaatctca attggtgtat caaccccca       420 aatggcatta ttgtagatcc taaaggttat tgtgaaggct tggaactgtc aaaaacttat      480
aagttattac ttgatcaatt agatatgtta agaagaaat cacttattat taataagaaa       540
agtattaatc agtgtagact tgttgatagt tcgaatatcg tctttgcaac agttaatata      600
caatctacac cgagattctt aaatcttggt cacacagtta gtaaccaacg tataacattc      660
ggtcaaggaa catatagtag cacttatatt ataactatac aagaggatgg attaactgat      720
gttcagtacc gagtatttga aataggatat atctcagatc aatttggaac cttcccttct      780
ctaatcgttt ccagagtact acctgtgcga atggtacttg aatggaatc ttgtacactg       840 accagtgaca agtttggggg ttattttta tgcatgaaca ttccgacacg ctctatatat       900
gattatgtca acataagaga cttaaagtca ctatacgtca caatccctca ttatggcaaa      960
attaattaca cttactttaa ttttgggaaa gtcagaagcc cacatgaaat tgataagatt      1020
tggcttacat cagaaagggg acagatgatt tcaggttact ttgcagcatt tgttacgatt      1080
acaattagaa attataacaa ttatccctat aaatgcttac ataacccgtg tcttgaaaga     1140
tctgagagtt attgcaaagg atggtacaaa aatattacag gtactgatga tgttccaata    1200
ttagcatatc tattagttga aatgaatgat gaggaaggac ccttaattac attggttgag    1260
ataccacctt acaattatac ggctccttct cataattccc tttactatga tgataaaatt    1320
aacaaattaa taatgacaac atctcatata ggatacattc aaatcaatga agtgcatgaa    1380
gtcattgtcg gggataatct taaggctatt ctcttaaaca gattatctga tgaacacccct   1440 actcttactg cttgtagatt taatcaggaa attaaagagc gacatatatc tgatggatta    1500
ataatatcta actctgctct tattgatata caagaacgta tgtatgttac agttaaggct    1560
gttccaccca taggaaatta taacttcacg gtagagttgc attcacggtc aaatacatct    1620
tacgtagggt tgccaaggca gttcaatgct aggtatgaca aactgcatct cgaatgcttt    1680
gcctgggata ggtcttggtg gtgcgctttg atacctcaat tttcattaag ttggaatgaa    1740
tctctttcag tagatactgc cattttcaac ttaataaact gtaattaa                  1788
```

<210> SEQ ID NO 5
<211> LENGTH: 1788
<212> TYPE: DNA
<213> ORGANISM: Feline paramyxovirus type 2
<220> FEATURE:
<221> NAME/KEY: misc_feature
<223> OTHER INFORMATION: FPaV-2 "Gordon strain" H antigen nucleic acid
    that has been codon-optimized for expression primarily in felines;
    given as DNA sequence

<400> SEQUENCE: 5

```
atggaaagca ataataacaa atactataaa gacagcaatc ggtacttcag caagatcctg       60
gacgagaata agacagtcaa taatcacctg tactccctgt ctatcaggat catcaccgtg      120
atcgccatcg tggtgtccct gatcgcaacc actatcacta tcatcaatgc catctctggc      180
agaaccactc tgaacaataa catggacatg ctgctgaacc agcaggataa gatcaataac      240
atcaaagaga tgatcttcga caggatctat ccactgatca acgcaatgag caccgagctg      300
```

-continued

```
gggctgcaca tccctaccct gctggacgaa ctgactaagt ccatcgatca gaagatcaaa    360
atcatgactc cacctctgga aaccactacc tctaatctga actggtgcat caatcccccca    420
aacggaatca tcgtggaccc aaaaggctac tgtgaggggc tggaactgtc caagacctat    480
aaactgctgc tggaccagct ggatatgctg aggaagaaaa gcctgatcat caataagaaa    540
tccatcaacc agtgcagact ggtggatagc tccaatatcg tgttcgccac cgtgaacatc    600
cagagcactc ctaggtttct gaatctggga cataccgtgt ccaaccagag aatcactttc    660
ggacagggta cttactctag cacctatatc atcactatcc aggaggacgg tctgaccgat    720
gtgcagtaca gagtgtttga aatcggctat atctctgacc agttcgggac ttttccttct    780
ctgatcgtga gcagggtgct gcccgtgaga atggtgctgg ggatggagtc ctgcactctg    840
acctctgata agttcggcgg gtacttcctg tgcatgaata tccccaccag gtctatctac    900
gactatgtga acatcagaga tctgaagagc ctgtacgtga ccatccccca ctacggcaaa    960
atcaattaca cttatttcaa ctttgggaag gtgaggagcc cacatgagat cgacaaaatc   1020
tggctgactt ctgaaagagg acagatgatc agcggttact tcgccgcatt tgtgactatc   1080
accatcagga actacaacaa ctacccttac aagtgcctgc acaacccatg tctggagaga   1140
agcgaatcct actgcaaggg atggtataag aacatcactg gtaccgacga tgtgcccatc   1200
ctggcctacc tgctggtgga gatgaacgat gaggaaggtc cactgatcac cctggtggaa   1260
atccctccct acaattatac tgcacctagc cataactccc tgtactatga cgataagatc   1320
aacaagctga tcatgactac ctcccacatc ggatatatcc agatcaacga ggtgcatgaa   1380
gtgatcgtgg gtgacaatct gaaggccatc ctgctgaaca ggctgagcga tgagcaccca   1440
actctgaccg catgtaggtt caatcaggag atcaaagaaa gacatatctc cgacggcctg   1500
atcatctcta acagcgccct gatcgatatc caggagagga tgtacgtgac cgtgaaggca   1560
gtgccaccta tcggcaatta taactttacc gtggaactgc actccagatc taatactagc   1620
tacgtggggc tgcctaggca gttcaacgca agatatgaca aactgcatct ggaatgcttt   1680
gcctgggata gatcctggtg gtgtgcactg atcccccagt tttctctgtc ctggaatgag   1740
agcctgtccg tggatactgc tattttcaac ctgataaact gtaactaa                1788
```

<210> SEQ ID NO 6
<211> LENGTH: 595
<212> TYPE: PRT
<213> ORGANISM: Feline paramyxovirus type 2
<220> FEATURE:
<221> NAME/KEY: MISC_FEATURE
<223> OTHER INFORMATION: FPaV-2 “Gordon strain” H antigen translated amino acid sequence

<400> SEQUENCE: 6

```
Met Glu Ser Asn Asn Asn Lys Tyr Tyr Lys Asp Ser Asn Arg Tyr Phe
1               5                   10                  15

Ser Lys Ile Leu Asp Glu Asn Lys Thr Val Asn Asn His Leu Tyr Ser
            20                  25                  30

Leu Ser Ile Arg Ile Ile Thr Val Ile Ala Ile Val Val Ser Leu Ile
        35                  40                  45

Ala Thr Thr Ile Thr Ile Ile Asn Ala Ile Ser Gly Arg Thr Thr Leu
    50                  55                  60

Asn Asn Asn Met Asp Met Leu Leu Asn Gln Gln Asp Lys Ile Asn Asn
65                  70                  75                  80

Ile Lys Glu Met Ile Phe Asp Arg Ile Tyr Pro Leu Ile Asn Ala Met
```

```
                85                  90                  95
Ser Thr Glu Leu Gly Leu His Ile Pro Thr Leu Leu Asp Glu Leu Thr
                100                 105                 110
Lys Ser Ile Asp Gln Lys Ile Lys Ile Met Thr Pro Pro Leu Glu Thr
                115                 120                 125
Thr Thr Ser Asn Leu Asn Trp Cys Ile Asn Pro Asn Gly Ile Ile
    130                 135                 140
Val Asp Pro Lys Gly Tyr Cys Glu Gly Leu Glu Leu Ser Lys Thr Tyr
145                 150                 155                 160
Lys Leu Leu Leu Asp Gln Leu Asp Met Leu Arg Lys Lys Ser Leu Ile
                165                 170                 175
Ile Asn Lys Lys Ser Ile Asn Gln Cys Arg Leu Val Asp Ser Ser Asn
                180                 185                 190
Ile Val Phe Ala Thr Val Asn Ile Gln Ser Thr Pro Arg Phe Leu Asn
                195                 200                 205
Leu Gly His Thr Val Ser Asn Gln Arg Ile Thr Phe Gly Gln Gly Thr
                210                 215                 220
Tyr Ser Ser Thr Tyr Ile Ile Thr Ile Gln Glu Asp Gly Leu Thr Asp
225                 230                 235                 240
Val Gln Tyr Arg Val Phe Glu Ile Gly Tyr Ile Ser Asp Gln Phe Gly
                245                 250                 255
Thr Phe Pro Ser Leu Ile Val Ser Arg Val Leu Pro Val Arg Met Val
                260                 265                 270
Leu Gly Met Glu Ser Cys Thr Leu Thr Ser Asp Lys Phe Gly Gly Tyr
                275                 280                 285
Phe Leu Cys Met Asn Ile Pro Thr Arg Ser Ile Tyr Asp Tyr Val Asn
290                 295                 300
Ile Arg Asp Leu Lys Ser Leu Tyr Val Thr Ile Pro His Tyr Gly Lys
305                 310                 315                 320
Ile Asn Tyr Thr Tyr Phe Asn Phe Gly Lys Val Arg Ser Pro His Glu
                325                 330                 335
Ile Asp Lys Ile Trp Leu Thr Ser Glu Arg Gly Gln Met Ile Ser Gly
                340                 345                 350
Tyr Phe Ala Ala Phe Val Thr Ile Thr Ile Arg Asn Tyr Asn Asn Tyr
                355                 360                 365
Pro Tyr Lys Cys Leu His Asn Pro Cys Leu Glu Arg Ser Glu Ser Tyr
                370                 375                 380
Cys Lys Gly Trp Tyr Lys Asn Ile Thr Gly Thr Asp Asp Val Pro Ile
385                 390                 395                 400
Leu Ala Tyr Leu Leu Val Glu Met Asn Asp Glu Gly Pro Leu Ile
                405                 410                 415
Thr Leu Val Glu Ile Pro Pro Tyr Asn Tyr Thr Ala Pro Ser His Asn
                420                 425                 430
Ser Leu Tyr Tyr Asp Asp Lys Ile Asn Lys Leu Ile Met Thr Thr Ser
                435                 440                 445
His Ile Gly Tyr Ile Gln Ile Asn Glu Val His Glu Val Ile Val Gly
                450                 455                 460
Asp Asn Leu Lys Ala Ile Leu Leu Asn Arg Leu Ser Asp Glu His Pro
465                 470                 475                 480
Thr Leu Thr Ala Cys Arg Phe Asn Gln Glu Ile Lys Glu Arg His Ile
                485                 490                 495
Ser Asp Gly Leu Ile Ile Ser Asn Ser Ala Leu Ile Asp Ile Gln Glu
                500                 505                 510
```

Arg Met Tyr Val Thr Val Lys Ala Val Pro Pro Ile Gly Asn Tyr Asn
              515                 520                 525

Phe Thr Val Glu Leu His Ser Arg Ser Asn Thr Ser Tyr Val Gly Leu
              530                 535                 540

Pro Arg Gln Phe Asn Ala Arg Tyr Asp Lys Leu His Leu Glu Cys Phe
545                 550                 555                 560

Ala Trp Asp Arg Ser Trp Trp Cys Ala Leu Ile Pro Gln Phe Ser Leu
                565                 570                 575

Ser Trp Asn Glu Ser Leu Ser Val Asp Thr Ala Ile Phe Asn Leu Ile
              580                 585                 590

Asn Cys Asn
      595

<210> SEQ ID NO 7
<211> LENGTH: 1014
<212> TYPE: DNA
<213> ORGANISM: Feline paramyxovirus type 2
<220> FEATURE:
<221> NAME/KEY: misc_feature
<223> OTHER INFORMATION: FPaV-2 "Gordon strain” M antigen “wild-type” nucleic acid; given as DNA sequence

<400> SEQUENCE: 7

```
atgactgaga tattcaatct ggatgaaagt tcatggtcag tcaagggaac actggaccca      60
ttgacgcctg atacttatcc tgatgggcgc ctagtaccca agattcgggt tattgatccc     120
ggtctaggtg atcgtaaaag tggaggatat atgtacttac tccttcacgg tgtcatcgag     180
gacagtgaga ccgtcataaa tccgaaaggg agagcatttg gagctttccc tttaggcgta     240
gggcaatcaa ccgagaaccc agaagactta tttaaggaaa tattaaccct caacattgtt     300
actcgcagga ctgctggctt caatgaaaaa ttggtgtatt ataatactac acctctaaat     360
ctactaaccc cttggaaaaa agtactagca tatggaagta tctttactgc taatcaggtc     420
tgcaataata caagttctat ccctatagac attcctcaga aatttcgacc tgtctattta     480
actgttacca agttatcgga tgatggatat tatcagatac ctaaaatgat acaggatttc     540
aaatcatcaa actctgttgc atttaacatc cttgtgcatc tatcaatggg aacaatttta     600
cttgactcat ctaaaggctc tcgagtagga aaccctgcag aaaatttgat cacattcatg     660
attcatattg ggaatttcaa acggaagaat aataaagctt attctcccga atattgtaag     720
aggaaaataa tgaggcttgg attaattttc tcactaggag ccattggtgg aacaagtttg     780
catattcgat gcacaggcaa aatgagtaag agattacaag cctacttagg gtttaaaaga     840
actttatgtt atcctctgat gtatgtcaat gagggtctaa ataaaacctt atggagaaat     900
gaatgcaaaa ttgagaaggt tcaagcagta ttacagccat cagttccgaa tgaatttaag     960
atttatgatg atataatcat tgataacacg aatggcctct ttaaggttaa gtaa          1014
```

<210> SEQ ID NO 8
<211> LENGTH: 1014
<212> TYPE: DNA
<213> ORGANISM: Feline paramyxovirus type 2
<220> FEATURE:
<221> NAME/KEY: misc_feature
<223> OTHER INFORMATION: FPaV-2 “Gordon strain” M antigen nucleic acid that has been codon-optimized for expression primarily in felines; given as DNA sequence

<400> SEQUENCE: 8

```
atgactgaga tcttcaacct ggacgaaagc tcttggagtg ttaaagggac cctggaccct      60
```

```
ctgacccccg atacctaccc cgatgggagg ctggtgccaa agatcagagt gatcgaccct    120
gggctggggg ataggaaaag cgggggctac atgtatctgc tgctgcacgg ggtgatcgag    180
gactctgaaa ccgtgatcaa ccccaagggg agagccttcg ggcatttcc actgggggtg     240 gggcagagca ccgagaatcc cgaagatctg ttcaaggaga tcctgactct gaacatcgtg    300
accaggagaa ctgccgggtt taatgaaaaa ctggtgtact ataacaccac tcctctgaat    360
ctgctgactc cctggaagaa agtgctggcc tacgggtcta tcttcaccgc aaaccaagtg    420
tgtaacaata ctagctccat ccccatcgac atcccacaga agtttaggcc tgtgtatctg    480
accgtgacta aactgagcga cgatgggtac tatcagatcc ccaagatgat ccaggacttc    540
aaatctagca actctgtggc atttaatatc ctggtgcacc tgagcatggg gaccatcctg    600
ctggattcct ctaaggggag cagggtgggg aacccagccg agaatctgat cactttcatg    660
atccatatcg ggaacttcaa gagaaagaac aacaaggcat actcccctga atattgcaag    720
aggaaaatca tgagactggg gctgatcttc agcctggggg caatcggggg cacctccctg    780
catatcaggt gcactgggaa gatgtccaaa agactgcagg catacctggg gtttaagagg    840
accctgtgtt accctctgat gtatgtgaac gaggggctga ataaaactct gtggagaaac    900
gagtgcaaga tcgaaaaagt gcaggccgtg ctgcagccat ctgtgcctaa tgagttcaaa    960
atatacgacg acattatcat agacaataca aacgggctgt tcaaagtcaa gtaa         1014
```

```

<210> SEQ ID NO 9
<211> LENGTH: 337
<212> TYPE: PRT
<213> ORGANISM: Feline paramyxovirus type 2
<220> FEATURE:
<221> NAME/KEY: MISC_FEATURE
<223> OTHER INFORMATION: FPaV-2 "Gordon strain" M antigen translated
      amino acid sequence

<400> SEQUENCE: 9

Met Thr Glu Ile Phe Asn Leu Asp Glu Ser Ser Trp Ser Val Lys Gly
1               5                   10                  15

Thr Leu Asp Pro Leu Thr Pro Asp Thr Tyr Pro Asp Gly Arg Leu Val
            20                  25                  30

Pro Lys Ile Arg Val Ile Asp Pro Gly Leu Gly Asp Arg Lys Ser Gly
        35                  40                  45

Gly Tyr Met Tyr Leu Leu Leu His Gly Val Ile Glu Asp Ser Glu Thr
    50                  55                  60

Val Ile Asn Pro Lys Gly Arg Ala Phe Gly Ala Phe Pro Leu Gly Val
65                  70                  75                  80

Gly Gln Ser Thr Glu Asn Pro Glu Asp Leu Phe Lys Glu Ile Leu Thr
                85                  90                  95

Leu Asn Ile Val Thr Arg Arg Thr Ala Gly Phe Asn Glu Lys Leu Val
            100                 105                 110

Tyr Tyr Asn Thr Thr Pro Leu Asn Leu Leu Thr Pro Trp Lys Lys Val
        115                 120                 125

Leu Ala Tyr Gly Ser Ile Phe Thr Ala Asn Gln Val Cys Asn Asn Thr
    130                 135                 140

Ser Ser Ile Pro Ile Asp Ile Pro Gln Lys Phe Arg Pro Val Tyr Leu
145                 150                 155                 160

Thr Val Thr Lys Leu Ser Asp Asp Gly Tyr Tyr Gln Ile Pro Lys Met
                165                 170                 175

Ile Gln Asp Phe Lys Ser Ser Asn Ser Val Ala Phe Asn Ile Leu Val
```

```
                180             185             190
His Leu Ser Met Gly Thr Ile Leu Leu Asp Ser Ser Lys Gly Ser Arg
                195                 200                 205

Val Gly Asn Pro Ala Glu Asn Leu Ile Thr Phe Met Ile His Ile Gly
            210                 215                 220

Asn Phe Lys Arg Lys Asn Asn Lys Ala Tyr Ser Pro Glu Tyr Cys Lys
225                 230                 235                 240

Arg Lys Ile Met Arg Leu Gly Leu Ile Phe Ser Leu Gly Ala Ile Gly
                245                 250                 255

Gly Thr Ser Leu His Ile Arg Cys Thr Gly Lys Met Ser Lys Arg Leu
                260                 265                 270

Gln Ala Tyr Leu Gly Phe Lys Arg Thr Leu Cys Tyr Pro Leu Met Tyr
            275                 280                 285

Val Asn Glu Gly Leu Asn Lys Thr Leu Trp Arg Asn Glu Cys Lys Ile
            290                 295                 300

Glu Lys Val Gln Ala Val Leu Gln Pro Ser Val Pro Asn Glu Phe Lys
305                 310                 315                 320

Ile Tyr Asp Asp Ile Ile Ile Asp Asn Thr Asn Gly Leu Phe Lys Val
                325                 330                 335

Lys
```

<210> SEQ ID NO 10
<211> LENGTH: 1632
<212> TYPE: DNA
<213> ORGANISM: Feline paramyxovirus type 2
<220> FEATURE:
<221> NAME/KEY: misc_feature
<223> OTHER INFORMATION: FPaV-2 "Gordon strain" F antigen "wild-type"
      nucleic acid; given as DNA sequence

<400> SEQUENCE: 10

```
atgtataaga ttaaggttgt aatcatgggt tttttactgt tatcagatat tacatttgca      60
caggtaggtt gggataattt aacctcaatt ggagttataa gtactaaaca atataactat     120
aagataacta ctttgaatac taatcaactc atggtgatca aaatggtacc aatatatca     180 tcaattatta actgtactaa acttgaatta gcaaaatata gggaactgat tacaggaata     240
ctgagaccaa ttaatgaatc attagaattg atgaattcat atatcaacat gagaacaggt     300
tcagagagat tcatagggc tgttatagca ggagtagctc taggggttgc aactgcggcg      360
cagataacat cgggaattgc cttacataat tcgattatga ataaaaaaca gatacaggaa     420
ttaaggaaag cccttagtac tacaaataag gcaattgatg agataaggat tgcaggtgaa     480
agaactctga tagctgtcca aggtgtgcaa gattacatta acaatgttat tatccctatg     540
caagagaaac tccagtgcga tattttagcc tcacagctat ctattgccct actcagatac     600
tatactaata tactgactgt ttttggacca agtataagag atcctattac tagtacaatt     660
tctatacaag ctctcagtca agcattcaat ggtaatctac aggcattgct tgatggatta     720
gggtatactg acaagactt acatgatctc atagaaagta gatctatcac tggtcaaatt     780
attcacgctg atatgactga tttattcctt gtattgagaa tcaattatcc atctattacg     840
gatatgcaag gagtggtaat atatgagctg aattctatca catatcatat tggacctgaa     900
gagtggtaca ctattatgcc taatttcata gctgttcagg gatttctggt atctaatttc     960
gatgaacgta atgttcaat tactaaaaca agtatactgt gtcaacagaa ttcaatttat    1020
cctatgtcaa ccgaaatgca aagatgtata aaaggtgaga ttaaattctg tccaaggtcc    1080
```

```
aaagcaattg ggacattagt taatcgattt atattaatta atgggaatct aatggccaat   1140
tgtttgggta ttatctgtag atgttatacc tcaggtcaaa ttataacgca agacccaaat   1200
aaattaatca caattatatc acaagaagaa tgtagagagg ttggtgttga tgggattcgt   1260
ataatggtgg ggcctaaaaa attaccggat gttatcttta atgccagact agaaataggt   1320
gtacctatct cattaagcaa gctggatgtt gggaccgact tggcaattgc ttcagctaaa   1380
ctcaataact ctaaggcact tttggagcag tctgataaaa tcttaaattc tatgtctaag   1440
ttggattctt taaattcacg tatcttagga tctgtcttta taattatgat aatcttcgtg   1500
actgtaattg tgattatttg gattatttgt aaaaagtgta gaaataagag gaacaaatta   1560
agtgcttcta ttgaacccct ctacatacct ccctcttata attcacccca tagcatagtt   1620
aaatctattt ga                                                         1632
```

```

<210> SEQ ID NO 11
<211> LENGTH: 1632
<212> TYPE: DNA
<213> ORGANISM: Feline paramyxovirus type 2
<220> FEATURE:
<221> NAME/KEY: misc_feature
<223> OTHER INFORMATION: FPaV-2 “Gordon strain” F antigen nucleic acid
      that has been codon-optimized for expression primarily in felines;
      given as DNA sequence

<400> SEQUENCE: 11
atgtacaaaa tcaaggtggt catcatgggg ttcctgctgc tgagcgacat cacattcgca     60
caggttggct gggacaatct gactagcatc ggggtgatca gcaccaagca gtacaactat    120
aaaatcacca ctctgaacac taatcagctg atggtgatca agatggtgcc caacatcagc    180
tccatcatca attgcaccaa gctggagctg gccaaataca gggaactgat cactggaatc    240
ctgaggccaa tcaatgagtc tctggaactg atgaacagct atatcaatat gaggaccgga    300
agcgagagat tcatcggtgc agtgatcgca ggtgttgcac tgggagtggc caccgccgca    360
cagatcacta gcggtatcgc actgcacaac tccatcatga ataagaaaca gatccaggaa    420
ctgaggaagg ccctgtccac cactaacaaa gcaatcgacg agatcaggat cgccggagaa    480
agaactctga tcgcagtgca gggtgtgcag gactacatca acaatgtgat catcccaatg    540
caggagaaac tgcagtgtga tatcctggcc tcccagctgt ctatcgcact gctgaggtac    600
tataccaaca tcctgactgt gttcggcccc tccatcaggg acccaatcac cagcactatc    660
tccatccagg ccctgtctca ggcatttaac ggcaatctgc aggccctgct ggatggcctg    720
gggtataccg ggcaggacct gcacgatctg atcgaatcta ggagcatcac cgggcagatc    780
atccatgcag acatgactga tctgttcctg gtgctgagaa tcaactaccc ttctatcact    840
gacatgcagg gagtggtgat ctacgagctg aatagcatca cctatcatat cggtcctgag    900
gaatggtata ctatcatgcc caactttatc gccgtgcagg gattcctggt gtccaatttt    960
gatgaaagga agtgctccat caccaaaact tctatcctgt gtcagcagaa cagcatctac   1020
ccaatgtcca ccgagatgca gagatgcatc aagggagaaa tcaaattctg tcctaggtct   1080
aaggccatcg gtactctggt gaacagattt atcctgatca acggcaatct gatggcaaat   1140
tgcctgggga tcatctgcag gtgttatacc agcggccaga tcatcactca ggatcctaac   1200
aaactgatca ccatcatctc ccaggaagag tgtagggagg ttggagtgga cggtatcaga   1260
atcatggtgg ggccaaagaa actgcctgat gtgatcttta atgccagact ggaaatcggc   1320
gtgcccatct ccctgtctaa gctggacgtg gggactgatc tggccatcgc atccgccaag   1380
```

```
ctgaacaatt ctaaagcact gctggagcag tctgacaaga tcctgaacag catgtccaaa    1440
ctggattctc tgaatagcag aatcctgggc agcgtgttca tcatcatgat catctttgtg    1500
accgtgatcg tgatcatctg gatcatctgc aagaaatgta ggaacaagag aaataaactg    1560
tctgcaagca ttgaaccect gtacattcca ccatcctata actcccctca ttccattgtg    1620
aaaagcattt ga                                                       1632
```

```
<210> SEQ ID NO 12
<211> LENGTH: 543
<212> TYPE: PRT
<213> ORGANISM: Feline paramyxovirus type 2
<220> FEATURE:
<221> NAME/KEY: MISC_FEATURE
<223> OTHER INFORMATION: FPaV-2 "Gordon strain" F antigen translated
      amino acid sequence

<400> SEQUENCE: 12

Met Tyr Lys Ile Lys Val Val Ile Met Gly Phe Leu Leu Leu Ser Asp
1               5                   10                  15

Ile Thr Phe Ala Gln Val Gly Trp Asp Asn Leu Thr Ser Ile Gly Val
            20                  25                  30

Ile Ser Thr Lys Gln Tyr Asn Tyr Lys Ile Thr Thr Leu Asn Thr Asn
        35                  40                  45

Gln Leu Met Val Ile Lys Met Val Pro Asn Ile Ser Ser Ile Ile Asn
    50                  55                  60

Cys Thr Lys Leu Glu Leu Ala Lys Tyr Arg Glu Leu Ile Thr Gly Ile
65                  70                  75                  80

Leu Arg Pro Ile Asn Glu Ser Leu Glu Leu Met Asn Ser Tyr Ile Asn
                85                  90                  95

Met Arg Thr Gly Ser Glu Arg Phe Ile Gly Ala Val Ile Ala Gly Val
            100                 105                 110

Ala Leu Gly Val Ala Thr Ala Ala Gln Ile Thr Ser Gly Ile Ala Leu
        115                 120                 125

His Asn Ser Ile Met Asn Lys Lys Gln Ile Gln Glu Leu Arg Lys Ala
    130                 135                 140

Leu Ser Thr Thr Asn Lys Ala Ile Asp Glu Ile Arg Ile Ala Gly Glu
145                 150                 155                 160

Arg Thr Leu Ile Ala Val Gln Gly Val Gln Asp Tyr Ile Asn Asn Val
                165                 170                 175

Ile Ile Pro Met Gln Glu Lys Leu Gln Cys Asp Ile Leu Ala Ser Gln
            180                 185                 190

Leu Ser Ile Ala Leu Leu Arg Tyr Tyr Thr Asn Ile Leu Thr Val Phe
        195                 200                 205

Gly Pro Ser Ile Arg Asp Pro Ile Thr Ser Thr Ile Ser Ile Gln Ala
    210                 215                 220

Leu Ser Gln Ala Phe Asn Gly Asn Leu Gln Ala Leu Leu Asp Gly Leu
225                 230                 235                 240

Gly Tyr Thr Gly Gln Asp Leu His Asp Leu Ile Glu Ser Arg Ser Ile
                245                 250                 255

Thr Gly Gln Ile Ile His Ala Asp Met Thr Asp Leu Phe Leu Val Leu
            260                 265                 270

Arg Ile Asn Tyr Pro Ser Ile Thr Asp Met Gln Gly Val Val Ile Tyr
        275                 280                 285

Glu Leu Asn Ser Ile Thr Tyr His Ile Gly Pro Glu Glu Trp Tyr Thr
    290                 295                 300
```

```
Ile Met Pro Asn Phe Ile Ala Val Gln Gly Phe Leu Val Ser Asn Phe
305                 310                 315                 320

Asp Glu Arg Lys Cys Ser Ile Thr Lys Thr Ser Ile Leu Cys Gln Gln
            325                 330                 335

Asn Ser Ile Tyr Pro Met Ser Thr Glu Met Gln Arg Cys Ile Lys Gly
        340                 345                 350

Glu Ile Lys Phe Cys Pro Arg Ser Lys Ala Ile Gly Thr Leu Val Asn
    355                 360                 365

Arg Phe Ile Leu Ile Asn Gly Asn Leu Met Ala Asn Cys Leu Gly Ile
370                 375                 380

Ile Cys Arg Cys Tyr Thr Ser Gly Gln Ile Ile Thr Gln Asp Pro Asn
385                 390                 395                 400

Lys Leu Ile Thr Ile Ile Ser Gln Glu Glu Cys Arg Glu Val Gly Val
            405                 410                 415

Asp Gly Ile Arg Ile Met Val Gly Pro Lys Lys Leu Pro Asp Val Ile
        420                 425                 430

Phe Asn Ala Arg Leu Glu Ile Gly Val Pro Ile Ser Leu Ser Lys Leu
    435                 440                 445

Asp Val Gly Thr Asp Leu Ala Ile Ala Ser Ala Lys Leu Asn Asn Ser
450                 455                 460

Lys Ala Leu Leu Glu Gln Ser Asp Lys Ile Leu Asn Ser Met Ser Lys
465                 470                 475                 480

Leu Asp Ser Leu Asn Ser Arg Ile Leu Gly Ser Val Phe Ile Ile Met
            485                 490                 495

Ile Ile Phe Val Thr Val Ile Val Ile Trp Ile Ile Cys Lys Lys
        500                 505                 510

Cys Arg Asn Lys Arg Asn Lys Leu Ser Ala Ser Ile Glu Pro Leu Tyr
    515                 520                 525

Ile Pro Pro Ser Tyr Asn Ser Pro His Ser Ile Val Lys Ser Ile
530                 535                 540

<210> SEQ ID NO 13
<211> LENGTH: 1560
<212> TYPE: DNA
<213> ORGANISM: Feline paramyxovirus type 2
<220> FEATURE:
<221> NAME/KEY: misc_feature
<223> OTHER INFORMATION: FPaV-2 "Gordon strain" N antigen "wild-type"
      nucleic acid; given as DNA sequence

<400> SEQUENCE: 13
atggctagtt tactcaggtc acttgcggca ttcaagaaac acagagaaca accaactgtt      60
ccttctgggt caggagggac gatcaaagga ttaaaaaata caattattgt gcctgttcct     120
ggagatacag tcatcactac cagatcgaac ttactgttca gattagtcta cataattggt     180
aatccagata caccttttaag cacttcaaca ggggcaataa tatcattgtt gacattattt     240
gttgaatctc caggtcaatt aattcaaaga atcgctgatg atcctgatgc tgttttttaaa     300 ttagtagagg tggttcctga ggttggtaat cctggagaat taacttttgc atctagagga     360
attaacttgg ataaacaagc tcaacaatac tttagattgg ctgagaaaaa tgatcaagga     420
tattatgtaa gttttgggggtt tgaaaatcca ccaaatgatg atgatataac gtcaagtcct     480
gaaatcttta attatatttt agcatctgta cttgcacaga tctggattct cctagctaag     540
gctgtaactg ctccagacac agctgctgag gctgaaaaacc gtaggtggat taaattgatg     600
caacaacgca gagtggatgg tgagcttaga ttaagtaaag gatggttgga cttagtgagg     660
```

```
aataaaatcg catcggatat cacaattaga aggtttatgg tagcattagt tcttgacatt    720
aaacgttctc ctggaacaag accaagaatt gctgaaatga tttgtgatat agacaattat    780
attgtggagg ccggactggc aagttttctg ttaactatca aatttggtat agaaacacgt    840
tacccggcat tagcgttaca tgagttttcg ggggaattag ccactattga aggactcatg    900
aaattgtacc agtctatggg agaaatggca ccatacatgg tcattctaga gaattcgatc    960
cagactaggt ttagtgctgg gtcttatccg ttactctgga gctatgctat gggtgttggt   1020
gtagaacttg aaagatcaat gagtggatta aacttcacaa gaagtttctt tgatcctacg   1080
tacttcaggt tgggtcagga gatggtaaga aggtcttcag gaatggttaa tagctcattt   1140
gccaaagaac ttggactatc tgaacatgaa acacaacttg ttagccagat cattaactca   1200
ggtggtgagt caggtatacc gaaatttgat ggatttagag caaacccaac aacatttcta   1260
ggggctaagg acaacatcac tgataggagt gaagatccat tgattgcaat tccagggtca   1320
tcaggacaac cattgccagg ttatgacccc aatatctcag gtgactcata tagaattgat   1380
agtagcacta aagacacaaa caatatatca gatggaggaa caaatccaag tcatgatgtt   1440
tccaattctg ctatggaaga gctgagaaga ttggtagagt ctaccaacaa gattgataca   1500
aagaaatctg aaagcccagg catcgttaat cattacaacg atactgacct tctgagataa   1560
```

<210> SEQ ID NO 14
<211> LENGTH: 519
<212> TYPE: PRT
<213> ORGANISM: Feline Paramyxovirus type 2
<220> FEATURE:
<221> NAME/KEY: MISC_FEATURE
<223> OTHER INFORMATION: FPaV-2 "Gordon strain" N antigen translated
      amino acid sequence

<400> SEQUENCE: 14

Met Ala Ser Leu Leu Arg Ser Leu Ala Ala Phe Lys Lys His Arg Glu
1               5                   10                  15

Gln Pro Thr Val Pro Ser Gly Ser Gly Gly Thr Ile Lys Gly Leu Lys
            20                  25                  30

Asn Thr Ile Ile Val Pro Val Pro Gly Asp Thr Val Ile Thr Thr Arg
        35                  40                  45

Ser Asn Leu Leu Phe Arg Leu Val Tyr Ile Ile Gly Asn Pro Asp Thr
    50                  55                  60

Pro Leu Ser Thr Ser Thr Gly Ala Ile Ile Ser Leu Leu Thr Leu Phe
65                  70                  75                  80

Val Glu Ser Pro Gly Gln Leu Ile Gln Arg Ile Ala Asp Asp Pro Asp
                85                  90                  95

Ala Val Phe Lys Leu Val Glu Val Pro Glu Val Gly Asn Pro Gly
            100                 105                 110

Glu Leu Thr Phe Ala Ser Arg Gly Ile Asn Leu Asp Lys Gln Ala Gln
        115                 120                 125

Gln Tyr Phe Arg Leu Ala Glu Lys Asn Asp Gln Gly Tyr Tyr Val Ser
    130                 135                 140

Leu Gly Phe Glu Asn Pro Pro Asn Asp Asp Asp Ile Thr Ser Ser Pro
145                 150                 155                 160

Glu Ile Phe Asn Tyr Ile Leu Ala Ser Val Leu Ala Gln Ile Trp Ile
                165                 170                 175

Leu Leu Ala Lys Ala Val Thr Ala Pro Asp Thr Ala Ala Glu Ala Glu
            180                 185                 190

Asn Arg Arg Trp Ile Lys Leu Met Gln Gln Arg Arg Val Asp Gly Glu

-continued

```
            195                 200                 205
Leu Arg Leu Ser Lys Gly Trp Leu Asp Leu Val Arg Asn Lys Ile Ala
210                 215                 220

Ser Asp Ile Thr Ile Arg Arg Phe Met Val Ala Leu Val Leu Asp Ile
225                 230                 235                 240

Lys Arg Ser Pro Gly Thr Arg Pro Arg Ile Ala Glu Met Ile Cys Asp
                245                 250                 255

Ile Asp Asn Tyr Ile Val Glu Ala Gly Leu Ala Ser Phe Leu Leu Thr
                260                 265                 270

Ile Lys Phe Gly Ile Glu Thr Arg Tyr Pro Ala Leu Ala Leu His Glu
                275                 280                 285

Phe Ser Gly Glu Leu Ala Thr Ile Glu Gly Leu Met Lys Leu Tyr Gln
290                 295                 300

Ser Met Gly Glu Met Ala Pro Tyr Met Val Ile Leu Glu Asn Ser Ile
305                 310                 315                 320

Gln Thr Arg Phe Ser Ala Gly Ser Tyr Pro Leu Leu Trp Ser Tyr Ala
                325                 330                 335

Met Gly Val Gly Val Glu Leu Glu Arg Ser Met Ser Gly Leu Asn Phe
                340                 345                 350

Thr Arg Ser Phe Phe Asp Pro Thr Tyr Phe Arg Leu Gly Gln Glu Met
                355                 360                 365

Val Arg Arg Ser Ser Gly Met Val Asn Ser Ser Phe Ala Lys Glu Leu
370                 375                 380

Gly Leu Ser Glu His Glu Thr Gln Leu Val Ser Gln Ile Ile Asn Ser
385                 390                 395                 400

Gly Gly Glu Ser Gly Ile Pro Lys Phe Asp Gly Phe Arg Ala Asn Pro
                405                 410                 415

Thr Thr Phe Leu Gly Ala Lys Asp Asn Ile Thr Asp Arg Ser Glu Asp
                420                 425                 430

Pro Leu Ile Ala Ile Pro Gly Ser Ser Gly Gln Pro Leu Pro Gly Tyr
                435                 440                 445

Asp Pro Asn Ile Ser Gly Asp Ser Tyr Arg Ile Asp Ser Ser Thr Lys
                450                 455                 460

Asp Thr Asn Asn Ile Ser Asp Gly Gly Thr Asn Pro Ser His Asp Val
465                 470                 475                 480

Ser Asn Ser Ala Met Glu Glu Leu Arg Arg Leu Val Glu Ser Thr Asn
                485                 490                 495

Lys Ile Asp Thr Lys Lys Ser Glu Ser Pro Gly Ile Val Asn His Tyr
                500                 505                 510

Asn Asp Thr Asp Leu Leu Arg
515
```

<210> SEQ ID NO 15
<211> LENGTH: 1476
<212> TYPE: DNA
<213> ORGANISM: Feline paramyxovirus type 2
<220> FEATURE:
<221> NAME/KEY: misc_feature
<223> OTHER INFORMATION: FPaV-2 “Gordon strain” P antigen “wild-type” nucleic acid; given as DNA sequence

<400> SEQUENCE: 15
atgtcagcag aacaaatcca acaagttaga catggccttg aatccttgca agagatcaaa 60
aacaaccctc caccctctca agatgtcaat cttgccaggg aaatttacga atccattaaa 120
caaacaggaa caccttcaac acaaggaggg accattacag gaaataatac tgcgtcaggg 180

```
tgtgacaatt actcaatgca tagccaggga tcaggtcctt ctgtttcagg tgctgacaag    240
aatatcgaga gacttactgg acccgattat tcagaattat gggatccaga aggtaacctc    300
tgcatgctat tcgaaagcga tgatgatgac aacaattatt cagagattaa tggccggtct    360
accgctatcg aaggattgga tgaacagaat aataaggacc aggtattaa acaatcagga    420 gatcagtgtt ctgaaggagt gtctaagatt aattcatctt ctagtcccca agaagctaca    480
ttatcttctg ggagatctga tatatctggg acaggagtat ctccctgtgc ctctttggat    540
ataactgtta atgaattaga agatgcaact gttaagaata gtaataatat gaaaggaaat    600
tggccaatcc caaagttgct tgtcaaacca ccaccaagaa tgaaatcact ttctgactct    660
gttacaccat aaaaggggc caccgacggg aaatcagtct acctgggat ggagattaca    720 ttgtccggga agaatggtgc aaccctacct gtacacccat ttacacaacc tataaaagac    780
tcaaatgcag atgtaagcaa tgtccgtcaa catgtcccaa gtgtgactga tggtcatagt    840
gatgataatg aggaagtacc cggtttgcat aaagaaacta tagacaaagc tgatctatct    900
atgcaggaca tatacaattt aattcttgga tttaaggatg attacaggaa actatcaaat    960
aaattggata tgatactaga gatgaaacaa gatattgata tcttaaaaa gagtagtgca   1020 aaaatacaac ttgcattatc aacaattgaa ggacatctgt ccagtgttat gattgctatt   1080
ccaggttcag gtattgatat aaatcaagat gagaagaagg atcaattaaa ctctgactta   1140
aagccattac tagggaggga ccattgccgt gcatttcgtg aagtcactaa tcctttagat   1200
gaaacgtcat tgaccaacgc tccgaccaaa catgttgcta agatcaacaa aaattgcact   1260
cttcagaaaa tcaataacaa tgagacatct gcaattaagt ttgtacctaa tgatagccat   1320
gcaagtatct cgactatcaa gtctattgtc aaatcctcaa accttaatca agagcttaaa   1380
gtcaagttac tgacaattct atctcaaatt aaggggtag acaatattaa ggagttttat   1440
gagaaagtta tgatattgat caagaataat aactga                            1476
```

<210> SEQ ID NO 16
<211> LENGTH: 491
<212> TYPE: PRT
<213> ORGANISM: Feline paramyxovirus type 2
<220> FEATURE:
<221> NAME/KEY: MISC_FEATURE
<223> OTHER INFORMATION: FPaV-2 “Gordon strain” P antigen translated amino acid sequence

<400> SEQUENCE: 16

```
Met Ser Ala Glu Gln Ile Gln Gln Val Arg His Gly Leu Glu Ser Leu
1               5                   10                  15

Gln Glu Ile Lys Asn Asn Pro Pro Pro Ser Gln Asp Val Asn Leu Ala
            20                  25                  30

Arg Glu Ile Tyr Glu Ser Ile Lys Gln Thr Gly Thr Pro Ser Thr Gln
        35                  40                  45

Gly Gly Thr Ile Thr Gly Asn Asn Thr Ala Ser Gly Cys Asp Asn Tyr
    50                  55                  60

Ser Met His Ser Gln Gly Ser Gly Pro Ser Val Ser Gly Ala Asp Lys
65                  70                  75                  80

Asn Ile Glu Arg Leu Thr Gly Pro Asp Tyr Ser Glu Leu Trp Asp Pro
                85                  90                  95

Glu Gly Asn Leu Cys Met Leu Phe Glu Ser Asp Asp Asp Asp Asn Asn
            100                 105                 110

Tyr Ser Glu Ile Asn Gly Arg Ser Thr Ala Ile Glu Gly Leu Asp Glu
```

```
                115                 120                 125
Gln Asn Asn Lys Asp Pro Gly Ile Lys Gln Ser Gly Asp Gln Cys Ser
        130                 135                 140

Glu Gly Val Ser Lys Ile Asn Ser Ser Ser Pro Gln Glu Ala Thr
145                 150                 155                 160

Leu Ser Ser Gly Arg Ser Asp Ile Ser Gly Thr Val Ser Pro Cys
                165                 170                 175

Ala Ser Leu Asp Ile Thr Val Asn Glu Leu Glu Asp Ala Thr Val Lys
                180                 185                 190

Asn Ser Asn Asn Met Lys Gly Asn Trp Pro Ile Pro Lys Leu Leu Val
                195                 200                 205

Lys Pro Pro Arg Met Lys Ser Leu Ser Asp Ser Val Thr Pro Leu
210                 215                 220

Lys Gly Ala Thr Asp Gly Lys Ser Val Leu Pro Gly Met Glu Ile Thr
225                 230                 235                 240

Leu Ser Gly Lys Asn Gly Ala Thr Leu Pro Val His Pro Phe Thr Gln
                245                 250                 255

Pro Ile Lys Asp Ser Asn Ala Asp Val Ser Asn Val Arg Gln His Val
                260                 265                 270

Pro Ser Val Thr Asp Gly His Ser Asp Asp Asn Glu Glu Val Pro Gly
                275                 280                 285

Leu His Lys Glu Thr Ile Asp Lys Ala Asp Leu Ser Met Gln Asp Ile
290                 295                 300

Tyr Asn Leu Ile Leu Gly Phe Lys Asp Asp Tyr Arg Lys Leu Ser Asn
305                 310                 315                 320

Lys Leu Asp Met Ile Leu Glu Met Lys Gln Asp Ile Asp Asn Leu Lys
                325                 330                 335

Lys Ser Ser Ala Lys Ile Gln Leu Ala Leu Ser Thr Ile Glu Gly His
                340                 345                 350

Leu Ser Ser Val Met Ile Ala Ile Pro Gly Ser Gly Ile Asp Ile Asn
                355                 360                 365

Gln Asp Glu Lys Lys Asp Gln Leu Asn Ser Asp Leu Lys Pro Leu Leu
370                 375                 380

Gly Arg Asp His Cys Arg Ala Phe Arg Glu Val Thr Asn Pro Leu Asp
385                 390                 395                 400

Glu Thr Ser Leu Thr Asn Ala Pro Thr Lys His Val Ala Lys Ile Asn
                405                 410                 415

Lys Asn Cys Thr Leu Gln Lys Ile Asn Asn Asn Glu Thr Ser Ala Ile
                420                 425                 430

Lys Phe Val Pro Asn Asp Ser His Ala Ser Ile Ser Thr Ile Lys Ser
                435                 440                 445

Ile Val Lys Ser Ser Asn Leu Asn Gln Glu Leu Lys Val Lys Leu Leu
                450                 455                 460

Thr Ile Leu Ser Gln Ile Lys Gly Val Asp Asn Ile Lys Glu Phe Tyr
465                 470                 475                 480

Glu Lys Val Met Ile Leu Ile Lys Asn Asn Asn
                485                 490
```

<210> SEQ ID NO 17
<211> LENGTH: 6609
<212> TYPE: DNA
<213> ORGANISM: Feline paramyxovirus type 2
<220> FEATURE:
<221> NAME/KEY: misc_feature
<223> OTHER INFORMATION: FPaV-2 "Gordon strain" L antigen "wild-type"

nucleic acid; given as DNA sequence

<400> SEQUENCE: 17

```
atggagcaat cagattatca agatatttta tatccagagg tacatctcaa cagtcctata      60
gttatctcta aattagtggg tattttggag tattctaagg ttgttcacaa tcagcagtta     120
tctgatcaca caatagtcaa gaatatacaa tttagattga gaaatggatt caatagtcca     180
agaatacaaa cactgttagt tatgggtgaa attatcaata aaatcaaaaa taaataccca     240
aattatttgc atacaccttta tcctgaatgt aatcaaaagt tatttaggat agctgacccg     300
gagttaacat ctaaactaga agccctcttg acaaaggtg acacattata tcttaagatt     360
aagacagaga tcatagcttg tttcgataag ttaaaaacta aaatgagcat aaccaatgat     420
ctgattagtg acaataggca gctaatttca gatctaccta taattgtcaa gggatctcaa     480
tggttttttcc cttttttgct ctggttctct gttaaaactg agactaggaa ctgtattcga     540
caaaatcaaa aaactcgtgt taggtcacaa taccgacctc atttgtcaga aactaaaaga     600
attacgctgg tcgttactca tgacttgatc acaatatttg accacgtcaa caatgtata    660
tatcatctga cttttgagat gttgttgatg tattgtgatg tagtagaagg gaggttaatg     720
accgaagcat ctatgagtct agatcacaga tttattaacc tattgtcgag ggtccagtat     780
atgtgggatc tattagatgg gatgtttgag agtctaggaa atcagctata ttcaatcatt     840
gcactcttag aacctctctc tcttgcctat ctacagttga tggatgcaga cccacagata     900
cggggtacat ttttacacca ttgcctttca gagttggaag aactcttatt tagtaaattc     960
ccttttgatc ctgtaattta tgaaaatcta attagtggac ttgattacat ctatttaaca    1020
gacgatattc atttaactgc tgagatattt tctttcttta gaagttttgg tcatccttat    1080
ttagaagcac aaaatgcagc tagcaatgtt aggaaatata tgaatcaacc taagttatc    1140
tcataccaga ctctaatgca aggacatgca attttttgtg cattataat aaatgggttc    1200
agagatcgtc acggagggac atggccaccc gtagagctac cacatcatgc atccgctgta    1260
attagaaatg ctcagttatc tggagaagga ttaacacctg agcagtgtgc tcaatactgg    1320
aggtcatttt gtggatttaa atttaaatgt tttatgccat taagtttaga tagcgacctc    1380
accatgtacc ttagagacaa ggcattatca cctattaaga atgagtggga ctctgtgtat    1440
gctaaagagt atttaagata caaccctggc ttaccgacta gctctcgaag attagtcaat    1500
gtatttcttg aagatgataa atttgatccg tacgaaatga ttatgtacgt aataaacggt    1560
gattatttaa gggataatga gttcaatctc tcatatagtc ttaaagaaaa ggagatcaag    1620
gaggtaggcc gattgttcgc taaaatgact tataaaatga gagcttgtca ggtaatagca    1680
gaaaatttaa ttgcaaatgg agttgggaaa ttttttaaag acaatgggat ggcgaaggat    1740
gaacataaat taaccaaaac attacataag ctggccatttt ctggtgtacc taagataat    1800
tttcaactct atttaagtga atgttgggaa caagtggtag aacaatgcgt aaccagtacg    1860
caaacaaaaa atcaaattat cagttcacac tcaagaaaat cagttgcatc aaagtttcca    1920
agatcaaatc ccaatgatag gggtattcta aatagtggca gacatttgaa taaacatcca    1980
aaacatcctt caaacaccga atactatgaa actgtcagta gttttataac tactgatctc    2040
aagaaatatt gcctcaactg gcgctatgaa tcaagtagtg tgtttgcaga aagactcaat    2100
gagatttatg ggttaccagg atttttttcat tggcttcata gaattttgga gaatctgta    2160
ttatatgtta gtgatccatc cagtccacct gattttgatc aacatgttga tattgattca    2220
gttccaaatg atcatatttt tatcaaatac ccaatgggtg ggatagaagg attttgtcaa    2280
```

```
aaattatgga caatcagcac aatcccattt ttatatttag cagcttttga tacaggggtt    2340
agaatatctt cgttggttca aggtgataat caagcaattg cagtgaccaa aagagttcca    2400
tcgtcctgga gttattcgag aaaaaaagag gagtcaacta agttacaac acaatatttt    2460 ttaaacttaa gacaacgctt acatgatata ggtcatgagt taaaggcaaa tgagactatt    2520
atatcttcac acttttttgt ttactctaag ggtatttatt atgatggtat acttctttca    2580
caatccctta aaagtattgc aagatgtgtt ttttggtccg agacaattgt cgatgagact    2640
aggtcagctt gcagcaatat atccactacc cttgctaaag ctattgaacg gggttatgat    2700
aaattcgtgg catacgctat taatatatat aagactatac accaggtctt aattgcatta    2760
tcttttacta ttaatcccac tatgactccg gacataacag aaccttttta taaaagtta    2820 gatttactta aaaacctcat tctgatacca gcaccattgg gtgggatgaa ttacatgaat    2880
atgagcagat tatttgttag aaacataggt gatcccatta cagcttcatt tgctgacatc    2940
aagcgtatga tcgaatgcgg gttattaggg cacaatgttc tctcacaaat aatgtatcag    3000
aaatgtggta cctcgaaata cttagattgg gctagtgacc cttattccat aaatcttcct    3060
tatagtcaaa gcatgaccaa agtattaaaa aatataaccg cgagatatgt tctcatgcac    3120
agtcctaacc ctatgctaaa agatttattc catgagaagt cacaagaaga agatgagatt    3180
cttgctgaat ttttgctgga tcgtcagtta ataatcccta gagctgcaca tgaaatttta    3240
tcgaattcag taacaggagc tagagagtcg attgcaggga tgcttgatac tactaaagga    3300
cttattcgag ccagtatgtc aagaggtggt ctgacatctt cacttgtgtt gaaattgtca    3360
acatatgatt atcaacaatt tagaacatgc cttgaatggc tttatgcccc taccacagga    3420
atagcagtaa gtgctgattc ttgttcagtt tttttagcca gagctattcg aaaaaggatg    3480
tgggttcacc tgactaaagg aagagaaatt tatggcctag aagtgcctga tatattagaa    3540
tgtatgcaga gcaatgtaat tgttgatcat gaagattgtt attcatgtat tcaaggatca    3600
agatactaca catggttttt tgtaccttct aattgtcagc ttgatcagat taacaagtct    3660
acaaattctc tacgggttcc ttacattggc tctactacag aggaaagaag tgacatgaaa    3720
ttatcatacg tcagatcccc tagtaggcca cttaaggcag cagtccgaat tgcagcagtc    3780
tacacatggg catacggtga tgacgatctg tcttggcgtg aggcttggta cttggcaagg    3840
actagggcaa atgttacttt cgatgagctt aaattagtaa cacccatagc tacctctacg    3900
aacttggcac atagattaag ggacaggagt actcaagtta gtattcagg aacttcatta    3960 gtaagagtgg cacgctatac aacaatatcc aatgataata tgtcatttgt cattaatgac    4020
aaaaaggtag atactaattt tgtctatcaa cagggcatgt tattgggttt gagtatccta    4080
gaatatatat ttagatactg taaaagtact ggtcaatcaa atactgtagt tcacttgcat    4140
gcagatgtta attgttgcat aatccaaatg acagatcaac cttatactcc aagcttaacg    4200
aaaaaattac ctgagattaa acctattaat aataagttga tttatgatcc agctcctata    4260
attgatactg atgcagctag gttatattct cagaagtact tatcacacct gatagatttt    4320
ccaaattggt caatgaatca gctaaatgta gttttagcaa aagtagttgc aatatctatt    4380
gtggacttga taactaaagc gagtaaagat catctcaatg aaattatggc agttgttgga    4440
gatgatgaca ttaatagctt tataacagaa ttttttgctag ttgatccgag gctatttaca    4500
ttgtacttag gtcaatacac gtcacttcaa tgggcatatg aaattcatta tcaccgaccc    4560
gtaggcaaat accagatggc agaagtgtta cacactttac tgtcaagagc aagtaaaggt    4620
```

-continued

```
atatttaata tattaactaa tgcttttagt catcctagag tttacaaaag attttgggaa    4680
tgtggattac tggagcctat ttatggacca tacataggga gccaaaattt atatagtaca    4740
gtaattgatt acctttacaa tgcttatata acttatttag atgcttatct atctgatcat    4800
atcgaagatg cagacatagt aatatgtgag acagaagaaa cttgtctagc taataggatt    4860
gataactatc aaggtaggca tctagccgta cttattgatc tttattgtga ttctactagg    4920
tgtcctaata taaagggtc agacacaatc atgcgaaact caattctcaa atcttttatt     4980
gataatgaga gaaggacaag tccattaggt ctaacatgga atcttgatcc attactcata    5040
gatcatttca gttgttcaat tacttatctg aggagaggta ttattaaaca gattaggcta    5100
aggtttgatc caaacatatc tattgagttg gttaaattgg caaaacctga agtgattcat    5160
caaggaccaa aaataccgtc ttcttgggcc cttatagata ttaatcctga ggtcaatgat    5220
cttaatacag ttttcggaga attaaatagt aaatggaaag atattcctat tggacaaatt    5280
agaattcaaa attatgagat ccatgcttac cgaagaattg gagttaattc aactgcatgt    5340
tataaagcat tggaaatgct atctgtacta acccggttta tgtctaaccc agcaggagct    5400
ttgtttttag gagagggtgc agggtcaatg ttagttacct atcgtgcgtt tatcccgttc    5460
aagagaattt attataatag tggaatttct atacaaaata ttcaaagcca agagaacta    5520 agtctatacc catctgaagt agccttggtt gataataaaa atcgtttgac cagtgatcct    5580
gatatcaaag tcttatttaa tggcaagcca gaatccacgt gggttgggaa tatagactgc    5640
tttgcttata ttctgagtca tattgaaact tctagtttaa cattaatcca cagtgatatt    5700
gaatctagct tgagtaaaac aaagaataag attcttgagg agctttgcca tattctatca    5760
atggcactga ttttaggaaa gattggatct gtattagtta ttaagctgtt accacgggtt    5820
ggtgactaca catattcatt ttgcaagtat gcgtcagaat tctaccaaca gaatttttt     5880 atttaccta gatttagcaa catgtcatca tctgaaattt actacgttgg agttcattta    5940
aataccaata gactggttga tccagatagg attgtgcaat atataatcag gaatctccaa    6000
tctactccag ttactttctt atcttacatt ttggaaacta aatatagaaa taatatggtt    6060
acaaattatg ggctctgctt gtctgatgga cataaaagcg attacttgtc atcaatcacc    6120
aagatagaaa atgttctttt atcatgtgga ttggaattga atggacctaa gattatacag    6180
caattatctg gacatgacta cgccaatgga gagattagct tagaatcaag tataatggta    6240
ctggttagag aatatctaaa tgcaactatc caaggtcggg aaacactagg tcttttttca    6300
ccttaccctg tgttacatga gagtcagtta agagaaatta acaggtgcat tgcattgaag    6360
tatgttgtat atttactttt ttactcaacc tctgtaggat ctagtagaca aatcatgagc    6420
aatctcagaa aaggagtatt aatgtatgac ttaagagatg agttttcat ggaaaggtta     6480 tcaacaaatt tcaagaaaaa aataatgtca caagaggtta aaactacatg gatctttaat    6540
attgatgtac caacaagaaa agctctgtat aaattagttg gttattcact tatcattaat    6600
cacgtataa                                                           6609
```

<210> SEQ ID NO 18
<211> LENGTH: 2202
<212> TYPE: PRT
<213> ORGANISM: Feline paramyxovirus type 2
<220> FEATURE:
<221> NAME/KEY: MISC_FEATURE
<223> OTHER INFORMATION: FPaV-2 "Gordon strain" L antigen translated amino acid sequence

<400> SEQUENCE: 18

-continued

```
Met Glu Gln Ser Asp Tyr Gln Asp Ile Leu Tyr Pro Glu Val His Leu
1               5                   10                  15

Asn Ser Pro Ile Val Ile Ser Lys Leu Val Gly Ile Leu Glu Tyr Ser
                20                  25                  30

Lys Val Val His Asn Gln Gln Leu Ser Asp His Thr Ile Val Lys Asn
            35                  40                  45

Ile Gln Phe Arg Leu Arg Asn Gly Phe Asn Ser Pro Arg Ile Gln Thr
        50                  55                  60

Leu Leu Val Met Gly Glu Ile Ile Asn Lys Ile Lys Asn Lys Tyr Pro
65                  70                  75                  80

Asn Tyr Leu His Ile Pro Tyr Pro Glu Cys Asn Gln Lys Leu Phe Arg
                85                  90                  95

Ile Ala Asp Pro Glu Leu Thr Ser Lys Leu Glu Ala Leu Leu Asp Lys
                100                 105                 110

Gly Asp Thr Leu Tyr Leu Lys Ile Lys Thr Glu Ile Ile Ala Cys Phe
            115                 120                 125

Asp Lys Leu Lys Thr Lys Met Ser Ile Thr Asn Asp Leu Ile Ser Asp
        130                 135                 140

Asn Arg Gln Leu Ile Ser Asp Leu Pro Ile Ile Val Lys Gly Ser Gln
145                 150                 155                 160

Trp Phe Phe Pro Phe Leu Leu Trp Phe Ser Val Lys Thr Glu Thr Arg
                165                 170                 175

Asn Cys Ile Arg Gln Asn Gln Lys Thr Arg Val Arg Ser Gln Tyr Arg
                180                 185                 190

Pro His Leu Ser Glu Thr Lys Arg Ile Thr Leu Val Thr His Asp
            195                 200                 205

Leu Ile Thr Ile Phe Asp His Val Asn Lys Cys Ile Tyr His Leu Thr
        210                 215                 220

Phe Glu Met Leu Leu Met Tyr Cys Asp Val Val Glu Gly Arg Leu Met
225                 230                 235                 240

Thr Glu Ala Ser Met Ser Leu Asp His Arg Phe Ile Asn Leu Leu Ser
                245                 250                 255

Arg Val Gln Tyr Met Trp Asp Leu Leu Asp Gly Met Phe Glu Ser Leu
                260                 265                 270

Gly Asn Gln Leu Tyr Ser Ile Ile Ala Leu Leu Glu Pro Leu Ser Leu
            275                 280                 285

Ala Tyr Leu Gln Leu Met Asp Ala Asp Pro Gln Ile Arg Gly Thr Phe
        290                 295                 300

Leu His His Cys Leu Ser Glu Leu Glu Glu Leu Leu Phe Ser Lys Phe
305                 310                 315                 320

Pro Phe Asp Pro Val Ile Tyr Glu Asn Leu Ile Ser Gly Leu Asp Tyr
                325                 330                 335

Ile Tyr Leu Thr Asp Asp Ile His Leu Thr Ala Glu Ile Phe Ser Phe
            340                 345                 350

Phe Arg Ser Phe Gly His Pro Tyr Leu Glu Ala Gln Asn Ala Ala Ser
        355                 360                 365

Asn Val Arg Lys Tyr Met Asn Gln Pro Lys Val Ile Ser Tyr Gln Thr
        370                 375                 380

Leu Met Gln Gly His Ala Ile Phe Cys Gly Ile Ile Ile Asn Gly Phe
385                 390                 395                 400

Arg Asp Arg His Gly Gly Thr Trp Pro Pro Val Glu Leu Pro His His
                405                 410                 415
```

```
Ala Ser Ala Val Ile Arg Asn Ala Gln Leu Ser Gly Glu Gly Leu Thr
            420                 425                 430

Pro Glu Gln Cys Ala Gln Tyr Trp Arg Ser Phe Cys Gly Phe Lys Phe
        435                 440                 445

Lys Cys Phe Met Pro Leu Ser Leu Asp Ser Asp Leu Thr Met Tyr Leu
    450                 455                 460

Arg Asp Lys Ala Leu Ser Pro Ile Lys Asn Glu Trp Asp Ser Val Tyr
465                 470                 475                 480

Ala Lys Glu Tyr Leu Arg Tyr Asn Pro Gly Leu Pro Thr Ser Ser Arg
                485                 490                 495

Arg Leu Val Asn Val Phe Leu Glu Asp Lys Phe Asp Pro Tyr Glu
            500                 505                 510

Met Ile Met Tyr Val Ile Asn Gly Asp Tyr Leu Arg Asp Asn Glu Phe
        515                 520                 525

Asn Leu Ser Tyr Ser Leu Lys Glu Lys Glu Ile Lys Glu Val Gly Arg
    530                 535                 540

Leu Phe Ala Lys Met Thr Tyr Lys Met Arg Ala Cys Gln Val Ile Ala
545                 550                 555                 560

Glu Asn Leu Ile Ala Asn Gly Val Gly Lys Phe Phe Lys Asp Asn Gly
                565                 570                 575

Met Ala Lys Asp Glu His Lys Leu Thr Lys Thr Leu His Lys Leu Ala
            580                 585                 590

Ile Ser Gly Val Pro Lys Asp Asn Phe Gln Leu Tyr Leu Ser Glu Cys
        595                 600                 605

Trp Glu Gln Val Val Glu Gln Cys Val Thr Ser Thr Gln Thr Lys Asn
    610                 615                 620

Gln Ile Ile Ser Ser His Ser Arg Lys Ser Val Ala Ser Lys Phe Pro
625                 630                 635                 640

Arg Ser Asn Pro Asn Asp Arg Gly Ile Leu Asn Ser Gly Arg His Leu
                645                 650                 655

Asn Lys His Pro Lys His Pro Ser Asn Thr Glu Tyr Tyr Glu Thr Val
            660                 665                 670

Ser Ser Phe Ile Thr Thr Asp Leu Lys Lys Tyr Cys Leu Asn Trp Arg
        675                 680                 685

Tyr Glu Ser Ser Ser Val Phe Ala Glu Arg Leu Asn Glu Ile Tyr Gly
    690                 695                 700

Leu Pro Gly Phe Phe His Trp Leu His Arg Ile Leu Glu Lys Ser Val
705                 710                 715                 720

Leu Tyr Val Ser Asp Pro Ser Pro Pro Asp Phe Asp Gln His Val
                725                 730                 735

Asp Ile Asp Ser Val Pro Asn Asp His Ile Phe Ile Lys Tyr Pro Met
            740                 745                 750

Gly Gly Ile Glu Gly Phe Cys Gln Lys Leu Trp Thr Ile Ser Thr Ile
        755                 760                 765

Pro Phe Leu Tyr Leu Ala Ala Phe Asp Thr Gly Val Arg Ile Ser Ser
    770                 775                 780

Leu Val Gln Gly Asp Asn Gln Ala Ile Ala Val Thr Lys Arg Val Pro
785                 790                 795                 800

Ser Ser Trp Ser Tyr Ser Arg Lys Lys Glu Ser Thr Lys Val Thr
                805                 810                 815

Thr Gln Tyr Phe Leu Asn Leu Arg Gln Arg Leu His Asp Ile Gly His
            820                 825                 830

Glu Leu Lys Ala Asn Glu Thr Ile Ile Ser Ser His Phe Phe Val Tyr
```

```
                835             840             845
Ser Lys Gly Ile Tyr Tyr Asp Gly Ile Leu Leu Ser Gln Ser Leu Lys
850                 855                 860
Ser Ile Ala Arg Cys Val Phe Trp Ser Glu Thr Ile Val Asp Glu Thr
865                 870                 875                 880
Arg Ser Ala Cys Ser Asn Ile Ser Thr Thr Leu Ala Lys Ala Ile Glu
                885                 890                 895
Arg Gly Tyr Asp Lys Phe Val Ala Tyr Ala Ile Asn Ile Tyr Lys Thr
                900                 905                 910
Ile His Gln Val Leu Ile Ala Leu Ser Phe Thr Ile Asn Pro Thr Met
                915                 920                 925
Thr Pro Asp Ile Thr Glu Pro Phe Tyr Lys Ser Leu Asp Leu Leu Lys
930                 935                 940
Asn Leu Ile Leu Ile Pro Ala Pro Leu Gly Gly Met Asn Tyr Met Asn
945                 950                 955                 960
Met Ser Arg Leu Phe Val Arg Asn Ile Gly Asp Pro Ile Thr Ala Ser
                965                 970                 975
Phe Ala Asp Ile Lys Arg Met Ile Glu Cys Gly Leu Leu Gly His Asn
                980                 985                 990
Val Leu Ser Gln Ile Met Tyr Gln Lys Cys Gly Thr Ser Lys Tyr Leu
                995                 1000                1005
Asp Trp Ala Ser Asp Pro Tyr Ser Ile Asn Leu Pro Tyr Ser Gln
1010                1015                1020
Ser Met Thr Lys Val Leu Lys Asn Ile Thr Ala Arg Tyr Val Leu
1025                1030                1035
Met His Ser Pro Asn Pro Met Leu Lys Asp Leu Phe His Glu Lys
1040                1045                1050
Ser Gln Glu Glu Asp Glu Ile Leu Ala Glu Phe Leu Leu Asp Arg
1055                1060                1065
Gln Leu Ile Ile Pro Arg Ala Ala His Glu Ile Leu Ser Asn Ser
1070                1075                1080
Val Thr Gly Ala Arg Glu Ser Ile Ala Gly Met Leu Asp Thr Thr
1085                1090                1095
Lys Gly Leu Ile Arg Ala Ser Met Ser Arg Gly Gly Leu Thr Ser
1100                1105                1110
Ser Leu Val Leu Lys Leu Ser Thr Tyr Asp Tyr Gln Gln Phe Arg
1115                1120                1125
Thr Cys Leu Glu Trp Leu Tyr Ala Pro Thr Thr Gly Ile Ala Val
1130                1135                1140
Ser Ala Asp Ser Cys Ser Val Phe Leu Ala Arg Ala Ile Arg Lys
1145                1150                1155
Arg Met Trp Val His Leu Thr Lys Gly Arg Glu Ile Tyr Gly Leu
1160                1165                1170
Glu Val Pro Asp Ile Leu Glu Cys Met Gln Ser Asn Val Ile Val
1175                1180                1185
Asp His Glu Asp Cys Tyr Ser Cys Ile Gln Gly Ser Arg Tyr Tyr
1190                1195                1200
Thr Trp Phe Phe Val Pro Ser Asn Cys Gln Leu Asp Gln Ile Asn
1205                1210                1215
Lys Ser Thr Asn Ser Leu Arg Val Pro Tyr Ile Gly Ser Thr Thr
1220                1225                1230
Glu Glu Arg Ser Asp Met Lys Leu Ser Tyr Val Arg Ser Pro Ser
1235                1240                1245
```

```
Arg Pro Leu Lys Ala Ala Val Arg Ile Ala Ala Val Tyr Thr Trp
    1250                1255                1260

Ala Tyr Gly Asp Asp Asp Leu Ser Trp Arg Glu Ala Trp Tyr Leu
    1265                1270                1275

Ala Arg Thr Arg Ala Asn Val Thr Phe Asp Glu Leu Lys Leu Val
    1280                1285                1290

Thr Pro Ile Ala Thr Ser Thr Asn Leu Ala His Arg Leu Arg Asp
    1295                1300                1305

Arg Ser Thr Gln Val Lys Tyr Ser Gly Thr Ser Leu Val Arg Val
    1310                1315                1320

Ala Arg Tyr Thr Thr Ile Ser Asn Asp Asn Met Ser Phe Val Ile
    1325                1330                1335

Asn Asp Lys Lys Val Asp Thr Asn Phe Val Tyr Gln Gln Gly Met
    1340                1345                1350

Leu Leu Gly Leu Ser Ile Leu Glu Tyr Ile Phe Arg Tyr Cys Lys
    1355                1360                1365

Ser Thr Gly Gln Ser Asn Thr Val Val His Leu His Ala Asp Val
    1370                1375                1380

Asn Cys Cys Ile Ile Gln Met Thr Asp Gln Pro Tyr Thr Pro Ser
    1385                1390                1395

Leu Thr Lys Lys Leu Pro Glu Ile Lys Pro Ile Asn Asn Lys Leu
    1400                1405                1410

Ile Tyr Asp Pro Ala Pro Ile Ile Asp Thr Asp Ala Ala Arg Leu
    1415                1420                1425

Tyr Ser Gln Lys Tyr Leu Ser His Leu Ile Asp Phe Pro Asn Trp
    1430                1435                1440

Ser Met Asn Gln Leu Asn Val Val Leu Ala Lys Val Val Ala Ile
    1445                1450                1455

Ser Ile Val Asp Leu Ile Thr Lys Ala Ser Lys Asp His Leu Asn
    1460                1465                1470

Glu Ile Met Ala Val Val Gly Asp Asp Ile Asn Ser Phe Ile
    1475                1480                1485

Thr Glu Phe Leu Leu Val Asp Pro Arg Leu Phe Thr Leu Tyr Leu
    1490                1495                1500

Gly Gln Tyr Thr Ser Leu Gln Trp Ala Tyr Glu Ile His Tyr His
    1505                1510                1515

Arg Pro Val Gly Lys Tyr Gln Met Ala Glu Val Leu His Thr Leu
    1520                1525                1530

Leu Ser Arg Ala Ser Lys Gly Ile Phe Asn Ile Leu Thr Asn Ala
    1535                1540                1545

Phe Ser His Pro Arg Val Tyr Lys Arg Phe Trp Glu Cys Gly Leu
    1550                1555                1560

Leu Glu Pro Ile Tyr Gly Pro Tyr Ile Gly Ser Gln Asn Leu Tyr
    1565                1570                1575

Ser Thr Val Ile Asp Tyr Leu Tyr Asn Ala Tyr Ile Thr Tyr Leu
    1580                1585                1590

Asp Ala Tyr Leu Ser Asp His Ile Glu Asp Ala Asp Ile Val Ile
    1595                1600                1605

Cys Glu Thr Glu Glu Thr Cys Leu Ala Asn Arg Ile Asp Asn Tyr
    1610                1615                1620

Gln Gly Arg His Leu Ala Val Leu Ile Asp Leu Tyr Cys Asp Ser
    1625                1630                1635
```

```
Thr Arg Cys Pro Asn Ile Lys Gly Ser Asp Thr Ile Met Arg Asn
1640                1645                1650

Ser Ile Leu Lys Ser Phe Ile Asp Asn Glu Arg Arg Thr Ser Pro
1655                1660                1665

Leu Gly Leu Thr Trp Asn Leu Asp Pro Leu Leu Ile Asp His Phe
1670                1675                1680

Ser Cys Ser Ile Thr Tyr Leu Arg Arg Gly Ile Ile Lys Gln Ile
1685                1690                1695

Arg Leu Arg Phe Asp Pro Asn Ile Ser Ile Glu Leu Val Lys Leu
1700                1705                1710

Ala Lys Pro Glu Val Ile His Gln Gly Pro Lys Ile Pro Ser Ser
1715                1720                1725

Trp Ala Leu Ile Asp Ile Asn Pro Glu Val Asn Asp Leu Asn Thr
1730                1735                1740

Val Phe Gly Glu Leu Asn Ser Lys Trp Lys Asp Ile Pro Ile Gly
1745                1750                1755

Gln Ile Arg Ile Gln Asn Tyr Glu Ile His Ala Tyr Arg Arg Ile
1760                1765                1770

Gly Val Asn Ser Thr Ala Cys Tyr Lys Ala Leu Glu Met Leu Ser
1775                1780                1785

Val Leu Thr Arg Phe Met Ser Asn Pro Ala Gly Ala Leu Phe Leu
1790                1795                1800

Gly Glu Gly Ala Gly Ser Met Leu Val Thr Tyr Arg Ala Phe Ile
1805                1810                1815

Pro Phe Lys Arg Ile Tyr Tyr Asn Ser Gly Ile Ser Ile Gln Asn
1820                1825                1830

Ile Gln Ser Gln Arg Glu Leu Ser Leu Tyr Pro Ser Glu Val Ala
1835                1840                1845

Leu Val Asp Asn Lys Asn Arg Leu Thr Ser Asp Pro Asp Ile Lys
1850                1855                1860

Val Leu Phe Asn Gly Lys Pro Glu Ser Thr Trp Val Gly Asn Ile
1865                1870                1875

Asp Cys Phe Ala Tyr Ile Leu Ser His Ile Glu Thr Ser Ser Leu
1880                1885                1890

Thr Leu Ile His Ser Asp Ile Glu Ser Ser Leu Ser Lys Thr Lys
1895                1900                1905

Asn Lys Ile Leu Glu Glu Leu Cys His Ile Leu Ser Met Ala Leu
1910                1915                1920

Ile Leu Gly Lys Ile Gly Ser Val Leu Val Ile Lys Leu Leu Pro
1925                1930                1935

Arg Val Gly Asp Tyr Thr Tyr Ser Phe Cys Lys Tyr Ala Ser Glu
1940                1945                1950

Phe Tyr Gln Gln Asn Phe Phe Ile Leu Pro Arg Phe Ser Asn Met
1955                1960                1965

Ser Ser Ser Glu Ile Tyr Tyr Val Gly Val His Leu Asn Thr Asn
1970                1975                1980

Arg Leu Val Asp Pro Asp Arg Ile Val Gln Tyr Ile Ile Arg Asn
1985                1990                1995

Leu Gln Ser Thr Pro Val Thr Phe Leu Ser Tyr Ile Leu Glu Thr
2000                2005                2010

Lys Tyr Arg Asn Asn Met Val Thr Asn Tyr Gly Leu Cys Leu Ser
2015                2020                2025

Asp Gly His Lys Ser Asp Tyr Leu Ser Ser Ile Thr Lys Ile Glu
```

| | | | | | | | | | |
|---|---|---|---|---|---|---|---|---|---|
| | | | 2030 | | | 2035 | | | 2040 |
| Asn | Val | Leu | Leu | Ser | Cys | Gly | Leu | Glu | Leu | Asn | Gly | Pro | Lys | Ile |
| | | | 2045 | | | 2050 | | | 2055 |
| Ile | Gln | Gln | Leu | Ser | Gly | His | Asp | Tyr | Ala | Asn | Gly | Glu | Ile | Ser |
| | | | 2060 | | | 2065 | | | 2070 |
| Leu | Glu | Ser | Ser | Ile | Met | Val | Leu | Val | Arg | Glu | Tyr | Leu | Asn | Ala |
| | | | 2075 | | | 2080 | | | 2085 |
| Thr | Ile | Gln | Gly | Arg | Glu | Thr | Leu | Gly | Leu | Phe | Ser | Pro | Tyr | Pro |
| | | | 2090 | | | 2095 | | | 2100 |
| Val | Leu | His | Glu | Ser | Gln | Leu | Arg | Glu | Ile | Asn | Arg | Cys | Ile | Ala |
| | | | 2105 | | | 2110 | | | 2115 |
| Leu | Lys | Tyr | Val | Val | Tyr | Leu | Leu | Phe | Tyr | Ser | Thr | Ser | Val | Gly |
| | | | 2120 | | | 2125 | | | 2130 |
| Ser | Ser | Arg | Gln | Ile | Met | Ser | Asn | Leu | Arg | Lys | Gly | Val | Leu | Met |
| | | | 2135 | | | 2140 | | | 2145 |
| Tyr | Asp | Leu | Arg | Asp | Glu | Phe | Phe | Met | Glu | Arg | Leu | Ser | Thr | Asn |
| | | | 2150 | | | 2155 | | | 2160 |
| Phe | Lys | Lys | Lys | Ile | Met | Ser | Gln | Glu | Val | Lys | Thr | Thr | Trp | Ile |
| | | | 2165 | | | 2170 | | | 2175 |
| Phe | Asn | Ile | Asp | Val | Pro | Thr | Arg | Lys | Ala | Leu | Tyr | Lys | Leu | Val |
| | | | 2180 | | | 2185 | | | 2190 |
| Gly | Tyr | Ser | Leu | Ile | Ile | Asn | His | Val |
| | | | 2195 | | | 2200 |

<210> SEQ ID NO 19
<211> LENGTH: 1788
<212> TYPE: DNA
<213> ORGANISM: Feline paramyxovirus type 2
<220> FEATURE:
<221> NAME/KEY: misc_feature
<223> OTHER INFORMATION: FPaV-2 "TV25 strain" H antigen "wild-type"
    nucleic acid; given as DNA sequence

<400> SEQUENCE: 19

```
atggagtcta ataacaacaa gtactataaa gattcaaacc ggtatttag caagatacta      60
gatgagaaca agacggtaaa taatcatctg tatagtctta gtataaggat aattaccgtt    120
atagctattg ttgtgagtct aattgcaaca acaataacca tcattaatgc tataagcgga    180
aggactactc ttaataataa tatggacatg ctactcaacc aacaagacaa gattaataat    240
atcaaggaaa tgatatttga tcgtatctat cccctgataa atgccatgag tacagagctt    300
ggtcttcaca ttccaacttt attggatgag ctgactaaat caattgatca aaaaatcaag    360
ataatgactc caccacttga aactacgaca tctaatctca attggtgtat caacccccca    420
aatggcatta ttgtagatcc taaaggttac tgtgaaggct tggaactgtc aaaaacttat    480
aagttattac ttgatcaatt agatatgtta agaaagaaat cacttattat taataagaaa    540
agtattaatc agtgtagact tgttgatagc tcgaatatca tctttgcaac agttaatata    600
caatctacac cgagattctt aaatcttggt cacacagtta gtaaccaacg tataacattc    660
ggtcaaggaa catatagtag cacttatatt ataactatac aagaggatgg attaactgat    720
gttcagtacc gagtatttga ataggatat atctcagatc aatttggaac cttcccttct    780
ctaatcgttt ctagagtact acctgtgcga atggtacttg gaatggaatc ttgtacactg    840
accagtgaca agttcggggg ttatttttta tgcatgaaca ttccgacacg ctctatatat    900
gattatgtca acataaagaga cttaaagtca ctatacgtca caatccctca ttatggcaaa    960
```

-continued

```
attaattaca cttactttaa ttttggaaaa gtcagaagcc cacatgaaat tgataagatt    1020
tggcttacat cagaaagggg acagatgatt tcaggttact ttgcagcatt tgttacgatt    1080
acaattagaa attataacaa ttatccctat aaatgcttac ataacccgtg tcttgaaaga    1140
tctgagagtt attgcaaagg atggtacaaa aatattacag gtactgatga tgttccaata    1200
ttagcatatc tattagttga aatgaaggat gaggaaggac ctttaattac actggttgaa    1260
ataccacctt acaattatac ggctccttct cataattccc tttactatga tgataaaatt    1320
aacaaattaa taatgacaac atctcatata ggatacattc aaatcaatga agtgcatgaa    1380
gtcattgtcg gggataatct taaggctatt ctcttaaaca gattatctga tgaacaccct    1440
actcttactg cttgtagatt taatcaggaa attaaagagc gacatatatc tgatgggtta    1500
ataatatcta actctgctct tattgatata caagaacgta tgtatattac agttaaggct    1560
gttccaccca taggaaatta taacttcacg gtagagttgc attcacggtc aaatacatct    1620
tacgtagggt tgccaaggca gttcaatgct aggtatgaca aactgcatct cgaatgcttt    1680
gcctgggata ggtcttggtg gtgcgctttg atacctcaat tttcattaag ttggaatgaa    1740
tctctttcag tagatactgc cattttcaac ttaataaact gtaattaa                 1788
```

<210> SEQ ID NO 20
<211> LENGTH: 595
<212> TYPE: PRT
<213> ORGANISM: Feline paramyxovirus type 2
<220> FEATURE:
<221> NAME/KEY: MISC_FEATURE
<223> OTHER INFORMATION: FPaV-2 "TV25 strain" H antigen translated amino
      acid sequence

<400> SEQUENCE: 20

```
Met Glu Ser Asn Asn Asn Lys Tyr Tyr Lys Asp Ser Asn Arg Tyr Phe
1               5                   10                  15

Ser Lys Ile Leu Asp Glu Asn Lys Thr Val Asn Asn His Leu Tyr Ser
            20                  25                  30

Leu Ser Ile Arg Ile Ile Thr Val Ile Ala Ile Val Val Ser Leu Ile
        35                  40                  45

Ala Thr Thr Ile Thr Ile Ile Asn Ala Ile Ser Gly Arg Thr Thr Leu
    50                  55                  60

Asn Asn Asn Met Asp Met Leu Leu Asn Gln Gln Asp Lys Ile Asn Asn
65                  70                  75                  80

Ile Lys Glu Met Ile Phe Asp Arg Ile Tyr Pro Leu Ile Asn Ala Met
                85                  90                  95

Ser Thr Glu Leu Gly Leu His Ile Pro Thr Leu Leu Asp Glu Leu Thr
            100                 105                 110

Lys Ser Ile Asp Gln Lys Ile Lys Ile Met Thr Pro Pro Leu Glu Thr
        115                 120                 125

Thr Thr Ser Asn Leu Asn Trp Cys Ile Asn Pro Pro Asn Gly Ile Ile
    130                 135                 140

Val Asp Pro Lys Gly Tyr Cys Glu Gly Leu Glu Leu Ser Lys Thr Tyr
145                 150                 155                 160

Lys Leu Leu Leu Asp Gln Leu Asp Met Leu Arg Lys Lys Ser Leu Ile
                165                 170                 175

Ile Asn Lys Lys Ser Ile Asn Gln Cys Arg Leu Val Asp Ser Ser Asn
            180                 185                 190

Ile Ile Phe Ala Thr Val Asn Ile Gln Ser Thr Pro Arg Phe Leu Asn
        195                 200                 205
```

```
Leu Gly His Thr Val Ser Asn Gln Arg Ile Thr Phe Gly Gln Gly Thr
210                 215                 220
Tyr Ser Ser Thr Tyr Ile Ile Thr Ile Gln Glu Asp Gly Leu Thr Asp
225                 230                 235                 240
Val Gln Tyr Arg Val Phe Glu Ile Gly Tyr Ile Ser Asp Gln Phe Gly
                245                 250                 255
Thr Phe Pro Ser Leu Ile Val Ser Arg Val Leu Pro Val Arg Met Val
            260                 265                 270
Leu Gly Met Glu Ser Cys Thr Leu Thr Ser Asp Lys Phe Gly Gly Tyr
        275                 280                 285
Phe Leu Cys Met Asn Ile Pro Thr Arg Ser Ile Tyr Asp Tyr Val Asn
    290                 295                 300
Ile Arg Asp Leu Lys Ser Leu Tyr Val Thr Ile Pro His Tyr Gly Lys
305                 310                 315                 320
Ile Asn Tyr Thr Tyr Phe Asn Phe Gly Lys Val Arg Ser Pro His Glu
                325                 330                 335
Ile Asp Lys Ile Trp Leu Thr Ser Glu Arg Gly Gln Met Ile Ser Gly
            340                 345                 350
Tyr Phe Ala Ala Phe Val Thr Ile Thr Ile Arg Asn Tyr Asn Asn Tyr
        355                 360                 365
Pro Tyr Lys Cys Leu His Asn Pro Cys Leu Glu Arg Ser Glu Ser Tyr
    370                 375                 380
Cys Lys Gly Trp Tyr Lys Asn Ile Thr Gly Thr Asp Asp Val Pro Ile
385                 390                 395                 400
Leu Ala Tyr Leu Leu Val Glu Met Lys Asp Glu Glu Gly Pro Leu Ile
                405                 410                 415
Thr Leu Val Glu Ile Pro Pro Tyr Asn Tyr Thr Ala Pro Ser His Asn
            420                 425                 430
Ser Leu Tyr Tyr Asp Asp Lys Ile Asn Lys Leu Ile Met Thr Thr Ser
        435                 440                 445
His Ile Gly Tyr Ile Gln Ile Asn Glu Val His Glu Val Ile Val Gly
    450                 455                 460
Asp Asn Leu Lys Ala Ile Leu Leu Asn Arg Leu Ser Asp Glu His Pro
465                 470                 475                 480
Thr Leu Thr Ala Cys Arg Phe Asn Gln Glu Ile Lys Glu Arg His Ile
                485                 490                 495
Ser Asp Gly Leu Ile Ile Ser Asn Ser Ala Leu Ile Asp Ile Gln Glu
            500                 505                 510
Arg Met Tyr Ile Thr Val Lys Ala Val Pro Pro Ile Gly Asn Tyr Asn
        515                 520                 525
Phe Thr Val Glu Leu His Ser Arg Ser Asn Thr Ser Tyr Val Gly Leu
    530                 535                 540
Pro Arg Gln Phe Asn Ala Arg Tyr Asp Lys Leu His Leu Glu Cys Phe
545                 550                 555                 560
Ala Trp Asp Arg Ser Trp Trp Cys Ala Leu Ile Pro Gln Phe Ser Leu
                565                 570                 575
Ser Trp Asn Glu Ser Leu Ser Val Asp Thr Ala Ile Phe Asn Leu Ile
            580                 585                 590

Asn Cys Asn
        595

<210> SEQ ID NO 21
<211> LENGTH: 1014
<212> TYPE: DNA
```

<213> ORGANISM: Feline paramyxovirus type 2
<220> FEATURE:
<221> NAME/KEY: misc_feature
<223> OTHER INFORMATION: FPaV-2 "TV25 strain" M antigen "wild-type"
      nucleic acid; given as DNA sequence

<400> SEQUENCE: 21

```
atgactgaga tattcaatct ggatgaaagt tcatggtcag tcaagggaac actggaccca    60
ttgacgcctg atacttatcc tgatgggcgc ctagtaccca agattcgggt tattgatccc   120
ggtctaggtg atcgtaaaag tggaggatat atgtacttac tccttcacgg tgtcatcgag   180
gacagtgaga ccgtcataaa tccgaaaggg agagcatttg gagctttccc tttaggtgta   240
gggcaatcaa ccgagaaccc agaagactta tttaaggaaa tattaaccct caacattgtt   300
actcgcagga ctgctggctt caatgaaaaa ttggtgtatt ataatactac acctctaaat   360
ctactaaccc cttggaaaaa agtactagca tatggaagta tctttactgc taatcaggtc   420
tgcaataata caagttctat ccctatagac attcctcaga aatttcgacc tgtctattta   480
actgttacca agttatcgga tgatggatat tatcagatac taaaatgat acaggatttc    540
aaatcatcaa actctgttgc atttaacatc cttgtgcatc tatcaatggg aacaatttta   600
cttgactcat ctaaaggctc tcgagtagga atcctgcag aaaatttgat cacattcatg    660
attcatattg ggaatttcaa acggaagaat aataaagctt attctcccga atattgtaag   720
aggaaaataa tgaggcttgg attaatcttc tcactaggag ccattggtgg aacaagtttg   780
catattcgat gcacaggcaa aatgagtaag cgattacaag cctacttagg gtttaaaaga   840
actttatgtt atcctctgat gtatgtcaat gagggtctaa acaaaacctt atggagaaat   900
gaatgcagaa ttgagaaggt tcaagcagta ttacagccat cagttccgaa tgaatttaag   960
atttatgatg atataatcat tgataacacg aatggcctct ttaaggttaa gtaa        1014
```

<210> SEQ ID NO 22
<211> LENGTH: 337
<212> TYPE: PRT
<213> ORGANISM: Feline paramyxovirus type 2
<220> FEATURE:
<221> NAME/KEY: MISC_FEATURE
<223> OTHER INFORMATION: FPaV-2 "TV25 strain" M antigen translated amino
      acid sequence

<400> SEQUENCE: 22

```
Met Thr Glu Ile Phe Asn Leu Asp Glu Ser Ser Trp Ser Val Lys Gly
1               5                   10                  15

Thr Leu Asp Pro Leu Thr Pro Asp Thr Tyr Pro Asp Gly Arg Leu Val
            20                  25                  30

Pro Lys Ile Arg Val Ile Asp Pro Gly Leu Gly Asp Arg Lys Ser Gly
        35                  40                  45

Gly Tyr Met Tyr Leu Leu Leu His Gly Val Ile Glu Asp Ser Glu Thr
    50                  55                  60

Val Ile Asn Pro Lys Gly Arg Ala Phe Gly Ala Phe Pro Leu Gly Val
65                  70                  75                  80

Gly Gln Ser Thr Glu Asn Pro Glu Asp Leu Phe Lys Glu Ile Leu Thr
                85                  90                  95

Leu Asn Ile Val Thr Arg Arg Thr Ala Gly Phe Asn Glu Lys Leu Val
            100                 105                 110

Tyr Tyr Asn Thr Thr Pro Leu Asn Leu Leu Thr Pro Trp Lys Lys Val
        115                 120                 125

Leu Ala Tyr Gly Ser Ile Phe Thr Ala Asn Gln Val Cys Asn Asn Thr
```

```
                130                 135                 140
Ser Ser Ile Pro Ile Asp Ile Pro Gln Lys Phe Arg Pro Val Tyr Leu
145                 150                 155                 160

Thr Val Thr Lys Leu Ser Asp Asp Gly Tyr Tyr Gln Ile Pro Lys Met
                165                 170                 175

Ile Gln Asp Phe Lys Ser Ser Asn Ser Val Ala Phe Asn Ile Leu Val
                180                 185                 190

His Leu Ser Met Gly Thr Ile Leu Leu Asp Ser Ser Lys Gly Ser Arg
                195                 200                 205

Val Gly Asn Pro Ala Glu Asn Leu Ile Thr Phe Met Ile His Ile Gly
210                 215                 220

Asn Phe Lys Arg Lys Asn Asn Lys Ala Tyr Ser Pro Glu Tyr Cys Lys
225                 230                 235                 240

Arg Lys Ile Met Arg Leu Gly Leu Ile Phe Ser Leu Gly Ala Ile Gly
                245                 250                 255

Gly Thr Ser Leu His Ile Arg Cys Thr Gly Lys Met Ser Lys Arg Leu
                260                 265                 270

Gln Ala Tyr Leu Gly Phe Lys Arg Thr Leu Cys Tyr Pro Leu Met Tyr
                275                 280                 285

Val Asn Glu Gly Leu Asn Lys Thr Leu Trp Arg Asn Glu Cys Arg Ile
                290                 295                 300

Glu Lys Val Gln Ala Val Leu Gln Pro Ser Val Pro Asn Glu Phe Lys
305                 310                 315                 320

Ile Tyr Asp Asp Ile Ile Ile Asp Asn Thr Asn Gly Leu Phe Lys Val
                325                 330                 335

Lys
```

<210> SEQ ID NO 23
<211> LENGTH: 1632
<212> TYPE: DNA
<213> ORGANISM: Feline paramyxovirus type 2
<220> FEATURE:
<221> NAME/KEY: misc_feature
<223> OTHER INFORMATION: FPaV-2 "TV25 strain" F antigen "wild-type" nucleic acid; given as DNA sequence

<400> SEQUENCE: 23

```
atgtataaga ttaaggttgt aatcatgggt tttttactgt tatcagatat tacatttgca    60
caggtaggtt gggataattt aacctcaatt ggagttataa gtactaaaca atataactat   120
aagataacta ctttgaatac taatcaactc atggtgatta aaatggtacc caatatatca   180
tcaattatta ctgtactaa  acttgaatta gcaaaatata gggaactgat tacaggaata   240
ctgagaccaa ttaatgaatc attagaattg atgaattcat atatcaacat gagaacaggt   300
tcagagagat tcataggggc tgttatagca ggagtagctc taggggttgc aactgcggcg   360
cagataacat cgggaattgc cttacataat tcgattatga ataaaaaaca gatacaggaa   420
ttaaggaaag cccttagtac tacaaataag gcaattgatg agataaggat tgcaggtgaa   480
agaactctga tagctgtcca aggtgtgcaa gattacatta caatgttat  tatccctatg   540 caagagaaac tccagtgcga tattttagcc tcacagctat ctattgccct actcagatac   600
tatactaata tactgactgt ttttggacca agtataagag atcctattac tagtacaatt   660
tctatacaag ctctcagtca agcattcaat ggtaatctac aggcattgct tgatggatta   720
gggtatactg acaagacttt acatgatctc atagaaagta gatctatcac tggtcaaata   780
attcacgctg atatgactga tttattcctt atattgagaa tcaattatcc atctattacg   840
```

```
gatatgcaag gagtggtaat atatgagctg aattctatca catatcatat tggacctgaa    900
gagtggtaca ctattatgcc taatttcata gctgttcagg gatttctggt atctaatttc    960
gatgaacgta aatgttcaat tactaaaaca agtatactgt gtcaacagaa ttcaatttat   1020
cctatgtcaa ccgaaatgca aagatgtata aaaggtgaga ttaaattctg tccaaggtcc   1080
aaagcaattg ggacattagt taatcgattt atattaatta atgggaatct aatggccaat   1140
tgtttgggta ttatttgtag atgttatacc tcaggtcaaa ttataacgca agacccaaat   1200
aaattaatca caattatatc acaagaagaa tgtagagagg ttggtgttga tgggattcgt   1260
ataatggtgg gacctaaaaa attaccggat gttatcttta atgccagact agaaataggt   1320
gtacctatct cattaagcaa gctggatgtt gggaccgatt tggcaattgc ttcagctaaa   1380
ctcaataact ctaaggcact tttggagcag tctgataaaa tcttaaattc tatgtctaag   1440
ttggattctt taaattcacg tatcttagga tctgtcttta taatgatgat aatctttgtg   1500
attgtaattg tgattatttg gattatttgt aagaagtgta gaaataagag gaacaaatta   1560
agtgcttcta ttgaacccct ctacatacct ccctcttata attcacccca tagcatagtt   1620
aaatctattt ga                                                       1632

<210> SEQ ID NO 24
<211> LENGTH: 543
<212> TYPE: PRT
<213> ORGANISM: Feline paramyxovirus type 2
<220> FEATURE:
<221> NAME/KEY: MISC_FEATURE
<223> OTHER INFORMATION: FPaV-2 “TV25 strain” F antigen translated amino
      acid sequence <400> SEQUENCE: 24

Met Tyr Lys Ile Lys Val Val Ile Met Gly Phe Leu Leu Leu Ser Asp
1               5                   10                  15

Ile Thr Phe Ala Gln Val Gly Trp Asp Asn Leu Thr Ser Ile Gly Val
            20                  25                  30

Ile Ser Thr Lys Gln Tyr Asn Tyr Lys Ile Thr Thr Leu Asn Thr Asn
        35                  40                  45

Gln Leu Met Val Ile Lys Met Val Pro Asn Ile Ser Ser Ile Ile Asn
    50                  55                  60

Cys Thr Lys Leu Glu Leu Ala Lys Tyr Arg Glu Leu Ile Thr Gly Ile
65                  70                  75                  80

Leu Arg Pro Ile Asn Glu Ser Leu Glu Leu Met Asn Ser Tyr Ile Asn
                85                  90                  95

Met Arg Thr Gly Ser Glu Arg Phe Ile Gly Ala Val Ile Ala Gly Val
            100                 105                 110

Ala Leu Gly Val Ala Thr Ala Ala Gln Ile Thr Ser Gly Ile Ala Leu
        115                 120                 125

His Asn Ser Ile Met Asn Lys Lys Gln Ile Gln Glu Leu Arg Lys Ala
    130                 135                 140

Leu Ser Thr Thr Asn Lys Ala Ile Asp Glu Ile Arg Ile Ala Gly Glu
145                 150                 155                 160

Arg Thr Leu Ile Ala Val Gln Gly Val Gln Asp Tyr Ile Asn Asn Val
                165                 170                 175

Ile Ile Pro Met Gln Glu Lys Leu Gln Cys Asp Ile Leu Ala Ser Gln
            180                 185                 190

Leu Ser Ile Ala Leu Leu Arg Tyr Tyr Thr Asn Ile Leu Thr Val Phe
        195                 200                 205
```

Gly Pro Ser Ile Arg Asp Pro Ile Thr Ser Thr Ile Ser Ile Gln Ala
210                 215                 220

Leu Ser Gln Ala Phe Asn Gly Asn Leu Gln Ala Leu Leu Asp Gly Leu
225                 230                 235                 240

Gly Tyr Thr Gly Gln Asp Leu His Asp Leu Ile Glu Ser Arg Ser Ile
            245                 250                 255

Thr Gly Gln Ile Ile His Ala Asp Met Thr Asp Leu Phe Leu Ile Leu
        260                 265                 270

Arg Ile Asn Tyr Pro Ser Ile Thr Asp Met Gln Gly Val Val Ile Tyr
    275                 280                 285

Glu Leu Asn Ser Ile Thr Tyr His Ile Gly Pro Glu Glu Trp Tyr Thr
290                 295                 300

Ile Met Pro Asn Phe Ile Ala Val Gln Gly Phe Leu Val Ser Asn Phe
305                 310                 315                 320

Asp Glu Arg Lys Cys Ser Ile Thr Lys Thr Ser Ile Leu Cys Gln Gln
                325                 330                 335

Asn Ser Ile Tyr Pro Met Ser Thr Glu Met Gln Arg Cys Ile Lys Gly
            340                 345                 350

Glu Ile Lys Phe Cys Pro Arg Ser Lys Ala Ile Gly Thr Leu Val Asn
        355                 360                 365

Arg Phe Ile Leu Ile Asn Gly Asn Leu Met Ala Asn Cys Leu Gly Ile
370                 375                 380

Ile Cys Arg Cys Tyr Thr Ser Gly Gln Ile Ile Thr Gln Asp Pro Asn
385                 390                 395                 400

Lys Leu Ile Thr Ile Ser Gln Glu Glu Cys Arg Glu Val Gly Val
                405                 410                 415

Asp Gly Ile Arg Ile Met Val Gly Pro Lys Lys Leu Pro Asp Val Ile
            420                 425                 430

Phe Asn Ala Arg Leu Glu Ile Gly Val Pro Ile Ser Leu Ser Lys Leu
        435                 440                 445

Asp Val Gly Thr Asp Leu Ala Ile Ala Ser Ala Lys Leu Asn Asn Ser
450                 455                 460

Lys Ala Leu Leu Glu Gln Ser Asp Lys Ile Leu Asn Ser Met Ser Lys
465                 470                 475                 480

Leu Asp Ser Leu Asn Ser Arg Ile Leu Gly Ser Val Phe Ile Met Met
                485                 490                 495

Ile Ile Phe Val Ile Val Ile Val Ile Ile Trp Ile Ile Cys Lys Lys
            500                 505                 510

Cys Arg Asn Lys Arg Asn Lys Leu Ser Ala Ser Ile Glu Pro Leu Tyr
        515                 520                 525

Ile Pro Pro Ser Tyr Asn Ser Pro His Ser Ile Val Lys Ser Ile
530                 535                 540

<210> SEQ ID NO 25
<211> LENGTH: 1560
<212> TYPE: DNA
<213> ORGANISM: Feline paramyxovirus type 2
<220> FEATURE:
<221> NAME/KEY: misc_feature
<223> OTHER INFORMATION: FPaV-2 "TV25 strain" N antigen "wild-type"
      nucleic acid; given as DNA sequence

<400> SEQUENCE: 25
atggctagtt tactcaggtc acttgcggca ttcaagaaac acagagaaca accaactgtt    60
ccttctgggt caggagggac gatcaaagga ttaaaaaata caattattgt gcctgttcct   120

```
ggagatacag tcatcactac cagatcgaac ttactgttca gattagtcta cataattggt    180
aatccagata caccctttaag cacttcaaca ggggcaataa tatcattgtt gacattattt    240
gttgaatctc caggtcaatt aattcaaaga atcgctgatg atcctgatgc tgtttttaaa    300
ttagtagagg tggttcctga ggttggtaat cctggagaat taacttttgc atctagagga    360
attaacttgg ataaacaagc tcaacaatac tttagattgg ctgagaaaaa tgatcaagga    420
tattatgtaa gtttggggtt tgaaaatcca ccaaatgatg atgatataac gtcaagtcct    480
gaaatcttaa attatatttt agcatctgta cttgcacaga tctggattct cctagctaag    540
gctgtaactg ctccagacac aggtggtgag gctgaaaatc gtaggtggat taaattgatg    600
caacaacgca gagtggatgg tgagcttaga ttaagtaaag gatggttgga cttagtgagg    660
aataaaatcg catcggatat cacaattaga aggtttatgg tagcattagt tcttgacatt    720
aaacgttctc ctggaacaag accaagaatt gctgaaatga tttgtgatat agacaattat    780
attgtggagg ccggactggc aagttttctg ttaactatca aatttggtat agaaacacgt    840
tacccagcat tggcgttaca tgagttttcg ggggaattag ccactattga aggactcatg    900
aaattgtacc agtctatggg agaaatggca ccatacatgg tcattctaga gaattcgatc    960
cagactaggt ttagtgctgg gtcttatccg ttactctgga gctatgctat gggtgttggt   1020
gtagaacttg agagatcaat gagtggatta aacttcacaa gaagtttctt tgatcctacg   1080
tacttcaggt tgggtcagga gatggtaaga aggtcttcag gaatggttaa tagctcattt   1140
gctaaagaac ttggactatc tgaacatgaa acacaacttg ttagccagat cattaactct   1200
ggtggtgaat caggtatacc gaaatttgat ggatttagag caaacccaac aacatttcta   1260
ggggctaagg acaacatcac tgataggagt gaagatccat tgattgcaat tccagggtca   1320
tcaggacaac cattgccagg tcatgacccc aatatctcag gtgactcata tagaattgat   1380
agtagcacta aagacacgaa caatatatca gatggaggaa caaatccaag tcatgatgtt   1440
tccaattctg ctatggaaga gctgagaaga ttggtagagt ctaccaacaa gattgataca   1500
aagaaatctg aaagcccagg cattgttaat cattcaacg atactgacct tctgagataa    1560
```

<210> SEQ ID NO 26  
<211> LENGTH: 519  
<212> TYPE: PRT  
<213> ORGANISM: Feline paramyxovirus type 2  
<220> FEATURE:  
<221> NAME/KEY: MISC_FEATURE  
<223> OTHER INFORMATION: FPaV-2 "TV25 strain" N antigen translated amino acid sequence

<400> SEQUENCE: 26

Met Ala Ser Leu Leu Arg Ser Leu Ala Ala Phe Lys Lys His Arg Glu
1               5                   10                  15

Gln Pro Thr Val Pro Ser Gly Ser Gly Gly Thr Ile Lys Gly Leu Lys
            20                  25                  30

Asn Thr Ile Ile Val Pro Val Pro Gly Asp Thr Val Ile Thr Thr Arg
        35                  40                  45

Ser Asn Leu Leu Phe Arg Leu Val Tyr Ile Ile Gly Asn Pro Asp Thr
    50                  55                  60

Pro Leu Ser Thr Ser Thr Gly Ala Ile Ile Ser Leu Leu Thr Leu Phe
65                  70                  75                  80

Val Glu Ser Pro Gly Gln Leu Ile Gln Arg Ile Ala Asp Asp Pro Asp
                85                  90                  95

Ala Val Phe Lys Leu Val Glu Val Val Pro Glu Val Gly Asn Pro Gly
                100                 105                 110

Glu Leu Thr Phe Ala Ser Arg Gly Ile Asn Leu Asp Lys Gln Ala Gln
            115                 120                 125

Gln Tyr Phe Arg Leu Ala Glu Lys Asn Asp Gln Gly Tyr Tyr Val Ser
        130                 135                 140

Leu Gly Phe Glu Asn Pro Pro Asn Asp Asp Asp Ile Thr Ser Ser Pro
145                 150                 155                 160

Glu Ile Leu Asn Tyr Ile Leu Ala Ser Val Leu Ala Gln Ile Trp Ile
                165                 170                 175

Leu Leu Ala Lys Ala Val Thr Ala Pro Asp Thr Gly Gly Glu Ala Glu
            180                 185                 190

Asn Arg Arg Trp Ile Lys Leu Met Gln Gln Arg Arg Val Asp Gly Glu
        195                 200                 205

Leu Arg Leu Ser Lys Gly Trp Leu Asp Leu Val Arg Asn Lys Ile Ala
210                 215                 220

Ser Asp Ile Thr Ile Arg Arg Phe Met Val Ala Leu Val Leu Asp Ile
225                 230                 235                 240

Lys Arg Ser Pro Gly Thr Arg Pro Arg Ile Ala Glu Met Ile Cys Asp
                245                 250                 255

Ile Asp Asn Tyr Ile Val Glu Ala Gly Leu Ala Ser Phe Leu Leu Thr
            260                 265                 270

Ile Lys Phe Gly Ile Glu Thr Arg Tyr Pro Ala Leu Ala Leu His Glu
        275                 280                 285

Phe Ser Gly Glu Leu Ala Thr Ile Glu Gly Leu Met Lys Leu Tyr Gln
290                 295                 300

Ser Met Gly Glu Met Ala Pro Tyr Met Val Ile Leu Glu Asn Ser Ile
305                 310                 315                 320

Gln Thr Arg Phe Ser Ala Gly Ser Tyr Pro Leu Leu Trp Ser Tyr Ala
                325                 330                 335

Met Gly Val Gly Val Glu Leu Glu Arg Ser Met Ser Gly Leu Asn Phe
            340                 345                 350

Thr Arg Ser Phe Phe Asp Pro Thr Tyr Phe Arg Leu Gly Gln Glu Met
        355                 360                 365

Val Arg Arg Ser Ser Gly Met Val Asn Ser Ser Phe Ala Lys Glu Leu
370                 375                 380

Gly Leu Ser Glu His Glu Thr Gln Leu Val Ser Gln Ile Ile Asn Ser
385                 390                 395                 400

Gly Gly Glu Ser Gly Ile Pro Lys Phe Asp Gly Phe Arg Ala Asn Pro
                405                 410                 415

Thr Thr Phe Leu Gly Ala Lys Asp Asn Ile Thr Asp Arg Ser Glu Asp
            420                 425                 430

Pro Leu Ile Ala Ile Pro Gly Ser Ser Gly Gln Pro Leu Pro Gly His
        435                 440                 445

Asp Pro Asn Ile Ser Gly Asp Ser Tyr Arg Ile Asp Ser Ser Thr Lys
450                 455                 460

Asp Thr Asn Asn Ile Ser Asp Gly Gly Thr Asn Pro Ser His Asp Val
465                 470                 475                 480

Ser Asn Ser Ala Met Glu Glu Leu Arg Arg Leu Val Glu Ser Thr Asn
                485                 490                 495

Lys Ile Asp Thr Lys Lys Ser Glu Ser Pro Gly Ile Val Asn His Tyr
            500                 505                 510

Asn Asp Thr Asp Leu Leu Arg

<210> SEQ ID NO 27
<211> LENGTH: 1476
<212> TYPE: DNA
<213> ORGANISM: Feline paramyxovirus type 2
<220> FEATURE:
<221> NAME/KEY: misc_feature
<223> OTHER INFORMATION: FPaV-2 "TV25 strain" P antigen "wild-type" nucleic acid; given as DNA sequence

<400> SEQUENCE: 27

```
atgtcagcag aacaaatcca acaagttaga catggccttg aatccttgca agagatcaaa     60
aacaaccctc caccctctca agatgtcaat cttgccaggg aaatttacga atccattaaa    120
caaacaggaa caccttcaac acaaggaggg accattacag gaaataatac tacgtcaggg    180
tgtgacaatt actcaatgca tagccaggga tcaggtcctt ctgtttcagg tgctgacaag    240
aatatcgaga gacttactgg acccgattat tcagaattat gggatccaga aggtaacctc    300
tgcatgctat tcgaaagcga tgatgatgac aacaattatt cagagattaa tggccggtct    360
accgctatcg aaggattgga tgaacagaat aataaggacc caggtattaa acaatcagga    420
gatcagtgtt ctgaaggagt gtctaagatt aattcatctt ctagtcccca agaagctaca    480
ttatcttctg ggagatctga tatatctggg acaggagtat ctccctgtgc ctctttggat    540
ataactgtta atgaattaga agatgcaact gttaagaata gtaataatat gaaaggaaat    600
tggccaatcc caaagttgct tgtcaaacca ccaccaagaa tgaaatcact ttctgactct    660
gttacaccat taaaaggggc caccgacggg aaatcagtct tacctgggat ggagattaca    720
ttgtccggga agaatggtgc aaccctacct gtacacccat ttacacaacc tgtaaaagac    780
tcaaatgcag atgtaagcaa tgtccgtcaa catgtcccaa gtgtgactga tggttatagt    840
gatgataatg aggaagtacc cggtttgcat aaagaaacta tagacaaagc tgatctatct    900
atgcaggaca tatacaattt aattcttgga tttaaggatg attacaggaa actatcaaat    960
aaattggata tgatactaga gatgaaacaa gatattgata atcttaaaaa gagtagtgca   1020
aaaatacaac ttgcattatc aacaattgaa ggacatctgt ccagtgttat gattgctatt   1080
ccaggttcag gtattgatat gaatcaagat gagaagaagg atcaattaaa ctctgactta   1140
aagccattac tagggaggga ccattgccgt gcatttcgtg aagtcactaa tcctttagat   1200
gaaacgtcat tgaccaacgc tccgaccaaa catgttgcta agatcaacaa aaattgcact   1260
cttcagaaaa tcaataagaa tgagacatct gcaattaagt ttgtacctaa tgatagctat   1320
gcaagtatct cgactatcaa gtctattgtc aaatcctcaa accttaatca agagcttaaa   1380
gtcaagttac tgacaattct atctcaaatt aaaggggtag acaatattaa ggagttttat   1440
gagaaagtta tgatattgat caagaataat aactga                             1476
```

<210> SEQ ID NO 28
<211> LENGTH: 491
<212> TYPE: PRT
<213> ORGANISM: Feline paramyxovirus type 2
<220> FEATURE:
<221> NAME/KEY: MISC_FEATURE
<223> OTHER INFORMATION: FPaV-2 "TV25 strain" P antigen translated amino acid sequence

<400> SEQUENCE: 28

```
Met Ser Ala Glu Gln Ile Gln Gln Val Arg His Gly Leu Glu Ser Leu
1               5                   10                  15
```

Gln Glu Ile Lys Asn Asn Pro Pro Ser Gln Asp Val Asn Leu Ala
             20                  25                  30

Arg Glu Ile Tyr Glu Ser Ile Lys Gln Thr Gly Thr Pro Ser Thr Gln
                 35                  40                  45

Gly Gly Thr Ile Thr Gly Asn Asn Thr Thr Ser Gly Cys Asp Asn Tyr
 50                  55                  60

Ser Met His Ser Gln Gly Ser Gly Pro Ser Val Ser Gly Ala Asp Lys
 65                  70                  75                  80

Asn Ile Glu Arg Leu Thr Gly Pro Asp Tyr Ser Glu Leu Trp Asp Pro
                 85                  90                  95

Glu Gly Asn Leu Cys Met Leu Phe Glu Ser Asp Asp Asp Asn Asn
                100                 105                 110

Tyr Ser Glu Ile Asn Gly Arg Ser Thr Ala Ile Glu Gly Leu Asp Glu
                115                 120                 125

Gln Asn Asn Lys Asp Pro Gly Ile Lys Gln Ser Gly Asp Gln Cys Ser
        130                 135                 140

Glu Gly Val Ser Lys Ile Asn Ser Ser Ser Pro Gln Glu Ala Thr
145                 150                 155                 160

Leu Ser Ser Gly Arg Ser Asp Ile Ser Gly Thr Gly Val Ser Pro Cys
                165                 170                 175

Ala Ser Leu Asp Ile Thr Val Asn Glu Leu Glu Asp Ala Thr Val Lys
                180                 185                 190

Asn Ser Asn Asn Met Lys Gly Asn Trp Pro Ile Pro Lys Leu Leu Val
                195                 200                 205

Lys Pro Pro Arg Met Lys Ser Leu Ser Asp Ser Val Thr Pro Leu
210                 215                 220

Lys Gly Ala Thr Asp Gly Lys Ser Val Leu Pro Gly Met Glu Ile Thr
225                 230                 235                 240

Leu Ser Gly Lys Asn Gly Ala Thr Leu Pro Val His Pro Phe Thr Gln
                245                 250                 255

Pro Val Lys Asp Ser Asn Ala Asp Val Ser Asn Val Arg Gln His Val
                260                 265                 270

Pro Ser Val Thr Asp Gly Tyr Ser Asp Asp Asn Glu Glu Val Pro Gly
                275                 280                 285

Leu His Lys Glu Thr Ile Asp Lys Ala Asp Leu Ser Met Gln Asp Ile
290                 295                 300

Tyr Asn Leu Ile Leu Gly Phe Lys Asp Asp Tyr Arg Lys Leu Ser Asn
305                 310                 315                 320

Lys Leu Asp Met Ile Leu Glu Met Lys Gln Asp Ile Asp Asn Leu Lys
                325                 330                 335

Lys Ser Ser Ala Lys Ile Gln Leu Ala Leu Ser Thr Ile Glu Gly His
                340                 345                 350

Leu Ser Ser Val Met Ile Ala Ile Pro Gly Ser Gly Ile Asp Met Asn
                355                 360                 365

Gln Asp Glu Lys Lys Asp Gln Leu Asn Ser Asp Leu Lys Pro Leu Leu
        370                 375                 380

Gly Arg Asp His Cys Arg Ala Phe Arg Glu Val Thr Asn Pro Leu Asp
385                 390                 395                 400

Glu Thr Ser Leu Thr Asn Ala Pro Thr Lys His Val Ala Lys Ile Asn
                405                 410                 415

Lys Asn Cys Thr Leu Gln Lys Ile Asn Lys Asn Glu Thr Ser Ala Ile
                420                 425                 430

Lys Phe Val Pro Asn Asp Ser Tyr Ala Ser Ile Ser Thr Ile Lys Ser

```
                435                 440                 445
Ile Val Lys Ser Ser Asn Leu Asn Gln Glu Leu Lys Val Lys Leu Leu
    450                 455                 460

Thr Ile Leu Ser Gln Ile Lys Gly Val Asp Asn Ile Lys Glu Phe Tyr
465                 470                 475                 480

Glu Lys Val Met Ile Leu Ile Lys Asn Asn Asn
                485                 490

<210> SEQ ID NO 29
<211> LENGTH: 6609
<212> TYPE: DNA
<213> ORGANISM: Feline paramyxovirus type 2
<220> FEATURE:
<221> NAME/KEY: misc_feature
<223> OTHER INFORMATION: FPaV-2 "TV25 strain" L antigen "wild-type"
      nucleic acid; given as DNA sequence

<400> SEQUENCE: 29
atggagcaat cagattatca agatatttta tatccagagg tacatctcaa cagtcctata      60
gttatctcta aattagtggg tattttggag tattctaagg ttgttcacaa tcagcagtta     120
tctgatcaca caatagtcaa gaatatacaa tttagattga aaatggatt caatagtcca      180 agagtacaaa cactgttagt tatgggtgaa attatcaata aaatcaaaaa taaatcccca     240
aattatttgc atacccttta tcctgaatgt aatcaaaagt tatttaggat ggctgacccg     300
gagttaacat ctaaactaga agccctcttg gacaaaggtg acacattata tcttaagatt     360
aagacagaga tcatagcttg tttcgataag ttaaaaacta aatgagcat aaccaatgat      420 ctgattagtg acaataggca gctaattcta gatctacctc taattgtcaa gggatctcaa     480 tggttttttcc ctttttttgct ctggttttct gttaaaactg agactaggaa ctgtattcga    540
caaaatcaaa aaactcgtgt taggtcacaa taccgacctc atttgtcaga aactaaaaga    600
attacgctgg tcgttacccc tgacttgatc acaatatttg accacgtcaa caaatgtata    660
tatcatctga ctttttgagat gttgttgatg tattgtgatg tagtagaagg gaggttaatg    720
accgaagcat ctatgagtct agatcacaga tttattaacc tattgtcgag gtccagtat    780 atgtgggatc tattagatgg gatgtttgag agtctaggaa atcagctata ttcaatcatt    840
gcactcttag aacctctctc tcttgcctat ctacagttga tggatgcaga cccacagata    900
cggggtacat ttttacacca ttgccttttca gagttggaag aactcttatt tagtaaatcc    960 cctttttgatc ctgtgatttta tgaaaatcta attagtggac ttgattacat ctatttaaca   1020
gacgatattc atttaactgc tgagatattt tctttcttta gaagttttgg tcatccttat    1080
ttagaagcac aaaatgcagc tagcaatgtt aggaaatata tgaatcaacc taaagttatc    1140
tcataccaga ctctaatgca aggacatgca atttttttgtg cattataat aaatgggttc    1200 agagatcgtc acggagggac atggccacct gtagagctac cacatcatgc atccgctgta    1260
attagaaatg ctcagttatc tggagaagga ttaacacctg agcagtgtgc tcaatactgg    1320
aggtcatttt gtggatttaa atttaaatgt tttatgccat taagtctaga tagcgacctc    1380
accatgtacc ttagagataa ggcattatca cctattaaga tgagtgggga ttctgtgtat    1440
gctaaagagt atttaagata caaccctggc ttaccgacta gctctcgaag attagtcaat    1500
gtatttctag aagatgataa atttgatccg tacgaaatga ttatgtacgt aataaacggt    1560
gattatttaa gggataatga gttcaatctc tcatatagtc ttaaagaaaa ggagatcaag    1620
gaggtaggcc gattgttcgc taaaatgact tataagatga gcttgtcca ggtaatagca    1680
```

```
gaaaatttaa ttgcaaatgg agttgggaaa tttttaaag acaatgggat ggcgaaggat      1740
gaacataaat taaccaaaac attacataag ctggctattt ctggtgtacc taaagataat      1800
tctcaactct atttaagtga atgttgggaa caagtggtag aacaatgcgt aaccagtacg      1860
caaacaaaaa atcaaattat cagttcacac tcaggaaaat cagttgcatc aaagttttca      1920
agatcaaatc ccaatgatag gggtattcta aatagtggta gacatttgaa taaacatcca      1980
aaacatccat caaacaccga atactatgaa actgtcagta gttttataac tactgatctc      2040
aagaaatatt gcctcaactg cgctatgaa tcaagtagtg tgtttgcaga aagactcaat      2100
gagatttatg ggttaccagg atttttccat tggcttcata gaattttgga gaaatctgta      2160
ttatatgtta gtgatccatc cagtccacct gattttgatc aacatgtcga tattgattca      2220
gttccaaatg atcatatttt tatcaaatac ccaatgggtg ggataaaagg attttgtcaa      2280
aaattatgga caatcagcac aatcccattt ttatatttag cagcctttga tacaggggtt      2340
agaatatctt cgttggttca aggtgataat caagcaattg cagtgaccaa aagagttcca      2400
tcatcctgga gttattcgag aaaaaagag gagtcaacta aagttacaac acaatatttt      2460
ttaaacttga acaacgctt acatgatata ggtcatgagt taaaggcaaa tgagactatt      2520
atatcttcac acttttttgt ttactctaag ggtatttatt atgatggtat acttctttca      2580
caatccctta aaagtattgc aagatgtgtt ttttggtccg agacaattgt cgatgagact      2640
aggtcagctt gcagcaatat atccactacc cttgctaaag ctattgaacg gggttatgat      2700
aaatttgtag catacgctat taatatatat aagactatac accaggtctt aattgcatta      2760
tcttttacta ttaatcccac tatgactccg gacataacag aaccttttta taaaagttta      2820
gatttactta aaaacctcat tctgatacca gcaccattgg gtgggatgaa ttacatgaat      2880
atgagcagat tatttgttag gaacataggt gatcccatta cagcttcatt tgctgacatc      2940
aagcgtatga tcgaatgcgg gttattaggg cacaatgttc tctcacaaat aatgtatcag      3000
aaatgtggta cctcgaaata cttagattgg gctagtgacc cttattccat aaatcttcct      3060
tatagtcaaa gcatgaccaa agtattaaaa aatataaccg cgagatatgt tctcatgcat      3120
agtcctaacc ctatgctaaa agattttattc catgagaagt cacaagaaga ggatgagatt      3180
cttgctgaat ttttgctgga tcgtcagtta ataatcccta gagctgcaca tgaaatttta      3240
tcgaattcag taacaggagc tagagagtcg attgcaggga tgcttgatac tactaaagga      3300
cttattcgag ccagtatgtc aagaggtggt ctgacatctt cacttgtttt gaaattgtca      3360
acatatgatt atcaacaatt tagaacatgc cttgaatggc tttatgcccc taccacagga      3420
atagcagtaa gtgctgattc ttgttcagtt tttttagcca gagctattcg aaaaaggatg      3480
tgggttcacc tgactaaagg aagagaaatt tatggcctag aagtgcctga tatattagaa      3540
tgtatgcaga gcaatgtaat tgttgatcat gaagattgtt attcatgtat tcaaggatca      3600
agatactaca catggttttt tgtaccttct aattgtcagc ttgatcagat taacaagtct      3660
acaaattctc tacgggttcc ttacattggc tctactacag aggaaagaag tgacatgaaa      3720
ttatcatacg tcagatcccc tagtaggcca cttaaggcag cagtccgaat tgcagcagtc      3780
tacacatggg catacggtga tgacgatctg tcttggcgtg aggcttggta cttggcaagg      3840
actagggcaa atgttacttt cgatgagctt aaattagtaa cacccatagc tacctctact      3900
aacttggcac atagattaag ggacaggagt actcaagtta agtattcagg aacttcattg      3960
gtaagagtgg cacgctatac aacaatatcc aatgataata tgtcatttgt tattaatgac      4020
aaaaaggtag atactaattt tgtctatcaa cagggcatgt tattgggttt gagtatccta      4080
```

```
gaatatatat ttagatactg taaaagtact ggtcaatcaa atactgtagt tcacttgcat    4140
gcagatgtta attgttgcat aatccaaatg acagatcaac cttatactcc aagcttaacg    4200
aaaaaattac ctgagattaa acctattaat aataaattga tttatgatcc agctcctata    4260
attgatactg atgcagctag gttatattct cagaagtact tatcacacct gatagatttt    4320
ccaaattggt caatgaatca gctaaatgta gttttagcaa aagtagttgc aatatctatt    4380
gtggacttga taactaaagc gagtaaagat catctcaatg aaattatggc agttgttgga    4440
gatgatgaca ttaatagctt tataacagaa ttttttgctag ttgatccgag gctatttaca    4500
ttgtacttag gtcaatacac gtcacttcaa tgggcatatg aaattcatta tcaccgaccc    4560
gtaggcaaat accagatggc agaagtgtta cacactttac tgtcaagagc aagtaaaggt    4620
atatttaata tattgactaa tgcctttagt catcctagag tttacaaaag attttgggaa    4680
tgtggattac tggagcctat ttatggacca tacataggga gccaaaattt atatagtaca    4740
gtaattgatt acctttacaa tgcttatata acttatttag atgcttatct atctgatcat    4800
atcgaagatg cagacatagt aatatgtgag acagaagaaa cttgtctagc taataggatt    4860
gataactatc aaggtaggca tctcgccgta cttattgatc tttattgtga ttctactagg    4920
tgtcctaata taaaagggtc agacacaatc atgcgaaact caattctcaa atctttttatt    4980 gataatgaga gaaggacaag tccattaggt ctaacatgga atcttgatcc attactcata    5040
gatcatttca gttgttcaat tacttatctg aggagaggta ttattaaaca gattaggcta    5100
aggtttgatc caaacatatc tattgagttg gttaaattgg caaaacctga agtgattcat    5160
caaggaccaa aaataccgtc ttcttgggcc cttatagata ttaatcctga ggtcaatgat    5220
cttaatacag ttttcggaga attaaatagt aaatggaaag atattcctat tggacaaatt    5280
agaattcaaa attttgagat ccatgcttac cgaagaattg gagttaattc aactgcatgt    5340
tataaagcat tggaaatgct atctgtacta actcggttta tgtctaaccc agcaggagct    5400
ttgtttttag gagagggtgc agggtcaatg ttagttacct atcgtgcgtt tatcccgttc    5460
aagagaattt attataatag tggagtttct atacaaaata ttcaaagcca aagggaacta    5520
agtctatacc catctgaagt agccttggtc gataataaaa atcgtttgac cagtgatcct    5580
gatatcaaag tcttatttaa tggcaagcca gaatccacgt gggttgggaa tatagactgc    5640
tttgcttata ttctgagtca tattgaaact tctagtttaa cattaatcca cagtgatatt    5700
gaatctagct tgagtaaaac aaagaataag attcttgagg agctttgcca tattctatca    5760
atggcactga ttctaggaaa gattggatct gtattagtta ttaagctatt accacgggtt    5820
ggtgactaca catattcatt ttgcaagtat gcgtcagaat tctaccaaca gaatttcttc    5880 atttttaccta gatttagtaa catgtcatca tctgaaattt actacgttgg agttcattta    5940
aataccaata gactggttga tccagatagg attgtgcaat atataatcag gaatctccaa    6000
tctactccag tcactttctt atcttacatt ttggaaacta aatatagaaa taatatggtt    6060
acaaattatg ggctctgttt gtctgatgga cataaaagcg attacttgtc atcaatcacc    6120
aagatagaaa atgttctttt atcatgtgga ttggaattga atggacctaa gattattcag    6180
caattatctg gacatgacta cgccaatgga gagattagct tagaatcaag tataatggta    6240
ctggtcagag aatatctaaa tgcaactatc caaggtcgag aaacactagg tcttttttca    6300
ccttaccctg tgttacatga gagtcagtta agagaaatta acaggtgcat tgcattgaag    6360
tatgttgtat atttactttt ttactcaacc tctgtaggat ctagtagaca gatcatgagc    6420
```

```
aatctcagaa aaggagtatt aatgtatgac ttaagagatg agttttcat ggaaaggtta    6480 tcaacaaatt tcaagaaaaa aataatgtca caagaggtta aaactacatg gatctttaat    6540
attgatgtac caacaagaaa agctctgtat aaattagttg gttattcact tatcattaat    6600
cacgtataa                                                             6609
```

<210> SEQ ID NO 30
<211> LENGTH: 2202
<212> TYPE: PRT
<213> ORGANISM: Feline paramyxovirus type 2
<220> FEATURE:
<221> NAME/KEY: MISC_FEATURE
<223> OTHER INFORMATION: FPaV-2 "TV25 strain" L antigen translated amino acid sequence

<400> SEQUENCE: 30

```
Met Glu Gln Ser Asp Tyr Gln Asp Ile Leu Tyr Pro Glu Val His Leu
1               5                   10                  15

Asn Ser Pro Ile Val Ile Ser Lys Leu Val Gly Ile Leu Glu Tyr Ser
            20                  25                  30

Lys Val Val His Asn Gln Gln Leu Ser Asp His Thr Ile Val Lys Asn
        35                  40                  45

Ile Gln Phe Arg Leu Arg Asn Gly Phe Asn Ser Pro Arg Val Gln Thr
    50                  55                  60

Leu Leu Val Met Gly Glu Ile Ile Asn Lys Ile Lys Asn Lys Tyr Pro
65                  70                  75                  80

Asn Tyr Leu His Ile Pro Tyr Pro Glu Cys Asn Gln Lys Leu Phe Arg
                85                  90                  95

Met Ala Asp Pro Glu Leu Thr Ser Lys Leu Glu Ala Leu Leu Asp Lys
            100                 105                 110

Gly Asp Thr Leu Tyr Leu Lys Ile Lys Thr Glu Ile Ile Ala Cys Phe
        115                 120                 125

Asp Lys Leu Lys Thr Lys Met Ser Ile Thr Asn Asp Leu Ile Ser Asp
    130                 135                 140

Asn Arg Gln Leu Ile Ser Asp Leu Pro Leu Ile Val Lys Gly Ser Gln
145                 150                 155                 160

Trp Phe Phe Pro Phe Leu Leu Trp Phe Ser Val Lys Thr Glu Thr Arg
                165                 170                 175

Asn Cys Ile Arg Gln Asn Gln Lys Thr Arg Val Arg Ser Gln Tyr Arg
            180                 185                 190

Pro His Leu Ser Glu Thr Lys Arg Ile Thr Leu Val Val Thr Pro Asp
        195                 200                 205

Leu Ile Thr Ile Phe Asp His Val Asn Lys Cys Ile Tyr His Leu Thr
    210                 215                 220

Phe Glu Met Leu Leu Met Tyr Cys Asp Val Val Glu Gly Arg Leu Met
225                 230                 235                 240

Thr Glu Ala Ser Met Ser Leu Asp His Arg Phe Ile Asn Leu Leu Ser
                245                 250                 255

Arg Val Gln Tyr Met Trp Asp Leu Leu Asp Gly Met Phe Glu Ser Leu
            260                 265                 270

Gly Asn Gln Leu Tyr Ser Ile Ile Ala Leu Leu Glu Pro Leu Ser Leu
        275                 280                 285

Ala Tyr Leu Gln Leu Met Asp Ala Asp Pro Gln Ile Arg Gly Thr Phe
    290                 295                 300

Leu His His Cys Leu Ser Glu Leu Glu Glu Leu Leu Phe Ser Lys Ser
305                 310                 315                 320
```

```
Pro Phe Asp Pro Val Ile Tyr Glu Asn Leu Ile Ser Gly Leu Asp Tyr
                325                 330                 335

Ile Tyr Leu Thr Asp Asp Ile His Leu Thr Ala Glu Ile Phe Ser Phe
        340                 345                 350

Phe Arg Ser Phe Gly His Pro Tyr Leu Glu Ala Gln Asn Ala Ala Ser
        355                 360                 365

Asn Val Arg Lys Tyr Met Asn Gln Pro Lys Val Ile Ser Tyr Gln Thr
    370                 375                 380

Leu Met Gln Gly His Ala Ile Phe Cys Gly Ile Ile Asn Gly Phe
385                 390                 395                 400

Arg Asp Arg His Gly Gly Thr Trp Pro Pro Val Glu Leu Pro His His
                405                 410                 415

Ala Ser Ala Val Ile Arg Asn Ala Gln Leu Ser Gly Glu Gly Leu Thr
            420                 425                 430

Pro Glu Gln Cys Ala Gln Tyr Trp Arg Ser Phe Cys Gly Phe Lys Phe
        435                 440                 445

Lys Cys Phe Met Pro Leu Ser Leu Asp Ser Asp Leu Thr Met Tyr Leu
    450                 455                 460

Arg Asp Lys Ala Leu Ser Pro Ile Lys Asn Glu Trp Asp Ser Val Tyr
465                 470                 475                 480

Ala Lys Glu Tyr Leu Arg Tyr Asn Pro Gly Leu Pro Thr Ser Ser Arg
                485                 490                 495

Arg Leu Val Asn Val Phe Leu Glu Asp Asp Lys Phe Asp Pro Tyr Glu
            500                 505                 510

Met Ile Met Tyr Val Ile Asn Gly Asp Tyr Leu Arg Asp Asn Glu Phe
        515                 520                 525

Asn Leu Ser Tyr Ser Leu Lys Glu Lys Glu Ile Lys Glu Val Gly Arg
    530                 535                 540

Leu Phe Ala Lys Met Thr Tyr Lys Met Arg Ala Cys Gln Val Ile Ala
545                 550                 555                 560

Glu Asn Leu Ile Ala Asn Gly Val Gly Lys Phe Phe Lys Asp Asn Gly
                565                 570                 575

Met Ala Lys Asp Glu His Lys Leu Thr Lys Thr Leu His Lys Leu Ala
            580                 585                 590

Ile Ser Gly Val Pro Lys Asp Asn Ser Gln Leu Tyr Leu Ser Glu Cys
        595                 600                 605

Trp Glu Gln Val Val Glu Gln Cys Val Thr Ser Thr Gln Thr Lys Asn
    610                 615                 620

Gln Ile Ile Ser Ser His Ser Gly Lys Ser Val Ala Ser Lys Phe Ser
625                 630                 635                 640

Arg Ser Asn Pro Asn Asp Arg Gly Ile Leu Asn Ser Gly Arg His Leu
                645                 650                 655

Asn Lys His Pro Lys His Pro Ser Asn Thr Glu Tyr Tyr Glu Thr Val
            660                 665                 670

Ser Ser Phe Ile Thr Thr Asp Leu Lys Lys Tyr Cys Leu Asn Trp Arg
        675                 680                 685

Tyr Glu Ser Ser Ser Val Phe Ala Glu Arg Leu Asn Glu Ile Tyr Gly
    690                 695                 700

Leu Pro Gly Phe Phe His Trp Leu His Arg Ile Leu Glu Lys Ser Val
705                 710                 715                 720

Leu Tyr Val Ser Asp Pro Ser Pro Pro Asp Phe Asp Gln His Val
                725                 730                 735
```

-continued

Asp Ile Asp Ser Val Pro Asn Asp His Ile Phe Ile Lys Tyr Pro Met
            740                 745                 750

Gly Gly Ile Lys Gly Phe Cys Gln Lys Leu Trp Thr Ile Ser Thr Ile
            755                 760                 765

Pro Phe Leu Tyr Leu Ala Ala Phe Asp Thr Gly Val Arg Ile Ser Ser
            770                 775                 780

Leu Val Gln Gly Asp Asn Gln Ala Ile Ala Val Thr Lys Arg Val Pro
785                 790                 795                 800

Ser Ser Trp Ser Tyr Ser Arg Lys Lys Glu Glu Ser Thr Lys Val Thr
            805                 810                 815

Thr Gln Tyr Phe Leu Asn Leu Arg Gln Arg Leu His Asp Ile Gly His
            820                 825                 830

Glu Leu Lys Ala Asn Glu Thr Ile Ile Ser Ser His Phe Phe Val Tyr
            835                 840                 845

Ser Lys Gly Ile Tyr Tyr Asp Gly Ile Leu Leu Ser Gln Ser Leu Lys
            850                 855                 860

Ser Ile Ala Arg Cys Val Phe Trp Ser Glu Thr Ile Val Asp Glu Thr
865                 870                 875                 880

Arg Ser Ala Cys Ser Asn Ile Ser Thr Thr Leu Ala Lys Ala Ile Glu
            885                 890                 895

Arg Gly Tyr Asp Lys Phe Val Ala Tyr Ala Ile Asn Ile Tyr Lys Thr
            900                 905                 910

Ile His Gln Val Leu Ile Ala Leu Ser Phe Thr Ile Asn Pro Thr Met
            915                 920                 925

Thr Pro Asp Ile Thr Glu Pro Phe Tyr Lys Ser Leu Asp Leu Leu Lys
            930                 935                 940

Asn Leu Ile Leu Ile Pro Ala Pro Leu Gly Gly Met Asn Tyr Met Asn
945                 950                 955                 960

Met Ser Arg Leu Phe Val Arg Asn Ile Gly Asp Pro Ile Thr Ala Ser
            965                 970                 975

Phe Ala Asp Ile Lys Arg Met Ile Glu Cys Gly Leu Leu Gly His Asn
            980                 985                 990

Val Leu Ser Gln Ile Met Tyr Gln Lys Cys Gly Thr Ser Lys Tyr Leu
            995                 1000                1005

Asp Trp Ala Ser Asp Pro Tyr Ser Ile Asn Leu Pro Tyr Ser Gln
            1010                1015                1020

Ser Met Thr Lys Val Leu Lys Asn Ile Thr Ala Arg Tyr Val Leu
            1025                1030                1035

Met His Ser Pro Asn Pro Met Leu Lys Asp Leu Phe His Glu Lys
            1040                1045                1050

Ser Gln Glu Glu Asp Glu Ile Leu Ala Glu Phe Leu Leu Asp Arg
            1055                1060                1065

Gln Leu Ile Ile Pro Arg Ala Ala His Glu Ile Leu Ser Asn Ser
            1070                1075                1080

Val Thr Gly Ala Arg Glu Ser Ile Ala Gly Met Leu Asp Thr Thr
            1085                1090                1095

Lys Gly Leu Ile Arg Ala Ser Met Ser Arg Gly Gly Leu Thr Ser
            1100                1105                1110

Ser Leu Val Leu Lys Leu Ser Thr Tyr Asp Tyr Gln Gln Phe Arg
            1115                1120                1125

Thr Cys Leu Glu Trp Leu Tyr Ala Pro Thr Thr Gly Ile Ala Val
            1130                1135                1140

Ser Ala Asp Ser Cys Ser Val Phe Leu Ala Arg Ala Ile Arg Lys

-continued

```
            1145                1150                1155

Arg Met Trp Val His Leu Thr Lys Gly Arg Glu Ile Tyr Gly Leu
    1160                1165                1170

Glu Val Pro Asp Ile Leu Glu Cys Met Gln Ser Asn Val Ile Val
    1175                1180                1185

Asp His Glu Asp Cys Tyr Ser Cys Ile Gln Gly Ser Arg Tyr Tyr
    1190                1195                1200

Thr Trp Phe Phe Val Pro Ser Asn Cys Gln Leu Asp Gln Ile Asn
    1205                1210                1215

Lys Ser Thr Asn Ser Leu Arg Val Pro Tyr Ile Gly Ser Thr Thr
    1220                1225                1230

Glu Glu Arg Ser Asp Met Lys Leu Ser Tyr Val Arg Ser Pro Ser
    1235                1240                1245

Arg Pro Leu Lys Ala Ala Val Arg Ile Ala Ala Val Tyr Thr Trp
    1250                1255                1260

Ala Tyr Gly Asp Asp Leu Ser Trp Arg Glu Ala Trp Tyr Leu
    1265                1270                1275

Ala Arg Thr Arg Ala Asn Val Thr Phe Asp Glu Leu Lys Leu Val
    1280                1285                1290

Thr Pro Ile Ala Thr Ser Thr Asn Leu Ala His Arg Leu Arg Asp
    1295                1300                1305

Arg Ser Thr Gln Val Lys Tyr Ser Gly Thr Ser Leu Val Arg Val
    1310                1315                1320

Ala Arg Tyr Thr Thr Ile Ser Asn Asp Asn Met Ser Phe Val Ile
    1325                1330                1335

Asn Asp Lys Lys Val Asp Thr Asn Phe Val Tyr Gln Gln Gly Met
    1340                1345                1350

Leu Leu Gly Leu Ser Ile Leu Glu Tyr Ile Phe Arg Tyr Cys Lys
    1355                1360                1365

Ser Thr Gly Gln Ser Asn Thr Val Val His Leu His Ala Asp Val
    1370                1375                1380

Asn Cys Cys Ile Ile Gln Met Thr Asp Gln Pro Tyr Thr Pro Ser
    1385                1390                1395

Leu Thr Lys Lys Leu Pro Glu Ile Lys Pro Ile Asn Asn Lys Leu
    1400                1405                1410

Ile Tyr Asp Pro Ala Pro Ile Ile Asp Thr Asp Ala Ala Arg Leu
    1415                1420                1425

Tyr Ser Gln Lys Tyr Leu Ser His Leu Ile Asp Phe Pro Asn Trp
    1430                1435                1440

Ser Met Asn Gln Leu Asn Val Val Leu Ala Lys Val Val Ala Ile
    1445                1450                1455

Ser Ile Val Asp Leu Ile Thr Lys Ala Ser Lys Asp His Leu Asn
    1460                1465                1470

Glu Ile Met Ala Val Val Gly Asp Asp Ile Asn Ser Phe Ile
    1475                1480                1485

Thr Glu Phe Leu Leu Val Asp Pro Arg Leu Phe Thr Leu Tyr Leu
    1490                1495                1500

Gly Gln Tyr Thr Ser Leu Gln Trp Ala Tyr Glu Ile His Tyr His
    1505                1510                1515

Arg Pro Val Gly Lys Tyr Gln Met Ala Glu Val Leu His Thr Leu
    1520                1525                1530

Leu Ser Arg Ala Ser Lys Gly Ile Phe Asn Ile Leu Thr Asn Ala
    1535                1540                1545
```

-continued

Phe Ser His Pro Arg Val Tyr Lys Arg Phe Trp Glu Cys Gly Leu
    1550            1555            1560

Leu Glu Pro Ile Tyr Gly Pro Tyr Ile Gly Ser Gln Asn Leu Tyr
    1565            1570            1575

Ser Thr Val Ile Asp Tyr Leu Tyr Asn Ala Tyr Ile Thr Tyr Leu
    1580            1585            1590

Asp Ala Tyr Leu Ser Asp His Ile Glu Asp Ala Asp Ile Val Ile
    1595            1600            1605

Cys Glu Thr Glu Thr Cys Leu Ala Asn Arg Ile Asp Asn Tyr
    1610            1615            1620

Gln Gly Arg His Leu Ala Val Leu Ile Asp Leu Tyr Cys Asp Ser
    1625            1630            1635

Thr Arg Cys Pro Asn Ile Lys Gly Ser Asp Thr Ile Met Arg Asn
    1640            1645            1650

Ser Ile Leu Lys Ser Phe Ile Asp Asn Glu Arg Arg Thr Ser Pro
    1655            1660            1665

Leu Gly Leu Thr Trp Asn Leu Asp Pro Leu Leu Ile Asp His Phe
    1670            1675            1680

Ser Cys Ser Ile Thr Tyr Leu Arg Arg Gly Ile Ile Lys Gln Ile
    1685            1690            1695

Arg Leu Arg Phe Asp Pro Asn Ile Ser Ile Glu Leu Val Lys Leu
    1700            1705            1710

Ala Lys Pro Glu Val Ile His Gln Gly Pro Lys Ile Pro Ser Ser
    1715            1720            1725

Trp Ala Leu Ile Asp Ile Asn Pro Glu Val Asn Asp Leu Asn Thr
    1730            1735            1740

Val Phe Gly Glu Leu Asn Ser Lys Trp Lys Asp Ile Pro Ile Gly
    1745            1750            1755

Gln Ile Arg Ile Gln Asn Phe Glu Ile His Ala Tyr Arg Arg Ile
    1760            1765            1770

Gly Val Asn Ser Thr Ala Cys Tyr Lys Ala Leu Glu Met Leu Ser
    1775            1780            1785

Val Leu Thr Arg Phe Met Ser Asn Pro Ala Gly Ala Leu Phe Leu
    1790            1795            1800

Gly Glu Gly Ala Gly Ser Met Leu Val Thr Tyr Arg Ala Phe Ile
    1805            1810            1815

Pro Phe Lys Arg Ile Tyr Tyr Asn Ser Gly Val Ser Ile Gln Asn
    1820            1825            1830

Ile Gln Ser Gln Arg Glu Leu Ser Leu Tyr Pro Ser Glu Val Ala
    1835            1840            1845

Leu Val Asp Asn Lys Asn Arg Leu Thr Ser Asp Pro Asp Ile Lys
    1850            1855            1860

Val Leu Phe Asn Gly Lys Pro Glu Ser Thr Trp Val Gly Asn Ile
    1865            1870            1875

Asp Cys Phe Ala Tyr Ile Leu Ser His Ile Glu Thr Ser Ser Leu
    1880            1885            1890

Thr Leu Ile His Ser Asp Ile Glu Ser Ser Leu Ser Lys Thr Lys
    1895            1900            1905

Asn Lys Ile Leu Glu Glu Leu Cys His Ile Leu Ser Met Ala Leu
    1910            1915            1920

Ile Leu Gly Lys Ile Gly Ser Val Leu Val Ile Lys Leu Leu Pro
    1925            1930            1935

```
Arg Val Gly Asp Tyr Thr Tyr Ser Phe Cys Lys Tyr Ala Ser Glu
    1940            1945                1950

Phe Tyr Gln Gln Asn Phe Phe Ile Leu Pro Arg Phe Ser Asn Met
1955                1960                1965

Ser Ser Ser Glu Ile Tyr Tyr Val Gly Val His Leu Asn Thr Asn
    1970            1975                1980

Arg Leu Val Asp Pro Asp Arg Ile Val Gln Tyr Ile Ile Arg Asn
    1985            1990                1995

Leu Gln Ser Thr Pro Val Thr Phe Leu Ser Tyr Ile Leu Glu Thr
    2000            2005                2010

Lys Tyr Arg Asn Asn Met Val Thr Asn Tyr Gly Leu Cys Leu Ser
    2015            2020                2025

Asp Gly His Lys Ser Asp Tyr Leu Ser Ser Ile Thr Lys Ile Glu
    2030            2035                2040

Asn Val Leu Leu Ser Cys Gly Leu Glu Leu Asn Gly Pro Lys Ile
    2045            2050                2055

Ile Gln Gln Leu Ser Gly His Asp Tyr Ala Asn Gly Glu Ile Ser
    2060            2065                2070

Leu Glu Ser Ser Ile Met Val Leu Val Arg Glu Tyr Leu Asn Ala
    2075            2080                2085

Thr Ile Gln Gly Arg Glu Thr Leu Gly Leu Phe Ser Pro Tyr Pro
    2090            2095                2100

Val Leu His Glu Ser Gln Leu Arg Glu Ile Asn Arg Cys Ile Ala
    2105            2110                2115

Leu Lys Tyr Val Val Tyr Leu Leu Phe Tyr Ser Thr Ser Val Gly
    2120            2125                2130

Ser Ser Arg Gln Ile Met Ser Asn Leu Arg Lys Gly Val Leu Met
    2135            2140                2145

Tyr Asp Leu Arg Asp Glu Phe Phe Met Glu Arg Leu Ser Thr Asn
    2150            2155                2160

Phe Lys Lys Lys Ile Met Ser Gln Glu Val Lys Thr Thr Trp Ile
    2165            2170                2175

Phe Asn Ile Asp Val Pro Thr Arg Lys Ala Leu Tyr Lys Leu Val
    2180            2185                2190

Gly Tyr Ser Leu Ile Ile Asn His Val
    2195            2200

<210> SEQ ID NO 31
<211> LENGTH: 1788
<212> TYPE: DNA
<213> ORGANISM: Feline Morbillivirus
<220> FEATURE:
<221> NAME/KEY: misc_feature
<223> OTHER INFORMATION: FeMoV "Lapon strain" H antigen "wild-type"
      nucleic acid; given as DNA sequence

<400> SEQUENCE: 31
atggagtcca acaacattaa atattacaaa gactctaatc ggtatcttgg taaaatatta      60
gatgaacaca agacagttaa taatcaattg tacaggttga gtattaaagt aattaccatt    120
attgctatta ttgtaagctt aattgcaaca ataataacta ttattaatgc acaagtgga    180 agaactaccc taaacagtaa tacagacata ctgcttagcc aaagagatga gattcatagt    240
attcatgaaa tgatatttga ccgtatttat cctttgataa ctgctatgag tacagagcta    300
ggacttcata ttcctacttt attagatgaa cttactaaag caattgatca aaaaattaaa    360
ataatgaatc ctcccgttga tactgtaaca tctgatctta actggtgtat caaacctcct    420
```

```
aatgggatta ttatggatcc aaaaggttat tgcgaaagta tggaattatc taaaacttac      480
aaattattgc ttgatcagtt agatgtctca agaaagaaat cgctcattat aaatagaaag      540
aatatcaacc agtgtcaatt agttgatgac tcaaagatca cttttgctac tgttaatata      600
caatctacac caaggttttt aaattttggt catacagtag caatcaacg tataacattt       660 ggtcaaggaa cttatagtag tacttatatt ataactatcc aagaagatgg aataaatgat      720
gttcaatatc gagtgtttga aattggatat atctctgatc agtttggttt tttcccctca      780
ttaatagtat ctagggtatt gcctatacgt atggtattgg gaatggaatc ctgtaccttg      840
acgagtgatc gacaaggtgg gtatttctta tgtatgaata cattaacacg gtctatatat      900
gattatgtca atataagaga tttgaaatca ctatacataa cacttcctca ttatggtaag      960
gttaattata cttacttcaa ttttgggaaa attaggagcc acatgagat tgataaaatt      1020 tggctaacgt ccgaaagagg tcaaattatt tctggttatt ttgcagcatt tgtcacaatt      1080
acgattcgaa attataataa ttatccctac aaatgtttga ataatccatg ttttgacaac      1140
tctgagaatt actgtagggg atggtataag aacataacag gcaccgatga tgttccaata      1200
ctagcatact tactagttga aatgtatgat gaagaaggac ctttaattac acttgtagca      1260
ataccacctt acaattatac agctccatct cataattctc tttactatga tgacaaaatt      1320
aataagttga taatgactac atctcacact gggtatatac agatcaatga ggtgcatgag      1380
gtgattgttg gtgatgattt aaaggctatt ctcctgaaca gattatctga tgaacaccct      1440
aatcttacag cctgtagact taatcaaggc attaaagagc agtacaagtc cgatggaacg      1500
ataatttcaa attctgcact tattgatata caagaacgaa tgtatattac agtcaaagct      1560
attccaccag taggtaacta taactttaca gttgagttgc actctagatc aaacacatct      1620
tatatattgt taccgaaaca gttcaatgcc aagtatgaca aattacatct tgagtgcttt      1680
aattgggaca gtcttggtg gtgtgctttg atacctcaat tttcattaag ttggaatgaa      1740 tcccttctg ttgatactgc tattttttaat ttaataaatt gtaaatga                  1788
```

<210> SEQ ID NO 32
<211> LENGTH: 1784
<212> TYPE: DNA
<213> ORGANISM: Feline Morbillivirus
<220> FEATURE:
<221> NAME/KEY: misc_feature
<223> OTHER INFORMATION: FeMoV "Lapon strain" H antigen nucleic acid that has been codon-optimized for expression primarily in felines; given as DNA sequence

<400> SEQUENCE: 32

```
atggaaagca ataacatcaa gtactataaa gacagcaaca ggtatctggg aaaaattctg       60
gacgaacata agacagtcaa taatcagctg tacaggctgt ctatcaaggt gatcaccatc      120
atcgccatca tcgtgagcct gatcgcaacc atcatcacta tcatcaacgc cacttccggc      180
agaaccactc tgaactctaa taccgacatc ctgctgagcc agagggatga gatccactcc      240
atccatgaaa tgatcttcga cagaatctat ccactgatca ccgccatgtc tactgagctg      300
gggctgcaca tccctactct gctggacgaa ctgaccaaag caatcgatca gaagatcaaa      360
atcatgaacc cacctgtgga caccgtgact agcgatctga actggtgcat caagccccca      420
aatggaatca tcatggatcc aaaaggttac tgtgagtcta tggaactgag caagaccctat     480 aaactgctgc tggaccagct ggatgtgtcc aggaagaaat ctctgatcat caacagaaag      540
aacatcaatc agtgccagct ggtggacgat agcaaaatca ccttcgcaac tgtgaatatc      600
```

-continued

```
cagtccactc ctaggttcct gaactttgga catactgtgt ccaatcagag aatcacctttg       660 ggacagggta cctacagctc cacttatatc atcaccatcc aggaagacgg tatcaacgat       720
gtgcagtaca gggtgttcga atcggctat atctctgacc agtttgggtt ctttcctagc        780
ctgatcgtgt ccagggtgct gcccatcaga atggtgctgg gcatggagtc ttgcaccctg       840
actagcgata gacagggcgg gtacttcctg tgtatgaaca ccctgactag gtccatctac       900
gactatgtga atatcagaga tctgaagtct ctgtacatca ctctgcccca ctatggaaaa       960
gtgaactaca cctatttcaa ttttggaaag atcaggagcc acatgagat cgacaaaatc       1020 tggctgaccc tgaaagagg ccagatcatc agcgggtact cgccgcatt tgtgaccatc        1080 actatcagga actataacaa ttaccccctat aagtgcctga caatccatg ttttgacaac       1140 tccgagaatt actgcagagg atggtataag aatatcaccg gtactgacga tgtgcccatc       1200
ctggcctacc tgctggtgga aatgtatgat gaggaaggac cactgatcac tctggtggcc      1260
atccctccct acaactatac cgcacctagc cacaattccc tgtactatga cgataagatc      1320
aacaaactga tcatgaccac tagccacact ggctacatcc agatcaatga ggtgcatgaa      1380
gtgatcgtgg gggacgatct gaaggccatc ctgctgaaca ggctgagcga tgagcatccc      1440
aacctgactg catgtagact gaatcagggc atcaaggaac agtataaatc cgacgggacc      1500
atcatctcta atagcgccct gatcgatatc caggagagga tgtacatcac tgtgaaagca      1560
atcccacctg tgggcaacta taatttcact gtggaactgc actccagatc taacacctcc      1620
tacatcctgc tgcctaagca gttcaatgcc aagtatgaca aactgcatct ggagtgcttt      1680
aactgggata atcctggtg gtgtgcactg atccccccagt tttctctgtc ctggaacgaa      1740
agcctgtccg tggataccgc aatcttcaat ctgataaact gtaa                        1784
```

<210> SEQ ID NO 33
<211> LENGTH: 595
<212> TYPE: PRT
<213> ORGANISM: Feline Morbillivirus
<220> FEATURE:
<221> NAME/KEY: MISC_FEATURE
<223> OTHER INFORMATION: FeMoV "Lapon strain" H antigen translated amino
      acid sequence

<400> SEQUENCE: 33

```
Met Glu Ser Asn Asn Ile Lys Tyr Tyr Lys Asp Ser Asn Arg Tyr Leu
1               5                   10                  15

Gly Lys Ile Leu Asp Glu His Lys Thr Val Asn Asn Gln Leu Tyr Arg
            20                  25                  30

Leu Ser Ile Lys Val Ile Thr Ile Ile Ala Ile Ile Val Ser Leu Ile
        35                  40                  45

Ala Thr Ile Ile Thr Ile Ile Asn Ala Thr Ser Gly Arg Thr Thr Leu
    50                  55                  60

Asn Ser Asn Thr Asp Ile Leu Leu Ser Gln Arg Asp Glu Ile His Ser
65                  70                  75                  80

Ile His Glu Met Ile Phe Asp Arg Ile Tyr Pro Leu Ile Thr Ala Met
                85                  90                  95

Ser Thr Glu Leu Gly Leu His Ile Pro Thr Leu Leu Asp Glu Leu Thr
            100                 105                 110

Lys Ala Ile Asp Gln Lys Ile Lys Ile Met Asn Pro Val Asp Thr
        115                 120                 125

Val Thr Ser Asp Leu Asn Trp Cys Ile Lys Pro Pro Asn Gly Ile Ile
    130                 135                 140
```

```
Met Asp Pro Lys Gly Tyr Cys Glu Ser Met Glu Leu Ser Lys Thr Tyr
145                 150                 155                 160

Lys Leu Leu Leu Asp Gln Leu Asp Val Ser Arg Lys Lys Ser Leu Ile
            165                 170                 175

Ile Asn Arg Lys Asn Ile Asn Gln Cys Gln Leu Val Asp Asp Ser Lys
        180                 185                 190

Ile Thr Phe Ala Thr Val Asn Ile Gln Ser Thr Pro Arg Phe Leu Asn
        195                 200                 205

Phe Gly His Thr Val Ser Asn Gln Arg Ile Thr Phe Gly Gln Gly Thr
    210                 215                 220

Tyr Ser Ser Thr Tyr Ile Ile Thr Ile Gln Glu Asp Gly Ile Asn Asp
225                 230                 235                 240

Val Gln Tyr Arg Val Phe Glu Ile Gly Tyr Ile Ser Asp Gln Phe Gly
            245                 250                 255

Phe Phe Pro Ser Leu Ile Val Ser Arg Val Leu Pro Ile Arg Met Val
            260                 265                 270

Leu Gly Met Glu Ser Cys Thr Leu Thr Ser Asp Arg Gln Gly Gly Tyr
        275                 280                 285

Phe Leu Cys Met Asn Thr Leu Thr Arg Ser Ile Tyr Asp Tyr Val Asn
    290                 295                 300

Ile Arg Asp Leu Lys Ser Leu Tyr Ile Thr Leu Pro His Tyr Gly Lys
305                 310                 315                 320

Val Asn Tyr Thr Tyr Phe Asn Phe Gly Lys Ile Arg Ser Pro His Glu
            325                 330                 335

Ile Asp Lys Ile Trp Leu Thr Ser Glu Arg Gly Gln Ile Ile Ser Gly
            340                 345                 350

Tyr Phe Ala Ala Phe Val Thr Ile Thr Ile Arg Asn Tyr Asn Asn Tyr
        355                 360                 365

Pro Tyr Lys Cys Leu Asn Asn Pro Cys Phe Asp Asn Ser Glu Asn Tyr
    370                 375                 380

Cys Arg Gly Trp Tyr Lys Asn Ile Thr Gly Thr Asp Asp Val Pro Ile
385                 390                 395                 400

Leu Ala Tyr Leu Leu Val Glu Met Tyr Asp Glu Glu Gly Pro Leu Ile
            405                 410                 415

Thr Leu Val Ala Ile Pro Pro Tyr Asn Tyr Thr Ala Pro Ser His Asn
            420                 425                 430

Ser Leu Tyr Tyr Asp Asp Lys Ile Asn Lys Leu Ile Met Thr Thr Ser
        435                 440                 445

His Thr Gly Tyr Ile Gln Ile Asn Glu Val His Glu Val Ile Val Gly
    450                 455                 460

Asp Asp Leu Lys Ala Ile Leu Leu Asn Arg Leu Ser Asp Glu His Pro
465                 470                 475                 480

Asn Leu Thr Ala Cys Arg Leu Asn Gln Gly Ile Lys Glu Gln Tyr Lys
            485                 490                 495

Ser Asp Gly Thr Ile Ile Ser Asn Ser Ala Leu Ile Asp Ile Gln Glu
            500                 505                 510

Arg Met Tyr Ile Thr Val Lys Ala Ile Pro Pro Val Gly Asn Tyr Asn
        515                 520                 525

Phe Thr Val Glu Leu His Ser Arg Ser Asn Thr Ser Tyr Ile Leu Leu
    530                 535                 540

Pro Lys Gln Phe Asn Ala Lys Tyr Asp Lys Leu His Leu Glu Cys Phe
545                 550                 555                 560
```

```
Asn Trp Asp Lys Ser Trp Trp Cys Ala Leu Ile Pro Gln Phe Ser Leu
            565                 570                 575

Ser Trp Asn Glu Ser Leu Ser Val Asp Thr Ala Ile Phe Asn Leu Ile
        580                 585                 590

Asn Cys Lys
        595

<210> SEQ ID NO 34
<211> LENGTH: 1014
<212> TYPE: DNA
<213> ORGANISM: Feline Morbillivirus
<220> FEATURE:
<221> NAME/KEY: misc_feature
<223> OTHER INFORMATION: FeMoV "Lapon strain" M antigen "wild-type"
      nucleic acid; given as DNA sequence

<400> SEQUENCE: 34
atgactgaga tattcaatct tgatgaaagc tcatggtcag tcaaaggaac acttgatcca      60
ctaacccctg atacctatcc tgatgggcga cttgtaccta agtccgggt aatcgatcca     120 ggtttaggag atcgcaagag tggagggtat atgtatctac ttcttcatgg tgtcatagaa     180
gatagtgaaa ccatggttag cccgaaagga agagcatttg gggcgttccc attaggagta     240
ggtcagtcaa ctgaaaaccc agaagatttg tttaaagaag tattaaccct caacattgta     300
actcgtagga ctgctggctt aatgaaaaaa ttagtttatt ataataccac gcctctacac     360
ttattgactc cctggaagaa agtgttggcg tatgggagca ttttcaatgc taatcaggtc     420
tgcagtgata caagttctat cccgatagat attccacaaa aatttagacc tgtatacttg     480
actattacaa aattatctga cgatggctat tatcagatac gaagatgat ccaagatttc      540 aaatcatcaa attctgttgc atttaatatc cttgtgcatt tatcaatggg cacaacttta     600
attgaccaat ccaaagaccc tcgattaaga agtgctccag aaactatgat cacattcatg     660
attcatattg gaatttcaa acggaagagt aacaaatctt attctcctga atactgcaag     720
agaaaaataa taagacttgg tttgatattc tcattaggtg caattggcgg cacaagctta     780
catattagat gtacaggtaa gatgagcaaa cggctacagg cttatctagg attcaaaagg     840
actctatgtt acccccctgat gtatgggaat gaagggttga ataaaactct ggggagaaat     900
gaatgtaaaa tagaaaaggt tcaagcggtt ctacagccat cagttccaaa tgaattcaag     960
atatacgatg atgtcattat tgacaatacc aatggtcttt tcaagattaa gtag          1014

<210> SEQ ID NO 35
<211> LENGTH: 1014
<212> TYPE: DNA
<213> ORGANISM: Feline Morbillivirus
<220> FEATURE:
<221> NAME/KEY: misc_feature
<223> OTHER INFORMATION: FeMoV "Lapon strain" M antigen nucleic acid
      that has been codon-optimized for expression primarily in felines;
      given as DNA sequence

<400> SEQUENCE: 35
atgaccgaga tcttcaacct ggacgagagc agctggagcg ttaaaggcac actggacccc      60
ctgacccctg acacttaccc tgacggaagg ctggtgccca agtgagagt gatcgaccca     120 ggcctggggg ataggaaatc cggcgggtac atgtatctgc tgctgcacgg cgtgatcgag     180
gacagcgaaa ccatggtgtc cctaagggga agagccttcg gtgcatttcc cctgggagtg     240
ggacagtcta ccgagaaccc agaagatctg ttcaagaggg tgctgactct gaatatcgtg     300
accaggagaa ctgccggctt aacgaaaaaa ctggtgtact ataataccac tcctctgcat     360
```

```
ctgctgaccc cctggaagaa agtgctggcc tacgggagca tcttcaacgc aaatcaagtg    420
tgttccgaca ctagctccat ccccatcgat atcccacaga agtttaggcc agtgtatctg    480
accatcacta aactgtctga cgatgggtac tatcagatcc ctaagatgat ccaggacttc    540
aaatctagca actctgtggc ctttaatatc ctggtgcacc tgagcatggg aaccactctg    600
atcgaccagt ctaaggaccc aaggctgaga agcgcacctg agactatgat cactttcatg    660
atccatatcg gtaacttcaa gagaaagagc aacaagtcct actctcccga atattgcaag    720
aggaaaatca tcagactggg cctgatcttc tccctgggg ccatcggagg tacctctctg    780
cacatcaggt gcactggaaa gatgtccaaa agactgcagg catacctggg ttttaagagg    840
accctgtgtt acccactgat gtatggcaac gaggggctga ataaaactct gggcagaaac    900
gagtgcaaga tcgaaaaagt gcaggcagtg ctgcagccat ccgtgcctaa tgagttcaag    960
atatacgacg atgtcataat agataatact aatggtctgt tcaagataaa atag         1014
```

<210> SEQ ID NO 36
<211> LENGTH: 337
<212> TYPE: PRT
<213> ORGANISM: Feline Morbillivirus
<220> FEATURE:
<221> NAME/KEY: MISC_FEATURE
<223> OTHER INFORMATION: FeMoV "Lapon strain” M antigen translated amino acid sequence

<400> SEQUENCE: 36

```
Met Thr Glu Ile Phe Asn Leu Asp Glu Ser Ser Trp Ser Val Lys Gly
1               5                   10                  15

Thr Leu Asp Pro Leu Thr Pro Asp Thr Tyr Pro Asp Gly Arg Leu Val
            20                  25                  30

Pro Lys Val Arg Val Ile Asp Pro Gly Leu Gly Asp Arg Lys Ser Gly
        35                  40                  45

Gly Tyr Met Tyr Leu Leu Leu His Gly Val Ile Glu Asp Ser Glu Thr
    50                  55                  60

Met Val Ser Pro Lys Gly Arg Ala Phe Gly Ala Phe Pro Leu Gly Val
65                  70                  75                  80

Gly Gln Ser Thr Glu Asn Pro Glu Asp Leu Phe Lys Glu Val Leu Thr
                85                  90                  95

Leu Asn Ile Val Thr Arg Arg Thr Ala Gly Phe Asn Glu Lys Leu Val
            100                 105                 110

Tyr Tyr Asn Thr Thr Pro Leu His Leu Leu Thr Pro Trp Lys Lys Val
        115                 120                 125

Leu Ala Tyr Gly Ser Ile Phe Asn Ala Asn Gln Val Cys Ser Asp Thr
    130                 135                 140

Ser Ser Ile Pro Ile Asp Ile Pro Gln Lys Phe Arg Pro Val Tyr Leu
145                 150                 155                 160

Thr Ile Thr Lys Leu Ser Asp Asp Gly Tyr Tyr Gln Ile Pro Lys Met
                165                 170                 175

Ile Gln Asp Phe Lys Ser Ser Asn Ser Val Ala Phe Asn Ile Leu Val
            180                 185                 190

His Leu Ser Met Gly Thr Thr Leu Ile Asp Gln Ser Lys Asp Pro Arg
        195                 200                 205

Leu Arg Ser Ala Pro Glu Thr Met Ile Thr Phe Met Ile His Ile Gly
    210                 215                 220

Asn Phe Lys Arg Lys Ser Asn Lys Ser Tyr Ser Pro Glu Tyr Cys Lys
225                 230                 235                 240
```

```
Arg Lys Ile Ile Arg Leu Gly Leu Ile Phe Ser Leu Gly Ala Ile Gly
                245                 250                 255
Gly Thr Ser Leu His Ile Arg Cys Thr Gly Lys Met Ser Lys Arg Leu
            260                 265                 270
Gln Ala Tyr Leu Gly Phe Lys Arg Thr Leu Cys Tyr Pro Leu Met Tyr
        275                 280                 285
Gly Asn Glu Gly Leu Asn Lys Thr Leu Gly Arg Asn Glu Cys Lys Ile
    290                 295                 300
Glu Lys Val Gln Ala Val Leu Gln Pro Ser Val Pro Asn Glu Phe Lys
305                 310                 315                 320
Ile Tyr Asp Asp Val Ile Ile Asp Asn Thr Asn Gly Leu Phe Lys Ile
                325                 330                 335
Lys
```

<210> SEQ ID NO 37
<211> LENGTH: 1632
<212> TYPE: DNA
<213> ORGANISM: Feline Morbillivirus
<220> FEATURE:
<221> NAME/KEY: misc_feature
<223> OTHER INFORMATION: FeMoV "Lapon strain" F antigen "wild-type"
      nucleic acid; given as DNA sequence

<400> SEQUENCE: 37

| | |
|---|---|
| atgggtaaaa ttaaggttat aataattagc tctttactac tatcaactat tacgactgca | 60 |
| caagtaggtt gggacaattt aacttcgatt ggagttataa gtactaagca atatgattat | 120 |
| aaaataacca ctttgaatac taaccagttg atggttataa agatggtccc caatatatca | 180 |
| tcaatcatca attgcaccaa gcctgagttg attaaatatc gagagttggt cttaggggtt | 240 |
| attagaccaa tcaatgaatc gttagaattg atgaattcat acattaacat gaggacaggt | 300 |
| tcagagagat tcatagggc tgtaatagct ggagttgcat tgggtgtggc aactgcagcg | 360 |
| caaataacat caggaattgc attacataac tcaattatga acaaaaagca aatacaagaa | 420 |
| ttgaggaagg ccctcagtac caccaataaa gcaattgatg aaataaggat tgcaggtgag | 480 |
| agaacattaa tagcagtcca aggtgtacaa gattacatta ataatataat tattcctatg | 540 |
| caggacaaac ttcaatgtga tattttatca tcacagcttg ctattgcctt actcaggtat | 600 |
| tatacaaata tattgacagt ttttgggcca agcatacgag atcctgttac tagtacaatc | 660 |
| tcaatacaag cacttagtca ggcgtttaat ggtaatctcc aggcattgct tgatggatta | 720 |
| ggatataccg ggagagactt acgtgatctt ttagagagta gatctattac tggtcagata | 780 |
| attcatgcag atataactga tttgttcctt gtcctcagaa ttaactatcc ttctataact | 840 |
| gaaatgcagg gagtaacgat atatgaactt aattcaatta catatcatat tggacctgag | 900 |
| gaatggtata ctattatgcc taatttttata gctgttcagg ttttttttaac atccaatttc | 960 |
| gatgaaagga agtgctcaat aactaaatca agtatactgt gccaacaaaa ttcaatttac | 1020 |
| ccgatgtcaa cagaaatgca aagatgtatc aagggtgaga taagattctg tccaagatcc | 1080 |
| aaagcaattg gaacattagt taataagttt atcttgacta aaggtaattt aatggctaat | 1140 |
| tgccttggta ttatatgcag gtgttatact tcaggccaaa ttataacaca agaccctagt | 1200 |
| aagttaatta caataatatc acaagaggaa tgcaaagaag ttggagttga tggtatccgt | 1260 |
| attatggtag gacctaggaa attaccagac attaccttta acgctaggtt agaggttggt | 1320 |
| gtgccgatat cattaagtaa attagatgta ggaactgatt tagcaattgc ttcagctaaa | 1380 |

```
cttaataatt ctaaggcact gttggaacaa tcagataaaa ttctggactc aatgtctaaa    1440
ttggattcta ttaattcacg aatcacaggg ttgatcttgg caatcatggt aatctttata    1500
atcatcgtta ctattgtctg gatcatatac aaaagatgca gaaataaaga taataaattc    1560
agtacttcaa ttgaaccgct ttatatacct ccttcttaca actcacctca cagtgtggtt    1620
aagtctattt ga                                                        1632
```

<210> SEQ ID NO 38
<211> LENGTH: 543
<212> TYPE: PRT
<213> ORGANISM: Feline Morbillivirus
<220> FEATURE:
<221> NAME/KEY: MISC_FEATURE
<223> OTHER INFORMATION: FeMoV "Lapon strain" F antigen translated amino acid sequence

<400> SEQUENCE: 38

```
Met Gly Lys Ile Lys Val Ile Ile Ser Ser Leu Leu Leu Ser Thr
1               5                   10                  15

Ile Thr Thr Ala Gln Val Gly Trp Asp Asn Leu Thr Ser Ile Gly Val
            20                  25                  30

Ile Ser Thr Lys Gln Tyr Asp Tyr Lys Ile Thr Thr Leu Asn Thr Asn
        35                  40                  45

Gln Leu Met Val Ile Lys Met Val Pro Asn Ile Ser Ser Ile Ile Asn
    50                  55                  60

Cys Thr Lys Pro Glu Leu Ile Lys Tyr Arg Glu Leu Val Leu Gly Val
65                  70                  75                  80

Ile Arg Pro Ile Asn Glu Ser Leu Glu Leu Met Asn Ser Tyr Ile Asn
                85                  90                  95

Met Arg Thr Gly Ser Glu Arg Phe Ile Gly Ala Val Ile Ala Gly Val
            100                 105                 110

Ala Leu Gly Val Ala Thr Ala Ala Gln Ile Thr Ser Gly Ile Ala Leu
        115                 120                 125

His Asn Ser Ile Met Asn Lys Lys Gln Ile Gln Glu Leu Arg Lys Ala
    130                 135                 140

Leu Ser Thr Thr Asn Lys Ala Ile Asp Glu Ile Arg Ile Ala Gly Glu
145                 150                 155                 160

Arg Thr Leu Ile Ala Val Gln Gly Val Gln Asp Tyr Ile Asn Asn Ile
                165                 170                 175

Ile Ile Pro Met Gln Asp Lys Leu Gln Cys Asp Ile Leu Ser Ser Gln
            180                 185                 190

Leu Ala Ile Ala Leu Leu Arg Tyr Tyr Thr Asn Ile Leu Thr Val Phe
        195                 200                 205

Gly Pro Ser Ile Arg Asp Pro Val Thr Ser Ile Ser Ile Gln Ala
    210                 215                 220

Leu Ser Gln Ala Phe Asn Gly Asn Leu Gln Ala Leu Leu Asp Gly Leu
225                 230                 235                 240

Gly Tyr Thr Gly Arg Asp Leu Arg Asp Leu Leu Glu Ser Arg Ser Ile
                245                 250                 255

Thr Gly Gln Ile Ile His Ala Asp Ile Thr Asp Leu Phe Leu Val Leu
            260                 265                 270

Arg Ile Asn Tyr Pro Ser Ile Thr Glu Met Gln Gly Val Thr Ile Tyr
        275                 280                 285

Glu Leu Asn Ser Ile Thr Tyr His Ile Gly Pro Glu Glu Trp Tyr Thr
    290                 295                 300
```

Ile Met Pro Asn Phe Ile Ala Val Gln Gly Phe Leu Thr Ser Asn Phe
305                 310                 315                 320

Asp Glu Arg Lys Cys Ser Ile Thr Lys Ser Ser Ile Leu Cys Gln Gln
            325                 330                 335

Asn Ser Ile Tyr Pro Met Ser Thr Glu Met Gln Arg Cys Ile Lys Gly
        340                 345                 350

Glu Ile Arg Phe Cys Pro Arg Ser Lys Ala Ile Gly Thr Leu Val Asn
    355                 360                 365

Lys Phe Ile Leu Thr Lys Gly Asn Leu Met Ala Asn Cys Leu Gly Ile
370                 375                 380

Ile Cys Arg Cys Tyr Thr Ser Gly Gln Ile Ile Thr Gln Asp Pro Ser
385                 390                 395                 400

Lys Leu Ile Thr Ile Ile Ser Gln Glu Glu Cys Lys Glu Val Gly Val
            405                 410                 415

Asp Gly Ile Arg Ile Met Val Gly Pro Arg Lys Leu Pro Asp Ile Thr
        420                 425                 430

Phe Asn Ala Arg Leu Glu Val Gly Val Pro Ile Ser Leu Ser Lys Leu
    435                 440                 445

Asp Val Gly Thr Asp Leu Ala Ile Ala Ser Ala Lys Leu Asn Asn Ser
450                 455                 460

Lys Ala Leu Leu Glu Gln Ser Asp Lys Ile Leu Asp Ser Met Ser Lys
465                 470                 475                 480

Leu Asp Ser Ile Asn Ser Arg Ile Thr Gly Leu Ile Leu Ala Ile Met
            485                 490                 495

Val Ile Phe Ile Ile Val Thr Ile Val Trp Ile Ile Tyr Lys Arg
        500                 505                 510

Cys Arg Asn Lys Asp Asn Lys Phe Ser Thr Ser Ile Glu Pro Leu Tyr
    515                 520                 525

Ile Pro Pro Ser Tyr Asn Ser Pro His Ser Val Val Lys Ser Ile
530                 535                 540

<210> SEQ ID NO 39
<211> LENGTH: 1560
<212> TYPE: DNA
<213> ORGANISM: Feline Morbillivirus
<220> FEATURE:
<221> NAME/KEY: misc_feature
<223> OTHER INFORMATION: FeMoV "Lapon strain" N antigen "wild-type"
      nucleic acid; given as DNA sequence

<400> SEQUENCE: 39
atgtcgagtc tactaaggtc acttgctgca tttaaaagac atagggagca accaactgca      60
ccgtcaggct caggtggtac aattaaagga ttgaagaata caattattgt tccagttcca     120
ggggatacag taattactac gaggtctaac ttgttattta gattagttta tataataggc     180
aatccagata caccttttaag tacctcaacg ggagcaataa tatcattgct gaccctattt     240
gttgaatccc ccgtcaatt aattcaaagg attgctgatg atcctgacgc agttttttaaa     300 ttagtagaag tcattcctga agtcggtaat cctggagagc tgacttttgc atctcgagga     360
attaatttgg ataagcaagc tcaacaatat ttcaaactgg ctgaaaaaaa tgatcagggg     420
tattacgtta gcttaggatt tgagaaccca ccaaatgatg acgatataac atctagtcct     480
gagatattta attatattct ggcatctgta cttgcacagg tttggattct tctggcaaaa     540
gctgttactg ccccagatac cgctgctgag gctgaaaaacc gtagatggat taagttgatg     600
cagcaacgta gagtggatgg tgaactaaga ttgagcaaag gatggctgga tctggtgagg     660

```
aacaagattg catcagatat acaataaga cgattcatgg tagcattagt ccttgatatc    720
aaacgttccc ccggaacaag accaagaata gctgagatga tttgtgatat tgataattat    780
attgtagaag cagggcttgc aagcttttg ttgactatca aatttggcat agaaacacgt    840
tacccagcat tggcattaca tgaatttct ggagaactag ctaccattga ggggcttatg    900
aaattgtacc aatctatggg ggaaatggca ccttacatgg taattctgga aaattcaatc    960
caaaccaggt tcagtgcagg gtcttatcct ctgttatgga gttatgctat gggtgttggc   1020
gtagagcttg aaagatcaat gggtggactt aattttacta ggagtttctt tgatcctaca   1080
tatttcagac ttggtcagga gatggtgcga agatcttcag ggatggttaa tagttcattt   1140
gcaagagaac ttgggttgtc tgaacatgag acacaacttg tcagccaaat tgtcaattct   1200
ggaggtgaat ctggtatacc taagtttgat ggattcagag caaatcctac aactttctta   1260
ggagccaagg acaacataaa tgatggaggt gaggaccagt caaattcagt atcaggattg   1320
cctggaccaa tattgccaag tcatgacttg aatctgtcag gtgattcata tgggaatgat   1380
agtggtatga aaaatgtcaa cgacagacta atgaaggata taagtccaga ccatgatgtt   1440
tctagctctg ccatggaaga attaaggaga ttggttgagt ctactaacag aattgacact   1500
aaaaagccag aggctccagg tgttactaac cattacaatg atactgacct tctgaaataa   1560
```

<210> SEQ ID NO 40
<211> LENGTH: 519
<212> TYPE: PRT
<213> ORGANISM: Feline Morbillivirus
<220> FEATURE:
<221> NAME/KEY: MISC_FEATURE
<223> OTHER INFORMATION: FeMoV "Lapon strain" N antigen translated amino
      acid sequence

<400> SEQUENCE: 40

```
Met Ser Ser Leu Leu Arg Ser Leu Ala Ala Phe Lys Arg His Arg Glu
1               5                   10                  15

Gln Pro Thr Ala Pro Ser Gly Ser Gly Gly Thr Ile Lys Gly Leu Lys
            20                  25                  30

Asn Thr Ile Ile Val Pro Val Pro Gly Asp Thr Val Ile Thr Thr Arg
        35                  40                  45

Ser Asn Leu Leu Phe Arg Leu Val Tyr Ile Ile Gly Asn Pro Asp Thr
    50                  55                  60

Pro Leu Ser Thr Ser Thr Gly Ala Ile Ile Ser Leu Leu Thr Leu Phe
65                  70                  75                  80

Val Glu Ser Pro Gly Gln Leu Ile Gln Arg Ile Ala Asp Asp Pro Asp
                85                  90                  95

Ala Val Phe Lys Leu Val Glu Val Ile Pro Glu Val Gly Asn Pro Gly
            100                 105                 110

Glu Leu Thr Phe Ala Ser Arg Gly Ile Asn Leu Asp Lys Gln Ala Gln
        115                 120                 125

Gln Tyr Phe Lys Leu Ala Glu Lys Asn Asp Gln Gly Tyr Tyr Val Ser
    130                 135                 140

Leu Gly Phe Glu Asn Pro Pro Asn Asp Asp Ile Thr Ser Ser Pro
145                 150                 155                 160

Glu Ile Phe Asn Tyr Ile Leu Ala Ser Val Leu Ala Gln Val Trp Ile
                165                 170                 175

Leu Leu Ala Lys Ala Val Thr Ala Pro Asp Thr Ala Ala Glu Ala Glu
            180                 185                 190

Asn Arg Arg Trp Ile Lys Leu Met Gln Gln Arg Arg Val Asp Gly Glu
```

```
            195                 200                 205
Leu Arg Leu Ser Lys Gly Trp Leu Asp Leu Val Arg Asn Lys Ile Ala
    210                 215                 220

Ser Asp Ile Thr Ile Arg Arg Phe Met Val Ala Leu Val Leu Asp Ile
225                 230                 235                 240

Lys Arg Ser Pro Gly Thr Arg Pro Arg Ile Ala Glu Met Ile Cys Asp
                245                 250                 255

Ile Asp Asn Tyr Ile Val Glu Ala Gly Leu Ala Ser Phe Leu Leu Thr
                260                 265                 270

Ile Lys Phe Gly Ile Glu Thr Arg Tyr Pro Ala Leu Ala Leu His Glu
            275                 280                 285

Phe Ser Gly Glu Leu Ala Thr Ile Glu Gly Leu Met Lys Leu Tyr Gln
    290                 295                 300

Ser Met Gly Glu Met Ala Pro Tyr Met Val Ile Leu Glu Asn Ser Ile
305                 310                 315                 320

Gln Thr Arg Phe Ser Ala Gly Ser Tyr Pro Leu Leu Trp Ser Tyr Ala
                325                 330                 335

Met Gly Val Gly Val Glu Leu Glu Arg Ser Met Gly Gly Leu Asn Phe
                340                 345                 350

Thr Arg Ser Phe Phe Asp Pro Thr Tyr Phe Arg Leu Gly Gln Glu Met
            355                 360                 365

Val Arg Arg Ser Ser Gly Met Val Asn Ser Ser Phe Ala Arg Glu Leu
    370                 375                 380

Gly Leu Ser Glu His Glu Thr Gln Leu Val Ser Gln Ile Val Asn Ser
385                 390                 395                 400

Gly Gly Glu Ser Gly Ile Pro Lys Phe Asp Gly Phe Arg Ala Asn Pro
                405                 410                 415

Thr Thr Phe Leu Gly Ala Lys Asp Asn Ile Asn Asp Gly Gly Glu Asp
                420                 425                 430

Gln Ser Asn Ser Val Ser Gly Leu Pro Gly Pro Ile Leu Pro Ser His
            435                 440                 445

Asp Leu Asn Leu Ser Gly Asp Ser Tyr Gly Asn Asp Ser Gly Met Lys
    450                 455                 460

Asn Val Asn Asp Arg Leu Asn Glu Gly Val Ser Pro Asp His Asp Val
465                 470                 475                 480

Ser Ser Ser Ala Met Glu Glu Leu Arg Arg Leu Val Glu Ser Thr Asn
                485                 490                 495

Arg Ile Asp Thr Lys Lys Pro Glu Ala Pro Gly Val Thr Asn His Tyr
                500                 505                 510

Asn Asp Thr Asp Leu Leu Lys
            515

<210> SEQ ID NO 41
<211> LENGTH: 1476
<212> TYPE: DNA
<213> ORGANISM: Feline Morbillivirus
<220> FEATURE:
<221> NAME/KEY: misc_feature
<223> OTHER INFORMATION: FeMoV "Lapon strain" P antigen "wild-type"
      nucleic acid; given as DNA sequence

<400> SEQUENCE: 41
atgtcctctc accaaatcca acaggttaaa catggcctcg aatctttaca agagatcaaa      60
aacaaccctc catcttccca agatgtcaat cttgccaggg agatttacga atccattaaa     120
caaacaggaa caccttcagt gcaaggagga gccattacgg gagataatac tacgccaggg     180
```

-continued

```
ggtaacaatt acacaatgta tagccaagga ccaagtcctt ctattccaag tgttaacaag      240
aatatcgaag gacttactgg atccgatcat tcaggactat gggatccaga ggataacctc      300
tgcatgttat tcgaaagcga tgatgatgaa accattatt cagagattaa tggccggcct      360
tccactatcg aaagattgga tgaacaggat aatgagaacc caagtattaa acaaccagga      420
aatcaatgta ctgaaggagt gtttaagact gattcatctt ctaattccca agaaactaca      480
ctacctgttg ggagatctga tatacctggg acaggaatat caacctgtgc ctctttggat      540
ataaccgtaa atgaactcga ggatgcaact gtaagaaata gcgacaatat gaagggaaac      600
tggccaatac caaagttact tgttaagcca ccacccaggg caaaatcaag cgttgatcat      660
agcaatccat taaaaggggc cacaggaggg aaattagtct tacctgggat ggagactaca      720
ttgtccggga gagtggtgt aaccccatct gtgcacctat ctactcaacc tgtaaacgac      780
ttcaatgtaa atgtaagcaa tgcccgtcaa cctgccccaa atgtgaataa tgatcacagt      840
gacagtgggg taatagtgcc caacttacat aaagacattg aagataagtc tgaaatatcc      900
attcaagata tatacaactt aatacttggg tttaaggatg attatagaaa attgtctaat      960
aaactggata tggtattaga gatgaaacaa gatattgaca atcttaaaaa gagtagtgct     1020
aaattacaat tggcattatc aactattgag ggacatctat ctagtgttat gatcgctatt     1080
ccagggtcag gtattgattc caccggggat gagaaaaagg atcagatgaa cactgactta     1140
aagccgttat tggggaggga tcattgcaga gcatttcgag aagttaccag tcctttagat     1200
gagatgtcat tagccaattc tcccacaaaa catgttgcta aaataaacaa aaactgcacc     1260
cttcagaaaa tcaataagaa tgaaacatct gcaatcaaat ttgtcccaa tgatagtcat     1320 gcaagcacat caaccatcag atcaatcatc agatcatcca atcttgatca ggatttgaaa     1380
acgaaactac tcacaattct atctcagatt cggggatag ataatattaa ggaattttat     1440 gaaaagtca tgatactaat aaagaatagg aactaa                                1476
```

<210> SEQ ID NO 42
<211> LENGTH: 491
<212> TYPE: PRT
<213> ORGANISM: Feline Morbillivirus
<220> FEATURE:
<221> NAME/KEY: MISC_FEATURE
<223> OTHER INFORMATION: FeMoV "Lapon strain" P antigen translated amino acid sequence
<400> SEQUENCE: 42

```
Met Ser Ser His Gln Ile Gln Gln Val Lys His Gly Leu Glu Ser Leu
1               5                   10                  15

Gln Glu Ile Lys Asn Asn Pro Pro Ser Ser Gln Asp Val Asn Leu Ala
            20                  25                  30

Arg Glu Ile Tyr Glu Ser Ile Lys Gln Thr Gly Thr Pro Ser Val Gln
        35                  40                  45

Gly Gly Ala Ile Thr Gly Asp Asn Thr Thr Pro Gly Gly Asn Asn Tyr
    50                  55                  60

Thr Met Tyr Ser Gln Gly Pro Ser Pro Ser Ile Pro Ser Val Asn Lys
65                  70                  75                  80

Asn Ile Glu Gly Leu Thr Gly Ser Asp His Ser Gly Leu Trp Asp Pro
                85                  90                  95

Glu Asp Asn Leu Cys Met Leu Phe Glu Ser Asp Asp Glu Asn His
            100                 105                 110

Tyr Ser Glu Ile Asn Gly Arg Pro Ser Thr Ile Glu Arg Leu Asp Glu
```

|  | 115 |  |  |  | 120 |  |  |  | 125 |  |  |
|---|---|---|---|---|---|---|---|---|---|---|---|

Gln Asp Asn Glu Asn Pro Ser Ile Lys Gln Pro Gly Asn Gln Cys Thr
    130                     135               140

Glu Gly Val Phe Lys Thr Asp Ser Ser Asn Ser Gln Glu Thr Thr
145                 150               155              160

Leu Pro Val Gly Arg Ser Asp Ile Pro Gly Thr Gly Ile Ser Thr Cys
               165               170              175

Ala Ser Leu Asp Ile Thr Val Asn Glu Leu Glu Asp Ala Thr Val Arg
    180                     185               190

Asn Ser Asp Asn Met Lys Gly Asn Trp Pro Ile Pro Lys Leu Leu Val
         195                 200              205

Lys Pro Pro Arg Ala Lys Ser Ser Val Asp His Ser Asn Pro Leu
210                 215               220

Lys Gly Ala Thr Gly Gly Lys Leu Val Leu Pro Gly Met Glu Thr Thr
225                 230               235              240

Leu Ser Gly Lys Ser Gly Val Thr Pro Ser Val His Leu Ser Thr Gln
         245                 250              255

Pro Val Asn Asp Phe Asn Val Asn Val Ser Asn Ala Arg Gln Pro Ala
    260                   265               270

Pro Asn Val Asn Asn Asp His Ser Asp Ser Gly Val Ile Val Pro Asn
         275                280              285

Leu His Lys Asp Ile Glu Asp Lys Ser Glu Ile Ser Ile Gln Asp Ile
290                 295               300

Tyr Asn Leu Ile Leu Gly Phe Lys Asp Asp Tyr Arg Lys Leu Ser Asn
305                 310               315              320

Lys Leu Asp Met Val Leu Glu Met Lys Gln Asp Ile Asp Asn Leu Lys
               325               330              335

Lys Ser Ser Ala Lys Leu Gln Leu Ala Leu Ser Thr Ile Glu Gly His
             340               345              350

Leu Ser Ser Val Met Ile Ala Ile Pro Gly Ser Gly Ile Asp Ser Thr
        355                 360              365

Gly Asp Glu Lys Lys Asp Gln Met Asn Thr Asp Leu Lys Pro Leu Leu
370                 375               380

Gly Arg Asp His Cys Arg Ala Phe Arg Glu Val Thr Ser Pro Leu Asp
385                 390               395              400

Glu Met Ser Leu Ala Asn Ser Pro Thr Lys His Val Ala Lys Ile Asn
             405               410              415

Lys Asn Cys Thr Leu Gln Lys Ile Asn Lys Asn Glu Thr Ser Ala Ile
        420                 425              430

Lys Phe Val Pro Asn Asp Ser His Ala Ser Thr Ser Thr Ile Arg Ser
    435                   440               445

Ile Ile Arg Ser Ser Asn Leu Asp Gln Asp Leu Lys Thr Lys Leu Leu
        450                455              460

Thr Ile Leu Ser Gln Ile Arg Gly Ile Asp Asn Ile Lys Glu Phe Tyr
465                 470               475              480

Glu Lys Val Met Ile Leu Ile Lys Asn Arg Asn
             485               490

<210> SEQ ID NO 43
<211> LENGTH: 6609
<212> TYPE: DNA
<213> ORGANISM: Feline Morbillivirus
<220> FEATURE:
<221> NAME/KEY: misc_feature
<223> OTHER INFORMATION: FeMoV "Lapon strain" L antigen "wild-type"

nucleic acid; given as DNA sequence

<400> SEQUENCE: 43

```
atggagcagt cagactacca agatattcta tatccagagg tacatcttaa cagtcctata      60
gtaatttcta aattggtagg cattttggag tatgctcaag ttattcataa tcaacaatta     120
acagatcata caattattaa gaatatccaa tttagattaa gaaatgggtt taatagtccc     180
aggatacaga cactgtcaac tatgggtgaa atcatcaaca aaattaaaaa caagtatcct     240
aattatattc atatacctta tcccgaatgc aaccaaaaat tgtttaggat agtagatcca     300
gaactaacat caaaattaga atctcttctg aacaaaggtg atacactatt tctcaaaatt     360
cggtcagata tcataaaatg tttcgataaa ctgaagatga agatgaatat aagtaatgat     420
cttcttaatg acaatagtca attaattttg gatcttcctt taattatcaa aggatctcaa     480
tggttttttcc cgttttttatt ttggttttct attaaaactg aaactagaag ctgtattcgc     540
caaaatccaa aagctcgtgt tagatcacaa tatcgacccc acttatcaga gactaaaaga     600
attacattag ttgttacatc tgatctgatt acaaatatttg atcatattaa taaatgcaca     660
ttttacctga cttttgaaat gctattgatg tattgcgatg tgatagaagg taggttaatg     720
actgaaacag ctatgagcct ggattgtcga tttaccaatc tgttaccaag agtgcaatat     780
atgtgggatt tactagacgg aatgtttgaa agtctaggta atcagttata ttcagttatt     840
gcattattag aacctctttc tcttgcttat ttgcaattga tagatgctga tccgcagatt     900
cggggaacat tcttgcatca ctgtttctca gagttagaag aaatcatatt tgacaaatct     960
cctttttgacc ctttttgtgta tgaaaatctt atcaacggac ttgattatat ttatcttaca    1020
gatgacattc atctaactgc agaagttttt tctttttta gaagttttgg tcatccttac    1080
ttagaagcac aaaatgctgc caacaatgtg aggaagtata tgaatcagcc taaagtgatc    1140
tcataccaga ccttaatgca aggacatgca attttctgtg gaattataat aaatgggttt    1200
agagatcgtc atggaggaac atggcctcct gtagaattgc cgagtcatgc atctgctgta    1260
atcagaaatg cccaactatc tggggaaggg ttaacatctg aacaatgtgc tcaacattgg    1320
agatcgtttt gtgggtttaa attcaaatgt tttatgccat taagtctaga tagtgatctt    1380
acaatgtacc ttcgagacaa agcattgtca cctgttagaa gtgagtggga ttctgtctat    1440
gctaaagagt atttaagata taatccagga ttacctacaa gttccagaag attagtgaat    1500
gtatttttag aagatgataa gtttgaccca tatgaaatga ttatgtacgt gataaatggt    1560
gattacctac gagataatga gttcaacctt tcatatagtc ttaaagaaaa agagatcaaa    1620
gaggttggtc gattgttcgc caaaatgact tataaaatga gggcttgtcm agtaatagct    1680
gaaaacttga ttgctaatgg agtagggaag tttttttaaag acaatggaat ggcaaaagat    1740
gaacataaac taactaagac attacacaaa ttagccattt caggtgtacc taaagataat    1800
tctcaacttt atctagatga atgctgggag caggtagttc gacagtgttc aagtgataca    1860
catacaacaa aaccgattat gagttcgcaa ccaaagagga taattgaatc aaagtcttct    1920
agaccacctc tcaatcatag ggatactttt aaaggtaaga gagacccgaa tacacagtta    1980
aagtaccctt caaacaccga atattatgag actatcagta gttttataac tactgacctc    2040
aaaaagtact gtcttaattg gcgatatgaa tcaagtagtg tatttgcgga gagacttaat    2100
gaaatttacg gattgcccgg atttttccag tggcttcata aaattttgga aaatccgtt    2160
ttgtatgtta gtgatccatc tagcccacct gactttgatc aacatgtcga tatagaatca    2220
gttccaaacg accacatctt tattaaatat ccaatgggtg ggatagaggg gttctgtcag    2280
```

```
aaattatgga ctattagtac aatcccattt ctatacttag cagcctttga tacaggtgtt   2340
agaatcgcat cattggttca gggcgataat caagcgatcg cagtgacaaa aagagttccg   2400
tcatcttgga gttactcgaa gaaaaaggaa gaatcaacta aaataacaac acagtatttc   2460
cttaatttaa ggcaacgtct gcatgatata ggtcatgaat tgaaagcaaa tgagactatc   2520
atatcctctc atttctttgt ttactctaaa ggtatttatt acgatggaat acttctttct   2580
caggcactta aaagtatggc aagatgtgtc ttttggtctg aaacaattgt tgatgagact   2640
agatcagctt gcagtaatat atccaccaca cttgcgaagg caattgaaag gggttatgat   2700
aaatttgtgg catatgccat caatatttat aaaaccatac atcaagtttt gattgcatta   2760
tcttttacca tcaatcctac tatgacacca gatatcacag aacctttcta caaaagctta   2820
gatctactta aaaacctagt cttaattcct gcaccattag gggtatgaa ctacatgaac   2880 atgagcaggt tgtttgttag aaatatagga gatcccatta ctgcttcatt tgctgatata   2940
aagcgcatga ttgaatgtgg gttgctggga tgtagtatct tgtcacagat aatgtaccaa   3000
aagtgtggtt cctctaagta tttagactgg gctagcgatc cttattcaat aaaccttccg   3060
tatagccaaa gtatgaccaa ggtattgaag aatgtaacgg caagatatgt gctcatgcat   3120
agccccaacc ctatgcttaa agatttgttc catgaaaagt cgcaagaaga ggatgagatt   3180
cttgctgagt ttttattaga ccgacattta ataattccta gggcagcaca tgaaatttta   3240
tcaaattcag taacaggtgc tagagaatct attgcaggta tgcttgacac tactaagggt   3300
ttgatccgtg ctagtatgtc gagaggtggt ttgacatcgt cacttgtttt aaaattatca   3360
acatatgatt atcagcagtt tagaacgtgt cttgaatggc tttatgctcc taccacggga   3420
attgctgtga gtgtcgattt atgttctgtt ttcttagcta agactatccg aaaaagaatg   3480
tgggttcacc taaccaaagg aagggagatt tacgggttgg aagtacctga cattttggaa   3540
tgcatgcaga acaatataat tatcgatcat gaagattgtt actcatgtat tcaaggatcg   3600
agatattata catggttttt tgtgccttca aattgtcaac tagatcagat aaataagtca   3660
acaaattctc tccgagttcc ttatgttgga tcaacaacag aagaaagaag tgatatgagg   3720
ttatcatatg tgaggtcacc aagtcgacca cttaaagcgg cagttagaat tgcagctgta   3780
tatacatggg cttatggtga tgatgattta tcttggcacg aggcttggta tttagcaagg   3840
accagagcaa atattccctt tgatgaactc aaattaataa cacctatagc cacatctacg   3900
aatttagcac acagattaag agataggagt acccaggtta atattcagg aacttcttta   3960 gtaagagtag cgcgctacac aacaatctcc aatgataata tgtcgttcat tattaacaac   4020
aagaaagtag atactaactt tgtctatcag caaggcatgt tgttaggctt gagtatacta   4080
gagtacatat ttagatattg tacaagcact ggacaatcaa atactgtaat tcacttacat   4140
gcagacgtta actgttgtat agtacagatg actgatcagc cctatacacc tagcttaaca   4200
aagaagctac ctgatattaa acctattaat aataaattga tatatgatcc ggctcctata   4260
attgatactg atgcagctag attatattct caaaagtacc tatcacatct aatagatttc   4320
ccaagctggt caactactca gcttaacaca gtattggcaa aagtggtggc agtatctatt   4380
gtggaattaa taacaaaggc aagtaaagac catcttaatg agataatagc agttgttggt   4440
gatgatgata ttaatagttt tattacggag tttctacttg ttgatccacg tctgtttaca   4500
ctatacttag gccaatatac atcattacaa tgggcatatg aagttcatta ccatagacca   4560
gtaggtaagt accagatggc cgaagtgtta cataatctac tgtcaagggc tagtcgaggt   4620
```

-continued

```
atatttagcg tattgactaa tgcctttagc caccctaggg tatatagaag attctgggaa      4680
tgtggtttac tagagcctat ttatgggccc tatataggga gtcagaatct acatactgca      4740
gtgattgatt atatttataa tgcatatatt acttatctgg atgcttattt atctgatcag      4800
gtagatgata ctgatatcat aatatgcgaa acagaggaga catgtctatc aaataggatc      4860
gacaattatc agagcaggca tttagctata cttatagatt tgtattgtga ttccactaga      4920
tgccctaaca taaggggtc agatacaatt atgcggaatt caattcttag atcttttata       4980
gacaatgaga gacgaacaaa tccactcggt ttggcatgga atcttgatcc gttacttgtg      5040
gatcacttta gctgttctat tacatatcta agaagaggta ttattaaaca gatgaggtta      5100
agatttgatc caaacatatc tcttgagttg gctaagatga tcaaacctga tgtaatttat      5160
caagcaccta agttccgtc ttcgtgggct cttatagata tcaatcctga agtcaatgat       5220
cttaatacaa ttttggaga gctaaatagc aaatggaaag atattcctat tgggcaaatc       5280
aggattcaga attatgaaat acatgcatat aggagaattg gggttaattc aactgcatgt      5340
tataaggctc tagagatatt atctgtttta aatcgattta tgtccaatcc attgggtgca      5400 ctgttttag gtgaaggagc aggatcaatg ctggtcacat accgtgcttt tattccattt       5460
aagacaatct attataatag tggtatttct gtgcaaaatg tgcaaggtca gagagaactg      5520
agtctatatc cttctgaagt ggcactggtt gacaacaaaa atcgtttggc taatgaccct      5580
aatatcaaag tcttgtttaa cggtaagccg gagtctacgt gggttgggaa tattgactgt      5640
tttgcctata ttcttagcca tattgagacc gcaagcttga cattgataca tagtgatatc      5700
gagtccagtt taagcaagac aaaaaataag attcttgaag agctatgcca catcctatca      5760
atggcactta tcttagggag acttggatcc gtgttagtca ttaaactact accaagggtc      5820
ggtgattata cctattcatt ttgcaagtat gcatcagagt tctatcagca aaactttctc      5880
atattaccca gatttagtaa tatgtcgtca tctgaagttt actacatagg agttcacctt      5940
aatacaaaca gattgattga tcctgataga atagtacaat acataattag aaatttgcaa      6000 cccacccag ttacatttt atcctatatc tttgagacta aatatagaaa caatatggtt        6060
acaaattatg gactatgctt gtcagatgga cacaaaagtg attacttatc atcaattacc      6120
aaaatagaga atgttcttct gtcatgtgaa ttagaattgg atggacctaa gattataccg      6180
ccattatcag gacatgacta tgcaaatggg gagactagcc tggaatcaag tataatgata      6240
ttagttagag aatatcttaa tgcaactatt caaggccgag aaacattagg cttgttttca      6300
ccttacccag tattacatga gagtcagcta agagaaatta ataagtgtat tgcattgaag      6360
tatattgtgt atttactctt ttactcgaac tctgtatcat ctagtaaaca gataatgagt      6420
aatcttagaa aagggatatt aatgtatgat ttgagagacg aattttcat atcaagatta       6480 tcagcaaatt acaagaaaaa agtaatgtca caggaagtta aaaccacatg gatatttaat      6540
attgatacgc caacaagaaa agcattatac aagttagtgg ttattcatt gataattcat       6600 cacgtataa                                                              6609
```

<210> SEQ ID NO 44
<211> LENGTH: 2201
<212> TYPE: PRT
<213> ORGANISM: Feline Morbillivirus
<220> FEATURE:
<221> NAME/KEY: MISC_FEATURE
<223> OTHER INFORMATION: FeMoV "Lapon strain" L antigen translated amino
      acid sequence

<400> SEQUENCE: 44

```
Met Glu Gln Ser Asp Tyr Gln Asp Ile Leu Tyr Pro Glu Val His Leu
1               5                   10                  15

Asn Ser Pro Ile Val Ile Ser Lys Leu Val Gly Ile Leu Glu Tyr Ala
            20                  25                  30

Gln Val Ile His Asn Gln Gln Leu Thr Asp His Thr Ile Ile Lys Asn
            35                  40                  45

Ile Gln Phe Arg Leu Arg Asn Gly Phe Asn Ser Pro Arg Ile Gln Thr
50                  55                  60

Leu Ser Thr Met Gly Glu Ile Ile Asn Lys Ile Lys Asn Lys Tyr Pro
65                  70                  75                  80

Asn Tyr Ile His Ile Pro Tyr Pro Glu Cys Asn Gln Lys Leu Phe Arg
                85                  90                  95

Ile Val Asp Pro Glu Leu Thr Ser Lys Leu Glu Ser Leu Leu Asn Lys
                100                 105                 110

Gly Asp Thr Leu Phe Leu Lys Ile Arg Ser Asp Ile Ile Lys Cys Phe
            115                 120                 125

Asp Lys Leu Lys Met Lys Met Asn Ile Ser Asn Asp Leu Leu Asn Asp
            130                 135                 140

Asn Ser Gln Leu Ile Leu Asp Leu Pro Leu Ile Ile Lys Gly Ser Gln
145                 150                 155                 160

Trp Phe Phe Pro Phe Leu Phe Trp Phe Ser Ile Lys Thr Glu Thr Arg
                165                 170                 175

Ser Cys Ile Arg Gln Asn Pro Lys Ala Arg Val Arg Ser Gln Tyr Arg
                180                 185                 190

Pro His Leu Ser Glu Thr Lys Arg Ile Thr Leu Val Val Thr Ser Asp
            195                 200                 205

Leu Ile Thr Ile Phe Asp His Ile Asn Lys Cys Thr Phe Tyr Leu Thr
210                 215                 220

Phe Glu Met Leu Leu Met Tyr Cys Asp Val Ile Glu Gly Arg Leu Met
225                 230                 235                 240

Thr Glu Thr Ala Met Ser Leu Asp Cys Arg Phe Thr Asn Leu Leu Pro
                245                 250                 255

Arg Val Gln Tyr Met Trp Asp Leu Leu Asp Gly Met Phe Glu Ser Leu
                260                 265                 270

Gly Asn Gln Leu Tyr Ser Val Ile Ala Leu Leu Glu Pro Leu Ser Leu
            275                 280                 285

Ala Tyr Leu Gln Leu Ile Asp Ala Asp Pro Gln Ile Arg Gly Thr Phe
            290                 295                 300

Leu His His Cys Phe Ser Glu Leu Glu Ile Ile Phe Asp Lys Ser
305                 310                 315                 320

Pro Phe Asp Pro Phe Val Tyr Glu Asn Leu Ile Asn Gly Leu Asp Tyr
                325                 330                 335

Ile Tyr Leu Thr Asp Asp Ile His Leu Thr Ala Glu Val Phe Ser Phe
            340                 345                 350

Phe Arg Ser Phe Gly His Pro Tyr Leu Glu Ala Gln Asn Ala Ala Asn
            355                 360                 365

Asn Val Arg Lys Tyr Met Asn Gln Pro Lys Val Ile Ser Tyr Gln Thr
            370                 375                 380

Leu Met Gln Gly His Ala Ile Phe Cys Gly Ile Ile Ile Asn Gly Phe
385                 390                 395                 400

Arg Asp Arg His Gly Gly Thr Trp Pro Pro Val Glu Leu Pro Ser His
                405                 410                 415
```

Ala Ser Ala Val Ile Arg Asn Ala Gln Leu Ser Gly Glu Gly Leu Thr
            420                 425                 430

Ser Glu Gln Cys Ala Gln His Trp Arg Ser Phe Cys Gly Phe Lys Phe
        435                 440                 445

Lys Cys Phe Met Pro Leu Ser Leu Asp Ser Asp Leu Thr Met Tyr Leu
450                 455                 460

Arg Asp Lys Ala Leu Ser Pro Val Arg Ser Glu Trp Asp Ser Val Tyr
465                 470                 475                 480

Ala Lys Glu Tyr Leu Arg Tyr Asn Pro Gly Leu Pro Thr Ser Ser Arg
                485                 490                 495

Arg Leu Val Asn Val Phe Leu Glu Asp Lys Phe Asp Pro Tyr Glu
            500                 505                 510

Met Ile Met Tyr Val Ile Asn Gly Asp Tyr Leu Arg Asp Asn Glu Phe
            515                 520                 525

Asn Leu Ser Tyr Ser Leu Lys Glu Lys Glu Ile Lys Glu Val Gly Arg
        530                 535                 540

Leu Phe Ala Lys Met Thr Tyr Lys Met Arg Ala Cys Val Ile Ala Glu
545                 550                 555                 560

Asn Leu Ile Ala Asn Gly Val Gly Lys Phe Phe Lys Asp Asn Gly Met
                565                 570                 575

Ala Lys Asp Glu His Lys Leu Thr Lys Thr Leu His Lys Leu Ala Ile
            580                 585                 590

Ser Gly Val Pro Lys Asp Asn Ser Gln Leu Tyr Leu Asp Glu Cys Trp
        595                 600                 605

Glu Gln Val Val Arg Gln Cys Ser Ser Asp Thr His Thr Thr Lys Pro
610                 615                 620

Ile Met Ser Ser Gln Pro Lys Arg Ile Ile Glu Ser Lys Ser Ser Arg
625                 630                 635                 640

Pro Pro Leu Asn His Arg Asp Thr Phe Lys Gly Lys Arg Asp Pro Asn
                645                 650                 655

Thr Gln Leu Lys Tyr Pro Ser Asn Thr Glu Tyr Glu Thr Ile Ser
            660                 665                 670

Ser Phe Ile Thr Thr Asp Leu Lys Lys Tyr Cys Leu Asn Trp Arg Tyr
        675                 680                 685

Glu Ser Ser Ser Val Phe Ala Glu Arg Leu Asn Glu Ile Tyr Gly Leu
        690                 695                 700

Pro Gly Phe Phe Gln Trp Leu His Lys Ile Leu Glu Lys Ser Val Leu
705                 710                 715                 720

Tyr Val Ser Asp Pro Ser Ser Pro Asp Phe Asp Gln His Val Asp
                725                 730                 735

Ile Glu Ser Val Pro Asn Asp His Ile Phe Ile Lys Tyr Pro Met Gly
            740                 745                 750

Gly Ile Glu Gly Phe Cys Gln Lys Leu Trp Thr Ile Ser Thr Ile Pro
        755                 760                 765

Phe Leu Tyr Leu Ala Ala Phe Asp Thr Gly Val Arg Ile Ala Ser Leu
770                 775                 780

Val Gln Gly Asp Asn Gln Ala Ile Ala Val Thr Lys Arg Val Pro Ser
785                 790                 795                 800

Ser Trp Ser Tyr Ser Lys Lys Glu Glu Ser Thr Lys Ile Thr Thr
                805                 810                 815

Gln Tyr Phe Leu Asn Leu Arg Gln Arg Leu His Asp Ile Gly His Glu
            820                 825                 830

Leu Lys Ala Asn Glu Thr Ile Ile Ser Ser His Phe Phe Val Tyr Ser 835                 840                 845
Lys Gly Ile Tyr Tyr Asp Gly Ile Leu Leu Ser Gln Ala Leu Lys Ser
            850                 855                 860
Met Ala Arg Cys Val Phe Trp Ser Glu Thr Ile Val Asp Glu Thr Arg
865                 870                 875                 880
Ser Ala Cys Ser Asn Ile Ser Thr Thr Leu Ala Lys Ala Ile Glu Arg
                885                 890                 895
Gly Tyr Asp Lys Phe Val Ala Tyr Ala Ile Asn Ile Tyr Lys Thr Ile
            900                 905                 910
His Gln Val Leu Ile Ala Leu Ser Phe Thr Ile Asn Pro Thr Met Thr
                915                 920                 925
Pro Asp Ile Thr Glu Pro Phe Tyr Lys Ser Leu Asp Leu Leu Lys Asn
            930                 935                 940
Leu Val Leu Ile Pro Ala Pro Leu Gly Gly Met Asn Tyr Met Asn Met
945                 950                 955                 960
Ser Arg Leu Phe Val Arg Asn Ile Gly Asp Pro Ile Thr Ala Ser Phe
                965                 970                 975
Ala Asp Ile Lys Arg Met Ile Glu Cys Gly Leu Leu Gly Cys Ser Ile
            980                 985                 990
Leu Ser Gln Ile Met Tyr Gln Lys Cys Gly Ser Ser Lys Tyr Leu Asp
            995                 1000                1005
Trp Ala Ser Asp Pro Tyr Ser Ile Asn Leu Pro Tyr Ser Gln Ser
        1010                1015                1020
Met Thr Lys Val Leu Lys Asn Val Thr Ala Arg Tyr Val Leu Met
        1025                1030                1035
His Ser Pro Asn Pro Met Leu Lys Asp Leu Phe His Glu Lys Ser
        1040                1045                1050
Gln Glu Glu Asp Glu Ile Leu Ala Glu Phe Leu Leu Asp Arg His
        1055                1060                1065
Leu Ile Ile Pro Arg Ala Ala His Glu Ile Leu Ser Asn Ser Val
        1070                1075                1080
Thr Gly Ala Arg Glu Ser Ile Ala Gly Met Leu Asp Thr Thr Lys
        1085                1090                1095
Gly Leu Ile Arg Ala Ser Met Ser Arg Gly Gly Leu Thr Ser Ser
        1100                1105                1110
Leu Val Leu Lys Leu Ser Thr Tyr Asp Tyr Gln Gln Phe Arg Thr
        1115                1120                1125
Cys Leu Glu Trp Leu Tyr Ala Pro Thr Thr Gly Ile Ala Val Ser
        1130                1135                1140
Val Asp Leu Cys Ser Val Phe Leu Ala Lys Thr Ile Arg Lys Arg
        1145                1150                1155
Met Trp Val His Leu Thr Lys Gly Arg Glu Ile Tyr Gly Leu Glu
        1160                1165                1170
Val Pro Asp Ile Leu Glu Cys Met Gln Asn Asn Ile Ile Ile Asp
        1175                1180                1185
His Glu Asp Cys Tyr Ser Cys Ile Gln Gly Ser Arg Tyr Tyr Thr
        1190                1195                1200
Trp Phe Phe Val Pro Ser Asn Cys Gln Leu Asp Gln Ile Asn Lys
        1205                1210                1215
Ser Thr Asn Ser Leu Arg Val Pro Tyr Val Gly Ser Thr Thr Glu
        1220                1225                1230
Glu Arg Ser Asp Met Arg Leu Ser Tyr Val Arg Ser Pro Ser Arg
        1235                1240                1245

```
Pro Leu Lys Ala Ala Val Arg Ile Ala Ala Val Tyr Thr Trp Ala
1250                1255                1260

Tyr Gly Asp Asp Asp Leu Ser Trp His Glu Ala Trp Tyr Leu Ala
    1265                1270                1275

Arg Thr Arg Ala Asn Ile Thr Phe Asp Glu Leu Lys Leu Ile Thr
    1280                1285                1290

Pro Ile Ala Thr Ser Thr Asn Leu Ala His Arg Leu Arg Asp Arg
    1295                1300                1305

Ser Thr Gln Val Lys Tyr Ser Gly Thr Ser Leu Val Arg Val Ala
    1310                1315                1320

Arg Tyr Thr Thr Ile Ser Asn Asp Asn Met Ser Phe Ile Ile Asn
    1325                1330                1335

Asn Lys Lys Val Asp Thr Asn Phe Val Tyr Gln Gln Gly Met Leu
    1340                1345                1350

Leu Gly Leu Ser Ile Leu Glu Tyr Ile Phe Arg Tyr Cys Thr Ser
    1355                1360                1365

Thr Gly Gln Ser Asn Thr Val Ile His Leu His Ala Asp Val Asn
    1370                1375                1380

Cys Cys Ile Val Gln Met Thr Asp Gln Pro Tyr Thr Pro Ser Leu
    1385                1390                1395

Thr Lys Lys Leu Pro Asp Ile Lys Pro Ile Asn Asn Lys Leu Ile
    1400                1405                1410

Tyr Asp Pro Ala Pro Ile Ile Asp Thr Asp Ala Ala Arg Leu Tyr
    1415                1420                1425

Ser Gln Lys Tyr Leu Ser His Leu Ile Asp Phe Pro Ser Trp Ser
    1430                1435                1440

Thr Thr Gln Leu Asn Thr Val Leu Ala Lys Val Val Ala Val Ser
    1445                1450                1455

Ile Val Glu Leu Ile Thr Lys Ala Ser Lys Asp His Leu Asn Glu
    1460                1465                1470

Ile Ile Ala Val Val Gly Asp Asp Ile Asn Ser Phe Ile Thr
    1475                1480                1485

Glu Phe Leu Leu Val Asp Pro Arg Leu Phe Thr Leu Tyr Leu Gly
    1490                1495                1500

Gln Tyr Thr Ser Leu Gln Trp Ala Tyr Glu Val His Tyr His Arg
    1505                1510                1515

Pro Val Gly Lys Tyr Gln Met Ala Glu Val Leu His Asn Leu Leu
    1520                1525                1530

Ser Arg Ala Ser Arg Gly Ile Phe Ser Val Leu Thr Asn Ala Phe
    1535                1540                1545

Ser His Pro Arg Val Tyr Arg Arg Phe Trp Glu Cys Gly Leu Leu
    1550                1555                1560

Glu Pro Ile Tyr Gly Pro Tyr Ile Gly Ser Gln Asn Leu His Thr
    1565                1570                1575

Ala Val Ile Asp Tyr Ile Tyr Asn Ala Tyr Ile Thr Tyr Leu Asp
    1580                1585                1590

Ala Tyr Leu Ser Asp Gln Val Asp Asp Thr Asp Ile Ile Ile Cys
    1595                1600                1605

Glu Thr Glu Glu Thr Cys Leu Ser Asn Arg Ile Asp Asn Tyr Gln
    1610                1615                1620

Ser Arg His Leu Ala Ile Leu Ile Asp Leu Tyr Cys Asp Ser Thr
    1625                1630                1635
```

Arg Cys Pro Asn Ile Lys Gly Ser Asp Thr Ile Met Arg Asn Ser
1640                1645                1650

Ile Leu Arg Ser Phe Ile Asp Asn Glu Arg Arg Thr Asn Pro Leu
1655                1660                1665

Gly Leu Ala Trp Asn Leu Asp Pro Leu Leu Val Asp His Phe Ser
1670                1675                1680

Cys Ser Ile Thr Tyr Leu Arg Arg Gly Ile Ile Lys Gln Met Arg
1685                1690                1695

Leu Arg Phe Asp Pro Asn Ile Ser Leu Glu Leu Ala Lys Met Ile
1700                1705                1710

Lys Pro Asp Val Ile Tyr Gln Ala Pro Lys Val Pro Ser Ser Trp
1715                1720                1725

Ala Leu Ile Asp Ile Asn Pro Glu Val Asn Asp Leu Asn Thr Ile
1730                1735                1740

Phe Gly Glu Leu Asn Ser Lys Trp Lys Asp Ile Pro Ile Gly Gln
1745                1750                1755

Ile Arg Ile Gln Asn Tyr Glu Ile His Ala Tyr Arg Arg Ile Gly
1760                1765                1770

Val Asn Ser Thr Ala Cys Tyr Lys Ala Leu Glu Ile Leu Ser Val
1775                1780                1785

Leu Asn Arg Phe Met Ser Asn Pro Leu Gly Ala Leu Phe Leu Gly
1790                1795                1800

Glu Gly Ala Gly Ser Met Leu Val Thr Tyr Arg Ala Phe Ile Pro
1805                1810                1815

Phe Lys Thr Ile Tyr Tyr Asn Ser Gly Ile Ser Val Gln Asn Val
1820                1825                1830

Gln Gly Gln Arg Glu Leu Ser Leu Tyr Pro Ser Glu Val Ala Leu
1835                1840                1845

Val Asp Asn Lys Asn Arg Leu Ala Asn Asp Pro Asn Ile Lys Val
1850                1855                1860

Leu Phe Asn Gly Lys Pro Glu Ser Thr Trp Val Gly Asn Ile Asp
1865                1870                1875

Cys Phe Ala Tyr Ile Leu Ser His Ile Glu Thr Ala Ser Leu Thr
1880                1885                1890

Leu Ile His Ser Asp Ile Glu Ser Ser Leu Ser Lys Thr Lys Asn
1895                1900                1905

Lys Ile Leu Glu Glu Leu Cys His Ile Leu Ser Met Ala Leu Ile
1910                1915                1920

Leu Gly Arg Leu Gly Ser Val Leu Val Ile Lys Leu Leu Pro Arg
1925                1930                1935

Val Gly Asp Tyr Thr Tyr Ser Phe Cys Lys Tyr Ala Ser Glu Phe
1940                1945                1950

Tyr Gln Gln Asn Phe Leu Ile Leu Pro Arg Phe Ser Asn Met Ser
1955                1960                1965

Ser Ser Glu Val Tyr Tyr Ile Gly Val His Leu Asn Thr Asn Arg
1970                1975                1980

Leu Ile Asp Pro Asp Arg Ile Val Gln Tyr Ile Ile Arg Asn Leu
1985                1990                1995

Gln Pro Thr Pro Val Thr Phe Leu Ser Tyr Ile Phe Glu Thr Lys
2000                2005                2010

Tyr Arg Asn Asn Met Val Thr Asn Tyr Gly Leu Cys Leu Ser Asp
2015                2020                2025

Gly His Lys Ser Asp Tyr Leu Ser Ser Ile Thr Lys Ile Glu Asn

```
                   2030            2035            2040
Val Leu Leu Ser Cys Glu Leu Glu Leu Asp Gly Pro Lys Ile Ile
        2045            2050            2055
Pro Pro Leu Ser Gly His Asp Tyr Ala Asn Gly Glu Thr Ser Leu
        2060            2065            2070
Glu Ser Ser Ile Met Ile Leu Val Arg Glu Tyr Leu Asn Ala Thr
        2075            2080            2085
Ile Gln Gly Arg Glu Thr Leu Gly Leu Phe Ser Pro Tyr Pro Val
        2090            2095            2100
Leu His Glu Ser Gln Leu Arg Glu Ile Asn Lys Cys Ile Ala Leu
        2105            2110            2115
Lys Tyr Ile Val Tyr Leu Leu Phe Tyr Ser Asn Ser Val Ser Ser
        2120            2125            2130
Ser Lys Gln Ile Met Ser Asn Leu Arg Lys Gly Ile Leu Met Tyr
        2135            2140            2145
Asp Leu Arg Asp Glu Phe Phe Ile Ser Arg Leu Ser Ala Asn Tyr
        2150            2155            2160
Lys Lys Lys Val Met Ser Gln Glu Val Lys Thr Thr Trp Ile Phe
        2165            2170            2175
Asn Ile Asp Thr Pro Thr Arg Lys Ala Leu Tyr Lys Leu Val Gly
        2180            2185            2190
Tyr Ser Leu Ile Ile His His Val
        2195            2200

<210> SEQ ID NO 45
<211> LENGTH: 940
<212> TYPE: DNA
<213> ORGANISM: Artificial Sequence
<220> FEATURE:
<223> OTHER INFORMATION: ALVAC insertion locus C3 flanking region left
      arm; given as DNA sequence

<400> SEQUENCE: 45
caaatgtgag ttaatattag tatactacat tactaattta ttacatattc atttatatca      60
atctagtagc atttagcttt tataaaacaa tataactgaa tagtacatac tttactaata     120
agttataaat aagagataca tatttatagt atttttacttt ctacactgaa tataataata    180
taattataca aatataattt ttaatactat atagtatata actgaaataa ataccagtg     240
taatatagtt attatacatt tataccacat caaagatgag ttataacatc agtgtcactg    300
ttagcaacag tagttatacg atgagtagtt actctcgtat ggcgttagta tgtatgtatc    360
ttctagtttt cttagtaggc attataggaa acgtcaagct tataaggtta ttaatggtat    420
ctagaaatat atctattata ccgtttctca acttgggaat agccgatttg ctgtttgtga    480
tattcatacc tttatacatt atatacatac taagtaattt ccattggcat tttggtaaag    540
cactttgtaa aattagttct ttctttttta cttctaacat gtttgcaagt atattttaa     600
taactgtaat aagcgtatat agatatgtaa aaattaccct tcctggattt acctataaat    660
atgttaacat tagaaatatg tacattacta tattttcat atggattatt tctattatac    720
tagggattcc tgctctttac tttagaaata ctatcgtaac aaaaaataac gacacgctgt    780
gtattaatca ttatcatgat aatagagaaa ttgctgaatt gatttacaaa gttattatct    840
gtatcagatt tattttagga tacctactac ctacgataat tatactcgta tgctatacgt    900
tactgatcta cagaactaac aatgcatgtc gacgcggccg                           940
```

<210> SEQ ID NO 46
<211> LENGTH: 1999
<212> TYPE: DNA
<213> ORGANISM: Artificial Sequence
<220> FEATURE:
<223> OTHER INFORMATION: ALVAC insertion locus C3 flanking region right arm; given as DNA sequence

<400> SEQUENCE: 46

```
atattattaa aactattaga taacatagct ttatgtaaag gagtatttcc agataactta      60
gctttagcat ttacgtaagc accgtggtca agtaagagtt taacaaattc tgttttcata     120
gaactaactg ccatgtatag aggagtgaaa cctttatgat tatagacgtt tacatagcaa     180
ccatataata agatcgcatt cagtatatta atatctttca tttctatagc tatgtgaata     240
acatgtttat ctaatcctac caactttgta tcagtaccgt acttcagtaa taagtttact     300
atagttttgt ttttagatgc aacagctata tttagaacgg tatctatatg attattaacc     360
acattaacat tagatcctct ttctaaaagt gtctttgttg tttcgatatc gttacgtgaa     420
acagcgtaat gtaagggact gcccatacag tcatctatta cgtttatatc agctcctaga     480
tttaacagaa gtgctgttac atcttttctt ctattaatta ccgaatgatg taatggggtt     540
ttacctaaat catcttgttc gtttataggc actccgtgat ttataagtaa cgctattata     600
tcgtaactac aattattttt aagtgccttt atgagatact gtttatgcaa aaataaactt     660
ttatctattt taatactatt atctaacaat atcctaatta aatctatatt cttatacttt     720
atagcgtaat gtaacggagt ttcaaaattt ctagtttgta tattaagatc aatattaaaa     780
tctataaata ttttatacat atcatcagat atcttatcat acagtacatc gtaataattt     840
agaaagaatc tattacaatt aacacctttt tttaataaat atctagttaa tgacttattg     900
tttctatata cagaaatata taacggacta tttccagaat gtatctgttc tatgtcagcg     960
ccagaatcta ttagtagttt agcaatttct gtattatcta aactagcagc tttatgaaga    1020
ggaggatttt tacattttaa aatatcggca ccgtgttcta gtaataattt taccatttct    1080
atatcagaaa tacttacggc taaatacaaa gacgttgata gtatatttac gttattgtat    1140
ttgcattttt taagtatata ccttactaaa tttatatctc tataccttat agctttatgc    1200
agttcattta taagtcttcc attactcatt tctggtaatg aagtattata tatcattatg    1260
atattatctc tattttattc taataaaaac cgttatcatg ttatttatta tttgttataa    1320
ttatactatt taataaatta taccaaatac ttagatactt attaatacca tcctagaact    1380
tgtatttctt gccccctaaa cttggacatg cactccatta ggcgtttctt gttttcgaca    1440
tcgtcctcct taacatatcc tactgttatg tgaggattcc acggattatc tactgtgata    1500
tcaccaaaca cgtccttcga acagggtacc gcattcagca gaacatttct tagggctcta    1560
agttcatcag atacctccag tttcataact acagcgcatc ctttcgctcc caactgttta    1620
gaggcgttac tctgaggaaa acacatctct tctttacaga ctatagaaat agtctgtaaa    1680
tcttgatcag ttatttgctt tttgaaattt tcaaatctat cacattgatc catatttgct    1740
attccaagag ttatatgagg aaaaatatca catcctgtca tgtatttttat tgtaacatta    1800
ttataatctg taacatcagt atctaaccta acgtcgtaaa agttaacaga tgcccagtta    1860
ctataatccc aaggaacctt aacatctaat cccattaaaa tagtatcctt tctactattt    1920
ttttcattgg caagtatgtg gcttagttta cacaaaattc ctgccatttt gtaacgatag    1980
cgaagcaata gcttgtatg                                                 1999
```

<210> SEQ ID NO 47
<211> LENGTH: 405
<212> TYPE: DNA
<213> ORGANISM: Artificial Sequence
<220> FEATURE:
<223> OTHER INFORMATION: ALVAC insertion locus C5 flanking region left
      arm; given as DNA sequence

<400> SEQUENCE: 47

```
cttataaaga tctaaaatgc ataatttcta aataatgaaa aaaagtacat catgagcaac      60
gcgttagtat attttacaat ggagattaac gctctatacc gttctatgtt tattgattca     120
gatgatgttt tagaaaagaa agttattgaa tatgaaaact ttaatgaaga tgaagatgac     180
gacgatgatt attgttgtaa atctgtttta gatgaagaag atgacgcgct aaagtatact     240
atggttacaa agtataagtc tatactacta atggcgactt gtgcaagaag gtatagtata     300
gtgaaaatgt tgttagatta tgattatgaa aaaccaaata aatcagatcc atatctaaag     360
gtatctcctt tgcacataat ttcatctatt cctagtttag aatac                     405
```

<210> SEQ ID NO 48
<211> LENGTH: 1536
<212> TYPE: DNA
<213> ORGANISM: Artificial Sequence
<220> FEATURE:
<223> OTHER INFORMATION: ALVAC insertion locus C5 flanking region right
      arm; given as DNA sequence

<400> SEQUENCE: 48

```
tgaatgttaa atgttatact ttggatgaag ctataaatat gcattggaaa aataatccat      60
ttaaagaaag gattcaaata ctacaaaacc taagcgataa tatgttaact aagcttattc     120
ttaacgacgc tttaaatata cacaaataaa cataattttt gtataaccta acaaataact     180
aaaacataaa aataataaaa ggaaatgtaa tatcgtaatt attttactca ggaatggggt     240
taaatattta tatcacgtgt atatctatac tgttatcgta tactctttac aattactatt     300
acgaatatgc aagagataat aagattacgt atttaagaga atcttgtcat gataattggg     360
tacgacatag tgataaatgc tatttcgcat cgttacataa agtcagttgg aaagatggat     420
ttgacagatg taacttaata ggtgcaaaaa tgttaaataa cagcattcta tcggaagata     480
ggataccagt tatattatac aaaaatcact ggttggataa aacagattct gcaatattcg     540
taaaagatga agattactgc gaatttgtaa actatgacaa taaaaagcca tttatctcaa     600
cgacatcgtg taattcttcc atgttttatg tatgtgtttc agatattatg agattactat     660
aaactttttg tatacttata ttccgtaaac tatattaatc atgaagaaaa tgaaaaagta     720
tagaagctgt tcacgagcgg ttgttgaaaa caacaaaatt atacattcaa gatggcttac     780
atatacgtct gtgaggctat catggataat gacaatgcat ctctaaatag gttttttggac     840 aatggattcg accctaacac ggaatatggt actctacaat ctcctcttga aatggctgta     900
atgttcaaga ataccgaggc tataaaaatc ttgatgaggt atggagctaa acctgtagtt     960
actgaatgca caacttcttg tctgcatgat gcggtgttga gagacgacta caaaatagtg    1020
aaagatctgt tgaagaataa ctatgtaaac aatgttcttt acagcggagg ctttactcct    1080 ttgtgttttgg cagcttacct taacaaagtt aatttggtta aacttctatt ggctcattcg    1140
gcggatgtag atatttcaaa cacggatcgg ttaactcctc tacatatagc cgtatcaaat    1200
aaaaatttaa caatggttaa acttctattg aacaaaggtg ctgatactga cttgctggat    1260
aacatgggac gtactccttt aatgatcgct gtacaatctg gaaatattga aatatgtagc    1320
```

```
acactactta aaaaaaataa aatgtccaga actgggaaaa attgatcttg ccagctgtaa    1380
ttcatggtag aaaagaagtg ctcaggctac ttttcaacaa aggagcagat gtaaactaca    1440
tctttgaaag aaatggaaaa tcatatactg ttttggaatt gattaaagaa agttactctg    1500
agacacaaaa gaggtagctg aagtggtact ctcaaa                              1536
```

<210> SEQ ID NO 49
<211> LENGTH: 4170
<212> TYPE: DNA
<213> ORGANISM: Artificial Sequence
<220> FEATURE:
<223> OTHER INFORMATION: passage 3 C5 insertion locus of vCP3025
      including C5 flanking region right arm, H6 vaccinia promoter,
      codon-optimized Gordon H antigen, C5 flanking region left arm,
      i.e. base pairs 304,701 to 308,870

<400> SEQUENCE: 49

```
aaatgactat gtaccgttat tgcatgaacg atattataaa tataggttct cgtaggagag      60
aactattgac tatggcaatg aatgttaaat gttatacttt ggatgaagct ataaatatgc     120
attggaaaaa taatccattt aaagaaagga ttcaaatact acaaaaccta agcgataata     180
tgttaactaa gcttattctt aacgacgctt taaatataca caaataaaca taattttttgt    240 ataacctaac aaataactaa aacataaaaa taataaaagg aaatgtaata tcgtaattat     300
tttactcagg aatgggggtta aatatttata tcacgtgtat atctatactg ttatcgtata    360
ctctttacaa ttactattac gaatatgcaa gagataataa gattacgtat ttaagagaat    420
cttgtcatga taattgggta cgacatagta ataaatgcta tttcgcatcg ttacataaag    480
tcagttggaa agatggattt gacagatgta acttaatagg tgcaaaaatg ttaaataaca    540
gcattctatc ggaagatagg ataccagtta tattatacaa aaatcactgg ttggataaaa    600
cagattctgc aatattcgta aaagatgaag attactgcga atttgtaaac tatgacaata    660
aaaagccatt tatctcaacg acatcgtgta attcttccat gttttatgta tgtgtttcag    720
atattatgag attactataa acttttttgta tacttatatt ccgtaaacta tattaatcat    780
gaagaaaatg aaaagtata gaagctgttc acgagcggtt gttgaaaaca acaaaattat     840
acattcaaga tggcttacat atacgtctgt gaggctatca tggataatga caatgcatct    900
ctaaataggt ttttggacaa tggattcgac cctaacacgg aatatggtac tctacaatct    960
cctcttgaaa tggctgtaat gttcaagaat accgaggcta taaaaatctt gatgaggtat   1020
ggagctaaac ctgtagttac tgaatgcaca acttcttgtc tgcatgatgc ggtgttgaga   1080
gacgactaca aaatagtgaa agatctgttg aagaataact atgtaaacaa tgttctttac   1140
agcggaggct ttactccttt gtgtttggca gcttacctta acaaagttaa tttggttaaa   1200
cttctattgg ctcattcggc ggatgtagat atttcaaaca cggatcggtt aactcctcta   1260
catatagccg tatcaaataa aaatttaaca atggttaaac ttctattgaa caaaggtgct   1320
gatactgact tgctggataa catgggacgt actcctttaa tgatcgctgt acaatctgga   1380
aatattgaaa tatgtagcac actacttaaa aaaataaaa tgtccagaac tgggaaaaat   1440
tgatcttgcc agctgtaatt catggtagaa aagaagtgct caggctactt ttcaacaaag   1500
gagcagatgt aaactacatc tttgaaagaa atggaaaatc atatactgtt ttggaattga   1560
ttaaagaaag ttactctgag acacaaaaga ggtagctgaa gtggtactct caaaggtacg   1620
tgactaatta gctataaaaa ggatccgggt taattaatta gtcatcaggc agggcgagaa   1680
cgagactatc tgctcgttaa ttaattagag cttctttatt ctatacttaa aaagtgaaaa   1740
```

-continued

```
taaatacaaa ggttcttgag ggttgtgtta aattgaaagc gagaaataat cataaattat   1800
ttcattatcg cgatatccgt taagtttgta tcgtaatgga aagcaataat aacaaatact   1860
ataaagacag caatcggtac ttcagcaaga tcctggacga gaataagaca gtcaataatc   1920
acctgtactc cctgtctatc aggatcatca ccgtgatcgc catcgtggtg tccctgatcg   1980
caaccactat cactatcatc aatgccatct ctggcagaac cactctgaac aataacatgg   2040
acatgctgct gaaccagcag gataagatca ataacatcaa agagatgatc ttcgacagga   2100
tctatccact gatcaacgca atgagcaccg agctggggct gcacatccct accctgctgg   2160
acgaactgac taagtccatc gatcagaaga tcaaaatcat gactccacct ctggaaacca   2220
ctacctctaa tctgaactgg tgcatcaatc ccccaaacgg aatcatcgtg gacccaaaag   2280
gctactgtga ggggctggaa ctgtccaaga cctataaact gctgctggac cagctggata   2340
tgctgaggaa gaaaagcctg atcatcaata agaaatccat caaccagtgc agactggtgg   2400
atagctccaa tatcgtgttc gccaccgtga acatccagag cactcctagg tttctgaatc   2460
tgggacatac cgtgtccaac cagagaatca ctttcggaca gggtacttac tctagcacct   2520
atatcatcac tatccaggag gacggtctga ccgatgtgca gtacagagtg tttgaaatcg   2580
gctatatctc tgaccagttc gggactttc cttctctgat cgtgagcagg gtgctgcccg   2640
tgagaatggt gctggggatg gagtcctgca ctctgacctc tgataagttc ggcgggtact   2700
tcctgtgcat gaatatcccc accaggtcta tctacgacta tgtgaacatc agagatctga   2760
agagcctgta cgtgaccatc ccccactacg gcaaaatcaa ttacacttat ttcaactttg   2820
ggaaggtgag gagcccacat gagatcgaca aaatctggct gacttctgaa agaggacaga   2880
tgatcagcgg ttacttcgcc gcatttgtga ctatcaccat caggaactac aacaactacc   2940
cttacaagtg cctgcacaac ccatgtctgg agagaagcga atcctactgc aagggatggt   3000
ataagaacat cactggtacc gacgatgtgc ccatcctggc ctacctgctg gtggagatga   3060
acgatgagga aggtccactg atcaccctgg tggaaatccc tcctacaat tatactgcac   3120
ctagccataa ctccctgtac tatgacgata agatcaacaa gctgatcatg actacctccc   3180
acatcggata tatccagatc aacgaggtgc atgaagtgat cgtgggtgac aatctgaagg   3240
ccatcctgct gaacaggctg agcgatgagc acccaactct gaccgcatgt aggttcaatc   3300
aggagatcaa agaaagacat atctccgacg gcctgatcat ctctaacagc gccctgatcg   3360
atatccagga gaggatgtac gtgaccgtga aggcagtgcc acctatcggc aattataact   3420
ttaccgtgga actgcactcc agatctaata ctagctacgt ggggctgcct aggcagttca   3480
acgcaagata tgacaaactg catctggaat gctttgcctg ggatagatcc tggtggtgtg   3540
cactgatccc ccagtttct ctgtcctgga atgagagcct gtccgtggat actgctattt   3600
tcaacctgat aaactgtaac taactcgagt ctagaatcga tcccgggttt ttatgactag   3660
ttaatcacgg ccgcttataa agatctaaaa tgcataattt ctaaataatg aaaaaaagta   3720
catcatgagc aacgcgttag tatattttac aatggagatt aacgctctat accgttctat   3780
gtttattgat tcagatgatg ttttagaaaa gaaagttatt gaatatgaaa actttaatga   3840
agatgaagat gacgacgatg attattgttg taaatctgtt ttagatgaag aagatgacgc   3900
gctaaagtat actatggtta caaagtataa gtctatacta ctaatggcga cttgtgcaag   3960
aaggtatagt atagtgaaaa tgttgttaga ttatgattat gaaaaccaa ataaatcaga   4020
tccatatcta aaggtatctc ctttgcacat aatttcatct attcctagtt tagaatactt   4080
ttcattatat ttgtttacag ctgaagacga aaaaaatata tcgataatag aagattatgt   4140
```
taactctgct aataagatga aattgaatga 4170

<210> SEQ ID NO 50
<211> LENGTH: 4215
<212> TYPE: DNA
<213> ORGANISM: Artificial Sequence
<220> FEATURE:
<223> OTHER INFORMATION: passage 3 C5 insertion locus of vCP3029 including C5 flanking region right arm, H6 vaccinia promoter, codon-optimized Gordon H antigen, C5 flanking region left arm, i.e. base pairs 304,166 to 308,380

<400> SEQUENCE: 50
tagttacttg gataaattaa tcgagacgcg tgataaaatg actatgtacc gttattgcat 60
gaacgatatt ataaatatag gttctcgtag gagagaacta ttgactatgg caatgaatgt 120
taaatgttat actttggatg aagctataaa tatgcattgg aaaaataatc catttaaaga 180
aaggattcaa atactacaaa acctaagcga taatatgtta actaagctta ttcttaacga 240
cgctttaaat atacacaaat aaacataatt tttgtataac ctaacaaata actaaaacat 300
aaaaataata aaaggaaatg taatatcgta attattttac tcaggaatgg ggttaaatat 360
ttatatcacg tgtatatcta tactgttatc gtatactctt tacaattact attacgaata 420
tgcaagagat aataagatta cgtatttaag agaatcttgt catgataatt gggtacgaca 480
tagtgataaa tgctatttcg catcgttaca taaagtcagt tggaaagatg gatttgacag 540
atgtaactta ataggtgcaa aaatgttaaa taacagcatt ctatcggaag ataggatacc 600
agttatatta tacaaaaatc actggttgga taaaacagat tctgcaatat tcgtaaaaga 660
tgaagattac tgcgaatttg taaactatga caataaaaag ccatttatct caacgacatc 720
gtgtaattct tccatgtttt atgtatgtgt ttcagatatt atgagattac tataaacttt 780
ttgtatactt atattccgta aactatatta atcatgaaga aaatgaaaaa gtatagaagc 840
tgttcacgag cggttgttga aaacaacaaa attatacatt caagatggct tacatatacg 900
tctgtgaggc tatcatggat aatgacaatg catctctaaa taggtttttg gacaatggat 960
tcgaccctaa cacggaatat ggtactctac aatctcctct tgaaatggct gtaatgttca 1020
agaataccga ggctataaaa atcttgatga ggtatggagc taaacctgta gttactgaat 1080
gcacaacttc ttgtctgcat gatgcggtgt tgagagacga ctacaaaata gtgaaagatc 1140
tgttgaagaa taactatgta aacaatgttc tttacagcgg aggctttact cctttgtgtt 1200
tggcagctta ccttaacaaa gttaatttgg ttaaacttct attggctcat tcggcggatg 1260
tagatatttc aaacacggat cggttaactc ctctacatat agccgtatca aataaaaatt 1320
taacaatggt taaacttcta ttgaacaaag gtgctgatac tgacttgctg gataacatgg 1380
gacgtactcc tttaatgatc gctgtacaat ctggaaatat tgaaatatgt agcacactac 1440
ttaaaaaaaa taaaatgtcc agaactggga aaaattgatc ttgccagctg taattcatgg 1500
tagaaaagaa gtgctcaggc tacttttcaa caaaggagca gatgtaaact acatctttga 1560
aagaaatgga aaatcatata ctgttttgga attgattaaa gaaagttact ctgagacaca 1620
aaagaggtag ctgaagtggt actctcaaag gtacgtgact aattagctat aaaaaggatc 1680
cgggttaatt aattagtcat caggcagggc gagaacgaga ctatctgctc gttaattaat 1740
tagagcttct ttattctata cttaaaaagt gaaaataaat acaaaggttc ttgagggttg 1800
tgttaaattg aaagcgagaa ataatcataa attatttcat tatcgcgata tccgttaagt 1860
ttgtatcgta atggaaagca ataataacaa atactataaa gacagcaatc ggtacttcag 1920

```
caagatcctg gacgagaata agacagtcaa taatcacctg tactccctgt ctatcaggat      1980
catcaccgtg atcgccatcg tggtgtccct gatcgcaacc actatcacta tcatcaatgc      2040
catctctggc agaaccactc tgaacaataa catggacatg ctgctgaacc agcaggataa      2100
gatcaataac atcaaagaga tgatcttcga caggatctat ccactgatca acgcaatgag      2160
caccgagctg gggctgcaca tccctaccct gctggacgaa ctgactaagt ccatcgatca      2220
gaagatcaaa atcatgactc cacctctgga aaccactacc tctaatctga actggtgcat      2280
caatccccca aacggaatca tcgtggaccc aaaaggctac tgtgaggggc tggaactgtc      2340
caagacctat aaactgctgc tggaccagct ggatatgctg aggaagaaaa gcctgatcat      2400
caataagaaa tccatcaacc agtgcagact ggtggatagc tccaatatcg tgttcgccac      2460
cgtgaacatc cagagcactc ctaggtttct gaatctggga cataccgtgt ccaaccagag      2520
aatcactttc ggacagggta cttactctag cacctatatc atcactatcc aggaggacgg      2580
tctgaccgat gtgcagtaca gagtgtttga atcggctat atctctgacc agttcgggac       2640
ttttccttct ctgatcgtga gcagggtgct gcccgtgaga atggtgctgg ggatggagtc      2700
ctgcactctg acctctgata agttcggcgg gtacttcctg tgcatgaata tccccaccag      2760
gtctatctac gactatgtga acatcagaga tctgaagagc ctgtacgtga ccatccccca      2820
ctacggcaaa atcaattaca cttatttcaa ctttgggaag gtgaggagcc acatgagat      2880 cgacaaaatc tggctgactt ctgaaagagg acagatgatc agcggttact tcgccgcatt      2940
tgtgactatc accatcagga actacaacaa ctaccttac aagtgcctgc acaacccatg       3000
tctggagaga agcgaatcct actgcaaggg atggtataag aacatcactg gtaccgacga      3060
tgtgcccatc ctggcctacc tgctggtgga gatgaacgat gaggaaggtc cactgatcac      3120
cctggtggaa atccctccct acaattatac tgcacctagc cataactccc tgtactatga      3180
cgataagatc aacaagctga tcatgactac ctcccacatc ggatatatcc agatcaacga      3240
ggtgcatgaa gtgatcgtgg gtgacaatct gaaggccatc ctgctgaaca ggctgagcga      3300
tgagcaccca actctgaccg catgtaggtt caatcaggag atcaaagaaa gacatatctc      3360
cgacggcctg atcatctcta acagcgccct gatcgatatc caggagagga tgtacgtgac      3420
cgtgaaggca gtgccaccta tcggcaatta aactttacc gtggaactgc actccagatc       3480
taatactagc tacgtgggc tgcctaggca gttcaacgca agatatgaca aactgcatct       3540
ggaatgcttt gcctgggata gatcctggtg gtgtgcactg atcccccagt tttctctgtc      3600
ctggaatgag agcctgtccg tggatactgc tattttcaac ctgataaact gtaactaact      3660
cgagtctaga atcgatcccg ggttttatg actagttaat cacggccgct tataaagatc       3720
taaaatgcat aatttctaaa taatgaaaaa agtacatca tgagcaacgc gttagtatat       3780
tttacaatgg agattaacgc tctataccgt tctatgttta ttgattcaga tgatgtttta      3840
gaaaagaaag ttattgaata tgaaaacttt aatgaagatg aagatgacga cgatgattat      3900
tgttgtaaat ctgtttttaga tgaagaagat gacgcgctaa agtatactat ggttacaaag      3960
tataagtcta tactactaat ggcgacttgt gcaagaaggt atagtatagt gaaaatgttg      4020
ttagattatg attatgaaaa accaaataaa tcagatccta atctaaaggt atctcctttg      4080
cacataattt catctattcc tagtttagaa tacttttcat tatatttgtt tacagctgaa      4140
gacgaaaaaa atatatcgat aatagaagat tatgttaact ctgctaataa gatgaaattg      4200
aatgagtctg tgata                                                       4215
```

<210> SEQ ID NO 51
<211> LENGTH: 4200
<212> TYPE: DNA
<213> ORGANISM: Artificial Sequence
<220> FEATURE:
<223> OTHER INFORMATION: passage 3 C3 insertion locus of vCP3029
including C3 flanking region right arm, 42k (long) poxviral
promoter, codon-optimized Gordon M antigen, C3 flanking region
left arm, i.e. base pairs 38,608 to 42,807

<400> SEQUENCE: 51
cgtattaccg tgattattta gagaattata gtcggcgtta taagataaaa gtaattttat 60
attattaaaa ctattagata acatagcttt atgtaaagga gtatttccag ataacttagc 120
tttagcattt acgtaagcac cgtggtcaag taagagttta acaaattctg ttttcataga 180
actaactgcc atgtatagag gagtgaaacc tttatgatta tagacgttta catagcaacc 240
atataataag atcgcattca gtatattaat atctttcatt tctatagcta tgtgaataac 300
atgtttatct aatcctacca actttgtatc agtaccgtac ttcagtaata agtttactat 360
agttttgttt ttagatgcaa cagctatatt tagaacggta tctatatgat tattaaccac 420
attaacatta gatcctcttt ctaaaagtgt ctttgttgtt tcgatatcgt tacgtgaaac 480
agcgtaatgt aagggactgc ccatacagtc atctattacg tttatatcag ctcctagatt 540
taacagaagt gctgttacat cttttcttct attaattacc gaatgatgta atggggtttt 600
acctaaatca tcttgttcgt ttataggcac tccgtgattt ataagtaacg ctattatatc 660
gtaactacaa ttatttttaa gtgcctttat gagatactgt ttatgcaaaa ataaactttt 720
atctatttta atactattat ctaacaatat cctaattaaa tctatattct tatactttat 780
agcgtaatgt aacggagttt caaaatttct agtttgtata ttaagatcaa tattaaaatc 840
tataaatatt ttatacatat catcagatat cttatcatac agtacatcgt aataatttag 900
aaagaatcta ttacaattaa cacctttttt taataaatat ctagttaatg acttattgtt 960
tctatataca gaaatatata acggactatt tccagaatgt atctgttcta tgtcagcgcc 1020
agaatctatt agtagtttag caatttctgt attatctaaa ctagcagctt tatgaagagg 1080
aggattttta cattttaaaa tatcggcacc gtgttctagt aataatttta ccatttctat 1140
atcagaaata cttacggcta aatacaaaga cgttgatagt atatttacgt tattgtattt 1200
gcatttttta agtatatacc ttactaaatt tatatctcta taccttatag ctttatgcag 1260
ttcatttata agtcttccat tactcatttc tggtaatgaa gtattatata tcattatgat 1320
attatctcta ttttattcta ataaaaaccg ttatcatgtt atttattatt tgttataatt 1380
atactattta ataaattata ccaaatactt agatacttat taataccatc ctagaacttg 1440
tatttcttgc cccctaaact tggacatgca ctccattagg cgtttcttgt tttcgacatc 1500
gtcctcctta acatatccta ctgttatgtg aggattccac ggattatcta ctgtgatatc 1560
accaaacacg tccttcgaac agggtaccgc attcagcaga acatttctta gggctctaag 1620
ttcatcagat acctccagtt tcataactac agcgcatcct ttcgctccca actgtttaga 1680
ggcgttactc tgaggaaaac acatctcttc tttacagact atagaaatag tctgtaaatc 1740
ttgatcagtt atttgctttt tgaaattttc aaatctatca cattgatcca tatttgctat 1800
tccaagagtt atatgaggaa aaatatcaca tcctgtcatg tattttattg taacattatt 1860
ataatctgta acatcagtat ctaacctaac gtcgtaaaag ttaacagatg cccagttact 1920
ataatcccaa ggaaccttaa catctaatcc cattaaaata gtatcctttc tactattttt 1980

```
ttcattggca agtatgtggc ttagtttaca caaaattcct gccattttgt aacgatagcg    2040
aagcaatagc ttgtatgctt tttatttgat taactagtca taaaaatcgg gatcctcaaa    2100
aaaatataaa tgattcacca tctgatagaa aaaaaattta ttgggagaat atgataatat    2160
tttgggattt caaaattgaa aatatatata taatataaa aatgactgag atcttcaacc    2220
tggacgaaag ctcttggagt gttaaaggga ccctggaccc tctgaccccc gatacctacc    2280
ccgatgggag gctggtgcca agatcagag tgatcgaccc tggctgggg gataggaaaa     2340 gcggggcta catgtatctg ctgctgcacg gggtgatcga ggactctgaa accgtgatca    2400
accccaaggg gagagccttc ggggcatttc cactgggggt ggggcagagc accgagaatc    2460
ccgaagatct gttcaaggag atcctgactc tgaacatcgt gaccaggaga actgccgggt    2520
ttaatgaaaa actggtgtac tataacacca ctccctctga tctgctgact ccctggaaga    2580
aagtgctggc ctacgggtct atcttcaccg caaaccaagt gtgtaacaat actagctcca    2640
tccccatcga catcccacag aagtttaggc ctgtgtatct gaccgtgact aaactgagcg    2700
acgatgggta ctatcagatc cccaagatga tccaggactt caaatctagc aactctgtgg    2760
catttaatat cctggtgcac ctgagcatgg ggaccatcct gctggattcc tctaagggga    2820
gcagggtggg gaacccagcc gagaatctga tcactttcat gatccatatc gggaacttca    2880
agagaaagaa caacaaggca tactcccctg aatattgcaa gaggaaaatc atgagactgg    2940
ggctgatctt cagcctgggg gcaatcgggg gcacctccct gcatatcagg tgcactggga    3000
agatgtccaa aagactgcag gcatacctgg ggtttaagag gaccctgtgt taccctctga    3060
tgtatgtgaa cgagggggctg aataaaaactc tgtggagaaa cgagtgcaag atcgaaaaag    3120
tgcaggccgt gctgcagcca tctgtgccta atgagttcaa aatatacgac gacattatca    3180
tagacaatac aaacgggctg ttcaaagtca agtaactcga ggaattcctg cagcccgggt    3240
ttttatagct aattagtcaa atgtgagtta atattagtat actacattac taatttatta    3300
catattcatt tatatcaatc tagtagcatt tagcttttat aaaacaatat aactgaatag    3360
tacatacttt actaataagt tataaataag agatacatat ttatagtatt ttactttcta    3420
cactgaatat aataatataa ttatacaaat ataattttta atactatata gtatataact    3480
gaaataaaat accagtgtaa tatagttatt atacatttat accacatcaa agatgagtta    3540
taacatcagt gtcactgtta gcaacagtag ttatacgatg agtagttact ctcgtatggc    3600
gttagtatgt atgtatcttc tagttttctt agtaggcatt ataggaaacg tcaagcttat    3660
aaggttatta atggtatcta gaaatatatc tattataccg tttctcaact tgggaatagc    3720
cgatttgctg tttgtgatat tcatacctt atacattata tacatactaa gtaatttcca    3780
ttggcatttt ggtaaagcac tttgtaaaat tagttctttc ttttttactt ctaacatgtt    3840
tgcaagtata ttttaataa ctgtaataag cgtatataga tatgtaaaaa ttacccttcc    3900
tggatttacc tataaatatg ttaacattag aaatatgtac attactatat ttttcatatg    3960
gattatttct attatactag ggattcctgc tctttacttt agaaatacta tcgtaacaaa    4020
aaataacgac acgctgtgta ttaatcatta tcatgataat agagaaattg ctgaattgat    4080
ttacaaagtt attatctgta tcagatttat tttaggatac ctactaccta cgataattat    4140
actcgtatgc tatacgttac tgatctacag aactaacaat gcatctaata tatctgataa    4200
```

<210> SEQ ID NO 52
<211> LENGTH: 23
<212> TYPE: DNA
<213> ORGANISM: Artificial Sequence

```
<220> FEATURE:
<223> OTHER INFORMATION: PCR Primer "Gordon_M_probe_F"

<400> SEQUENCE: 52
ggagatcctg actctgaaca tcg                                        23

<210> SEQ ID NO 53
<211> LENGTH: 23
<212> TYPE: DNA
<213> ORGANISM: Artificial Sequence
<220> FEATURE:
<223> OTHER INFORMATION: PCR Primer "Gordon_M_probe_R"

<400> SEQUENCE: 53
ctccacagag ttttattcag ccc                                        23

<210> SEQ ID NO 54
<211> LENGTH: 25
<212> TYPE: DNA
<213> ORGANISM: Artificial Sequence
<220> FEATURE:
<223> OTHER INFORMATION: PCR Primer "C3F"

<400> SEQUENCE: 54
cgtagagttt tttgtctagt tctat                                      25

<210> SEQ ID NO 55
<211> LENGTH: 25
<212> TYPE: DNA
<213> ORGANISM: Artificial Sequence
<220> FEATURE:
<223> OTHER INFORMATION: PCR Primer "C3R"

<400> SEQUENCE: 55
gttgttttat gcggtaaaga ataat                                      25

<210> SEQ ID NO 56
<211> LENGTH: 24
<212> TYPE: DNA
<213> ORGANISM: Artificial Sequence
<220> FEATURE:
<223> OTHER INFORMATION: PCR Primer "7520"

<400> SEQUENCE: 56
tcttgcttcg cagtcatcgt tctg                                       24

<210> SEQ ID NO 57
<211> LENGTH: 21
<212> TYPE: DNA
<213> ORGANISM: Artificial Sequence
<220> FEATURE:
<223> OTHER INFORMATION: PCR Primer "7521"

<400> SEQUENCE: 57
tctaaaatgc ataatttcta a                                          21

<210> SEQ ID NO 58
<211> LENGTH: 26
<212> TYPE: DNA
<213> ORGANISM: Artificial Sequence
<220> FEATURE:
<223> OTHER INFORMATION: PCR Primer "C3-PCR-F"

<400> SEQUENCE: 58
gctaacacaa gttagaggcg tattac                                     26
```

<210> SEQ ID NO 59
<211> LENGTH: 27
<212> TYPE: DNA
<213> ORGANISM: Artificial Sequence
<220> FEATURE:
<223> OTHER INFORMATION: PCR Primer "C3-PCR-R"

<400> SEQUENCE: 59
cattaattat gtgatgaggc atccaac                                27

<210> SEQ ID NO 60
<211> LENGTH: 20
<212> TYPE: DNA
<213> ORGANISM: Artificial Sequence
<220> FEATURE:
<223> OTHER INFORMATION: PCR Primer "C3-R1"

<400> SEQUENCE: 60
tttataggta aatccaggaa                                        20

<210> SEQ ID NO 61
<211> LENGTH: 25
<212> TYPE: DNA
<213> ORGANISM: Artificial Sequence
<220> FEATURE:
<223> OTHER INFORMATION: PCR Primer "C3-R2"

<400> SEQUENCE: 61
gcctactaag aaaactagaa gatac                                  25

<210> SEQ ID NO 62
<211> LENGTH: 24
<212> TYPE: DNA
<213> ORGANISM: Artificial Sequence
<220> FEATURE:
<223> OTHER INFORMATION: PCR Primer "C3-R3"

<400> SEQUENCE: 62
agattgatat aaatgaatat gtaa                                   24

<210> SEQ ID NO 63
<211> LENGTH: 20
<212> TYPE: DNA
<213> ORGANISM: Artificial Sequence
<220> FEATURE:
<223> OTHER INFORMATION: PCR Primer "C3-R4"

<400> SEQUENCE: 63
cgacgttagg ttagatactg                                        20

<210> SEQ ID NO 64
<211> LENGTH: 20
<212> TYPE: DNA
<213> ORGANISM: Artificial Sequence
<220> FEATURE:
<223> OTHER INFORMATION: PCR Primer "C3-R5"

<400> SEQUENCE: 64
atgcggtacc ctgttcgaag                                        20

<210> SEQ ID NO 65
<211> LENGTH: 20
<212> TYPE: DNA
<213> ORGANISM: Artificial Sequence
<220> FEATURE:
<223> OTHER INFORMATION: PCR Primer "C3-R6"

<400> SEQUENCE: 65
cagaaatgag taatggaaga                                           20

<210> SEQ ID NO 66
<211> LENGTH: 20
<212> TYPE: DNA
<213> ORGANISM: Artificial Sequence
<220> FEATURE:
<223> OTHER INFORMATION: PCR Primer "C3-R7"

<400> SEQUENCE: 66
ctggaaatag tccgttatat                                           20

<210> SEQ ID NO 67
<211> LENGTH: 22
<212> TYPE: DNA
<213> ORGANISM: Artificial Sequence
<220> FEATURE:
<223> OTHER INFORMATION: PCR Primer "C3-R8"

<400> SEQUENCE: 67
cagtatctca taaaggcact ta                                        22

<210> SEQ ID NO 68
<211> LENGTH: 24
<212> TYPE: DNA
<213> ORGANISM: Artificial Sequence
<220> FEATURE:
<223> OTHER INFORMATION: PCR Primer "C3-R9"

<400> SEQUENCE: 68
ccgttctaaa tatagctgtt gcat                                      24

<210> SEQ ID NO 69
<211> LENGTH: 22
<212> TYPE: DNA
<213> ORGANISM: Artificial Sequence
<220> FEATURE:
<223> OTHER INFORMATION: PCR Primer "Gordon_M_1F"

<400> SEQUENCE: 69
atgactgaga tcttcaacct gg                                        22

<210> SEQ ID NO 70
<211> LENGTH: 20
<212> TYPE: DNA
<213> ORGANISM: Artificial Sequence
<220> FEATURE:
<223> OTHER INFORMATION: PCR Primer "Gordon_M_2F"

<400> SEQUENCE: 70
tgagcatggg gaccatcctg                                           20

<210> SEQ ID NO 71
<211> LENGTH: 23
<212> TYPE: DNA
<213> ORGANISM: Artificial Sequence
<220> FEATURE:
<223> OTHER INFORMATION: PCR Primer "Gordon_M_3F"

<400> SEQUENCE: 71
gggctgaata aaactctgtg gag                                       23

<210> SEQ ID NO 72

```
<211> LENGTH: 23
<212> TYPE: DNA
<213> ORGANISM: Artificial Sequence
<220> FEATURE:
<223> OTHER INFORMATION: PCR Primer "Gordon_M_1R"

<400> SEQUENCE: 72
cgatgttcag agtcaggatc tcc                                              23

<210> SEQ ID NO 73
<211> LENGTH: 20
<212> TYPE: DNA
<213> ORGANISM: Artificial Sequence
<220> FEATURE:
<223> OTHER INFORMATION: PCR Primer "C3-F5"

<400> SEQUENCE: 73
cacggattat ctactgtgat                                                  20

<210> SEQ ID NO 74
<211> LENGTH: 22
<212> TYPE: DNA
<213> ORGANISM: Artificial Sequence
<220> FEATURE:
<223> OTHER INFORMATION: PCR Primer "C3-F7"

<400> SEQUENCE: 74
gcaacagtag ttatacgatg ag                                               22

<210> SEQ ID NO 75
<211> LENGTH: 25
<212> TYPE: DNA
<213> ORGANISM: Artificial Sequence
<220> FEATURE:
<223> OTHER INFORMATION: PCR Primer "7931"

<400> SEQUENCE: 75
gaatctgtta gttagttact tggat                                            25

<210> SEQ ID NO 76
<211> LENGTH: 25
<212> TYPE: DNA
<213> ORGANISM: Artificial Sequence
<220> FEATURE:
<223> OTHER INFORMATION: PCR Primer "7932"

<400> SEQUENCE: 76
tgattatagc tattatcaca gactc                                            25

<210> SEQ ID NO 77
<211> LENGTH: 26
<212> TYPE: DNA
<213> ORGANISM: Artificial Sequence
<220> FEATURE:
<223> OTHER INFORMATION: PCR Primer "7927.DC"

<400> SEQUENCE: 77
ctcttgcata ttcgtaatag taattg                                           26

<210> SEQ ID NO 78
<211> LENGTH: 25
<212> TYPE: DNA
<213> ORGANISM: Artificial Sequence
<220> FEATURE:
<223> OTHER INFORMATION: PCR Primer "7696.CXL"

<400> SEQUENCE: 78
```
attctatcgg aagataggat accag       25

<210> SEQ ID NO 79
<211> LENGTH: 26
<212> TYPE: DNA
<213> ORGANISM: Artificial Sequence
<220> FEATURE:
<223> OTHER INFORMATION: PCR Primer "7697.CXL"

<400> SEQUENCE: 79
atgcacaact tcttgtctgc atgatg       26

<210> SEQ ID NO 80
<211> LENGTH: 26
<212> TYPE: DNA
<213> ORGANISM: Artificial Sequence
<220> FEATURE:
<223> OTHER INFORMATION: PCR Primer "7925.DC"

<400> SEQUENCE: 80
tacggctata tgtagaggag ttaacc       26

<210> SEQ ID NO 81
<211> LENGTH: 25
<212> TYPE: DNA
<213> ORGANISM: Artificial Sequence
<220> FEATURE:
<223> OTHER INFORMATION: PCR Primer "7792.SL"

<400> SEQUENCE: 81
ctctgagaca caaaagaggt agctg       25

<210> SEQ ID NO 82
<211> LENGTH: 25
<212> TYPE: DNA
<213> ORGANISM: Artificial Sequence
<220> FEATURE:
<223> OTHER INFORMATION: PCR Primer "7793SL"

<400> SEQUENCE: 82
catagaacgg tatagagcgt taatc       25

<210> SEQ ID NO 83
<211> LENGTH: 25
<212> TYPE: DNA
<213> ORGANISM: Artificial Sequence
<220> FEATURE:
<223> OTHER INFORMATION: PCR Primer "7928.DC"

<400> SEQUENCE: 83
catcatgagc aacgcgttag tatat       25

<210> SEQ ID NO 84
<211> LENGTH: 25
<212> TYPE: DNA
<213> ORGANISM: Artificial Sequence
<220> FEATURE:
<223> OTHER INFORMATION: PCR Primer "7929.DC"

<400> SEQUENCE: 84 ggagataacct ttagatatgg atctg       25

<210> SEQ ID NO 85
<211> LENGTH: 25
<212> TYPE: DNA

```
<213> ORGANISM: Artificial Sequence
<220> FEATURE:
<223> OTHER INFORMATION: PCR Primer "7926.DC"

<400> SEQUENCE: 85
tcaacaaccg ctcgtgaaca gcttc                                     25

<210> SEQ ID NO 86
<211> LENGTH: 20
<212> TYPE: DNA
<213> ORGANISM: Artificial Sequence
<220> FEATURE:
<223> OTHER INFORMATION: PCR Primer "Gordon_H_1R"

<400> SEQUENCE: 86
gctcggtgct cattgcgttg                                           20

<210> SEQ ID NO 87
<211> LENGTH: 20
<212> TYPE: DNA
<213> ORGANISM: Artificial Sequence
<220> FEATURE:
<223> OTHER INFORMATION: PCR Primer "Gordon_H_2F"

<400> SEQUENCE: 87
caacgcaatg agcaccgagc                                           20

<210> SEQ ID NO 88
<211> LENGTH: 19
<212> TYPE: DNA
<213> ORGANISM: Artificial Sequence
<220> FEATURE:
<223> OTHER INFORMATION: PCR Primer "Gordon_H_probe_R"

<400> SEQUENCE: 88
cactgccttc acggtcacg                                            19

<210> SEQ ID NO 89
<211> LENGTH: 20
<212> TYPE: DNA
<213> ORGANISM: Artificial Sequence
<220> FEATURE:
<223> OTHER INFORMATION: PCR Primer "Gordon_H_probe_F"

<400> SEQUENCE: 89
gttcgccacc gtgaacatcc                                           20

<210> SEQ ID NO 90
<211> LENGTH: 23
<212> TYPE: DNA
<213> ORGANISM: Artificial Sequence
<220> FEATURE:
<223> OTHER INFORMATION: PCR Primer "Gordon_H_1F"

<400> SEQUENCE: 90
tcgcgatatc cgttaagttt gta                                       23

<210> SEQ ID NO 91
<211> LENGTH: 25
<212> TYPE: DNA
<213> ORGANISM: Artificial Sequence
<220> FEATURE:
<223> OTHER INFORMATION: PCR Primer "Gordon_H_3F"

<400> SEQUENCE: 91
gaatatcccc accaggtcta tctac                                     25
```

```
<210> SEQ ID NO 92
<211> LENGTH: 20
<212> TYPE: DNA
<213> ORGANISM: Artificial Sequence
<220> FEATURE:
<223> OTHER INFORMATION: PCR Primer "Gordon_H_4F"

<400> SEQUENCE: 92
taccgacgat gtgcccatcc                                              20

<210> SEQ ID NO 93
<211> LENGTH: 20
<212> TYPE: DNA
<213> ORGANISM: Artificial Sequence
<220> FEATURE:
<223> OTHER INFORMATION: PCR Primer "Gordon_H_5F"

<400> SEQUENCE: 93
atctccgacg gcctgatcat                                              20

<210> SEQ ID NO 94
<211> LENGTH: 1788
<212> TYPE: DNA
<213> ORGANISM: Feline Morbillivirus
<220> FEATURE:
<221> NAME/KEY: misc_feature
<223> OTHER INFORMATION: FeMoV "Lapon strain" H antigen "wild-type" -
      without BamH1 restriction enzyme site - nucleic acid; given as DNA
      sequence

<400> SEQUENCE: 94
atggagtcca acaacattaa atattacaaa gactctaatc ggtatcttgg taaaatatta    60
gatgaacaca agacagttaa taatcaattg tacaggttga gtattaaagt aattaccatt   120
attgctatta ttgtaagctt aattgcaaca ataataacta ttattaatgc cacaagtgga   180
agaactaccc taaacagtaa tacagacata ctgcttagcc aaagagatga gattcatagt   240
attcatgaaa tgatatttga ccgtatttat cctttgataa ctgctatgag tacagagcta   300
ggacttcata ttcctacttt attagatgaa cttactaaag caattgatca aaaaattaaa   360
ataatgaatc ctcccgttga tactgtaaca tctgatctta actggtgtat caaacctcct   420
aatgggatta ttatggaccc aaaaggttat tgcgaaagta tggaattatc taaaacttac   480
aaattattgc ttgatcagtt agatgtctca agaaagaaat cgctcattat aaatagaaag   540
aatatcaacc agtgtcaatt agttgatgac tcaaagatca cttttgctac tgttaatata   600
caatctacac caaggttttt aaatttggt catacagtca gcaatcaacg tataacattt   660
ggtcaaggaa cttatagtag tacttatatt ataactatcc aagaagatgg aataaatgat   720
gttcaatatc gagtgtttga aattggatat atctctgatc agtttggttt tttcccctca   780
ttaatagtat ctagggtatt gcctatacgt atggtattgg aatggaatc ctgtaccttg   840 acgagtgatc gacaaggtgg gtatttctta tgtatgaata cattaacacg gtctatatat   900
gattatgtca atataagaga tttgaaatca ctatacataa cacttcctca ttatggtaag   960
gttaattata cttacttcaa ttttgggaaa attaggagcc cacatgagat tgataaaatt  1020
tggctaacgt ccgaaagagg tcaaattatt tctggttatt ttgcagcatt tgtcacaatt  1080
acgattcgaa attataataa ttatccctac aaatgtttga ataatccatg ttttgacaac  1140
tctgagaatt actgtagggg atggtataag aacataacag gcaccgatga tgttccaata  1200
ctagcatact tactagttga aatgtatgat gaagaaggac ctttaattac acttgtagca  1260
```

-continued

```
ataccacctt acaattatac agctccatct cataattctc tttactatga tgacaaaatt    1320
aataagttga taatgactac atctcacact gggtatatac agatcaatga ggtgcatgag    1380
gtgattgttg gtgatgattt aaaggctatt ctcctgaaca gattatctga tgaacaccct    1440
aatcttacag cctgtagact taatcaaggc attaaagagc agtacaagtc cgatggaacg    1500
ataatttcaa attctgcact tattgatata caagaacgaa tgtatattac agtcaaagct    1560
attccaccag taggtaacta taactttaca gttgagttgc actctagatc aaacacatct    1620
tatatattgt taccgaaaca gttcaatgcc aagtatgaca aattacatct tgagtgcttt    1680
aattgggaca gtcttggtg gtgtgctttg atacctcaat tttcattaag ttggaatgaa    1740 tcccttctg ttgatactgc tattttttaat ttaataaatt gtaaatga                1788
```

<210> SEQ ID NO 95
<211> LENGTH: 4900
<212> TYPE: DNA
<213> ORGANISM: Artificial Sequence
<220> FEATURE:
<223> OTHER INFORMATION: vCP3041:cloned insertion locus C3 and its
    theoretical nucleotide sequence from 38,619 to 43,588 bp
    including C3 right flanking sequence, 42k (long) promoter, Lapon H
    (wt; no BamH I restriction enzyme site) and C3 left flanking
    sequence

<400> SEQUENCE: 95

```
atattattaa aactattaga taacatagct ttatgtaaag gagtatttcc agataactta     60
gctttagcat ttacgtaagc accgtggtca agtaagagtt taacaaattc tgttttcata    120
gaactaactg ccatgtatag aggagtgaaa cctttatgat tatagacgtt tacatagcaa    180
ccatataata agatcgcatt cagtatatta atatctttca tttctatagc tatgtgaata    240
acatgtttat ctaatcctac caactttgta tcagtaccgt acttcagtaa taagtttact    300
atagttttgt ttttagatgc aacagctata tttagaacgg tatctatatg attattaacc    360
acattaacat tagatcctct ttctaaaagt gtctttgttg tttcgatatc gttacgtgaa    420
acagcgtaat gtaagggact gcccatacag tcatctatta cgtttatatc agctcctaga    480
tttaacagaa gtgctgttac atcttttctt ctattaatta ccgaatgatg taatgggtt     540 ttacctaaat catcttgttc gtttataggc actccgtgat ttataagtaa cgctattata    600
tcgtaactac aattattttt aagtgccttt atgagatact gttatgcaa aaataaactt     660 ttatctattt taatactatt atctaacaat atcctaatta aatctatatt cttatacttt    720
atagcgtaat gtaacggagt ttcaaaattt ctagtttgta tattaagatc aatattaaaa    780
tctataaata ttttatacat atcatcagat atcttatcat acagtacatc gtaataattt    840
agaaagaatc tattacaatt aacacctttt tttaataaat atctagttaa tgacttattg    900
tttctatata cagaaatata taacggacta tttccagaat gtatctgttc tatgtcagcg    960
ccagaatcta ttagtagttt agcaatttct gtattatcta aactagcagc tttatgaaga    1020
ggaggatttt tacattttaa aatatcggca ccgtgttcta gtaataattt taccattct     1080 atatcagaaa tacttacggc taaatacaaa gacgttgata gtatatttac gttattgtat    1140
ttgcattttt taagtatata ccttactaaa tttatatctc tataccttat agctttatgc    1200
agttcattta taagtcttcc attactcatt tctggtaatg aagtattata tatcattatg    1260
atattatctc tatttttattc taataaaaac cgttatcatg ttatttatta tttgttataa    1320
ttatactatt taataaaatta taccaaatac ttagatactt attaatacca tcctagaact    1380
```

```
tgtatttctt gcccctaaa cttggacatg cactccatta ggcgtttctt gttttcgaca      1440
tcgtcctcct taacatatcc tactgttatg tgaggattcc acggattatc tactgtgata      1500
tcaccaaaca cgtccttcga acagggtacc gcattcagca gaacatttct tagggctcta     1560
agttcatcag atacctccag tttcataact acagcgcatc ctttcgctcc caactgttta     1620
gaggcgttac tctgaggaaa acacatctct tctttacaga ctatagaaat agtctgtaaa     1680
tcttgatcag ttatttgctt tttgaaattt tcaaatctat cacattgatc catatttgct     1740
attccaagag ttatatgagg aaaaatatca catcctgtca tgtattttat tgtaacatta     1800
ttataatctg taacatcagt atctaaccta acgtcgtaaa agttaacaga tgcccagtta     1860
ctataatccc aaggaacctt aacatctaat cccattaaaa tagtatcctt tctactattt     1920
ttttcattgg caagtatgtg cttagtttta cacaaaattc ctgccatttt gtaacgatag     1980
cgaagcaata gcttgtatgc tttttatttg attaactagt cataaaaatc gggatcctca     2040
aaaaaatata aatgattcac catctgatag aaaaaaaatt tattgggaga atatgataat     2100
attttgggat ttcaaaattg aaaatatata attacaatat aaaatggagt ccaacaacat     2160
taaatattac aaagactcta atcggtatct tggtaaaata ttagatgaac acaagacagt     2220
taataatcaa ttgtacaggt tgagtattaa agtaattacc attattgcta ttattgtaag     2280
cttaattgca acaataataa ctattattaa tgccacaagt ggaagaacta ccctaaacag     2340
taatacagac atactgctta gccaaagaga tgagattcat agtattcatg aaatgatatt     2400
tgaccgtatt tatcctttga taactgctat gagtacagag ctaggacttc atattcctac     2460
tttattagat gaacttacta aagcaattga tcaaaaaatt aaaataatga atcctcccgt     2520
tgatactgta acatctgatc ttaactggtg tatcaaacct cctaatggga ttattatgga     2580
cccaaaaggt tattgcgaaa gtatggaatt atctaaaact acaaattat tgcttgatca      2640 gttagatgtc tcaagaaaga aatcgctcat tataaataga aagaatatca accagtgtca     2700
attagttgat gactcaaaga tcacttttgc tactgttaat atacaatcta caccaaggtt     2760
tttaaatttt ggtcatacag tcagcaatca acgtataaca tttggtcaag aacttatag     2820 tagtacttat attataacta tccaagaaga tggaataaat gatgttcaat atcgagtgtt     2880
tgaaattgga tatatctctg atcagtttgg ttttttcccc tcattaatag tatctagggt     2940
attgcctata cgtatggtat tgggaatgga atcctgtacc ttgacgagtg atcgacaagg     3000
tgggtatttc ttatgtatga atacattaac acggtctata tatgattatg tcaatataag     3060
agatttgaaa tcactataca taacacttcc tcattatggt aaggttaatt atacttactt     3120
caattttggg aaaattagga gcccacatga gattgataaa atttggctaa cgtccgaaag     3180
aggtcaaatt atttctggtt attttgcagc atttgtcaca attacgattc gaaattataa     3240
taattatccc tacaaatgtt tgaataatcc atgttttgac aactctgaga attactgtag     3300
gggatggtat aagaacataa caggcaccga tgatgttcca atactagcat acttactagt     3360
tgaaatgtat gatgaagaag gacctttaat tacacttgta gcaataccac cttacaatta     3420
tacagctcca tctcataatt ctctttacta tgatgacaaa attaataagt tgataatgac     3480
tacatctcac actgggtata tacagatcaa tgaggtgcat gaggtgattg ttggtgatga     3540
tttaaaggct attctcctga acagattatc tgatgaacac cctaatctta cagcctgtag     3600
acttaatcaa ggcattaaag agcagtacaa gtccgatgga acgataattt caaattctgc     3660
acttattgat atacaagaac gaatgtatat tacagtcaaa gctattccac cagtaggtaa     3720
ctataacttt acagttgagt tgcactctag atcaaacaca tcttatatat tgttaccgaa     3780
```

-continued

```
acagttcaat gccaagtatg acaaattaca tcttgagtgc tttaattggg acaagtcttg   3840
gtggtgtgct ttgatacctc aattttcatt aagttggaat gaatcccttt ctgttgatac   3900
tgctattttt aatttaataa attgtaaatg actcgaggaa ttcctgcagc ccgggttttt   3960
atagctaatt agtcaaatgt gagttaatat tagtatacta cattactaat ttattacata   4020
ttcatttata tcaatctagt agcatttagc ttttataaaa caatataact gaatagtaca   4080
tactttacta ataagttata aataagagat acatatttat agtattttac tttctacact   4140
gaatataata atataattat acaaatataa tttttaatac tatatagtat ataactgaaa   4200
taaaatacca gtgtaatata gttattatac atttatacca catcaaagat gagttataac   4260
atcagtgtca ctgttagcaa cagtagttat acgatgagta gttactctcg tatggcgtta   4320
gtatgtatgt atcttctagt tttcttagta ggcattatag gaaacgtcaa gcttataagg   4380
ttattaatgg tatctagaaa tatatctatt ataccgtttc tcaacttggg aatagccgat   4440
ttgctgtttg tgatattcat acctttatac attatataca tactaagtaa tttccattgg   4500
cattttggta aagcactttg taaaattagt tctttctttt ttacttctaa catgtttgca   4560
agtatatttt taataactgt aataagcgta tatagatatg taaaaattac ccttcctgga   4620
tttacctata aatatgttaa cattagaaat atgtacatta ctatattttt catatggatt   4680
atttctatta tactagggat tcctgctctt tactttagaa atactatcgt aacaaaaaat   4740
aacgacacgc tgtgtattaa tcattatcat gataatagag aaattgctga attgatttac   4800
aaagttatta tctgtatcag atttatttta ggatacctac tacctacgat aattatactc   4860
gtatgctata cgttactgat ctacagaact aacaatgcat                         4900
```